US011510993B2

(12) United States Patent
Brandish et al.

(10) Patent No.: US 11,510,993 B2
(45) Date of Patent: Nov. 29, 2022

(54) ANTIBODY DRUG CONJUGATE FOR ANTI-INFLAMMATORY APPLICATIONS

(71) Applicants: Merck Sharp & Dohme Corp., Rahway, NJ (US); Ambrx, Inc., La Jolla, CA (US)

(72) Inventors: Philip E. Brandish, Needham, MA (US); Robert M. Garbaccio, Lansdale, PA (US); Jeffrey Kern, Gilbertsville, PA (US); Linda Liang, Mountain View, CA (US); Sanjiv Shah, Wakefield, MA (US); Dennis Zaller, Boston, MA (US); Andrew Beck, San Diego, CA (US); Dennis Gately, San Diego, CA (US); Nick Knudsen, Escondido, CA (US); Anthony Manibusan, San Diego, CA (US); Jianing Wang, San Diego, CA (US); Ying Sun, San Diego, CA (US)

(73) Assignees: Merck Sharp & Dohme LLC, Rahway, NJ (US); Ambrx, Inc., La Jolla, CA (US)

(*) Notice: Subject to any disclaimer, the term of this patent is extended or adjusted under 35 U.S.C. 154(b) by 776 days.

(21) Appl. No.: 15/765,515

(22) PCT Filed: Sep. 30, 2016

(86) PCT No.: PCT/US2016/054658
§ 371 (c)(1),
(2) Date: Apr. 3, 2018

(87) PCT Pub. No.: WO2017/062271
PCT Pub. Date: Apr. 13, 2017

(65) Prior Publication Data
US 2020/0164085 A1    May 28, 2020

Related U.S. Application Data

(60) Provisional application No. 62/237,668, filed on Oct. 6, 2015.

(51) Int. Cl.
*A61K 47/68* (2017.01)
*C07K 16/28* (2006.01)
*A61K 45/06* (2006.01)

(52) U.S. Cl.
CPC ...... *A61K 47/6889* (2017.08); *A61K 47/6803* (2017.08); *A61K 47/6849* (2017.08); *C07K 16/2833* (2013.01); *C07K 16/2896* (2013.01); *A61K 45/06* (2013.01); *C07K 2317/51* (2013.01); *C07K 2317/515* (2013.01); *C07K 2317/565* (2013.01)

(58) Field of Classification Search
None
See application file for complete search history.

(56) References Cited

U.S. PATENT DOCUMENTS

| 5,094,848 | A  | * | 3/1992  | Brixner ............. A61K 51/1093 424/1.53 |
|---|---|---|---|---|
| 5,621,002 | A  |   | 4/1997  | Bosslet et al. |
| 6,214,345 | B1 |   | 4/2001  | Firestone et al. |
| 6,218,519 | B1 |   | 4/2001  | Kenten et al. |
| 6,268,488 | B1 |   | 7/2001  | Barbas, III |
| 6,677,435 | B2 |   | 1/2004  | Barbas, III et al. |
| 6,759,509 | B1 |   | 7/2004  | King et al. |
| 6,835,807 | B1 |   | 12/2004 | Susaki et al. |
| 7,229,618 | B2 |   | 6/2007  | Johnson et al. |
| 10,550,190 | B2 |  | 2/2020  | Garbaccio |
| 2002/0042539 | A1 | | 4/2002  | Arstad et al. |
| 2002/0102590 | A1 | | 8/2002  | Taing et al. |
| 2003/0096743 | A1 | | 5/2003  | Senter et al. |
| 2003/0130189 | A1 | | 7/2003  | Senter et al. |
| 2004/0018194 | A1 | | 1/2004  | Francisco et al. |
| 2004/0052793 | A1 | | 3/2004  | Carter et al. |
| 2004/0121940 | A1 | | 6/2004  | De Groot et al. |
| 2004/0219203 | A1 | * | 11/2004 | Griffiths ................. A61K 45/00 424/450 |
| 2006/0122143 | A1 | | 6/2006  | Boyer et al. |
| 2007/0048773 | A1 | | 3/2007  | Lee et al. |
| 2010/0249072 | A1 | | 9/2010  | Borch et al. |
| 2012/0058473 | A1 | | 3/2012  | Yue et al. |
| 2015/0017187 | A1 | | 1/2015  | Thanos et al. |
| 2015/0065393 | A1 | | 3/2015  | Jacobson |
| 2017/0182181 | A1 | | 6/2017  | Garbaccio |
| 2019/0030171 | A1 | | 1/2019  | Garbaccio |
| 2019/0071483 | A1 | | 3/2019  | Carrington |

FOREIGN PATENT DOCUMENTS

| WO | WO199813059 A1 | 4/1998 |
|---|---|---|
| WO | WO2004032828 A2 | 4/2004 |
| WO | 2009058734 A1 | 5/2009 |

(Continued)

OTHER PUBLICATIONS

Edwards et al J. Mol. Biol., 334:103-118, 2003.*
Timmermans et al, Frontiers in Immunology, 10:1545, pp. 1-17, 2019.*
Ostrovskis et al., Application of Metal Free Click Chemistry in Biological Studies, Current Organic Chemistry, 2013,vol. 17, pp. 610-640.
Alley et al., Contribution of Linker Stability to the Activity of Anticancer Immunoconjugates, Bioconjugate Chem., 2008, pp. 759-765, 19.
Austin et al., Oxidizing Potential of Endosomes and Lysosomes Limits Intracellular Cleavage of Disulfide Based Antibody Drug Conjugates, Proc. Natl. Acad. Sci., USA, 2005, pp. 17987-17992, 102.

(Continued)

*Primary Examiner* — Patricia Duffy
(74) *Attorney, Agent, or Firm* — John David Reilly; Anna L. Cocuzzo

(57) ABSTRACT

Antibody drug conjugates (ADCs) comprising an antibody conjugated to an anti-inflammatory therapeutic agent via a phosphate-based linker with tunable extracellular and intracellular stability are described.

20 Claims, 10 Drawing Sheets

Specification includes a Sequence Listing.

(56) References Cited

FOREIGN PATENT DOCUMENTS

| WO | WO2010096142 A1 | 8/2010 |
|---|---|---|
| WO | WO2014153164 A1 | 8/2010 |
| WO | WO2011116387 | 9/2011 |
| WO | 2014073845 A1 | 5/2014 |
| WO | 2015006736 A2 | 1/2015 |
| WO | WO2015153401 | 10/2015 |

OTHER PUBLICATIONS

Blattler et al., New Heterobifunctional Protein Cross-linking Reagent that forms an Acid Labile Link, Biochem., 1985, pp. 1517-1524, 24.

Carl et al., A Novel Connector Linkage Applicable in Prodrug Design, J. Med. Chem., 1981, pp. 479-480, 24.

Chakravarty et al., Plasmin-activated Prodrugs for Cancer Chemotherapy, J. Med. Chem., 1983, pp. 638-644, 26.

Chari et al., Targeted Delivery of Chemotherapeutics: Tumor-activated Prodrug Therapy, Adv. Drug Delivery Rev., 1998, pp. 89-104, 31.

De Groot et al., Design, Synthesis, and Biological Evaluation of a Dual Tumor Specific Motive, Molecular Cancer Therapeutics, 2002, pp. 901-911, 1.

De Groot et al., Elongated Multiple Electronic Cascade and Cyclization Spacer Systems in Activatible Anticancer Prodrugs for Enhanced Drug Release, Journal of Organic Chemistry, 2001, pp. 8815-8830, 66.

De Groot et al., Synthesis and Biological Evaluation of Novel Prodrugs of Anthracyclines for Selective Activation by the Tumor-Associated Protease Plasmin, J. Med. Chem., 1999, pp. 5277-5283, 42.

Doronina et al., Enhanced Activity of Monomethylauristatin F through Monoclonal Antibody Delivery, Bioconj. Chem., 2006, pp. 114-124, 17.

Erickson et al., Antibody-Maytansinoid Conjugates are Activated in Targeted Cancer Cells by Lysomomal Degradation, Cancer Research, 2006, pp. 4426-4433, 66.

Hamann et al., An Anti-MUC1 Antibody Calicheamicin Conjugate for Treatment of Solid Tumors, Bioconj. Chem., 2005, pp. 346-353, 16.

Hashimoto et al., Significance of Cathepsin B Accumulation in Synovial luid of Rheumatoid Arthritis, Biochem Biophys. Res. Commun., 2001, pp. 334-339, 288.

Hong et al., Nucleoside Conjugates as Potential Antitumor Agents, Journal of Medicinal Chemistry, 1979, No. 11, pp. 1428-1432, 22.

King et al., Monoclonal Antibody Conjugates of Doxorubicin Prepared with Branched Peptide Linkers, J. Med. Chem., 2002, pp. 4336-4343, 45.

Lewis et al., Targeting HER2-Positive Brease Cancer with Trastuzumab-DM1, An Antibody-Cytotoxic Drug Conjugate, Cancer Research, 2008, pp. 9280-9290, 68.

NA, Pub Chern Compound Summary, CID21125146, 2007, pp. 1 and 2, NA.

Sinha et al., Plasma Membrane Association of Cathepsin B in Human Prostate Cancer, Prostate, 2001, pp. 172-184, 49.

Widdison et al., Semisynthetic Maytansine Analogues for the Targeted Treatment of Cancer, J. Med. Chem., 2006, pp. 4392-4408, 49.

Chabenne, J. et al., A Glucagon Analog Chemically Stabilized for Immediate Treatment of Life-threatening hypoglycemia, Molecular Metabolism, 2014, No. 3, pp. 293-300, 3.

Hallam, Trevor J. et al., Antibody Conjugates with Unnatural Amino Acids, Molecular Pharmaceutics, 2015, 1848-1862, 12.

Kern, Jeffrey C., Discovery of Pyrophosphate Diesters as Tunable, Soluble, and Bioorthogonal Linkers for Site-Specific Antibody-Drug Conjugates, Journal of the American Chemical Society, 2015, 1430-1445, vol. 138.

Graversen, JH, Targeting the Hemoglobin Scavenger receptor CD163 in Macrophages Highly Increases the Anti-inflammatory Potency of Dexamethasone, The Journal of the American Society of Gene Therapy, 2012, pp. 1550-1558, vol. 20, No. 8.

Stein, Rhona et al., Combining Milatuzumab with Bortezomib, Doxorubicin, or Dexamethasone Improves Responses in Multiple Myeloma Cell Lines, Clinical Cancer Research, 2009, 2808-2817, 15(8).

\* cited by examiner

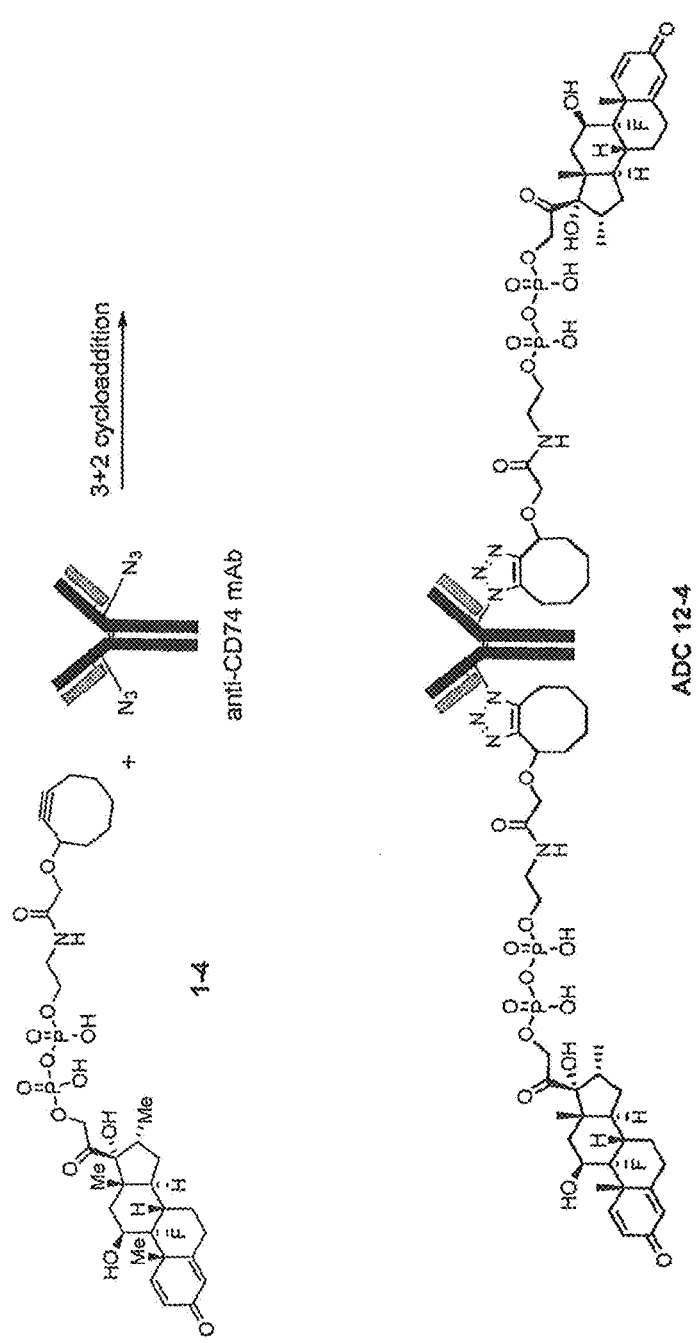
FIG 1: Synthesis of antibody-drug conjugate ADC 12-4.

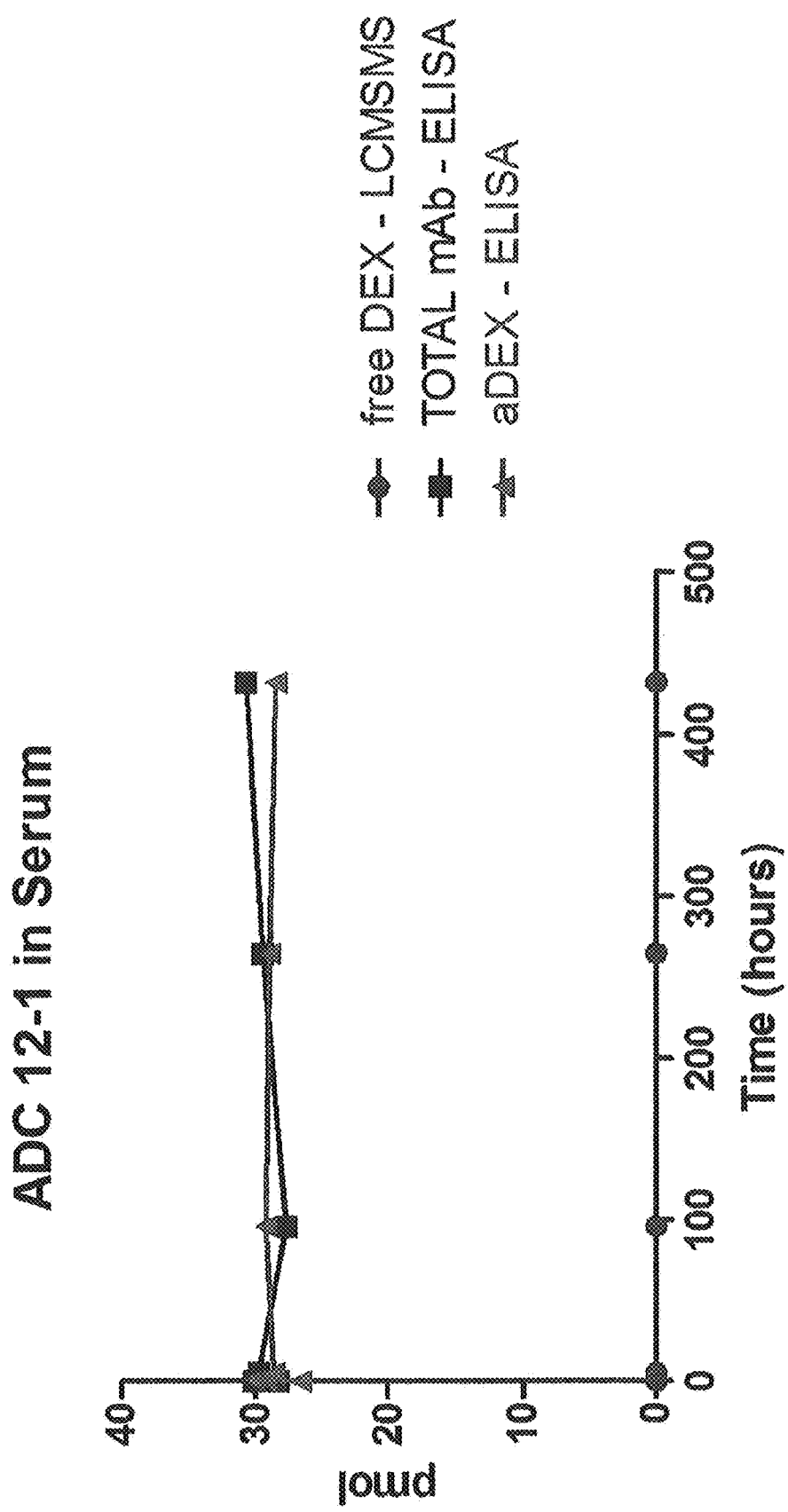
FIG. 2. Mouse serum stability of antibody-drug conjugate 12-1

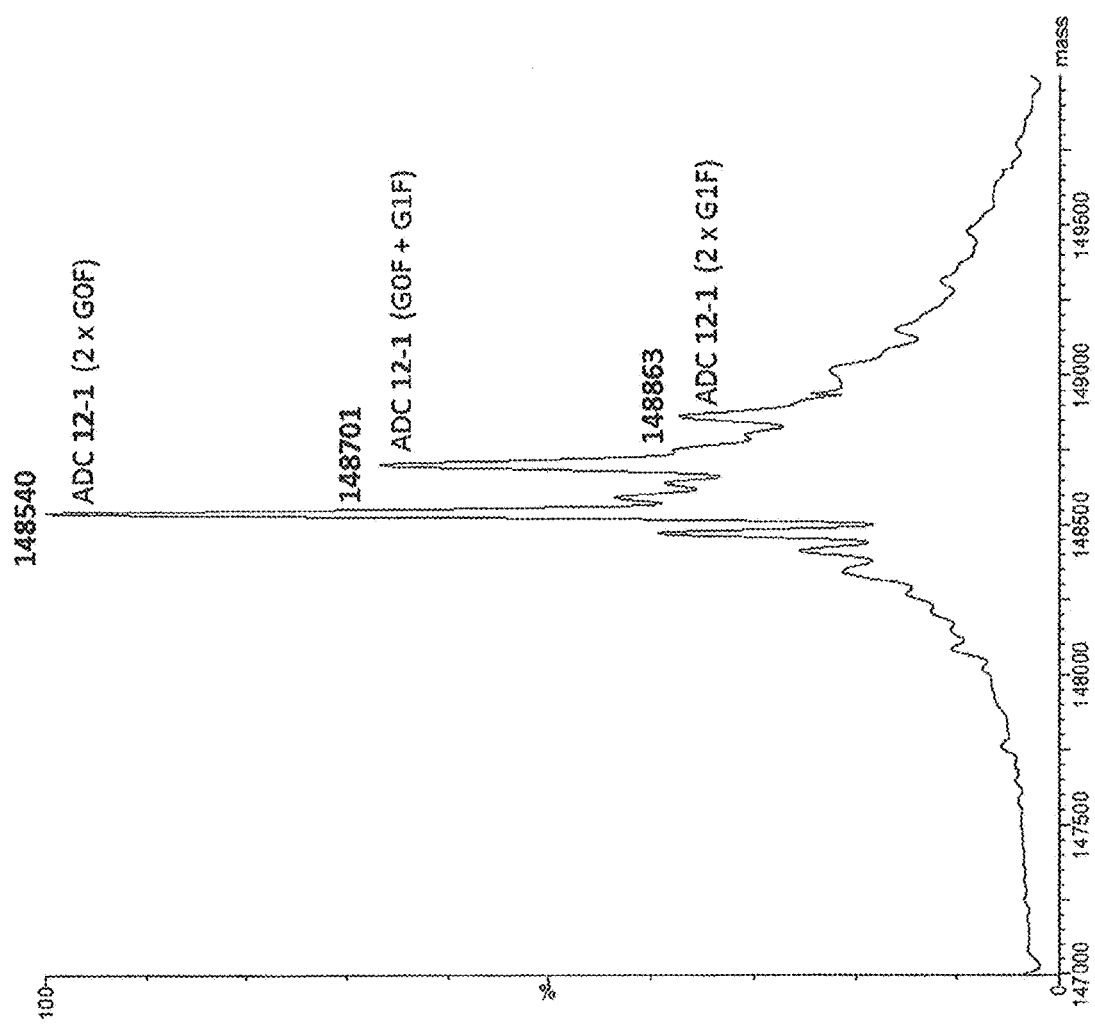
FIG. 3: Deconvoluted intact mass spectrum for 12-1 stock solution.

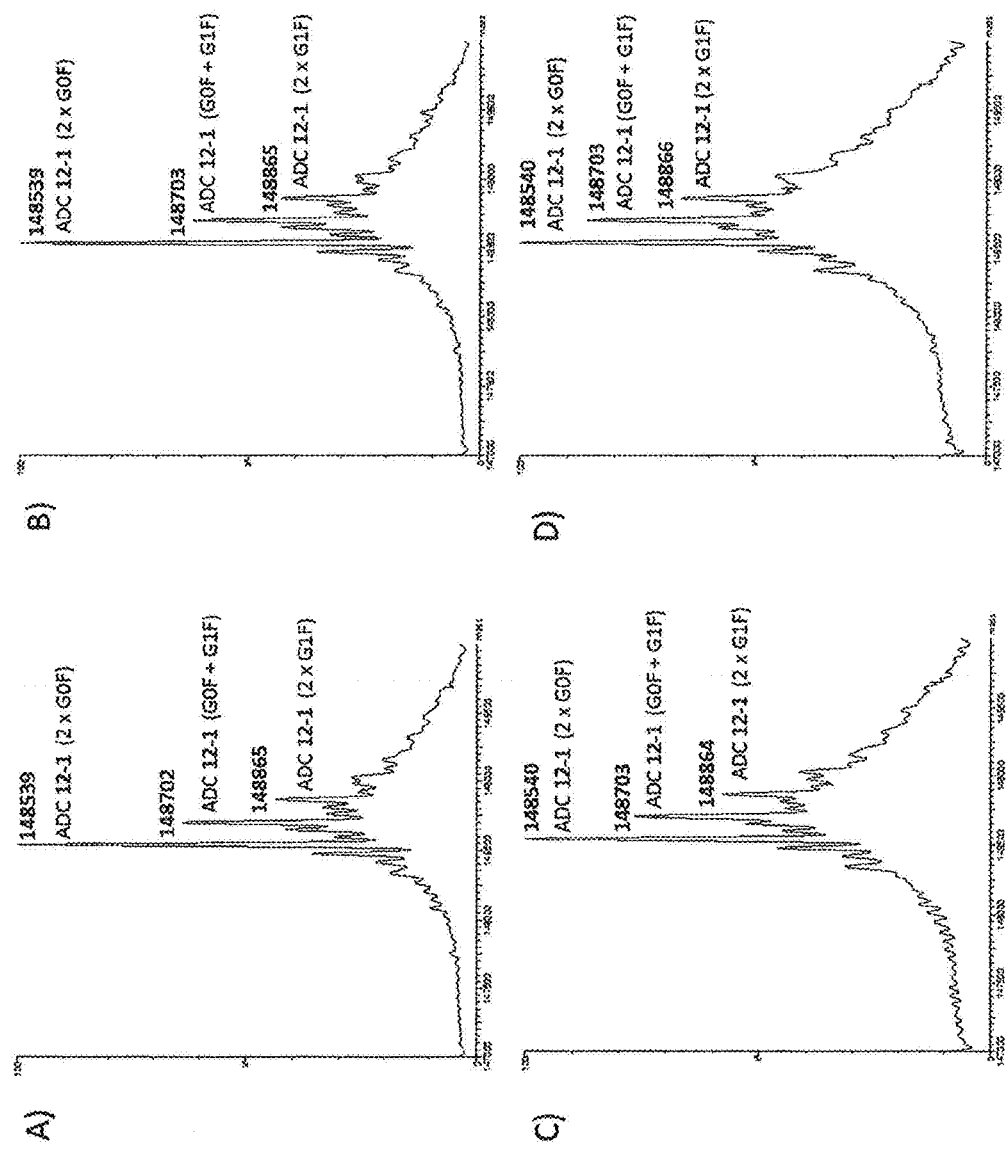
FIG. 4: Deconvoluted intact mass spectra for *in-vitro* stability samples incubated at 37°C for: A) 1 hour, B) 8 hours, C) 14 days and D) 21 days.

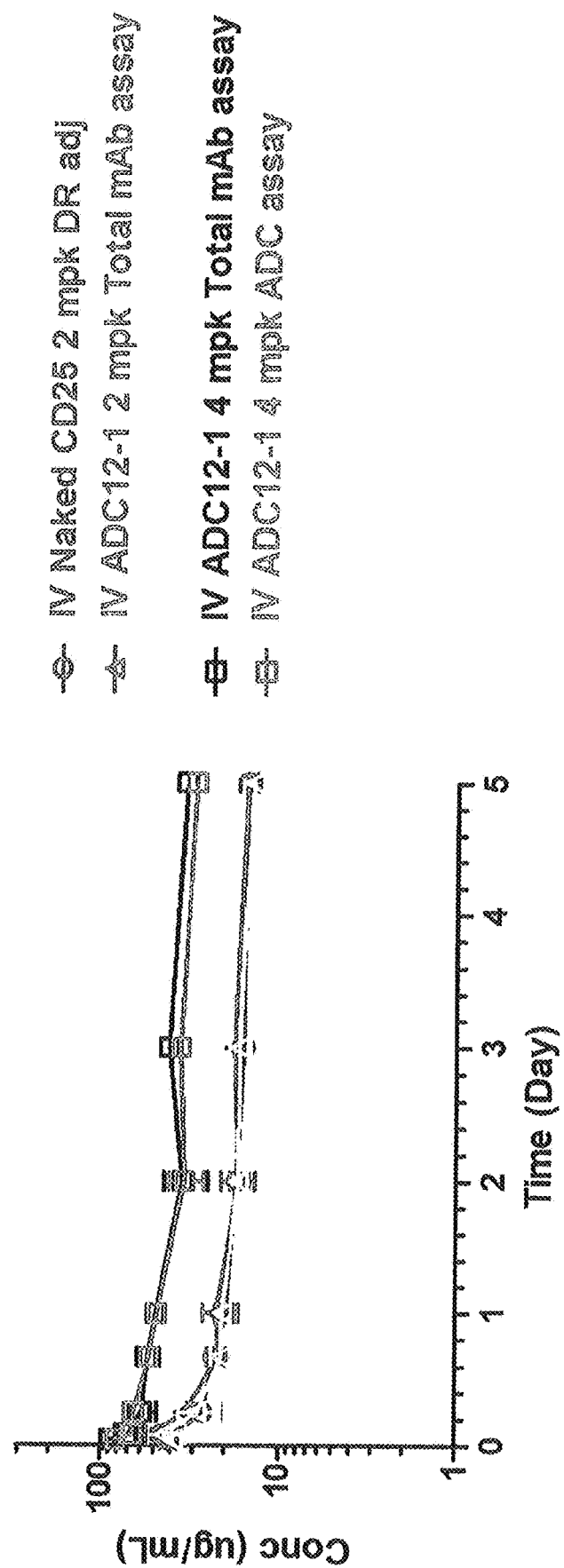
FIG 5: *In vivo* stability of antibody-drug conjugate 12-1 following IV dosing to DBA1 mice

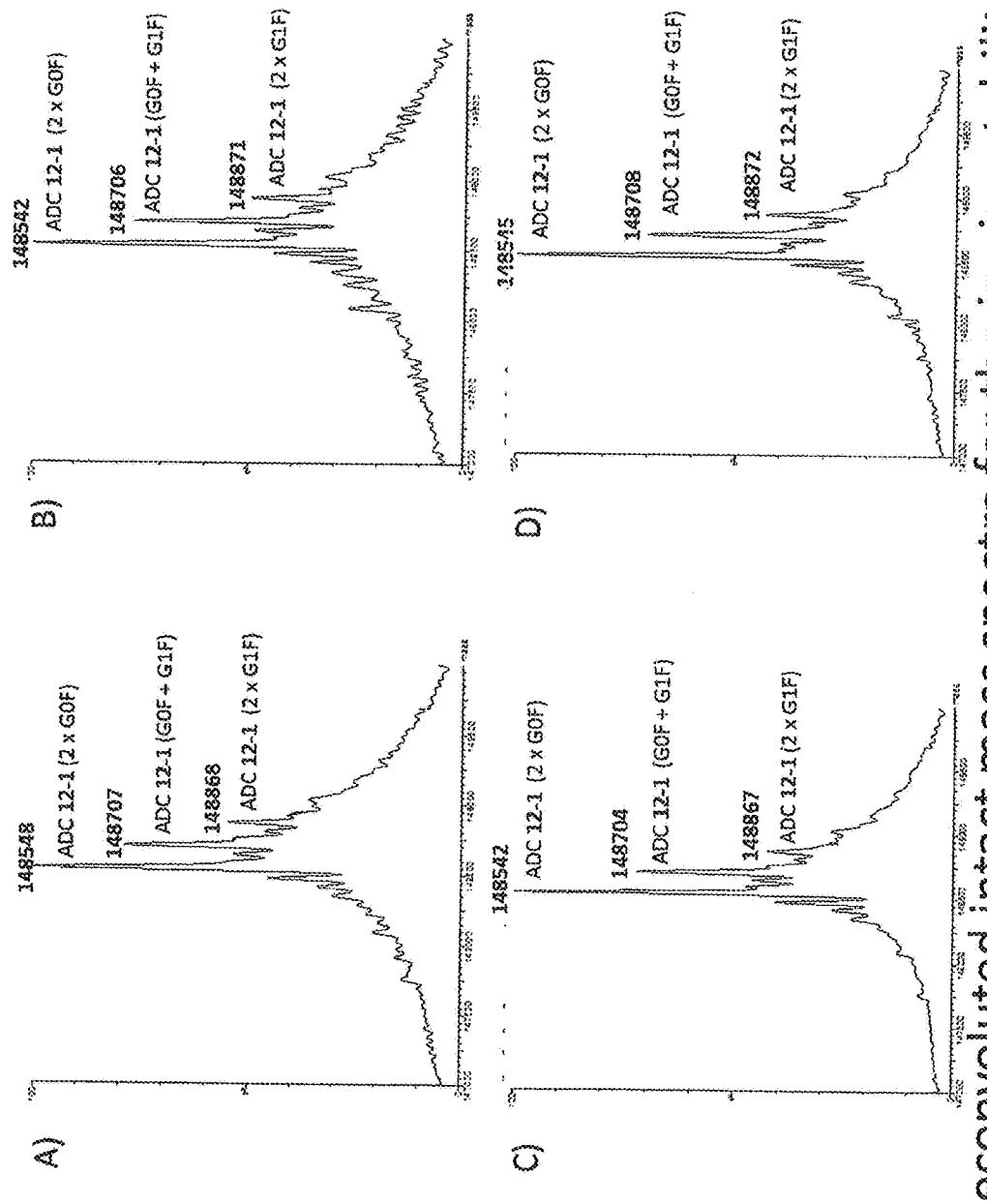
FIG 6: Deconvoluted intact mass spectra for the *in vivo* stability samples: A) sample B1 at 1 hour, B) sample H3 at 5 days, C) sample B7 at 1 hour and D) sample H9 at 5 days.

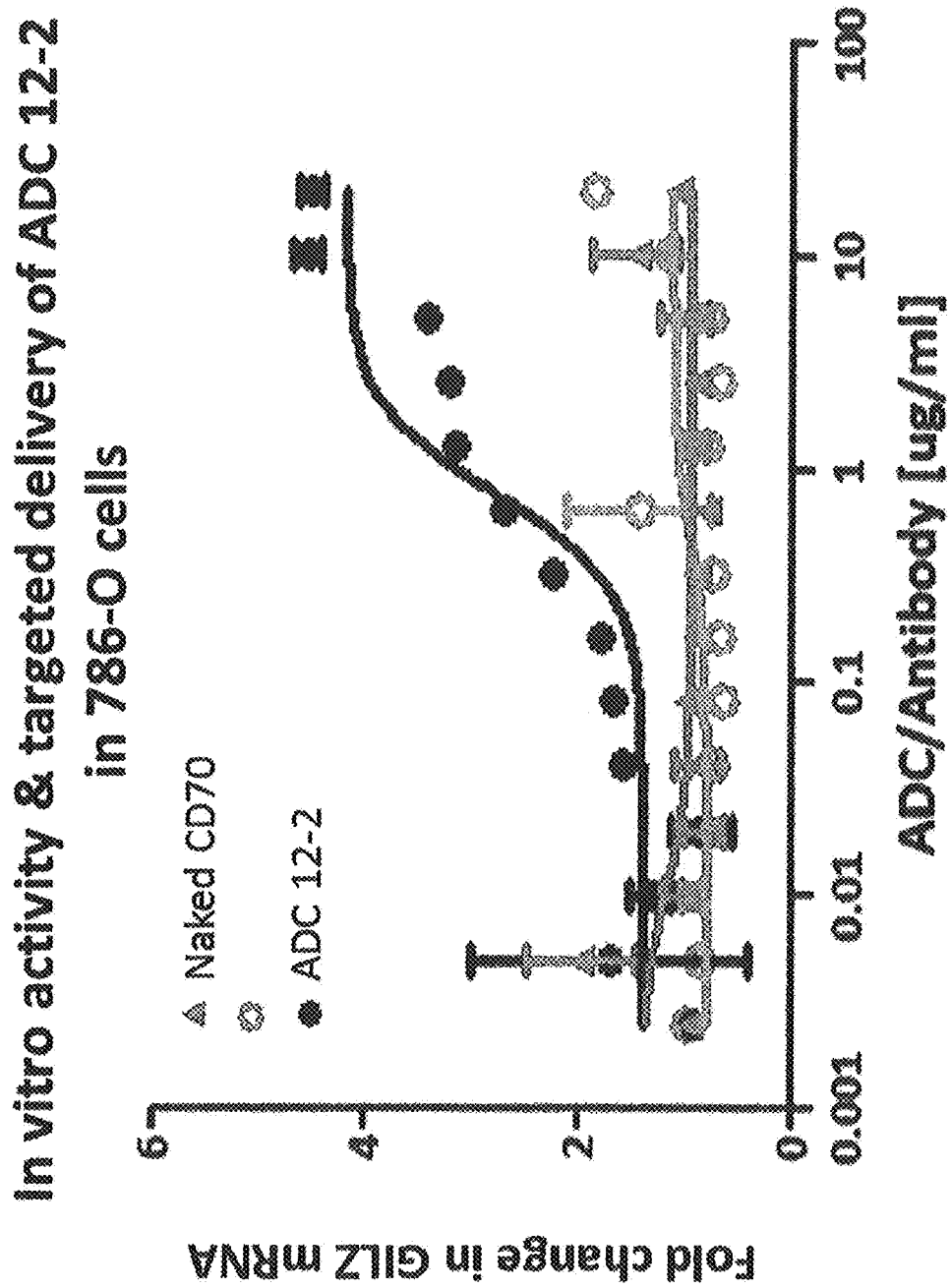
FIG 7: In vitro activity of ADC 12-2 in 786-O cells.

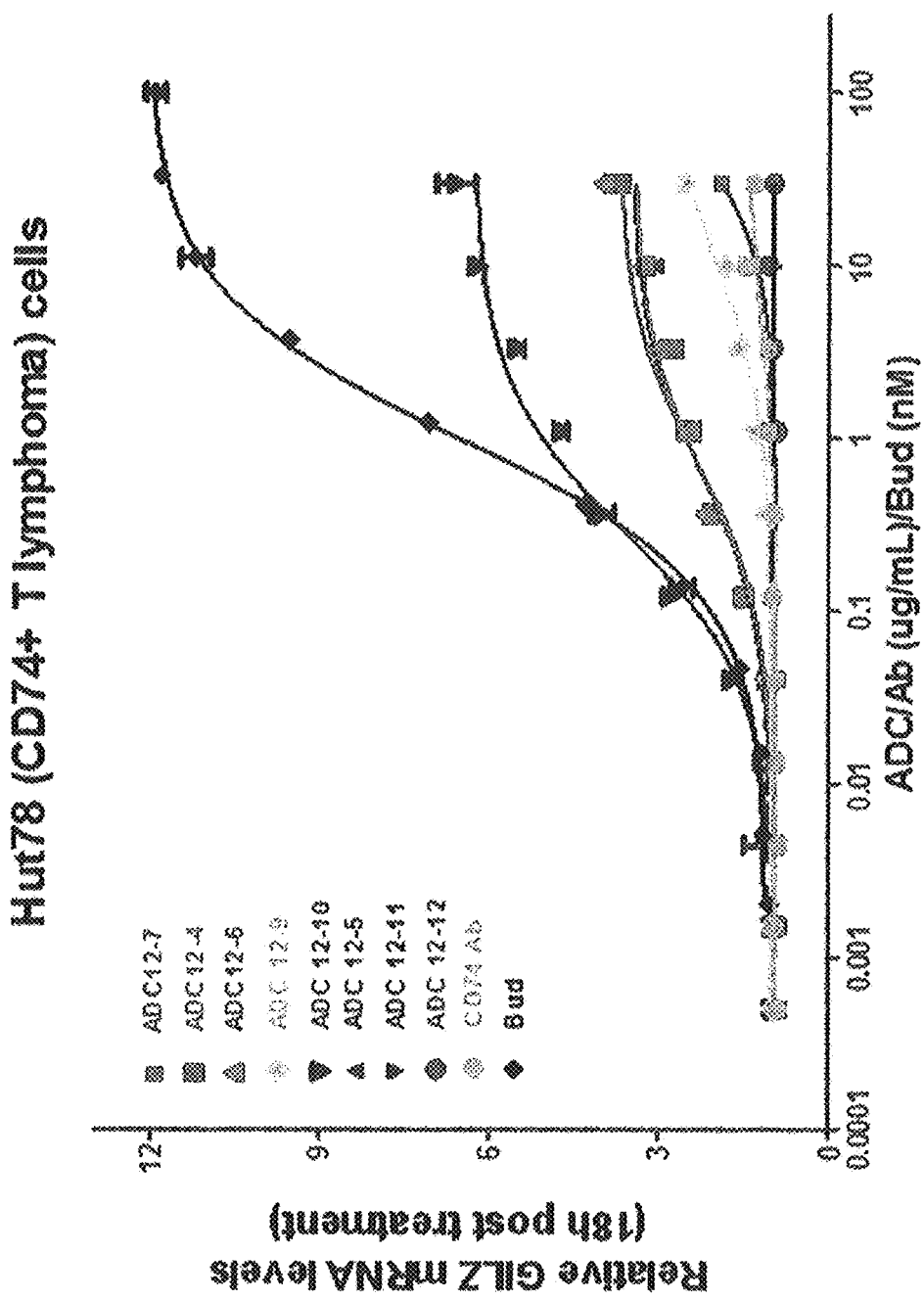
Fig. 8 Activity of anti-hC74 (LL1) ADCs in Hut78 cells

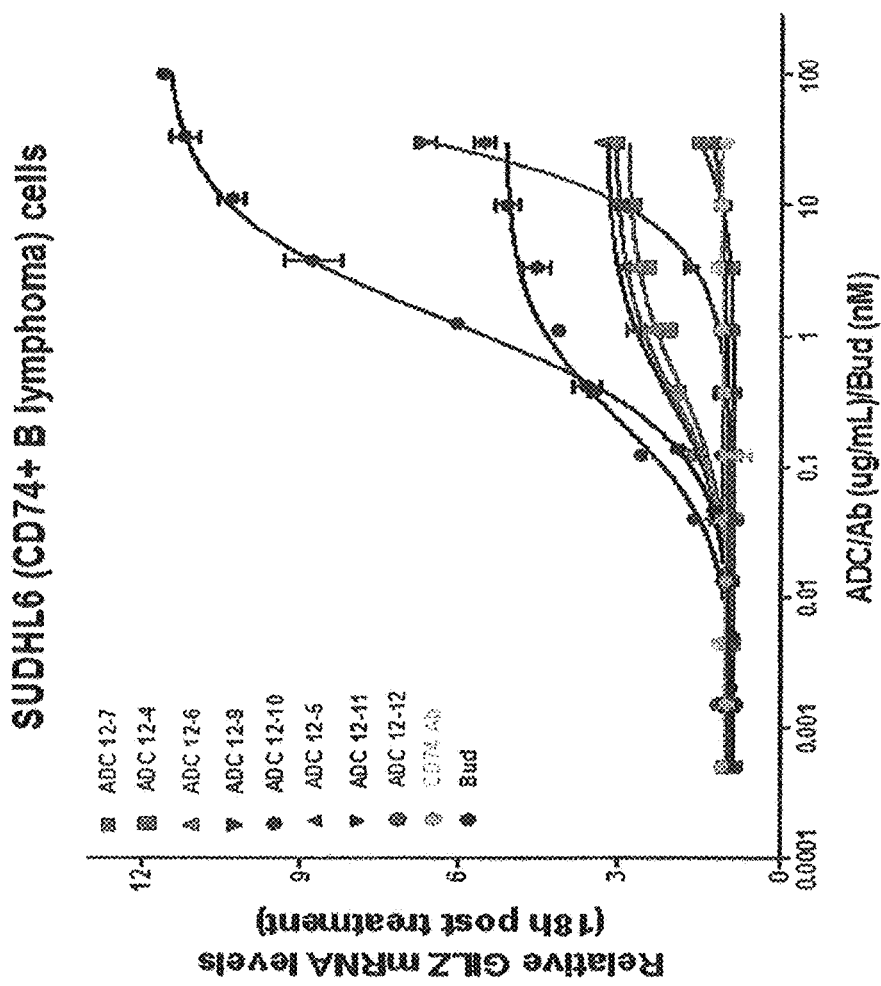
Fig. 9 Activity of anti-hC74 (LL1) ADCs in SUDHL-6 cells

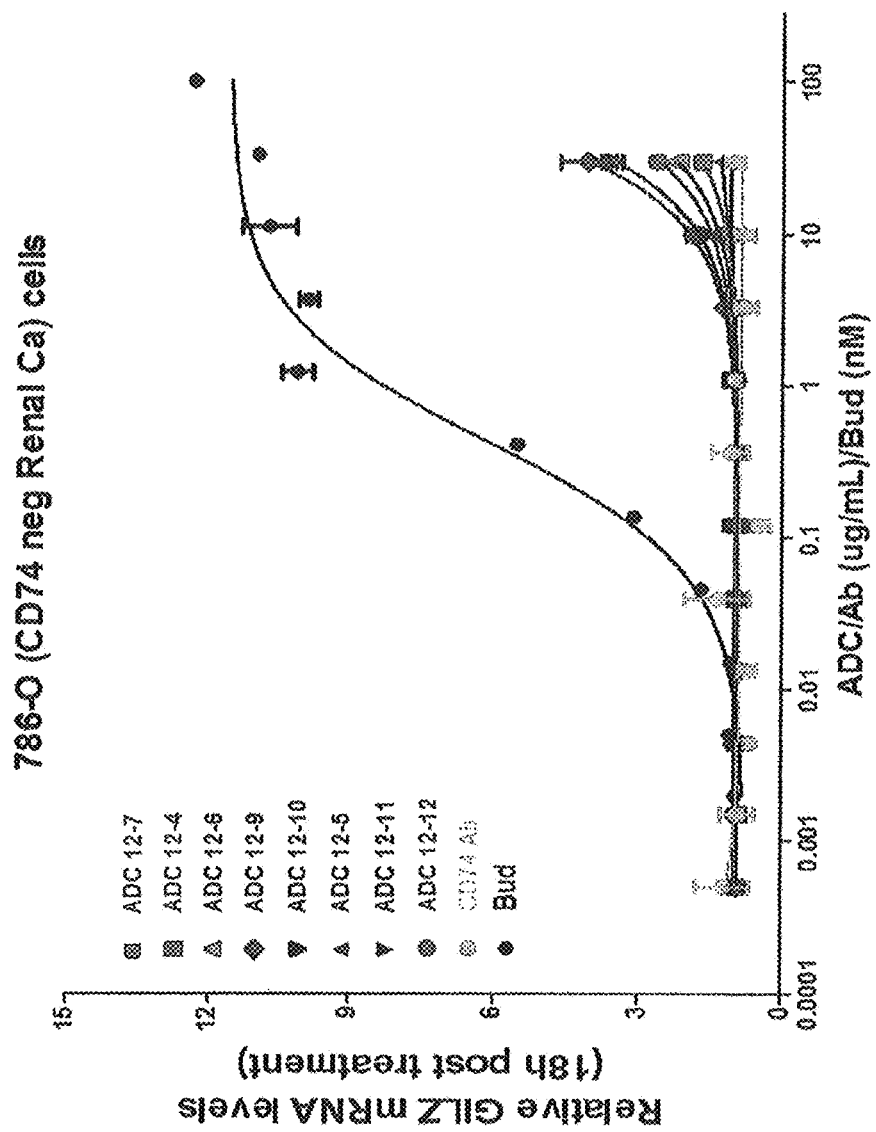
Fig. 10 Activity of anti-hC74 (LL1) ADCs in 786-O cells

ANTIBODY DRUG CONJUGATE FOR ANTI-INFLAMMATORY APPLICATIONS

CROSS REFERENCE TO RELATED APPLICATIONS

This application is a National Stage Application of PCT/US2016/054658 filed Sep. 30, 2016, and claims benefit under 35 U.S.C. 119(e) of U.S. Provisional Application No. 62/237,668, filed Oct. 6, 2015, both of which are incorporated herein in their entities.

BACKGROUND OF THE INVENTION

(1) Field of the Invention

The present invention relates to antibody drug conjugates (ADCs) comprising an antibody conjugated to an anti-inflammatory therapeutic agent via a phosphate-based linker having tunable extracellular and intracellular stability.

(2) Description of Related Art

Antibody drug conjugates (ADC) are targeted chemotherapeutic molecules combining the ideal properties of both antibodies and cytotoxic drugs by targeting potent cytotoxic drugs to antigen-expressing tumor cells. The antigen-expressing tumor cells internalize the ADC, which then releases the drug from the ADC, thereby enhancing the drug's anti-tumor activity. This strategy has met limited success in part because many cytotoxic drugs tend to be inactive or less active when conjugated to large antibodies or protein receptor ligands. Promising advancements with immunoconjugates have seen cytotoxic drugs linked to antibodies through a linker that is cleaved at the tumor site or inside tumor cells.

The successful ADC development for a given target antigen depends on optimization of antibody selection, linker design and stability, drug potency and mode of drug and linker conjugation to the antibody. Linker properties such as pH and redox sensitivities and protease susceptibility influence circulatory stability and release of the drug moiety. The intracellular cleavage of disulfide containing linkers of an ADC is limited by the oxidizing potential of endosomes and lysosomes and are probably not released by reductive cleavage within the endocytic pathway (Austin et al., Proc. Natl. Acad. Sci. USA 102: 17987-17992 (2005)). Reductive cleavage may occur at the cell membrane and impart a bystander killing effect of tumor and susceptible normal cells by free drug. Inappropriate release of drug likely contributes to toxicity. Linker stability plays an important role in both the efficacy and toxicity of ADC (Alley et al., Bioconjugate Chem. 19:759-765 (2008)). Stable, non-cleavable linkers such as mcc are more efficacious and safer than unstable, disulfide linkers, widening the therapeutic window. However, while mcc linkers are more stable than disulfides, they can only be used for drugs that can tolerate residual linker on it and still be potent. Thus, self-immolative linkers are needed for drugs that do not have this flexible structure activity relationship (SAR).

A chemical solution to targeted delivery of cytotoxic or cytostatic drugs conjugated to cell-specific ligands is the "self-immolative linker", PABC or PAB (para-aminobenzyloxycarbonyl) linker, attaching the drug moiety to the ligand in the conjugate (Carl et al., J. Med. Chem. 24: 479-480 (1981); Chakravarty et al., J. Med. Chem. 26: 638-644 (1983)). The PAB linker unit is also referred to as an electronic cascade spacer. The amide bond linking the carboxy terminus of a peptide unit and the para-aminobenzyl of PAB may be a substrate and cleavable by certain proteases. Following cleavage, the aromatic amine becomes electron-donating and initiates an electronic cascade that leads to the expulsion of the leaving group, which releases the free drug after elimination of carbon dioxide (de Groot, et al. Journal of Organic Chemistry 66: 8815-8830 (2001)). Cathepsin B is a ubiquitous cysteine protease with increasing activity within low pH environments (i.e. lysosomes). It is an intracellular enzyme, except in pathological conditions, such as metastatic tumors (Sinha et al., Prostate 49: 172-184 (2001)) or rheumatoid arthritis (Hashimoto et al., Biochem. Biophys. Res. Commun. 283: 334-339 (2001)). Therefore, conjugates produced with cathepsin B-cleavable linkers are likely to be stable in circulation. Upon cleavage of a peptide bond adjacent to the PABC, i.e. by an intracellular enzyme, the drug is released from the ligand whereby no remaining portion of the linker is bound (de Groot et al., Molecular Cancer Therapeutics 1: 901-911 (2002); de Groot et al., J. Med. Chem. 42: 5277-5283 (1999)).

Linkers containing the para-aminobenzyloxycarbonyl (PAB or PABC) unit, in conjunction with a peptide unit, have been developed with a "self-immolating" or "self-immolative" mechanism of 1,6 elimination and fragmentation under enzymatic, hydrolytic, or other metabolic conditions to release a drug moiety from a targeting ligand, such as an antibody (U.S. Pat. Nos. 6,214,345; 6,677,435 5,621,002; 6,218,519; 6,835,807; 6,268,488; and 6,759,509; US Pat. Pub. Nos. 20030130189; 20030096743; 20040052793; 20040018194; 20040052793; and 20040121940; PCT Pub. Nos. WO 98/13059 and WO2004/032828).

Limitations of the PAB type self-immolating linkers are the propensity to cause poor solubility and aggregation of the conjugates. In addition, some PAB-containing conjugates may not be suitable substrates for certain cleaving enzymes or cleave too slowly to achieve efficacy. While the PAB/PABC linkers have been exemplified for amine-terminus payloads that form stable carbamate bonds, for payloads that do not contain a linkable amine, the carbonate that is formed may not be stable and so there is a need for self-immolative linkers that can handle payloads with an oxygen terminus, for example, dexamethasone.

In light of the above, there is a need for linkers for constructing drug-ligand conjugates with improved therapeutic efficacy.

BRIEF SUMMARY OF THE INVENTION

The present invention provides antibody-drug conjugates (ADCs) for use in treatments where it is desirable that the treatment include an anti-inflammatory component. The antibody-drug conjugates comprise an antibody that targets a CD74 or CD163 protein conjugated to an anti-inflammatory therapeutic agent via a phosphate-based linker with tunable stability for intracellular delivery of the therapeutic agent. The phosphate-based linker comprises a monophosphate, diphosphate, triphosphate, or tetraphosphate group (phosphate group) covalently linked to the distal end of a linker arm comprising from the distal to the proximal direction a tuning element, optionally a spacer element, and a reactive functional group. The phosphate group of the phosphate-based linker is capable of being conjugated to the therapeutic agent and the reactive functional group is capable of being conjugated to the side chain of an amino acid (natural or non-natural amino acid) comprising the antibody. The phosphate-based linker has a differentiated and tunable stability in blood vs. an intracellular environment (e.g., lysosomal compartment). The inventors have discovered that the rate at which the phosphate group is cleaved in the intracellular environment to release the anti-inflammatory agent in its native or active form may be affected by the structure of the tuning element with further effects mediated by substitutions of the phosphate group as well as whether the phosphate group is a monophosphate, diphosphate, triphosphate, or tetraphosphate.

Therefore, the present invention provides composition comprising a compound having formula (I)

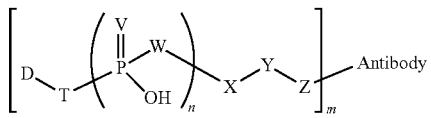

wherein V is selected from O and S; W is selected from O, N, and $CH_2$; X is a tuning element selected from a covalent bond; a carbon atom; a heteroatom; an optionally substituted group selected from the group consisting of acyl, aliphatic, heteroaliphatic, aryl, heteroaryl, and heterocyclic; nucleoside, protease sensitive group, cathepsin B sensitive group, or glycosidase sensitive group; Y is selected from a covalent bond or a bivalent, straight or branched, saturated or unsaturated, optionally substituted $C_{1-30}$ hydrocarbon chain wherein one or more methylene units of Y are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group; T is an NR, $CR_2$, O, or S; D is an anti-inflammatory agent; antibody is a chimeric, humanized, or human antibody having a light chain and a heavy chain wherein the antibody binds the human CD25, human CD70, human CD74 protein, or human CD163 protein (anti-CD25 antibody, anti-CD70 antibody, anti-CD74, or anti-CD163 antibody, respectively); Z is a linkage formed between (i) a reactive functional group selected from the group consisting of N-hydroxysuccinimide, para-nitrophenyl carbonate, para-nitrophenyl carbamate, pentafluorophenyl, haloacetamide, maleimide, hydroxylamine, strained cycloalkyne, and heterocycloalkyne, alkyne, diene, azadiene, and heterocyclic azadience, wherein halo is iodine (I), bromine (Br), fluorine (F), or chlorine (Cl) and hetero is N, O, or S, and (ii) the side chain of an amino acid in the heavy chain or light chain of the antibody; each occurrence of R is independently hydrogen, a suitable protecting group, an acyl moiety, arylalkyl moiety, aliphatic moiety, aryl moiety, heteroaryl moiety, or heteroaliphatic moiety; n is 1, 2, 3, or 4; m is 1, 2, 3, 4, 5, 6, 7, 8, 9, or 10; and, a pharmaceutically acceptable carrier.

In a further embodiment, the present invention provides a method for treating an inflammatory disease or disorder by providing to a subject having the disease or disorder a composition comprising a compound having formula (I)

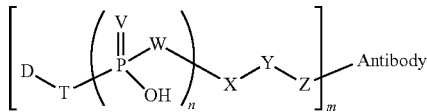

wherein V is selected from O and S; W is selected from O, N, and $CH_2$; X is a tuning element selected from a covalent bond; a carbon atom; a heteroatom; an optionally substituted group selected from the group consisting of acyl, aliphatic, heteroaliphatic, aryl, heteroaryl, and heterocyclic; nucleoside, protease sensitive group, cathepsin B sensitive group, or glycosidase sensitive group; Y is selected from a covalent bond or a bivalent, straight or branched, saturated or unsaturated, optionally substituted $C_{1-30}$ hydrocarbon chain wherein one or more methylene units of Y are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group; T is an NR, $CR_2$, O, or S; D is an anti-inflammatory agent; antibody is a chimeric, humanized, or human antibody having a light chain and a heavy chain wherein the antibody binds the human CD25, human CD70, human CD74 protein, or human CD163 protein (anti-CD25 antibody, anti-CD70 antibody, anti-CD74, or anti-CD163 antibody, respectively); Z is a linkage formed between (i) a reactive functional group selected from the group consisting of N-hydroxysuccinimide, para-nitrophenyl carbonate, para-nitrophenyl carbamate, pentafluorophenyl, haloacetamide, maleimide, hydroxylamine, strained cycloalkyne, and heterocycloalkyne, alkyne, diene, azadiene, and heterocyclic azadience, wherein halo is iodine (I), bromine (Br), fluorine (F), or chlorine (Cl) and hetero is N, O, or S, and (ii) the side chain of an amino acid in the heavy chain or light chain of the antibody; each occurrence of R is independently hydrogen, a suitable protecting group, an acyl moiety, arylalkyl moiety, aliphatic moiety, aryl moiety, heteroaryl moiety, or heteroaliphatic moiety; n is 1, 2, 3, or 4; m is 1, 2, 3, 4, 5, 6, 7, 8, 9, or 10; and, a pharmaceutically acceptable carrier to treat the inflammatory disease or disorder.

In a further embodiment, the present invention provides for the use of a composition comprising a compound having formula (I)

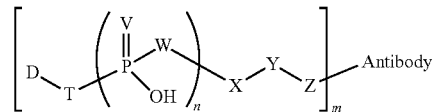

wherein V is selected from O and S; W is selected from O, N, and $CH_2$; X is a tuning element selected from a covalent bond; a carbon atom; a heteroatom; an optionally substituted group selected from the group consisting of acyl, aliphatic, heteroaliphatic, aryl, heteroaryl, and heterocyclic; nucleoside, protease sensitive group, cathepsin B sensitive group, or glycosidase sensitive group; Y is selected from a covalent bond or a bivalent, straight or branched, saturated or unsaturated, optionally substituted $C_{1-30}$ hydrocarbon chain wherein one or more methylene units of Y are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group; T is an NR, $CR_2$, O, or S; D is an anti-inflammatory agent; antibody is a chimeric, humanized, or human antibody having a light chain and a heavy chain wherein the antibody binds the human CD25, human CD70, human CD74 protein, or human CD163 protein (anti-CD25 antibody, anti-CD70 antibody, anti-CD74, or anti-CD163 antibody, respectively); Z is a linkage formed between (i) a reactive functional group selected from the group consisting of N-hydroxysuccinimide, para-nitrophenyl carbonate, para-nitrophenyl carbamate, pentafluorophenyl, haloacetamide, maleimide, hydroxylamine, strained cycloalkyne, and heterocycloalkyne, alkyne, diene, azadiene, and heterocyclic azadience, wherein halo is iodine (I), bromine (Br), fluorine (F), or chlorine (Cl) and hetero is N, O, or S, and (ii) the side chain of an amino acid in the heavy chain or light chain of the antibody; each occurrence of R is independently hydrogen, a suitable protecting group, an acyl moiety, arylalkyl moiety, aliphatic moiety, aryl moiety, heteroaryl moiety, or heteroaliphatic moiety; n is 1, 2, 3, or 4; m is 1, 2, 3, 4, 5, 6, 7, 8, 9, or 10; and, a pharmaceutically acceptable carrier for the treatment of an inflammatory disease or disorder.

The present invention provides composition comprising a compound having formula (I)

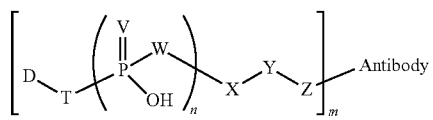

wherein V is selected from O and S; W is selected from O, N, and $CH_2$; X is a tuning element selected from a covalent bond; a carbon atom; a heteroatom; an optionally substituted group selected from the group consisting of acyl, aliphatic, heteroaliphatic, aryl, heteroaryl, and heterocyclic; nucleoside, protease sensitive group, cathepsin B sensitive group, or glycosidase sensitive group; Y is selected from a covalent bond or a bivalent, straight or branched, saturated or unsaturated, optionally substituted $C_{1-30}$ hydrocarbon chain wherein one or more methylene units of Y are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group; T is an NR, $CR_2$, O, or S; D is an anti-inflammatory agent; antibody is a chimeric, humanized, or human antibody having a light chain and a heavy chain wherein the antibody binds the human CD74 protein (an anti-CD74 antibody); Z is a linkage formed between (i) a reactive functional group selected from the group consisting of N-hydroxysuccinimide, para-nitrophenyl carbonate, para-nitrophenyl carbamate, pentafluorophenyl, haloacetamide, maleimide, hydroxylamine, strained cycloalkyne, and heterocycloalkyne, alkyne, diene, azadiene, and heterocyclic azadience, wherein halo is iodine (I), bromine (Br), fluorine (F), or chlorine (Cl) and hetero is N, O, or S, and (ii) the side chain of an amino acid in the heavy chain or light chain of the antibody; each occurrence of R is independently hydrogen, a suitable protecting group, an acyl moiety, arylalkyl moiety, aliphatic moiety, aryl moiety, heteroaryl moiety, or heteroaliphatic moiety; n is 1, 2, 3, or 4; m is 1, 2, 3, 4, 5, 6, 7, 8, 9, or 10; and, a pharmaceutically acceptable carrier.

In a further embodiment, the present invention provides a method for treating an inflammatory disease or disorder by providing to a subject having the disease or disorder a composition comprising a compound having formula (I)

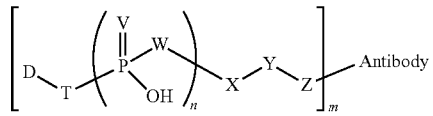

wherein V is selected from O and S; W is selected from O, N, and $CH_2$; X is a tuning element selected from a covalent bond; a carbon atom; a heteroatom; an optionally substituted group selected from the group consisting of acyl, aliphatic, heteroaliphatic, aryl, heteroaryl, and heterocyclic; nucleoside, protease sensitive group, cathepsin B sensitive group, or glycosidase sensitive group; Y is selected from a covalent bond or a bivalent, straight or branched, saturated or unsaturated, optionally substituted $C_{1-30}$ hydrocarbon chain wherein one or more methylene units of Y are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group; T is an NR, $CR_2$, O, or S; D is an anti-inflammatory agent; antibody is a chimeric, humanized, or human antibody having a light chain and a heavy chain wherein the antibody binds the human CD74 protein (an anti-CD74 antibody); Z is a linkage formed between (i) a reactive functional group selected from the group consisting of N-hydroxysuccinimide, para-nitrophenyl carbonate, para-nitrophenyl carbamate, pentafluorophenyl, haloacetamide, maleimide, hydroxylamine, strained cycloalkyne, and heterocycloalkyne, alkyne, diene, azadiene, and heterocyclic azadience, wherein halo is iodine (I), bromine (Br), fluorine (F), or chlorine (Cl) and hetero is N, O, or S, and (ii) the side chain of an amino acid in the heavy chain or light chain of the antibody; each occurrence of R is independently hydrogen, a suitable protecting group, an acyl moiety, arylalkyl moiety, aliphatic moiety, aryl moiety, heteroaryl moiety, or heteroaliphatic moiety; n is 1, 2, 3, or 4; m is 1, 2, 3, 4, 5, 6, 7, 8, 9, or 10; and, a pharmaceutically acceptable carrier to treat the inflammatory disease or disorder.

In a further embodiment, the present invention provides for the use of a composition comprising a compound having formula (I)

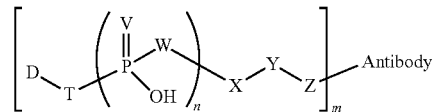

wherein V is selected from O and S; W is selected from O, N, and $CH_2$; X is a tuning element selected from a covalent bond; a carbon atom; a heteroatom; an optionally substituted group selected from the group consisting of acyl, aliphatic, heteroaliphatic, aryl, heteroaryl, and heterocyclic; nucleoside, protease sensitive group, cathepsin B sensitive group, or glycosidase sensitive group; Y is selected from a covalent bond or a bivalent, straight or branched, saturated or unsaturated, optionally substituted $C_{1-30}$ hydrocarbon chain wherein one or more methylene units of Y are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group; T is an NR, $CR_2$, O, or S; D is an anti-inflammatory agent; antibody is a chimeric, humanized, or human antibody having a light chain and a heavy chain wherein the antibody binds the human CD74 protein (an anti-CD74 antibody); Z is a linkage formed between (i) a reactive functional group selected from the group consisting of N-hydroxysuccinimide, para-nitrophenyl carbonate, para-nitrophenyl carbamate, pentafluorophenyl, haloacetamide, maleimide, hydroxylamine, strained cycloalkyne, and heterocycloalkyne, alkyne, diene, azadiene, and heterocyclic azadience, wherein halo is iodine (I), bromine (Br), fluorine (F), or chlorine (Cl) and hetero is N, O, or S, and (ii) the side chain of an amino acid in the heavy chain or light chain of the antibody; each occurrence of R is independently hydrogen, a suitable protecting group, an acyl moiety, arylalkyl moiety, aliphatic moiety, aryl moiety, heteroaryl moiety, or heteroaliphatic moiety; n is 1, 2, 3, or 4; m is 1, 2, 3, 4, 5, 6, 7, 8, 9, or 10; and, a pharmaceutically acceptable carrier for the treatment of an inflammatory disease or disorder.

The present invention provides composition comprising a compound having formula (I)

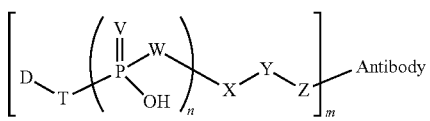

wherein V is selected from O and S; W is selected from O, N, and CH$_2$; X is a tuning element selected from a covalent bond; a carbon atom; a heteroatom; an optionally substituted group selected from the group consisting of acyl, aliphatic, heteroaliphatic, aryl, heteroaryl, and heterocyclic; nucleoside, protease sensitive group, cathepsin B sensitive group, or glycosidase sensitive group; Y is selected from a covalent bond or a bivalent, straight or branched, saturated or unsaturated, optionally substituted C$_{1-30}$ hydrocarbon chain wherein one or more methylene units of Y are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group; T is an NR, CR$_2$, O, or S; D is an anti-inflammatory agent; antibody is a chimeric, humanized, or human antibody having a light chain and a heavy chain wherein the antibody binds the human CD163 protein(an anti-CD163 antibody); Z is a linkage formed between (i) a reactive functional group selected from the group consisting of N-hydroxysuccinimide, para-nitrophenyl carbonate, para-nitrophenyl carbamate, pentafluorophenyl, haloacetamide, maleimide, hydroxylamine, strained cycloalkyne, and heterocycloalkyne, alkyne, diene, azadiene, and heterocyclic azadience, wherein halo is iodine (I), bromine (Br), fluorine (F), or chlorine (Cl) and hetero is N, O, or S, and (ii) the side chain of an amino acid in the heavy chain or light chain of the antibody; each occurrence of R is independently hydrogen, a suitable protecting group, an acyl moiety, arylalkyl moiety, aliphatic moiety, aryl moiety, heteroaryl moiety, or heteroaliphatic moiety; n is 1, 2, 3, or 4; m is 1, 2, 3, 4, 5, 6, 7, 8, 9, or 10; and, a pharmaceutically acceptable carrier.

In a further embodiment, the present invention provides a method for treating an inflammatory disease or disorder by providing to a subject having the disease or disorder a composition comprising a compound having formula (I)

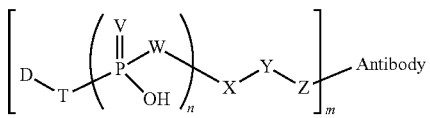

wherein V is selected from O and S; W is selected from O, N, and CH$_2$; X is a tuning element selected from a covalent bond; a carbon atom; a heteroatom; an optionally substituted group selected from the group consisting of acyl, aliphatic, heteroaliphatic, aryl, heteroaryl, and heterocyclic; nucleoside, protease sensitive group, cathepsin B sensitive group, or glycosidase sensitive group; Y is selected from a covalent bond or a bivalent, straight or branched, saturated or unsaturated, optionally substituted C$_{1-30}$ hydrocarbon chain wherein one or more methylene units of Y are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group; T is an NR, CR$_2$, O, or S; D is an anti-inflammatory agent; antibody is a chimeric, humanized, or human antibody having a light chain and a heavy chain wherein the antibody binds the human CD163 protein(an anti-CD163 antibody); Z is a linkage formed between (i) a reactive functional group selected from the group consisting of N-hydroxysuccinimide, para-nitrophenyl carbonate, para-nitrophenyl carbamate, pentafluorophenyl, haloacetamide, maleimide, hydroxylamine, strained cycloalkyne, and heterocycloalkyne, alkyne, diene, azadiene, and heterocyclic azadience, wherein halo is iodine (I), bromine (Br), fluorine (F), or chlorine (Cl) and hetero is N, O, or S, and (ii) the side chain of an amino acid in the heavy chain or light chain of the antibody; each occurrence of R is independently hydrogen, a suitable protecting group, an acyl moiety, arylalkyl moiety, aliphatic moiety, aryl moiety, heteroaryl moiety, or heteroaliphatic moiety; n is 1, 2, 3, or 4; m is 1, 2, 3, 4, 5, 6, 7, 8, 9, or 10; and, a pharmaceutically acceptable carrier to treat the inflammatory disease or disorder.

In a further embodiment, the present invention provides for the use of a composition comprising a compound having formula (I)

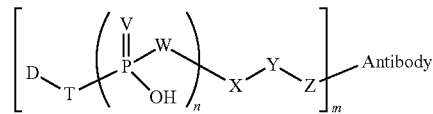

wherein V is selected from O and S; W is selected from O, N, and CH$_2$; X is a tuning element selected from a covalent bond; a carbon atom; a heteroatom; an optionally substituted group selected from the group consisting of acyl, aliphatic, heteroaliphatic, aryl, heteroaryl, and heterocyclic; nucleoside, protease sensitive group, cathepsin B sensitive group, or glycosidase sensitive group; Y is selected from a covalent bond or a bivalent, straight or branched, saturated or unsaturated, optionally substituted C$_{1-30}$ hydrocarbon chain wherein one or more methylene units of Y are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group; T is an NR, CR$_2$, O, or S; D is an anti-inflammatory agent; antibody is a chimeric, humanized, or human antibody having a light chain and a heavy chain wherein the antibody binds the human CD163 protein (an anti-CD163 antibody); Z is a linkage formed between (i) a reactive functional group selected from the group consisting of N-hydroxysuccinimide, para-nitrophenyl carbonate, para-nitrophenyl carbamate, pentafluorophenyl, haloacetamide, maleimide, hydroxylamine, strained cycloalkyne, and heterocycloalkyne, alkyne, diene, azadiene, and heterocyclic azadience, wherein halo is iodine (I), bromine (Br), fluorine (F), or chlorine (Cl) and hetero is N, O, or S, and (ii) the side chain of an amino acid in the heavy chain or light chain of the antibody; each occurrence of R is independently hydrogen, a suitable protecting group, an acyl moiety, arylalkyl moiety, aliphatic moiety, aryl moiety, heteroaryl moiety, or heteroaliphatic moiety; n is 1, 2, 3, or 4; m is 1, 2, 3, 4, 5, 6, 7, 8, 9, or 10; and, a pharmaceutically acceptable carrier for the treatment of an inflammatory disease or disorder.

In particular aspects, the anti-inflammatory agent comprises a glucocorticoid receptor agonist. In particular aspects, the anti-inflammatory agent comprises Cortisol, cortisone acetate, beclometasone, prednisone, prednisolone, methylprednisolone, betamethasone, trimcinolone, budesonide, dexamethasone, fluticasone, or mometasone.

In particular aspects, the antibody comprises a substitution of an amino acid in the heavy chain or light chain of the antibody with pAzF and the reactive functional group comprises a strained cycloalkyne.

In particular aspects, the inflammatory disease or disorder comprises Alzheimer's disease, ankylosing spondylitis arthritis (osteoarthritis, rheumatoid arthritis (RA), psoriatic arthritis), asthma, atherosclerosis, Crohn's disease, colitis, dermatitis, diverticulitis, fibromyalgia, hepatitis, irritable bowel syndrome (IBS), systemic lupus erythematous (SLE), nephritis, Parkinson's disease, or ulcerative colitis.

In further aspects of the compound of formula I, the m comprises 2. In further still aspects of the compound of formula I, n comprises 2. In further still aspects, n comprises 3.

In a further embodiment, the present invention provides an anti-CD74 antibody (antibody that binds CD74) comprising a para-azidophenylalanine (pAzF) residue conjugated to a molecule selected from the group of molecules consisting of 1-4, 2-7, 3-4, 4-3, 5-3, 6-2, 7-1, 8-5, 9-1, 10-1, 11-5, 21-1, 13-1, 14-5, 15-1, 16-5, and 17-2.

In particular aspects, the anti-CD74 antibody comprises light chain complementarity-determining region (CDR) sequences CDR1 (RSSQSLVHRNGNTYLH; SEQ ID NO:44), CDR2 (TVSNRFS; SEQ ID NO:45), and CDR3 (SQSSHVPPT; SEQ ID NO:46) and heavy chain CDR sequences CDR1 (NYGVN; SEQ ID NO:47), CDR2 (WINPNTGEPTFDDDFKG; SEQ ID NO:48), and CDR3 (SRGKNEAWFAY; SEQ ID NO:49). In particular aspects, the anti-CD74 antibody comprises a non-natural amino acid, which is a further aspect, may be pAzF.

In particular aspects, the anti-CD74 antibody comprises at least one, two, three, four, five, or six CDR(s) selected from SEQ ID NO:44, SEQ ID NO: 45, SEQ ID NO:46, SEQ ID NO:47, SEQ ID NO:48, and SEQ ID NO:49. In particular aspects, the anti-CD74 antibody comprises a non-natural amino acid, which is a further aspect, may be pAzF.

In particular aspects, the anti-CD74 antibody comprises a heavy chain (HC) comprising an amino acid sequence selected from SEQ ID NO:69, 70, 71, and 72 and a light chain (LC) comprising the amino acid sequence of SEQ ID NO:73. In particular aspects, the anti-CD74 antibody comprises a non-natural amino acid, which is a further aspect, may be pAzF.

In particular aspects, the anti-CD74 antibody comprises light chain CDR sequences CDR1 (QGISSW; SEQ ID NO:50), CDR2 (AAS), and CDR3 (QQYNSYPLT; SEQ ID NO:51) and heavy chain CDR sequences CDR1 (GFTFSSYA; SEQ ID NO:52), CDR2 (ISYDGSNK; SEQ ID NO:53), and CDR3 (ASGRYYGSGSYSSYFD; SEQ ID NO:54). In particular aspects, the anti-CD74 antibody comprises a non-natural amino acid, which is a further aspect, may be pAzF.

In particular aspects, the anti-CD74 antibody comprises light chain CDR sequences CDR1 (QGISSW; SEQ ID NO:50), CDR2 (AAS), and CDR3 (QQYNSYPLT; SEQ ID NO:51) and heavy chain CDR sequences CDR1 (GFTFSSYA; SEQ ID NO:52), CDR2 (ISYDGSIK; SEQ ID NO:55), and CDR3 (ARGREYTSQNIVILLD; SEQ ID NO:56). In particular aspects, the anti-CD74 antibody comprises a non-natural amino acid, which is a further aspect, may be pAzF.

In particular aspects, the anti-CD74 antibody comprises light chain CDR sequences CDR1 (QGISSW; SEQ ID NO:50), CDR2 (AAS), and CDR3 (QQYNSYPLT; SEQ ID NO:51) and heavy chain CDR sequences CDR1 (GFTFSSYA; SEQ ID NO:52), CDR2 (ISYDGSNK; SEQ ID NO:53), and CDR3 (ARGREITSQNIVILLD; SEQ ID NO:57). In particular aspects, the anti-CD74 antibody comprises a non-natural amino acid, which is a further aspect, may be pAzF.

In particular aspects, the anti-CD74 antibody comprises light chain CDR sequences CDR1 (QGISSW; SEQ ID NO:50), CDR2 (AAS), and CDR3 (QQYNSYPLT; SEQ ID NO:51) and heavy chain CDR sequences CDR1 (GFTFSSYA; SEQ ID NO:52), CDR2 (IWYDGSNK; SEQ ID NO:58), and CDR3 (ARGGTLVRGAMYGTDV; SEQ ID NO:59). In particular aspects, the anti-CD74 antibody comprises a non-natural amino acid, which is a further aspect, may be pAzF.

In particular aspects, the anti-CD74 antibody comprises at least one, two, three, four, five, or six CDR(s) having an amino acid sequence selected from AAS, SEQ ID NO:50, SEQ ID NO: 51, SEQ ID NO:52, SEQ ID NO:53, SEQ ID NO:54, SEQ ID NO:55, SEQ ID NO:56, SEQ ID NO:57, SEQ ID NO:58, and SEQ ID NO:59. In particular aspects, the anti-CD74 antibody comprises a non-natural amino acid, which is a further aspect, may be pAzF.

In particular aspects, the anti-CD74 antibody comprises a heavy chain (HC) comprising an amino acid sequence selected from SEQ ID NO:74, 75, 76, and 77 and a light chain (LC) comprising the amino acid sequence of SEQ ID NO:78. In particular aspects, the anti-CD74 antibody comprises a non-natural amino acid, which is a further aspect, may be pAzF.

In a further embodiment, the present invention provides an anti-CD163 antibody (antibody that binds CD163) comprising a para-azidophenylalanine (pAzF) residue conjugated to a molecule selected from the group of molecules consisting of 1-4, 2-7, 3-4, 4-3, 5-3, 6-2, 7-1, 8-5, 9-1, 10-1, 11-5, 21-1, 13-1, 14-5, 15-5, 16-5, and 17-2.

In particular aspects, the anti-CD163 antibody comprises light chain CDR sequences CDR1 (ASQSVSSDV; SEQ ID NO:60), CDR2 (YAS), and CDR3 (QDYTSPRT; SEQ ID NO:61) and heavy chain complementarity-determining region (CDR) sequences CDR1 (GYSITSDY; SEQ ID NO:62), CDR2 (YSG), and CDR3 (CVSGTYYFDYWG; SEQ ID NO:63). In particular aspects, the anti-CD163 antibody comprises a non-natural amino acid, which is a further aspect, may be pAzF.

In particular aspects, the anti-CD163 antibody comprises light chain CDR sequences CDR1 (ASQSVSHDV; SEQ ID NO:54), CDR2 (YTS), and CDR3 (QDYSSPRT; SEQ ID NO:65) and heavy chain CDR sequences CDR1 (GYSITSDY; SEQ ID NO:62), CDR2 (YSG), and CDR3 (CVSGTYYFDYWG; SEQ ID NO:63).

In particular aspects, the anti-CD163 antibody comprises at least one, two, three, four, five, or six CDR(s) having an amino acid sequence selected from YYAS, YSG, YTS, SEQ ID NO:60, SEQ ID NO: 61, SEQ ID NO:62, SEQ ID NO:63, SEQ ID NO:64, and SEQ ID NO:65. In particular aspects, the anti-CD 163 antibody comprises a non-natural amino acid, which is a further aspect, may be pAzF.

In particular aspects, the antibody is selected from the group consisting of ADC 12-1, ADC 12-2, ADC 12-3, ADC 12-4, ADC 12-5, ADC 12-6, ADC 12-7, ADC 12-8, ADC 12-9, ADC 12-10, ADC 12-13, ADC 12-14, and ADC 12-15.

Definitions

Definitions of specific functional groups, chemical terms, and general terms used throughout the specification are described in more detail below. For purposes of this invention, the chemical elements are identified in accordance with the Periodic Table of the Elements, CAS version, Handbook of Chemistry and Physics, $75^{th}$ Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March March's Advanced Organic Chemistry, $5^{th}$ Edition, John Wiley & Sons, Inc., New York, 2001; Larock, Comprehensive Organic Transformations, VCH Publishers, Inc., New York, 1989; Carruthers, Some Modern Methods of Organic Synthesis, $3^{rd}$ Edition, Cambridge University Press, Cambridge, 1987.

Acyl—As used herein, the term "acyl," refers to a group having the general formula —C(=O)$R^{X1}$, —C(=O)O$R^{X1}$, —C(=O)—O—C(=O)$R^{X1}$, —C(=O)S$R^{X1}$, —C(=O)N($R^{X1}$)$_2$, —C(=S)$R^{X1}$, —C(=S)N($R^{X1}$)$_2$, and —C(=S)S($R^{X1}$), —C(=N$R^{X1}$)$R^{X1}$, —C(=N$R^{X1}$)O$R^{X1}$, —C(=N$R^{X1}$)S$R^{X1}$, and —C(=N$R^{X1}$)N($R^{X1}$)$_2$, wherein $R^{X1}$ is hydrogen; halogen; substituted or unsubstituted hydroxyl; substituted or unsubstituted thiol; substituted or unsubstituted amino; substituted or unsubstituted acyl; cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl, substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^{X1}$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

Aliphatic—As used herein, the term "aliphatic" or "aliphatic group" denotes an optionally substituted hydrocarbon moiety that may be straight-chain (i.e., unbranched), branched, or cyclic ("carbocyclic") and may be completely saturated or may contain one or more units of unsaturation, but which is not aromatic. Unless otherwise specified, aliphatic groups contain 1-12 carbon atoms. In some embodiments, aliphatic groups contain 1-6 carbon atoms. In some embodiments, aliphatic groups contain 1-4 carbon atoms, and in yet other embodiments aliphatic groups contain 1-3 carbon atoms. Suitable aliphatic groups include, but are not limited to, linear or branched, alkyl, alkenyl, and alkynyl groups, and hybrids thereof such as (cycloalkyl) alkyl, (cycloalkenyl)alkyl or (cycloalkyl)alkenyl.

Alkenyl—As used herein, the term "alkenyl" denotes an optionally substituted monovalent group derived from a straight- or branched-chain aliphatic moiety having at least one carbon-carbon double bond by the removal of a single hydrogen atom. In certain embodiments, the alkenyl group employed in the invention contains 2-6 carbon atoms. In certain embodiments, the alkenyl group employed in the invention contains 2-5 carbon atoms. In some embodiments, the alkenyl group employed in the invention contains 2-4 carbon atoms. In another embodiment, the alkenyl group employed contains 2-3 carbon atoms. Alkenyl groups include, for example, ethenyl, propenyl, butenyl, 1-methyl-2-buten-1-yl, and the like.

Alkyl—As used herein, the term "alkyl" refers to optionally substituted saturated, straight- or branched-chain hydrocarbon radicals derived from an aliphatic moiety containing between 1-6 carbon atoms by removal of a single hydrogen atom. In some embodiments, the alkyl group employed in the invention contains 1-5 carbon atoms. In another embodiment, the alkyl group employed contains 1-4 carbon atoms. In still other embodiments, the alkyl group contains 1-3 carbon atoms. In yet another embodiment, the alkyl group contains 1-2 carbons. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

Alkynyl—As used herein, the term "alkynyl" refers to an optionally substituted monovalent group derived from a straight- or branched-chain aliphatic moiety having at least one carbon-carbon triple bond by the removal of a single hydrogen atom. In certain embodiments, the alkynyl group employed in the invention contains 2-6 carbon atoms. In certain embodiments, the alkynyl group employed in the invention contains 2-5 carbon atoms. In some embodiments, the alkynyl group employed in the invention contains 2-4 carbon atoms. In another embodiment, the alkynyl group employed contains 2-3 carbon atoms. Representative alkynyl groups include, but are not limited to, ethynyl, 2-propynyl (propargyl), 1-propynyl, and the like.

Aryl—As used herein, the term "aryl" used alone or as part of a larger moiety as in "aralkyl", "aralkoxy", or "aryloxyalkyl", refers to an optionally substituted monocyclic and bicyclic ring systems having a total of five to 10 ring members, wherein at least one ring in the system is aromatic and wherein each ring in the system contains three to seven ring members. The term "aryl" may be used interchangeably with the term "aryl ring". In certain embodiments of the present invention, "aryl" refers to an aromatic ring system which includes, but not limited to, phenyl, biphenyl, naphthyl, anthracyl and the like, which may bear one or more substituents.

Arylalkyl—As used herein, the term "arylalkyl" refers to an alkyl group substituted with an aryl group (e.g., an aromatic or heteroaromatic group).

Bivalent hydrocarbon chain—As used herein, the term "bivalent hydrocarbon chain" (also referred to as a "bivalent alkylene group") is a polymethylene group, i.e., —$(CH_2)_z$—, wherein z is a positive integer from 1 to 30, from 1 to 20, from 1 to 12, from 1 to 8, from 1 to 6, from 1 to 4, from 1 to 3, from 1 to 2, from 2 to 30, from 2 to 20, from 2 to 10, from 2 to 8, from 2 to 6, from 2 to 4, or from 2 to 3. A substituted bivalent hydrocarbon chain is a polymethylene group in which one or more methylene hydrogen atoms are replaced with a substituent. Suitable substituents include those described below for a substituted aliphatic group.

Carbonyl—As used herein, the term "carbonyl" refers to a monovalent or bivalent moiety containing a carbon-oxygen double bond. Non-limiting examples of carbonyl groups include aldehydes, ketones, carboxylic acids, ester, amide, enones, acyl halides, anhydrides, ureas, carbamates, carbonates, thioesters, lactones, lactams, hydroxamates, isocyanates, and chloroformates.

Cycloaliphatic—As used herein, the terms "cycloaliphatic", "carbocycle", or "carbocyclic", used alone or as part of a larger moiety, refer to an optionally substituted saturated or partially unsaturated cyclic aliphatic monocyclic or bicyclic ring systems, as described herein, having from 3 to 10 members. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloalkyl has 3-6 carbons.

Halogen—As used herein, the terms "halo" and "halogen" refer to an atom selected from fluorine (fluoro, —F), chlorine (chloro, —Cl), bromine (bromo, —Br), and iodine (iodo, —I).

Heteroaliphatic—As used herein, the terms "heteroaliphatic" or "heteroaliphatic group", denote an optionally substituted hydrocarbon moiety having, in addition to carbon atoms, from one to five heteroatoms, that may be straight-chain (i.e., unbranched), branched, or cyclic ("heterocyclic") and may be completely saturated or may contain one or more units of unsaturation, but which is not aromatic. Unless otherwise specified, heteroaliphatic groups contain 1-6 carbon atoms wherein 1-3 carbon atoms are optionally and independently replaced with heteroatoms selected from oxygen, nitrogen and sulfur. In some embodiments, heteroaliphatic groups contain 1-4 carbon atoms, wherein 1-2 carbon atoms are optionally and independently replaced with heteroatoms selected from oxygen, nitrogen and sulfur. In yet other embodiments, heteroaliphatic groups contain 1-3 carbon atoms, wherein 1 carbon atom is optionally and independently replaced with a heteroatom selected from oxygen, nitrogen and sulfur. Suitable heteroaliphatic groups include, but are not limited to, linear or branched, heteroalkyl, heteroalkenyl, and heteroalkynyl groups.

Heteroaralkyl—As used herein, the term "heteroaralkyl" refers to an alkyl group substituted by a heteroaryl, wherein the alkyl and heteroaryl portions independently are optionally substituted.

Heteroaryl—As used herein, the term "heteroaryl" used alone or as part of a larger moiety, e.g., "heteroaralkyl", or "heteroaralkoxy", refers to an optionally substituted group having 5 to 10 ring atoms, preferably 5, 6, or 9 ring atoms; having 6, 10, or 14 π electrons shared in a cyclic array; and having, in addition to carbon atoms, from one to five heteroatoms. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, carbocyclic, or heterocyclic rings, where the radical or point of attachment is on the heteroaromatic ring. Non limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, and tetrahydroisoquinolinyl. A heteroaryl group may be mono- or bicyclic. The term "heteroaryl" may be used interchangeably with the terms "heteroaryl ring", "heteroaryl group", or "heteroaromatic", any of which terms include rings that are optionally substituted.

Heteroatom—As used herein, the term "heteroatom" refers to nitrogen, oxygen, or sulfur, and includes any oxidized form of nitrogen or sulfur, and any quaternized form of a basic nitrogen. The term "nitrogen" also includes a substituted nitrogen.

Heterocyclic—As used herein, the terms "heterocycle", "heterocyclyl", "heterocyclic radical", and "heterocyclic ring" are used interchangeably and refer to a stable optionally substituted 5- to 7-membered monocyclic or 7- to 10-membered bicyclic heterocyclic moiety that is either saturated or partially unsaturated, and having, in addition to carbon atoms, one or more heteroatoms, as defined above. A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or carbocyclic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

Unsaturated—As used herein, the term "unsaturated", means that a moiety has one or more double or triple bonds.

Partially unsaturated—As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

Optionally substituted—As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R^{\circ}$; —$(CH_2)_{0-4}OR^{\circ}$; —O—$(CH_2)_{0-4}C(O)OR^{\circ}$; —$(CH_2)_{0-4}CH(OR^{\circ})_2$; —$(CH_2)_{0-4}SR^{\circ}$; —$(CH_2)_{0-4}Ph$, which may be substituted with $R^{\circ}$; —$(CH_2)_{0-4}O(CH_2)_{0-1}Ph$ which may be substituted with $R^{\circ}$; —CH=CHPh, which may be substituted with $R^{\circ}$; —$NO_2$; —CN; —$N_3$; —$(CH_2)_{0-4}N(R^{\circ})_2$; —$(CH_2)_{0-4}N(R^{\circ})C(O)R^{\circ}$; —$N(R^{\circ})C(S)R^{\circ}$; —$(CH_2)_{0-4}N(R^{\circ})C(O)NR^{\circ}_2$; —$N(R^{\circ})C(S)NR^{\circ}_2$; —$(CH_2)_{0-4}N(R^{\circ})C(O)OR^{\circ}$; —$N(R^{\circ})N(R^{\circ})C(O)R^{\circ}$; —$N(R^{\circ})N(R^{\circ})C(O)NR^{\circ}_2$; —$N(R^{\circ})N(R^{\circ})C(O)OR^{\circ}$; —$(CH_2)_{0-4}C(O)R^{\circ}$; —$C(S)R^{\circ}$; —$(CH_2)_{0-4}C(O)OR^{\circ}$; —$(CH_2)_{0-4}C(O)SR^{\circ}$; —$(CH_2)_{0-4}C(O)OSiR^{\circ}_3$; —$(CH_2)_{0-4}C(O)R^{\circ}$; —$OC(O)(CH_2)_{0-4}SR$—, $SC(S)SR^{\circ}$; —$(CH_2)_{0-4}SC(O)R^{\circ}$; —$(CH_2)_{0-4}C(O)NR^{\circ}_2$; —$C(S)NR^{\circ}_2$; —$C(S)SR^{\circ}$; —$SC(S)SR^{\circ}$, —$(CH_2)_{0-4}C(O)NR^{\circ}_2$; —$C(O)N(OR^{\circ})R^{\circ}$; —$C(O)C(O)R^{\circ}$; —$C(O)CH_2C(O)R^{\circ}$; —$C(NOR^{\circ})R^{\circ}$; —$(CH_2)_{0-4}SSR^{\circ}$; —$(CH_2)_{0-4}S(O)_2R^{\circ}$; —$(CH_2)_{0-4}S(O)_2OR^{\circ}$; —$(CH_2)_{0-4}OS(O)_2R^{\circ}$; —$S(O)_2NR^{\circ}_2$; —$(CH_2)_{0-4}S(O)R^{\circ}$; —$N(R^{\circ})S(O)_2NR^{\circ}_2$; —$N(R^{\circ})S(O)_2R^{\circ}$; —$N(OR^{\circ})R^{\circ}$; —$C(NH)NR^{\circ}_2$; —$P(O)_2R^{\circ}$; —$P(O)R^{\circ}_2$; —$OP(O)R^{\circ}_2$; —$OP(O)(OR^{\circ})_2$; $SiR^{\circ}_3$; —$(C_{1-4}$ straight or branched alkylene)O—$N(R^{\circ})_2$; or —$(C_{1-4}$ straight or branched alkylene)C(O)O—$N(R^{\circ})_2$, wherein each $R^{\circ}$ may be substituted as defined below and is independently hydrogen, $C_{1-6}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur, or, notwithstanding the definition above, two independent occurrences of $R^{\circ}$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^{\circ}$ (or the ring formed by taking two independent occurrences of $R^{\circ}$ together with their intervening atoms), are independently halogen, —$(CH_2)_{0-2}R^{\bullet}$, -(haloR$^{\bullet}$), —$(CH_2)_{0-2}OH$, —$(CH_2)_{0-2}OR^{\bullet}$, —$(CH_2)_{0-2}CH(OR^{\bullet})_2$; —$O(haloR^{\bullet})$, —CN, —$N_3$, —$(CH_2)_{0-2}C(O)R^{\bullet}$, —$(CH_2)_{0-2}C(O)OH$, —$(CH_2)_{0-2}C(O)OR^{\bullet}$, —$(CH_2)_{0-2}SR$, —$(CH_2)_{0-2}SH$, —$(CH_2)_{0-2}NH_2$, —$(CH_2)_{0-2}NHR^{\bullet}$, —$(CH_2)_{0-2}NR_2^{\bullet}$, —$NO_2$, —$SiR^{\bullet}_3$, —$OSiR^{\bullet}_3$, —$C(O)SR^{\bullet}$, —$(C_{1-4}$ straight or branched alkylene)C(O)OR$^{\bullet}$, or —$SSR^{\bullet}$ wherein each $R^{\bullet}$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^{\circ}$ include =O and =S.

Suitable divalent substituents on a saturated carbon atom of an "optionally substituted" group include the following: =O, =S, =$NNR^*_2$, =$NNHC(O)R^*$, =$NNHC(O)OR^*$, =$NNHS(O)_2R^*$, =$NR^*$, =$NOR^*$, —$O(C(R^*_2))_{2-3}O$—, or —$S(C(R^*_2))_{2-3}S$—, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —$O(CR^*_2)_{2-3}O$—, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, —$R^{\bullet}$, -(halo$R^{\bullet}$), —OH, —$OR^{\bullet}$, —$O(haloR^{\bullet})$, —CN, —C(O)OH, —$C(O)OR^{\bullet}$, —$NH_2$, —$NHR^{\bullet}$, —$NR^{\bullet}_2$, or —$NO_2$, wherein each $R^{\bullet}$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —$R^{\dagger}$, —$NR^{\dagger}_2$, —$C(O)R^{\dagger}$, —$C(O)OR^{\dagger}$, —$C(O)C(O)R^{\dagger}$, —$C(O)CH_2C(O)R^{\dagger}$, —$S(O)_2R^{\dagger}$, —$S(O)_2NR^{\dagger}_2$, —$C(S)NR^{\dagger}_2$, —$C(NH)NR^{\dagger}_2$, or —$N(R^{\dagger})S(O)_2R^{\dagger}$; wherein each $R^{\dagger}$ is independently hydrogen, $C_{1-6}$ aliphatic which may be substituted as defined below, unsubstituted—OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^{\dagger}$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^{\dagger}$ are independently halogen, —$R^{\bullet}$, -(halo$R^{\bullet}$), —OH, —$OR^{\bullet}$, —$O(haloR^{\bullet})$, —CN, —C(O)OH, —$C(O)OR^{\bullet}$, —$NH_2$, —$NHR^{\bullet}$, —$NR^{\bullet}_2$, or —$NO_2$, wherein each $R^{\bullet}$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

In any case where a chemical variable (e.g., an R group) is shown attached to a bond that crosses a bond of ring, this means that one or more such variables are optionally attached to the ring having the crossed bond. Each R group on such a ring can be attached at any suitable position, this is generally understood to mean that the group is attached in place of a hydrogen atom on the parent ring. This includes the possibility that two R groups can be attached to the same ring atom.

Furthermore, when more than one R group is present on a ring, each may be the same or different than other R groups attached thereto, and each group is defined independently of other groups that may be attached elsewhere on the same molecule, even though they may be represented by the same identifier.

Antibody—As used herein the term "antibody" includes monoclonal antibodies, polyclonal antibodies, monospecific antibodies, and multispecific antibodies (e.g., bispecific antibodies) and the term "antibody" is used interchangeably with the terms "immunoglobulin," "immunoglobulins" and "immunoglobulin molecule". Each antibody molecule has a unique structure that allows it to bind its specific antigen, but all antibodies have the same overall structure as described herein. The basic immunoglobulin structural unit is known to comprise a tetramer of subunits. Each tetramer has two identical pairs of polypeptide chains, each pair having one "light" chain (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Light chains are classified as either kappa or lambda. Heavy chains are classified as gamma, mu, alpha, delta, or epsilon, and define the antibody's isotype as IgG, IgM, IgA, IgD and IgE, respectively. Thus, an antibody as defined herein can be of any type or class (e.g., IgG, IgE, IgM, IgD, and IgA) or subclass (e.g., IgG1, IgG2, IgG3, IgG4, IgA1 and IgA2).

The light and heavy chains are subdivided into variable regions and constant regions (See generally, Fundamental Immunology (Paul, W., ed., 2nd ed. Raven Press, N.Y., 1989), Ch. 7. The variable regions of each light/heavy chain pair form the antibody binding site. Thus, an intact antibody has two binding sites. Except in bifunctional or bispecific antibodies, the two binding sites are the same. The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. The terms include naturally occurring forms, as well as fragments and derivatives. Included within the scope of the term are classes of immunoglobulins (Igs), namely, IgG, IgA, IgE, IgM, and IgD. Also included within the scope of the terms are the subtypes of IgGs, namely, IgG1, IgG2, IgG3 and IgG4. The term is used in the broadest sense and includes single monoclonal antibodies (including agonist and antagonist antibodies) as well as antibody compositions which will bind to multiple epitopes or antigens. The terms specifically cover monoclonal antibodies (including full length monoclonal antibodies), polyclonal antibodies, multispecific antibodies (for example, bispecific antibodies), and antibody fragments so long as they contain or are modified to contain at least the portion of the $C_H2$ domain of the heavy chain immunoglobulin constant region which comprises an N-linked glycosylation site of the $C_H2$ domain, or a variant thereof. Included within the terms are molecules comprising only the Fc region, such as immunoadhesins (U.S. Published Patent Application No. 20040136986), Fc fusions, and antibody-like molecules. Alternatively, these terms can refer to an antibody fragment of at least the Fab region that at least contains an N-linked glycosylation site.

The term "Fc" fragment refers to the 'fragment crystallized' C-terminal region of the antibody containing the CH2 and CH3 domains. The term "Fab" fragment refers to the 'fragment antigen binding' region of the antibody containing the $V_H$, $C_H1$, $V_L$ and $C_L$ domains.

The term "antibodies" further includes chemical analogues and derivatives of antibodies and antibody fragments, provided that the antibody or antibody fragment maintains its ability to bind specifically to its target antigen. Thus, for example, chemical modifications are possible (e.g., glycosylation, acetylation, PEGylation and other modifications without limitation) provided specific binding ability of the antibody is retained. An antibody may be, for example, human, humanized, or chimeric A "monoclonal antibody" is an antibody obtained from a population of substantially homogeneous antibodies, i.e., individual antibodies comprising the population are identical except for possible naturally-occurring mutations that may be present in minor amounts. Monoclonal antibodies (mAbs) are highly specific, being directed against a single antigenic site. Furthermore, in contrast to conventional (polyclonal) antibody preparations which typically include different antibodies directed against different determinants (epitopes), each mAb is directed against a single determinant on the antigen. In addition to their specificity, monoclonal antibodies are advantageous in that they can be synthesized by hybridoma culture, uncontaminated by other immunoglobulins. The term "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., (1975) Nature, 256:495, or may be made by recombinant DNA methods (See, for example, U.S. Pat. No. 4,816,567 to Cabilly et al.).

Monoclonal antibodies further include chimeric antibodies in which a portion of the heavy and/or light chain is identical to or homologous with the corresponding s of antibodies derived from a particular species or belonging to a particular antibody class or subclass, while the remainder of the chain(s) is identical to or homologous with the corresponding sequences of antibodies derived from another species or belonging to another antibody class or subclass, as well as fragments of such antibodies, so long as they exhibit the desired biological activity.

An "intact antibody" is one that comprises an antigen-binding variable region as well as a light chain constant domain ($C_L$) and heavy chain constant domains, $C_H1$, $C_H^2$, $C_H^3$ and $C_H^4$, as appropriate for the antibody class. The constant domains may be native sequence constant domains such as human native sequence constant domains or amino acid sequence variants thereof. An intact antibody may or may not have one or more "effector functions", which refers to those biological activities attributable to the Fc region (e.g., a native sequence Fc region or amino acid sequence variant Fc region) of an antibody. Examples of antibody effector functions include complement dependent cytotoxicity, antibody-dependent cell-mediated cytotoxicity (ADCC) and antibody-dependent cell-mediated phagocytosis.

An "antibody fragment" comprises a portion of an intact antibody, preferably comprising the antigen-binding or variable region thereof. Examples of antibody fragments include Fab, Fab', F(ab')$_2$, and Fv fragments, diabodies, triabodies, tetrabodies, linear antibodies, single-chain antibody molecules, scFv, scFv-Fc, multispecific antibody fragments formed from antibody fragment(s), a fragment(s) produced by a Fab expression library, camelids, or an epitope-binding fragments of any of the above which immunospecifically bind to a target antigen (e.g., a cancer cell antigen).

"Humanized" forms of non-human (e.g., rodent) antibodies are chimeric antibodies that contain minimal sequence derived from non-human immunoglobulin. The term "capable of specific binding" refers to protein or peptide (e.g., antibody) binding to a predetermined target substance (e.g., an antigen and/or groups of antigens), e.g. a target substance that is expressed on the surface of a cell; thus the term "binding to a target cell" or "binding to a cancer cell" is to be understand as referring to protein or peptide (e.g., antibody) binding to a predetermined target substance (e.g. antigen or antigens) that is expressed on such a cell.

Typically, the protein or peptide (e.g., antibody) binds with an affinity of at least about $1\times10^7$ $M^1$, and/or binds to the predetermined target substance (e.g., antigen, antigens or cell) with an affinity that is at least two-fold greater than its affinity for binding to a non-specific control substance (e.g., BSA, casein, non-cancer cells) other than the predetermined target substance or a closely-related target substance.

Drug—As used herein, the term "drug" refers to small molecules or biomolecules that alter, inhibit, activate, or otherwise affect a biological event. For example, drugs may include, but are not limited to, anti-AIDS substances, anti-cancer substances, antibiotics, anti-diabetic substances, immunosuppressants, anti-viral substances, enzyme inhibitors, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, anti-secretory factors, anticoagulants and/or anti-thrombotic agents, local anesthetics, ophthalmics, prostaglandins, anti-depressants, anti-psychotic substances, anti-emetics, and imaging agents. A more complete listing of exemplary drugs suitable for use in the present invention may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", edited by Susan Budavari et al., CRC Press, 1996, and the United States Pharmacopeia-25/National Formulary-20, published by the United States Pharmcopeial Convention, Inc., Rockville Md., 2001.

Polymer—As used herein, a "polymer" or "polymeric structure" is a structure that includes a string of covalently bound monomers. A polymer can be made from one type of monomer or more than one type of monomer. The term "polymer" therefore encompasses copolymers, including block-copolymers in which different types of monomer are grouped separately within the overall polymer. A polymer can be linear or branched.

Treat—As used herein, the term "treat" (or "treating", "treated", "treatment", etc.) refers to the administration of a conjugate of the present disclosure to a subject in need thereof with the purpose to alleviate, relieve, alter, ameliorate, improve or affect a condition (e.g., diabetes, cancer, inflammatory disease), a symptom or symptoms of a condition (e.g., hyperglycemia), or the predisposition toward a condition.

BRIEF DESCRIPTION OF THE DRAWINGS

FIG. 1 shows a scheme for synthesis of ADC 12-4.

FIG. 2 is a graph showing stability of ADC 12-1 in mouse serum. (aDEX is ADC 12-1).

FIG. 3 is a graph showing deconvoluted intact mass spectrum for ADC 12-1 stock solution.

FIG. 4A is a graph showing deconvoluted intact mass spectra for in-vitro stability samples of ADC 12-1. incubated at 37° C. for 1 hour.

FIG. 4B is a graph showing deconvoluted intact mass spectra for in-vitro stability samples of ADC 12-1. incubated at 37° C. for 8 hours.

FIG. 4C is a graph showing deconvoluted intact mass spectra for in-vitro stability samples of ADC 12-1. incubated at 37° C. for 14 days.

FIG. 4D is a graph showing deconvoluted intact mass spectra for in-vitro stability samples of ADC 12-1. incubated at 37° C. for 21 days.

FIG. 5 is a graph showing In vivo stability of ADC 12-1 versus "naked" antibody (non-conjugated) following IV dosing to DBA1 mice.

FIG. 6A is a graph showing deconvoluted intact mass spectra for the in vivo stability samples of ADC 12-1 from FIG. 5: sample B1 at 1 hour.

FIG. 6B is a graph showing deconvoluted intact mass spectra for the in vivo stability samples of ADC 12-1 from FIG. 5: sample H3 at 5 days.

FIG. 6C is a graph showing deconvoluted intact mass spectra for the in vivo stability samples of ADC 12-1 from FIG. 5: sample B7 at 1 hour.

FIG. 6D is a graph showing deconvoluted intact mass spectra for the in vivo stability samples of ADC 12-1 from FIG. 5: sample H9 at 5 days.

FIG. 7 is a graph showing In vitro activity of ADC 12-2 versus "naked" antibody (non-conjugated) in 786-O cells.

FIG. 8 shows the activity of anti-hC74 (LL1) ADCs in Hut78 cells.

FIG. 9 shows the activity of anti-hC74 (LL1) ADCs in SUDHL-6 cells.

FIG. 10 shows the activity of anti-hC74 (LL1) ADCs in 786-O cells.

DETAILED DESCRIPTION OF THE INVENTION

The present invention provides antibody-drug conjugates (ADCs) for use in treatments where it is desirable that the treatment include an anti-inflammatory therapeutic component. The antibody-drug conjugates comprise an antibody that targets or binds the human CD25, human CD70, human CD74 protein, or human CD163 protein (anti-CD25 antibody, anti-CD70 antibody, anti-CD74, or anti-CD163 antibody, respectively) conjugated to an anti-inflammatory therapeutic agent via a phosphate-based linker with tunable stability for intracellular delivery of the therapeutic agent. The phosphate-based linker comprises a monophosphate, diphosphate, triphosphate, or tetraphosphate group (phosphate group) covalently linked to the distal end of a linker arm comprising from the distal to the proximal direction a tuning element, optionally a spacer element, and a reactive functional group. The phosphate group of the phosphate-based linker is capable of being conjugated to the therapeutic agent and the reactive functional group is capable of being conjugated the antibody. The phosphate-based linker has a differentiated and tunable stability in blood vs. an intracellular environment (e.g., lysosomal compartment). The inventors have discovered that the rate at which the phosphate group is cleaved in the intracellular environment to release the payload in its native or active form may be affected by the structure of the tuning element with further effects mediated by substitutions of the phosphate group as well as whether the phosphate group is a monophosphate, diphosphate, triphosphate, or tetraphosphate.

The phosphate-based linkers comprise a monophosphate, diphosphate, triphosphate, or tetraphosphate group and a linker arm comprising a tuning element, an optional spacer element, and a reactive functional group. The phosphate-based linkers have a distal end and a proximal end. The distal end of the phosphate-based linker comprises a monophosphate, diphosphate, or triphosphate group (phosphate group) linked to the distal end of the tuning element comprising the linker arm. The phosphate group is covalently linked to an anti-inflammatory therapeutic agent. The proximal end of the linker arm comprises a reactive functional group capable of reacting with a group (side chain of an amino acid) on an antibody to covalently link the phosphate-based linker to the antibody. Interspersed between the tuning element and the reactive functional group of the linker arm may be an optional spacer element. Such a compound comprises formula (I)

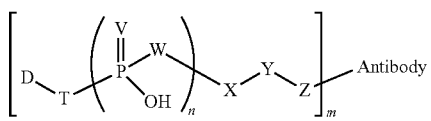

Wherein V is selected from O and S; W is selected from O, N, and $CH_2$; X is a tuning element selected from a covalent bond; a carbon atom; a heteroatom; an optionally substituted group selected from the group consisting of acyl, aliphatic, heteroaliphatic, aryl, heteroaryl, and heterocyclic; nucleoside, protease sensitive group, cathepsin K sensitive group, or glycosidase sensitive group; Y is selected from a covalent bond or a bivalent, straight or branched, saturated or unsaturated, optionally substituted $C_{1-30}$ hydrocarbon chain wherein one or more methylene units of Y are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group; T is an NR, $CR_2$, O, or S; D is an anti-inflammatory therapeutic agent; wherein the antibody binds the human CD25, human CD70, human CD74 protein, or human CD163 protein (anti-CD25 antibody, anti-CD70 antibody, anti-CD74, or anti-CD163 antibody, respectively); Z is a linkage formed between (i) a reactive functional group selected from the group consisting of N-hydroxysuccinimide, para-nitrophenyl carbonate, para-nitrophenyl carbamate, pentafluorophenyl, haloacetamide, maleimide, hydroxylamine, strained cycloalkyne, and heterocycloalkyne, alkyne, diene, azadiene, and heterocyclic azadience, wherein halo is iodine (I), bromine (Br), fluorine (F), or chlorine (Cl) and hetero is N, O, or S, and (ii) a side chain of an amino acid of the antibody; each occurrence of R is independently hydrogen, a suitable protecting group, an acyl moiety, arylalkyl moiety, aliphatic moiety, aryl moiety, heteroaryl moiety, or heteroaliphatic moiety; n is 1, 2, 3, or 4; and m is 1, 2, 3, 4, 5, 6, 7, 8, 9, or 10.

The phosphate-therapeutic agent is stabile extracellularly and labile intracellularly, for example, when present in the lysosomal compartment of the target cell. The tuning element provides a tunable stability to the phosphate-therapeutic agent linkage when the conjugate is within the lysosomal compartment of the target cell. The intracellular stability of the phosphate-therapeutic agent linkage or rate of intracellular release of the therapeutic agent from the conjugate may be adjusted or tuned by the particular tuning element adjacent to the phosphate group and/or by adjusting the number of the phosphate groups.

The link between the antibody and the anti-inflammatory therapeutic agent plays an important role in an antibody drug conjugate (ADC), as the type and structure of the linker may significantly affect the potency, selectivity, and the pharmacokinetics of the resulting conjugate (Widdeson et al, J. Med. Chem. 49: 4392-4408 (2006); Doronina et al., Bioconj. Chem. 17: 114-124 (2006); Hamann et al., Bioconj. Chem. 16: 346-353 (2005); King et al., J. Med. Chem. 45: 4336-4343 (2002); Alley et al., Bioconj. 19: 759-765 (2008); Blattler et al., Biochem. 24: 1517-1524 (1985). ADC delivery of a drug moiety to its intracellular target occurs via an multistep sequence of events: binding to the cell surface, endocytosis, trafficking (within an endosome) to a lysosome, proteolytic degradation of the conjugate, and diffusion of the released drug moiety across the lysosomal or endosomal membrane toward its intracellular target and its interaction with the target. Therefore, the linker should be sufficiently stable while in circulation to allow delivery of the intact ADC to the target cell but, on the other hand, sufficiently labile to allow release of the drug moiety from the ADC once inside the targeted cell. In general, four types of linkers have been used for preparation of ADCs that have currently entered the clinic: (a) acid-labile linkers, exploiting the acidic endosomal and lysosomal intracellular microenvironment (Hamann et al., op. cit.; Blattler et al., op. cit.); (b) linkers cleavable by lysosomal proteases (Dronina et al. op. cit.; King et al. op. cit.); (c) chemically stable thioether linkers that release a lysyl adduct after proteolytic degradation of the antibody inside the cell; (Lewis et al Cancer Res. 68: 9280-9290 (2008); Erickson et al., Cancer Res. 66: 4426-4433 (2006) and (d) disulfide containing linkers (Chari, Adv. Drug Delivery Rev. 31: 89-104 (1998); Widdeson et al., op. cit.), which are cleaved upon exposure to an intracellular thiol. While U.S. Pat. No. 5,094,848 discloses conjugates comprising a diphosphate or amidated diposphate group and a linker arm wherein the linker arm may preferably be an oligopeptide having preferably 2-10 amino acids, in particular embodiments the tuning element of the phosphate-based linkers disclosed herein may include a di-peptide.

The linker-therapeutic agent conjugates of the present invention wherein the therapeutic agent is covalently linked to a tuning element of the linker via a monophosphate, diphosphate, triphosphate, or tetraphosphate linkage have a differentiated and tunable stability of the phosphate linkage in blood vs. an intracellular environment (e.g. lysosomal compartment). Due to location of enzymes that recognize the phosphate linkage, conjugates that have a phosphate group linking a therapeutic agent to a tuning element of the linker are stable in circulation (plasma or blood) but reactive in intracellular compartments (e.g., lysosomes) making them suitable for intracellular delivery of therapeutic agent conjugates. The exemplary therapeutic agent-phosphate-based linker conjugates in the Examples show that the therapeutic agent-phosphate-based linker conjugates of the present invention are stable in blood, which is advantageous for extending the half-life and to prevent premature release of therapeutic agent from the conjugates.

Importantly, the inventors have discovered that by modifying the tuning element and/or V and/or W, and/or the number of phosphate groups, the ability to tune reactivity or cleavage of the phosphate linkage in a lysosomal environment so as to release the therapeutic agent from the conjugate. In general, the rate of release of the therapeutic agent is dependent on the proximal substitution of the tuning element. The ability to cleave the phosphate linkage between the payload and the tuning element efficiently in a lysosome is advantageous for the release of the therapeutic agent from the conjugate once it has been delivered to a cell and internalized through an endosomal pathway. Of note is that unlike other linkers known in the art, there is no need to for the phosphate-based linkers of the present invention to be self-immolative. In addition, the excellent solubility of the therapeutic agent-phosphate-based linker facilitates conjugation to a ligand or cell-targeting moiety and minimizes aggregation of the conjugates. In addition, the phosphate contributes to retention of the therapeutic agent to the conjugate within cell until phosphate linkage is fully cleaved and limits permeability of conjugates containing the payload from entering non-target cells.

The phosphate-based linkers provide greater solubility relative to disulfide linkers, cathepsin B-cleavable linkers, esters and acid-sensitive linkers such as hydrazones. They enable the release of the payload in its parent or unadultered form unlike some of the alternative linkers, and may offer an improved blood/lysosome stability profile. Specifically, these phosphate-based linkers will provide superior blood stability relative to esters and disuflides. Phosphate-based linkers, following lysosomal cleavage will release an alcohol or amine-containing payload whereas the other linker formats may require self-immolative tethers to accomplish this or leave residual linker on the therapeutic agent after lysosomal cleavage. The phosphate-based linker may have greater blood stability relative to the self-immolative cathepsin B linkers in the art, particularly when attached via the oxygen atom of a hydroxyl group of an alcohol-containing therapeutic agent. The enzymatic hydrolysis of the phosphate linkage may be more rapid than the acid-hydrolysis of hyrdazones. The phosphate-based linkers disclosed herein minimize the propensity for conjugates comprising particular therapeutic agent to aggregate. Thus, the phosphate-based linkers disclosed herein are particularly useful for conjugating therapeutic agents that are prone to forming aggregates to a cell-specific targeting ligand to provide a conjugate with a reduced or no detectable propensity for aggregation.

Phosphate Group

The phosphate group comprising the phosphate-based linkers disclosed herein may comprise 1, 2, 3, or 4 phosphate atoms. In particular embodiments, the phosphate group may be a phosphate ester

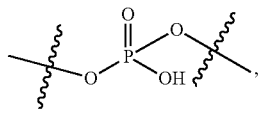 [SMILES: *OP(=O)(O)O*]

pyrophosphate ester

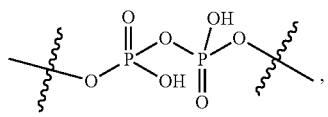

triphosphate ester

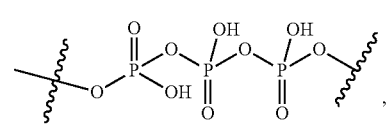 [SMILES: *OP(=O)(O)OP(=O)(O)OP(=O)(O)O*]

or tetraphosphate ester

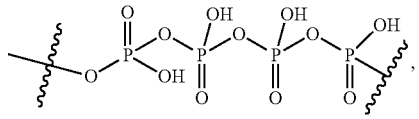 [SMILES: *OP(=O)(O)OP(=O)(O)OP(=O)(O)OP(*)(=O)O]

In further embodiments the phosphate group may be a phosphoramidate

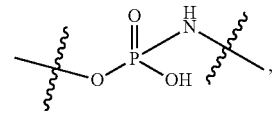 [SMILES: *NP(=O)(O)O*]

pyrophosphoramidate

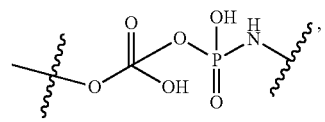

triphosphophoramidate

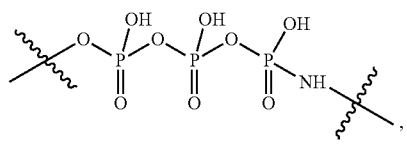 [SMILES: *NP(=O)(O)OP(=O)(O)OP(=O)(O)O*]

or tetraphosphoramidate

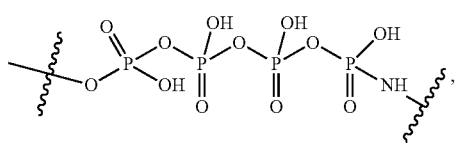 [SMILES: *NP(=O)(O)OP(=O)(O)OP(=O)(O)OP(=O)(O)O*]

In further still embodiments, the phosphate group may be a phosphonate

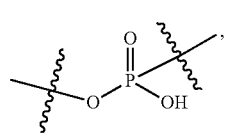 [SMILES: *OP(*)(=O)O]

a diposphonate

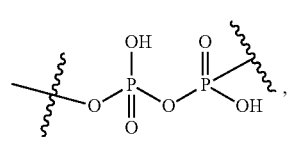 [SMILES: *OP(=O)(O)OP(*)(=O)O]

a phosphorthioate

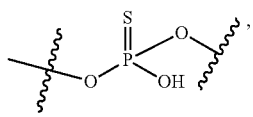

or a diphosphorthioate

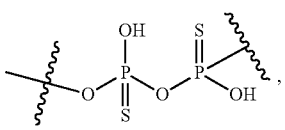 [SMILES: *OP(O)(=S)OP(*)(O)=S]

The wavy lines shown indicate the covalent attachment sites to the payload at the distal end (left) and the tuning element on the proximal end (right).

Anti-Inflammatory Therapeutic Agent

Anti-inflammatory therapeutic agents comprise glucocorticoid receptor agonists, which include but are not limited to glucocorticoids such as Cortisol, cortisone acetate, beclometasone, prednisone, prednisolone, methylprednisolone, betamethasone, trimcinolone, budesonide, dexamethasone, fluticasone, and mometasone.

Linker Arm

The linker arm of the phosphate-based linkers disclosed herein comprises a tuning element at the distal end covalently linked to a phosphate group and a functional reactive group at the proximal end capable of covalent linkage to a cell-targeting ligand. Optionally, the linker arm may further include a spacer element interposed between the tuning element and the reactive functional group. Examples of tuning elements include but are not limited to

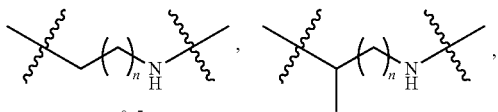

n = 0-5            n = 0-5

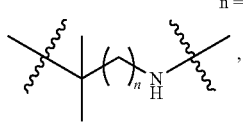

n = 0-5

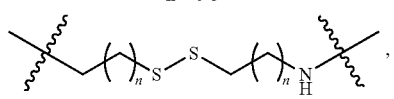

n = 0-5

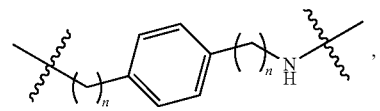

n = 0-5

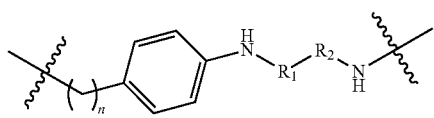

n = 0-5

$R_1$ and $R_2$ each independently any amino acid

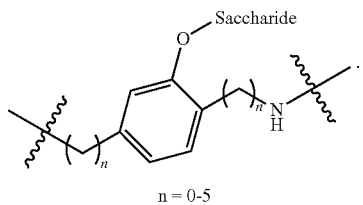

n = 0-5

The wavy lines indicate the covalent attachment sites to the phosphate group at the distal end (left) and the functional reactive group on the proximal end (right), or optionally, a spacer element.

Further examples of tuning elements include but are not limited to

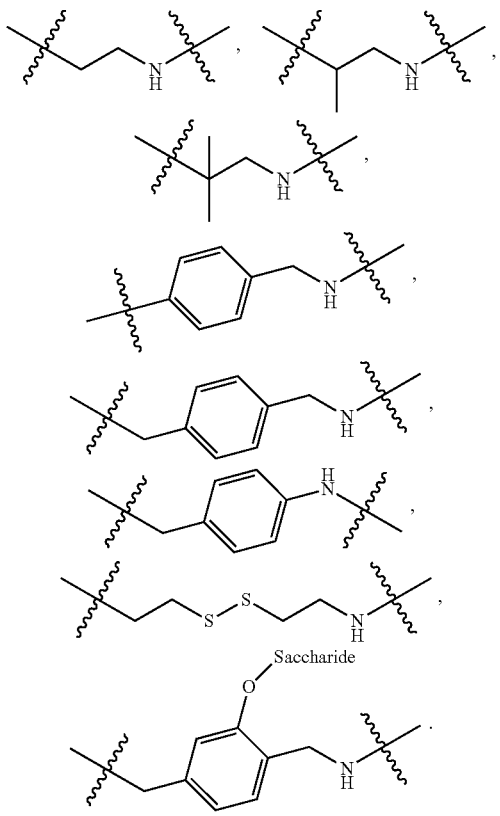

The wavy lines indicate the covalent attachment sites to the phosphate group at the distal end (left) and the functional reactive group on the proximal end (right), or optionally, a spacer element.

In general, the spacer element is to allow for distance control away from the cell-targeting ligand. In some embodiments, this distance may have an impact on the stability/cleavability of the linker. Examples of spacer elements include straight polyethylglycol (PEG) chains (of a defined length) and straight carbon chains with or without solubilizing groups attached thereto.

Targeting Antibody

The linker arm and anti-inflammatory therapeutic agent may be linked to an antibody that selectively delivers the therapeutic agent to a cell, organ, or region of the body that expresses the human CD25 protein, human CD74 protein, human CD74 protein, or human CD163 protein. Antibodies may be either polyclonal or monoclonal, but most preferably are monoclonal and may be human, humanized, or human chimeric antibodies. The antibody may be of any type or class (e.g., IgG, IgE, IgM, IgD, and IgA) or subclass (e.g., $IgG_1$, $IgG_2$, $IgG_3$, $IgG_4$, $IgA_1$ and $IgA_2$). The term "CD" refers to "cluster of differentiation".

The antibody may be attached to the linker arm by any available reactive group that can react with the reactive functional group on the proximal end of the linker arm. For example, the antibody may be attached through an amine, carboxyl, sulfhydryl, or hydroxyl group. Such a group may reside at N-terminus or at a site internal to the protein chain, for example, the side chain of an amino acid. The antibody may be further derivatized at one or more sites to allow for the attachment of appropriate reactive groups onto the peptide or protein. See, Chrisey et al. Nucleic Acids Res. 24:3031-3039 (1996). In addition, the antibody may be synthesized to contain one or more non-natural amino acids, the side chain thereof which may then serve as a site for attachment of the linker arm comprising the payload-phosphate-based linker. Antibodies comprising non-natural amino acids for conjugation and methods for making such antibodies have been disclosed in U.S. Pat. No. 7,632,924, which is incorporated herein by reference. As exemplified herein the antibody may comprise a substitution of an amino acid residue in the heavy chain or light chain with the non-natural amino acid para-azidophenylalanine (pAzF). The azido group on the side chain of the pAzF residue may be conjugated to a reactive functional group of the therapeutic agent-linker such as a strained cycloalkyne, for example, cyclooctyne.

In particular aspects, the antibody is a chimeric, humanized, or fully human anti-CD25 antibody comprising the light chain CDR sequences CDR1 (RASQSVSSSYLA; SEQ ID NO: 1), CDR2 (GASSRAT; SEQ ID NO: 2), and CDR3 (QQYSSSPLT; SEQ ID NO: 3) and the heavy chain complementarity-determining region (CDR) sequences CDR1 (RYIIN; SEQ ID NO: 4), CDR2 (RIIPILGVENYAQKFQG; SEQ ID NO: 5), and CDR3 (KDWFDY; SEQ ID NO: 6). In particular aspects, the antibody is a chimeric, humanized, or fully human anti-CD25 antibody comprising the light chain CDR sequences CDR1 (RASQSVSSSFLA; SEQ ID NO: 1), CDR2 (GASSRAT; SEQ ID NO: 2), and CDR3 (QQYSSSPLT; SEQ ID NO: 3) and the heavy chain complementarity-determining region (CDR) sequences CDR1 (RYPIN; SEQ ID NO: 7), CDR2 (RIIPILGIADYAQRFQG; SEQ ID NO: 8), and CDR3 (RDWGDY; SEQ ID NO: 9). In particular aspects, the antibody is a chimeric, humanized, or fully human anti-CD25 antibody comprising the light chain CDR sequences CDR1 (RASQSGSSSYLA; SEQ ID NO: 1), CDR2 (GASSRAT; SEQ ID NO: 2), and CDR3 (QQYGSSPIT; SEQ ID NO: 10) and the heavy chain complementarity-determining region (CDR) sequences CDR1 (RYAIN; SEQ ID NO: 11), CDR2 (RIIPILDIADYAQKFQD; SEQ ID NO: 12), and CDR3 (KDWFDP; SEQ ID NO: 13). In particular aspects, the antibody is a chimeric, humanized, or fully human anti-CD25 antibody comprising the light chain CDR sequences CDR1 (RASQSVSSSFLA; SEQ ID NO: 1), CDR2 (GASSRAT; SEQ ID NO:2), and CDR3 (QQYSSSPLT; SEQ ID NO:3) and the heavy chain complementarity-determining region (CDR) sequences CDR1 (RYPIN; SEQ ID NO: 14), CDR2 (RIIPILGIADYAQRFQG; SEQ ID NO:8), and CDR3 (RDWGDY; SEQ ID NO:9). In particular aspects, the antibody is a chimeric, humanized, or fully human anti-CD25 antibody comprising at least one, two, three, four, five, or six CDR(s) having an amino acid sequence selected from SEQ ID NO: 1, SEQ ID NO:2, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, and SEQ ID NO: 14. In particular aspects the antibody is a chimeric, humanized, or fully human anti-CD25 antibody that competes with any one of the aforementioned antibodies for binding to the CD25. The aforementioned anti-CD70 antibodies comprising said CDR sequences have been disclosed in U.S. Pat. No. 7,438,907, which is incorporated herein by reference.

In particular aspects, the antibody is a chimeric, humanized, or fully human anti-CD70 antibody comprising the light chain CDR sequences CDR1 (RASQSVSSYLA; SEQ ID NO: 15), CDR2 (YDASNRAT; SEQ ID NO: 16), and CDR3 (QQRTNWPLT; SEQ ID NO: 17) and the heavy chain complementarity-determining region (CDR) sequences CDR1 (SYIMH; SEQ ID NO: 18), CDR2 (VISYDGRNKYYADSVK; SEQ ID NO: 19), and CDR3 (DTDGYDFDY; SEQ ID NO:20). In particular aspects, the antibody is a chimeric, humanized, or fully human anti-CD70 antibody comprising the light chain CDR sequences CDR1 (RASQGISSALA; SEQ ID NO:21), CDR2 (DASSLES; SEQ ID NO:22), and CDR3 (QQFNSYPFT; SEQ ID NO:23) and the heavy chain complementarity-determining region (CDR) sequences CDR1 (YYAMH; SEQ ID NO:24), CDR2 (VISYDGSIKYYADSVK; SEQ ID NO:25), and CDR3 (EGPYSNYLDY; SEQ ID NO:26). In particular aspects, the antibody is a chimeric, humanized, or fully human anti-CD70 antibody comprising the light chain CDR sequences CDR1 (RASQGISSWLA; SEQ ID NO:27), CDR2 (AASSLQS; SEQ ID NO:28), and CDR3 (QQYNSYPLT; SEQ ID NO:29) and the heavy chain complementarity-determining region (CDR) sequences CDR1 (DYGMH; SEQ ID NO:30), CDR2 (VIWYDGSNKYYADSVK; SEQ ID NO:31), and CDR3 (DSIVMVRGDY; SEQ ID NO:32). In particular aspects, the antibody is a chimeric, humanized, or fully human anti-CD70 antibody comprising the light chain CDR sequences CDR1 (RASQGISSWLA; SEQ ID NO:33), CDR2 (AASSLQS; SEQ ID NO:34), and CDR3 (QQYNSYPLT; SEQ ID NO:35) and the heavy chain complementarity-determining region (CDR) sequences CDR1 (DHGMH; SEQ ID NO:36), CDR2 (VIWYDGSNKYYADSVK; SEQ ID NO:37), and CDR3 (DSIMVRGDY; SEQ ID NO:38). In particular aspects, the antibody is a chimeric, humanized, or fully human anti-CD70 antibody comprising the light chain CDR sequences CDR1 (RASQSVSSYLA; SEQ ID NO: 15), CDR2 (DASNRAT; SEQ ID NO:39), and CDR3 (QQRSNWPLT; SEQ ID NO:40) and the heavy chain complementarity-determining region (CDR) sequences CDR1 (SDYYWS; SEQ ID NO:41), CDR2 (YIYYSGSTNYDPSLKS; SEQ ID NO:42), and CDR3 (GDGDYGGNCFDY; SEQ ID NO:43). In particular aspects, the antibody is a chimeric, humanized, or fully human anti-CD74 antibody comprising at least one, two, three, four, five, or six CDR(s) having an amino acid sequence selected from SEQ ID NO: 15, SEQ ID NO: 16, SEQ ID NO: 17, SEQ ID NO: 18, SEQ ID NO: 19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, and SEQ ID NO:43. In particular aspects the antibody is a chimeric, humanized, or fully human anti-CD70 antibody that competes with any one of the aforementioned antibodies for binding to the CD70. The aforementioned anti-CD70 antibodies comprising said CDR sequences have been disclosed in U.S. Pat. No. 8,124,738, which is incorporated herein by reference.

In particular aspects, the antibody is a chimeric, humanized, or fully human anti-CD74 antibody comprising the light chain complementarity-determining region (CDR) sequences CDR1 (RSSQSLVHRNGNTYLH; SEQ ID NO:44), CDR2 (TVSNRFS; SEQ ID NO:45), and CDR3 (SQSSHVPPT; SEQ ID NO:46) and the heavy chain CDR sequences CDR1 (NYGVN; SEQ ID NO:47), CDR2 (WINPNTGEPTFDDDFKG; SEQ ID NO:48), and CDR3 (SRGKNEAWFAY; SEQ ID NO:49). In particular aspects, the antibody is a chimeric, humanized, or fully human anti-CD74 antibody comprising at least one, two, three, four, five, or six CDR(s) selected from SEQ ID NO:44, SEQ ID NO: 45, SEQ ID NO:46, SEQ ID NO:47, SEQ ID NO:48, and SEQ ID NO:49. In particular aspects the antibody is a chimeric, humanized, or fully human anti-CD74 antibody that competes with any one of the aforementioned antibodies for binding to the CD74. Antibodies comprising said CDR sequences have been disclosed in U.S. Pat. No. 7,772,373, which is incorporated herein by reference. In a particular aspect, the anti-CD74 antibody comprises a heavy chain (HC) comprising an amino acid sequence selected from SEQ ID NO:69, 70, 71, and 72 and a light chain (LC) comprising the amino acid sequence of SEQ ID NO:73.

In particular aspects, the antibody is a chimeric, humanized, or fully human anti-CD74 antibody comprising the light chain complementarity-determining region (CDR) sequences CDR1 (QGISSW; SEQ ID NO:50), CDR2 (AAS), and CDR3 (QQYNSYPLT; SEQ ID NO:51) and the heavy chain CDR sequences CDR1 (GFTFSSYA; SEQ ID NO:52), CDR2 (ISYDGSNK; SEQ ID NO:53), and CDR3 (ASGRYYGSGSYSSYFD; SEQ ID NO:54); or the heavy chain CDR sequences CDR1 (GFTFSSYA; SEQ ID NO:52), CDR2 (ISYDGSIK; SEQ ID NO:55), and CDR3 (ARGREYTSQNIVILLD; SEQ ID NO:56); or the heavy chain CDR sequences CDR1 (GFTFSSYA; SEQ ID NO:52), CDR2 (ISYDGSNK; SEQ ID NO:53), and CDR3 (ARGREITSQNIVILLD; SEQ ID NO:57); or the heavy chain CDR sequences CDR1 (GFTFSSYA; SEQ ID NO:52), CDR2 (IWYDGSNK; SEQ ID NO:58), and CDR3 (ARGGTLVRGAMYGTDV; SEQ ID NO:59). In particular aspects, the antibody is a chimeric, humanized, or fully human anti-CD74 antibody comprising at least one, two, three, four, five, or six CDR(s) having an amino acid sequence selected from AAS, SEQ ID NO:50, SEQ ID NO: 51, SEQ ID NO:52, SEQ ID NO:53, SEQ ID NO:54, SEQ ID NO:55, SEQ ID NO:56, SEQ ID NO:57, SEQ ID NO:58, and SEQ ID NO:59. In particular aspects the antibody is a chimeric, humanized, or fully human anti-CD74 antibody that competes with any one of the aforementioned antibodies for binding to the CD74. Antibodies comprising said CDR sequences have been disclosed in U.S. Patent Application Publication No. 20140030273, which is incorporated herein by reference. In a particular aspect, the anti-CD74 antibody comprises a heavy chain (HC) comprising an amino acid sequence selected from SEQ ID NO:74, 75, 76, and 77 and a light chain (LC) comprising the amino acid sequence of SEQ ID NO:78.

In particular aspects, the antibody is a chimeric, humanized, or fully human anti-CD163 antibody comprising the light chain CDR sequences CDR1 (ASQSVSSDV; SEQ ID NO:60), CDR2 (YAS), and CDR3 (QDYTSPRT; SEQ ID NO:61) and the heavy chain complementarity-determining region (CDR) sequences CDR1 (GYSITSDY; SEQ ID NO:62), CDR2 (YSG), and CDR3 (CVSGTYYFDYWG; SEQ ID NO:63); or the light chain CDR sequences CDR1 (ASQSVSHDV; SEQ ID NO:54), CDR2 (YTS), and CDR3 (QDYSSPRT; SEQ ID NO:65) and the heavy chain CDR sequences CDR1 (GYSITSDY; SEQ ID NO:62), CDR2 (YSG), and CDR3 (CVSGTYYFDYWG; SEQ ID NO:63).

In particular aspects, the antibody is a chimeric, humanized, or fully human anti-CD163 antibody comprising at least one, two, three, four, five, or six CDR(s) having an amino acid sequence selected from YYAS, YSG, YTS, SEQ ID NO:60, SEQ ID NO: 61, SEQ ID NO:62, SEQ ID NO:63, SEQ ID NO:64, and SEQ ID NO:65. In particular aspects the antibody is a chimeric, humanized, or fully human anti-CD163 antibody that competes with any one of the aforementioned antibodies for binding to the CD163. Antibodies comprising said CDR sequences have been disclosed in U.S. Patent Application Publication No. 20120258107 and 20120276193, which are incorporated herein by reference.

In particular embodiments, the antibody has reduced effector function or lacks effector function compared to a wild-type or native $IgG_1$ antibody. Reducing or eliminating effector function may be achieved by providing an antibody with an $IgG_4$ framework or constant domain. In one embodiment, the $IgG_4$ constant domain may differ from the native human $IgG_4$ constant domain (Swiss-Prot Accession No. P01861.1) at a position corresponding to position 228 in the EU system and position 241 as determined in the KABAT numbering scheme (See, e.g., Elvin A. Kabat ((1991) Sequences of Proteins of Immunological Interest, 5th Ed. Public Health Service, National Institutes of Health, Bethesda, Md.)), where the native $Ser_{108}$ is replaced with Pro, in order to prevent a potential inter-chain disulfide bond between $Cys_{106}$ and $Cys_{109}$ (corresponding to positions $Cys_{226}$ and $Cys_{229}$ in the EU system and positions $Cys_{239}$ and $Cys_{242}$ in the KABAT system) that could interfere with proper intra-chain disulfide bond formation (See Angal et al. Mol. Imunol. 30:105 (1993)). In other instances, a modified IgG1 constant domain which has been modified to increase half-life or reduce effector function can be used.

In particular aspects, the antibody that has reduced or lacks effector function is an aglycosylated antibody that lacks the N-glycan at position 297 of the heavy chain (as determined using the KABAT Numbering scheme). Aglycosylated antibodies may be produced in a prokaryote expression system, for example, E. coli. The antibody may be encoded by a nucleic acid molecule that introduces an amino acid substitution in any of positions 297-299 of the heavy chain such that the antibody is substantially aglycosylated when the nucleic acid molecule is expressed in a mammalian cell. In $IgG_1$, the glycosylation site is $Asn_{297}$ within the amino acid sequence QYNS (SEQ ID NO:66). In other immunoglobulin isotypes, the glycosylation site corresponds to $Asn_{297}$ of IgG1. For example, in $IgG_2$ and $IgG_4$, the glycosylation site is the asparagine within the amino acid sequence QFNS (SEQ ID NO:67). Accordingly, a mutation of $Asn_{297}$ of $IgG_1$ removes the glycosylation site in an Fc portion derived from $IgG_1$. In one embodiment, $Asn_{297}$ is replaced with Gln. In other embodiments, the tyrosine within the amino acid sequence QYNS (SEQ ID NO:66) is further mutated to eliminate a potential non-self T-cell epitope resulting from asparagine mutation. As used herein, a T-cell epitope is a polypeptide sequence in a protein that interacts with or binds an MHC class II molecule. For example, the amino acid sequence QYNS (SEQ ID NO:66)

within an IgG$_1$ heavy chain can be replaced with a QAQS (SEQ ID NO:68) amino acid sequence. Similarly, in IgG$_2$ or IgG$_4$, a mutation of asparagine within the amino acid sequence QFNS (SEQ ID NO:67) removes the glycosylation site in an Fc portion derived from IgG$_2$ or IgG$_4$ heavy chain. In one embodiment, the asparagine is replaced with a glutamine. In other embodiments, the phenylalanine within the amino acid sequence QFNS (SEQ ID NO:67) is further mutated to eliminate a potential non-self T-cell epitope resulting from asparagine mutation. For example, the amino acid sequence QFNS (SEQ ID NO:67) within an IgG$_2$ or IgG$_4$ heavy chain can be replaced with a QAQS (SEQ ID NO:68) amino acid sequence.

In particular aspects, the antibody comprises a substitution of one or more of the amino acids at position 318, 320, 322, 234, 235, 236, 237, or 297 of the antibody wherein the antibody with the substitution has a reduced effector function compared to an antibody comprising the native or wild-type amino acid at the position. The effector function may be binding affinity for Clq and/or binding affinity for the Fc receptor. These amino acid substitutions and their effect on reducing effector function have been disclosed in U.S. Pat. No. 5,648,260, which is incorporated herein by reference.

In particular aspects, the Fc region is modified to decrease the ability of the antibody to mediate effector function and/or to increase anti-inflammatory properties by modifying residues 243 and 264. In one embodiment, the Fc region of the antibody is modified by changing the residues at positions 243 and 264 to alanine. In one embodiment, the Fc region is modified to decrease the ability of the antibody to mediate effector function and/or to increase anti-inflammatory properties by modifying residues 243, 264, 267 and 328.

Pharmaceutical Formulations and Administration

The conjugates disclosed herein are useful for the manufacture of medicaments for the treatment of diseases or disorders such as an inflammatory disease or cancer. The conjugates disclosed herein may be formulated into pharmaceutical formulations for use in treating diseases or disorders such as an inflammatory disease or cancer.

The present invention provides a pharmaceutical formulation comprising a compound of the invention and a pharmaceutically acceptable carrier. The compounds described herein including pharmaceutically acceptable carriers such as addition salts or hydrates thereof, can be delivered to a patient using a wide variety of routes or modes of administration. Suitable routes of administration include, but are not limited to, inhalation, transdermal, oral, rectal, transmucosal, intestinal and parenteral administration, including intramuscular, subcutaneous and intravenous injections.

In particular embodiments, the conjugates of the invention comprising an antibody or antibody fragment as the targeting moiety are administered parenterally, more preferably intravenously. As used herein, the terms "administering" or "administration" are intended to encompass all means for directly and indirectly delivering a compound to its intended site of action. The compounds described herein, or pharmaceutically acceptable salts and/or hydrates thereof, may be administered singly, in combination with other compounds of the invention, and/or in cocktails combined with other therapeutic agents. The choice of therapeutic agents that can be co-administered with the compounds of the invention will depend, in part, on the condition being treated.

The active compound(s) of the invention are administered per se or in the form of a pharmaceutical composition wherein the active compound(s) is in admixture with one or more pharmaceutically acceptable carriers, excipients or diluents. Pharmaceutical compositions for use in accordance with the present invention are typically formulated in a conventional manner using one or more physiologically acceptable carriers comprising excipients and auxiliaries, which facilitate processing of the active compounds into preparations which, can be used pharmaceutically. Proper formulation is dependent upon the route of administration chosen.

For transmucosal administration, penetrants appropriate to the barrier to be permeated are used in the formulation. Such penetrants are generally known in the art.

For oral administration, the compounds can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores.

Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxyniethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations, which can be used orally, include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Injection is a preferred method of administration for the compositions of the current invention. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents may be added, such as the cross-linked polyvinyl pyrrolidone, agar, or alginic acid or a salt thereof such as sodium alginate.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances, which increase the viscosity of the suspension, such as sodium carboxymethyl cellulose, sorbitol, or dextran. Optionally, the suspension may also contain suitable stabilizers or agents, which increase the solubility of the compounds to allow for the preparation of highly, concentrated solutions. For injection, the agents of the invention may be formulated in aqueous solutions, preferably in physiologically compatible buffers such as Hanks's solution, Ringer's solution, or physiological saline buffer. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation or transcutaneous delivery (e.g., subcutaneously or intramuscularly), intramuscular injection or a transdermal patch. Thus, for example, the compounds may be formulated with suitable polymeric or hydrophobic materials (e.g., as an emulsion in an acceptable oil) or ion exchange resins, or as sparingly soluble derivatives, for example, as a sparingly soluble salt. The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

The following examples are intended to promote a further understanding of the present invention.

Example 1

The synthesis of dexamethasone linker 2-(2-(cyclooct-2-yn-1-yloxy)acetamido)ethyl(2-((8 S,9R,10S,11S,13 S,14 S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) dihydrogen pyrophosphate (1-4) was as follows.

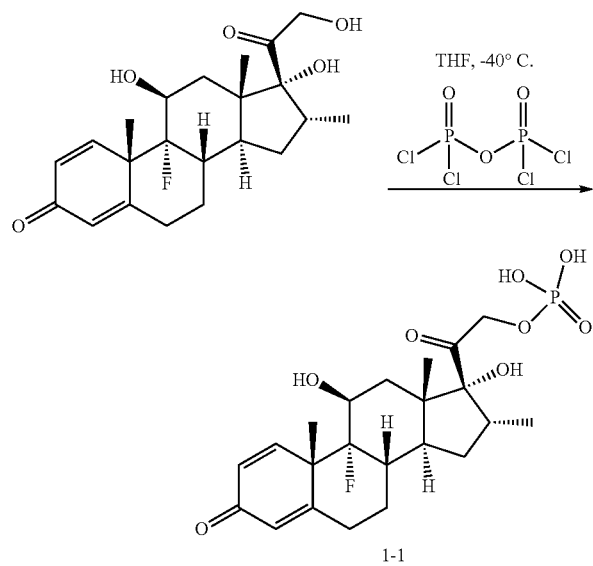

1-1

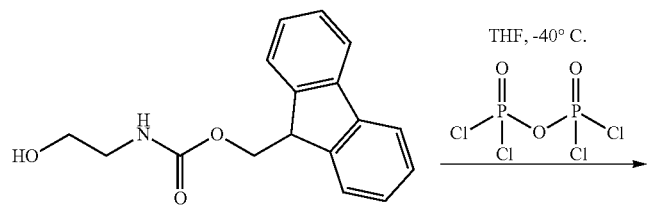

-continued
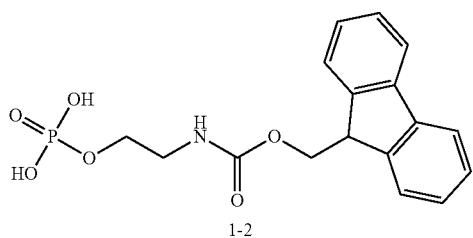
1-2
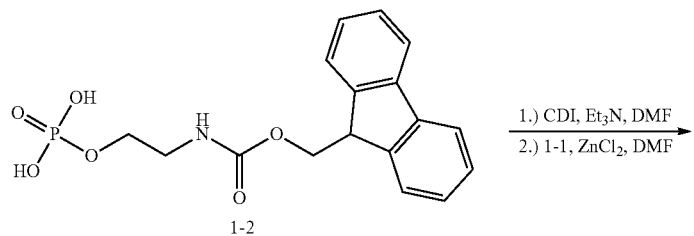
1.) CDI, Et₃N, DMF
2.) 1-1, ZnCl₂, DMF
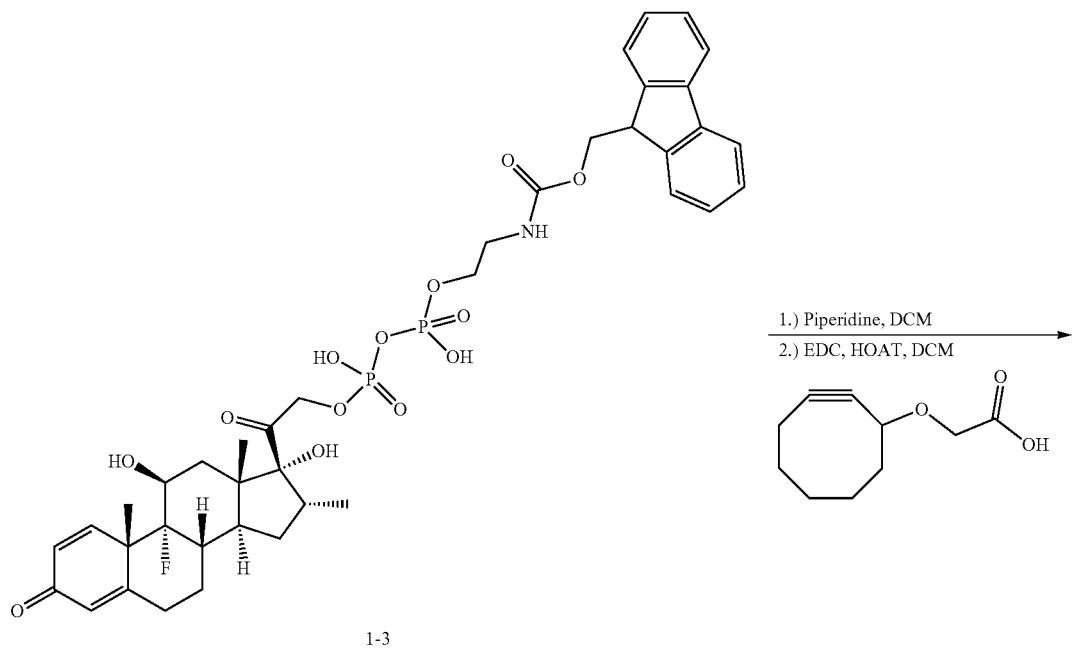
1-3
1.) Piperidine, DCM
2.) EDC, HOAT, DCM

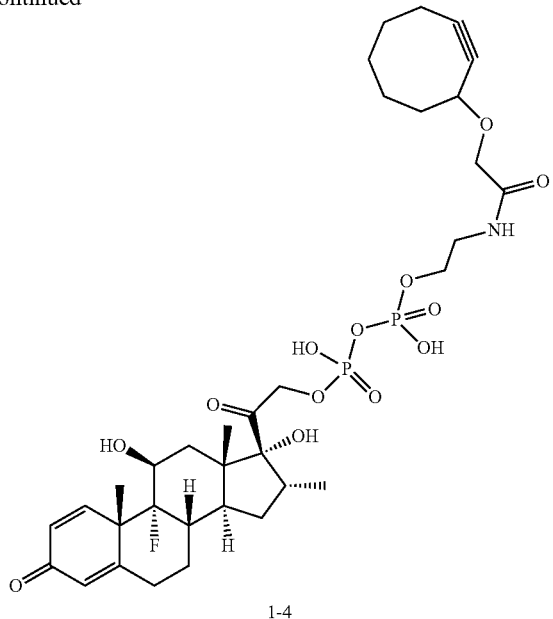

1-4

Step A: 2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl dihydrogen phosphate (1-1)

To a stirred solution of dexamethasone (0.40 g, 1.02 mmol) in THF (2.0 mL) at −40° C. was added diphosphoryl chloride (0.31 mL, 2.24 mmol) and the resulting mixture was stirred at −40° C. for 1 hr. The reaction was quenched with water, and treated with saturated sodium bicarbonate solution until pH ~8. The solution was made acidic using 1N HCl solution and extracted several times with ethyl acetate. The combined organic phase washed with brine, dried over sodium sulfate and concentrated to give 1-1 as a solid (497 mg, 103%). LRMS (ES) (M+H)+: observed=473.3, calculated=473.4.

Step B: (9H-fluoren-9-yl)methyl (2-((hydroxy(1H-imidazol-1-yl)phosphoryl)oxy)ethyl)carbamate (1-2)

The title compound was prepared from N-(9-fluorenylmethoxycarbonyl)ethanolamine according to the protocol outlined in Example 1-1 to afford 1-2. LRMS (ES) (M+H)+: observed=414.3, calculated=414.4

Step C: (9H-fluoren-9-yl)methyl (2-(((((2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethoxy)(hydroxy)phosphoryl)oxy)(hydroxy)phosphoryl)oxy)ethyl)carbamate (1-3)

To a stirred solution of 1-2 (0.15 g, 0.41 mmol) in DMF (1.2 mL) was added triethylamine (0.06 mL, 0.41 mmol) and CDI (0.17 g, 1.03 mmol). The resulting solution was stirred at room temperature for 30 minutes. To this mixture was added 1-1 (0.19 g, 0.41 mmol) and ZnCl$_2$ (0.45 g, 3.31 mmol) and the mixture was allowed to stir at room temperature overnight. The reaction was diluted with 1 N HCl and extracted several times with ethyl acetate. The combined organic layers were concentrated and reverse phase preparative chromatography (Phenomenex Gemini-NX C18 OBD 5 uM 30×100 mm; 5-35% MeCN/water w/0.1% NH$_4$OH modifier over 20 min) gave 1-3 as a solid (134 mg, 40%). LRMS (ES) (M+H)+: observed=818.6, calculated=818.7.

Step D: 2-(2-(cyclooct-2-yn-1-yloxy)acetamido)ethyl (2-((8S,9R,10S,11S,13S14S,14S,6R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) dihydrogen pyrophosphate (1-4)

To a stirred solution of 1-3 (0.19 g, 0.23 mmol) in DCM (3 mL) was added piperidine (0.15 mL, 1.51 mmol) and the resulting mixture was stirred at room temperature for 3 hrs. The solution was concentrated to dryness and redissolved in DCM (2 mL). In a separate vial a stirred solution of 2-(cyclooct-2-yn-1-yloxy)acetic acid (0.045 g, 0.25 mmol) in dichloromethane (1 mL) was added HOAT (0.034 g, 0.25 mmol), EDC (0.056 g, 0.30 mmol) and triethylamine (0.1 mL, 0.68 mmol). The resulting solution was stirred at room temperature for 40 minutes. The two solutions were combined and stirred at room temperature. Additional 2-(cyclooct-2-yn-1-yloxy)acetic acid activated with HOAT/EDC was added as necessary to complete reaction. Upon completion, the mixture was concentrated and reverse phase preparative chromatography (Phenomenex Gemini-NX C18 OBD 5 uM 30×100 mm; 5-30% MeCN/water w/0.1% NH$_4$OH modifier over 20 min) gave 1-4 as a solid (59 mg, 34%). LRMS (ES) (M+H)+: observed=760.6, calculated=760.7. $^1$H NMR (400 MHz, DMSO-d$_6$): δ 8.64 (br s, 1H), 7.29 (d, J=9.15 Hz, 1H), 6.21 (dd, J=10.05, 1.93 Hz, 1H), 6.00 (s, 1H), 4.57 (d, J=8.3 Hz, 2H), 4.31 (t, J=5.4 Hz, 1H), 4.12 (d, J=11.22 Hz, 1H), 3.92 (dd, J=14.43, 8.59 Hz, 1H), 3.80-3.76 (complex, 3H), 3.30-3.16 (complex, 2H), 3.02-2.91 (complex, 2H), 2.63 (m, 1H), 2.40-2.19 (complex, 3H), 2.17-2.03 (complex, 4H), 1.96-1.82 (m, 3H), 1.80-1.72

(complex, 3H), 1.66-1.52 (complex, 4H), 1.50 (s, 3H), 1.40-1.31 (complex, 2H), 1.07-1.02 (m, 1H), 0.88 (s, 3H), 0.77 (d, J=7.17 Hz, 3H)
Example 2
The synthesis of dexamethasone linker 2-(2-(cyclooct-2-yn-1-yloxy)acetamido)ethyl (2-((8S,9R,10S,11 S,13 S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) trihydrogen triphosphate (2-7) was as follows.
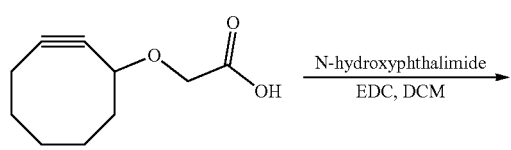
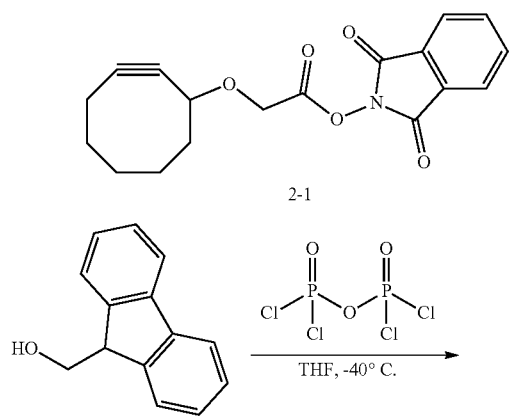
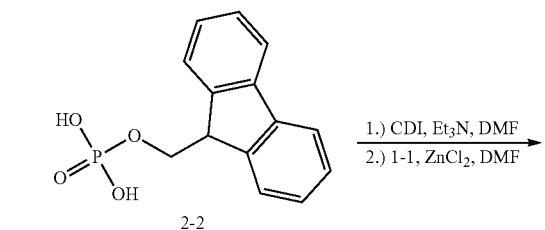
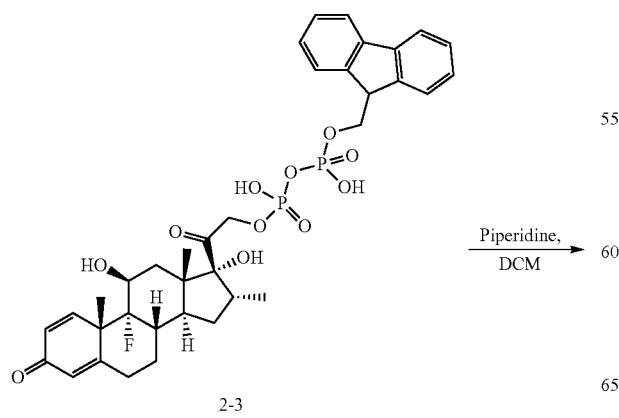
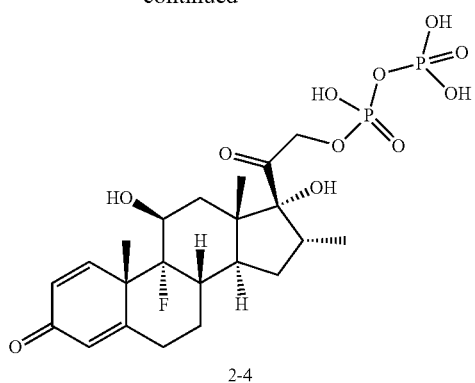
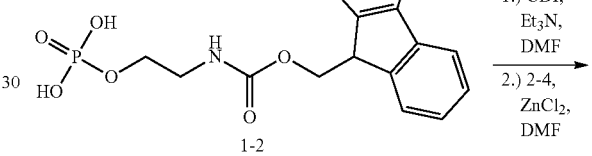
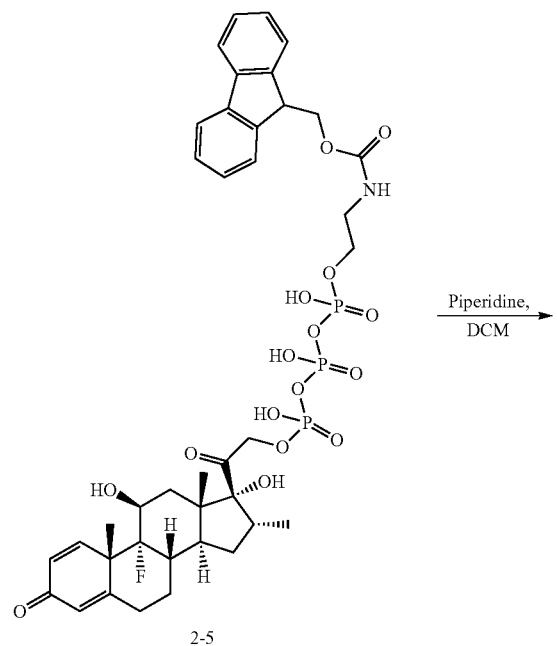

-continued

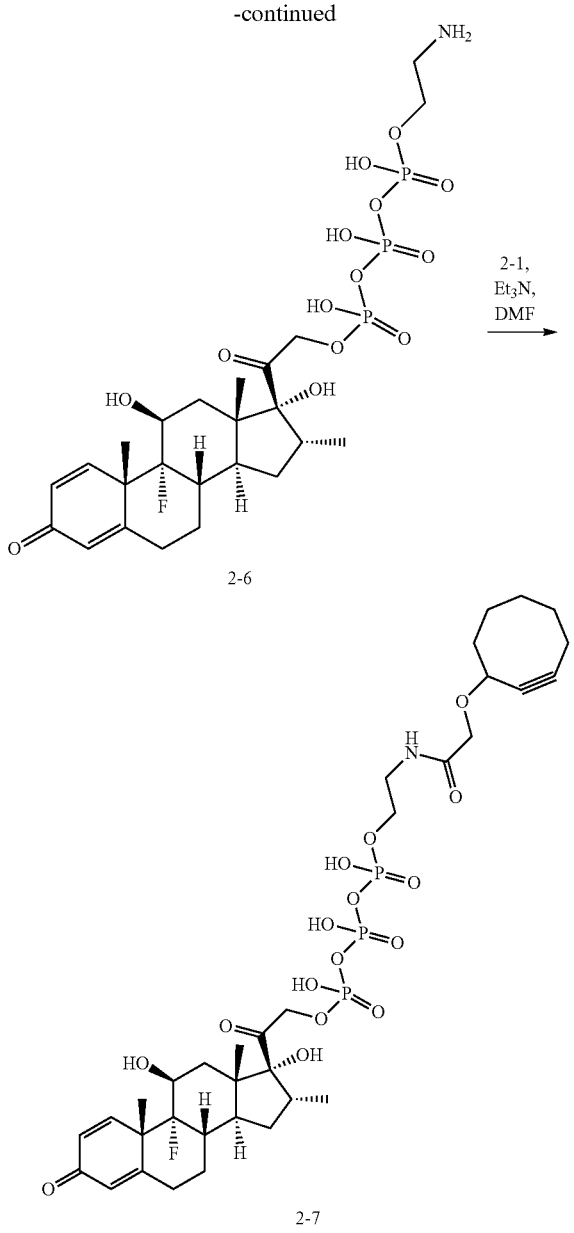

Step A: 1,3-dioxoisoindolin-2-yl 2-(cyclooct-2-yn-1-yloxy)acetate (2-1)

To a stirred solution of 2-(cyclooct-2-yn-1-yloxy)acetic acid (0.20 g, 1.10 mmol) in DCM (4.0 mL) was added N-hydroxyphthalimide (0.36 g, 2.20 mmol) and EDC (0.42 g, 2.20 mmol). The resulting mixture was stirred at room temperature for 45 minutes. The reaction was directly injected onto a silica gel column and flash column separation using a 0-50% ethyl acetate/hexane gradient gave 2-1 as a solid (335 mg, 93%)

Step B: (9H-fluoren-9-yl)methyl dihydrogen phosphate (2-2)

The title compound was prepared from (9H-fluoren-9-yl)methanol according to the protocol outlined in Example 1-1 to afford 2-2. LRMS (ES) (M+H)+: observed=277.1, calculated=276.2

Step C: ((9H-fluoren-9-yl)methyl) (2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) dihydrogen pyrophosphate (2-3)

The title compound was prepared from 2-2 and 1-1 according to the protocol outlined in Example 1 to produce 1-3 to afford 2-3. LRMS (ES) (M+H)+: observed=731.2, calculated=730.6

Step D: 2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl trihydrogen diphosphate (2-4)

To a stirred solution of 2-3 (0.29 g, 0.39 mmol) in DCM (2 mL) was added piperidine (0.23 mL, 2.36 mmol) and the resulting mixture was stirred at room temperature for 80 minutes. The solution was concentrated and reverse phase preparative chromatography (Phenomenex Gemini-NX C18 OBD 5 uM 30×100 mm; 3-25% MeCN/water w/0.1% NH4OH modifier over 20 min) gave 2-4 as a solid (123 mg, 56%). LRMS (ES) (M+H)+: observed=553.2, calculated=552.4

Step E: (9H-fluoren-9-yl)methyl (2-(((((((2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethoxy)(hydroxy)phosphoryl)oxy)(hydroxy)phosphoryl)oxy)(hydroxy)phosphoryl)oxy)ethyl)carba mate (2-5)

The title compound was prepared from 2-4 and 1-2 according to the protocol outlined in Example 1 to produce 1-3 to afford 2-5. LRMS (ES) (M+H)+: observed=898.3, calculated=897.7

Step F: 2-amionethyl (2-((8S,9R,10S,1 S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) trihydrogen triphosphate (2-6)

The title compound was prepared from 2-5 according to the protocol outlined in Example 2 to produce 2-4 to afford 2-6. LRMS (ES) (M+H)+: observed=676.2, calculated=675.4

Step G: 2-(2-(cyclooct-2-yn-1-yloxy)acetamido)ethyl (2-((8S,9R,10S,11 S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) trihydrogen triphosphate (2-7)

To a stirred solution of 2-6 (0.027 g, 0.04 mmol) in DMF (0.8 mL) was added triethylamine (0.02 mL, 0.16 mmol) and 2-1 and the resulting mixture was stirred at room temperature for 30 minutes. The solution was concentrated and reverse phase preparative chromatography (Phenomenex Gemini-NX C18 OBD 5 uM 30×100 mm; 5-40% MeCN/water w/0.1% NH4OH modifier over 20 min) gave 2-7 as a solid (8 mg, 24%). 1H NMR (499 MHz, DMSO): 0.78 (d, J=7.1 Hz, 3H); 0.88 (s, 3H); 1.10-0.99 (complex, 1H);

1.44-1.28 (complex, 2H); 1.50 (s, 3H); 1.67-1.52 (complex, 4H); 1.80-1.67 (complex, 3H); 1.93-1.83 (m, 3H); 2.17-2.01 (complex, 3H); 2.42-2.17 (complex, 3H); 2.67-2.57 (complex, 1H); 2.81 (d, J=79.7 Hz, 1H); 3.02-2.91 (complex, 1H); 3.17 (s, 1H); 3.26-3.21 (complex, 2H); 3.84-3.74 (complex, 2H); 3.91 (d, J=14.5 Hz, 1H); 4.15 (d, J=11.4 Hz, 1H); 4.31 (t, J=5.1 Hz, 1H); 4.57 (dd, J=18.0, 8.1 Hz, 1H); 4.71 (dd, J=17.9, 7.1 Hz, 1H); 5.99 (s, 1H); 6.20 (d, J=10.1 Hz, 1H); 7.30 (d, J=10.6 Hz, 1H); 8.48 (s, 1H). LRMS (ES) (M+H)$^+$: observed=840.4, calculated=839.6

Example 3

The synthesis of dexamethasone linker 4-(2-(cyclooct-2-yn-1-yloxy)acetamido)phenyl (2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) dihydrogen pyrophosphate (3-4) was as follows.

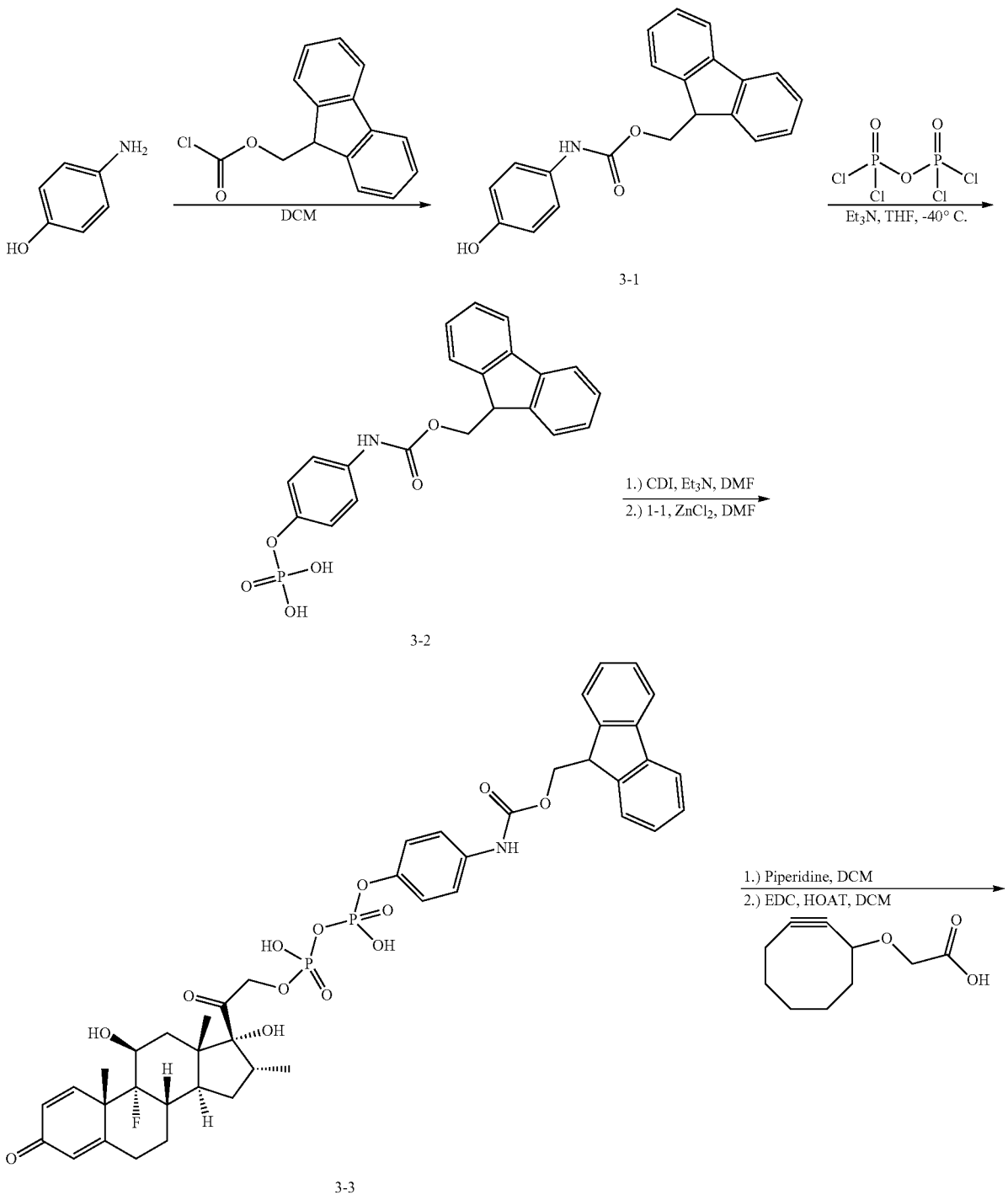

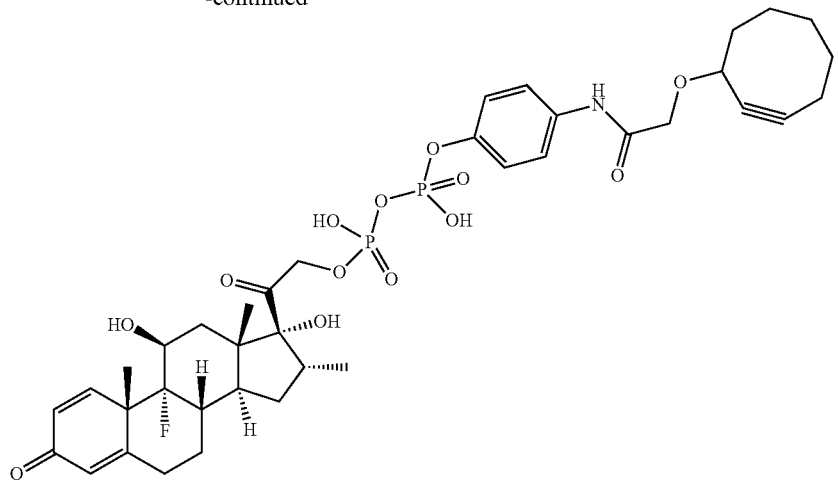

3-4

Step A: (9H-fluoren-9-yl)methyl (4-hydroxyphenyl) carbamate (3-1)

To a stirred solution of 4-aminophenol (0.30 g, 2.75 mmol) in DCM (9 mL) was added (9H-fluoren-9-yl)methyl carbonochloridate (0.71 g, 2.75 mmol) and the resulting mixture was stirred at room temperature for 2 hours. The mixture was partitioned between ethyl acetate and 1 N HCl solution. To the organic phase was added methanol until the solution cleared. The organic phase was dried over sodium sulfate and concentrated onto silica gel and flash column separation using a 100% ethyl acetate gave 3-1 as a solid (634 mg, 70%). LRMS (ES) (M+H)$^+$: observed=332.3, calculated=331.3

Step B: (9H-fluoren-9-yl)methyl (4-(phosphonooxy)phenyl)carbamate (3-2)

To a stirred solution of 3-1 (0.31 g, 0.95 mmol) in THF (1.9 mL) at −40° C. was added diphosphoryl chloride (0.31 mL, 2.24 mmol) and triethylamine (1.32 mL, 9.51 mmol) and the resulting mixture was stirred at −40° C. for 3 hr. The reaction was quenched with water, and treated with saturated sodium bicarbonate solution until pH ~8. The solution was made acidic using 1N HCl solution and extracted several times with ethyl acetate. The combined organic phase washed with brine, dried over sodium sulfate and concentrated to give 3-2 as a solid (342 mg, 87%). LRMS (ES) (M+H)$^+$: observed=412.3, calculated=411.3

Step C: (9H-fluoren-9-yl)methyl (4-(((((2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethoxy) (hydroxy) phosphoryl)oxy) (hydroxy)phosphoryl)oxy)phenyl) carbamate (3-3)

The title compound was prepared from 3-2 and 1-1 according to the protocol outlined in Example 1 to produce 1-3 to afford 3-3. LRMS (ES) (M+H)$^+$: observed=866.5, calculated=865.7

Step D: 4-(2-(cyclooct-2-yn-1-yloxy)acetamido) phenyl (2-((8S,9R,10S,11S,13S,14S,14S,6R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) dihydrogen pyrophosphate (3-4)

The title compound was prepared from 3-3 according to the protocol outlined in Example 1 to produce 1-4 to afford 3-4. LRMS (ES) (M+H)$^+$: observed=808.4, calculated=807.7

Example 4

The synthesis of dexamethasone linker 2-(2-(cyclooct-2-yn-1-yloxy)acetamido)ethyl (2-((8 S,9R,10S,11S,13 S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) hydrogen phosphate (4-3) was as follows.

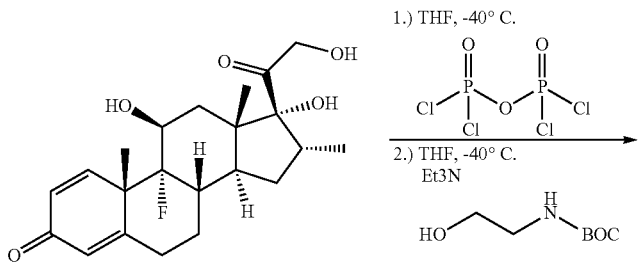

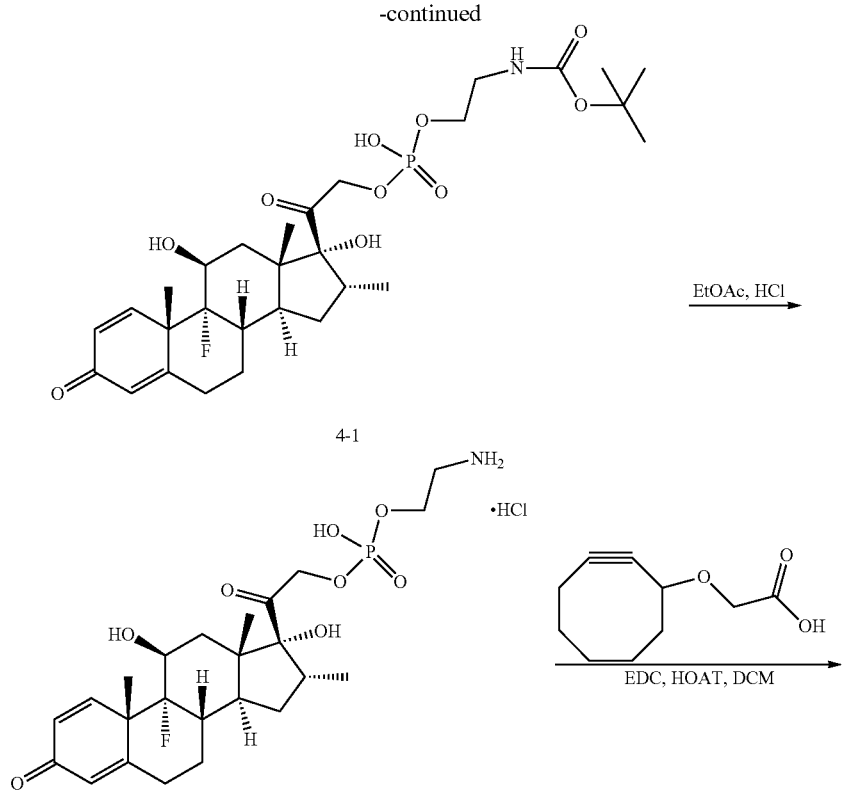

Step A: tert-butyl (2-(((2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethoxy) (hydroxy)phosphoryl)oxy)ethyl) carbamate (4-1)

To a stirred solution of dexamethasone (0.10 g, 0.26 mmol) in THF (0.5 mL) at −40° C. was added diphosphoryl chloride (0.12 g, 0.48 mmol) and the resulting mixture was stirred at −40° C. for 1 hr. To this was added tert-butyl N-(2-hydroxyethyl)carbamate (0.12 g, 0.76 mmol) and triethylamine (0.14 mL, 1.0 mmol). The resulting mixture was stirred at −40° C. for 4 hr. The reaction was quenched with water, and treated with saturated sodium bicarbonate solution until pH ~8. The solution was made acidic using 1N HCl solution and extracted several times with ethyl acetate. The combined organic phase was concentrated onto silica gel. Flash column separation using a 0-10% isopropanol/dichloromethane gradient gave 4-1 as a solid (115 mg, 73%). LRMS (ES) (M+H)+: observed=616.5, calculated=616.6.

Step B: 2-aminoethyl (2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) hydrogen phosphate, HCl (4-2)

To a stirred solution of 4-1 (0.11 g, 0.18 mmol) in ethyl acetate (1 mL) at 0° C. was bubbled in HCl gas until saturated. The resulting solution was stirred at 0° C. for 1 hr and concentrated to give 4-2 as a solid (99 mg, 100%). LRMS (ES) (M+H)+: observed=516.4, calculated=516.5.

Step C: 2-(2-(cyclooct-2-yn-1-yloxy)acetamido) ethyl (2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) hydrogen phosphate (4-3)

To a stirred solution of 2-(cyclooct-2-yn-1-yloxy)acetic acid (0.036 g, 0.20 mmol) in dichloromethane (1 mL) was added HOAT (0.027 g, 0.20 mmol), EDC (0.041 g, 0.22 mmol) and triethylamine (0.05 mL, 0.36 mmol). The resulting solution was stirred at room temperature for 40 minutes. This solution was added to 4-2 (0.10 g, 0.18 mmol) in DCM (1 mL). Additional 2-(cyclooct-2-yn-1-yloxy)acetic acid activated with HOAT/EDC was added as necessary to complete reaction. Upon completion, the mixture was concentrated and reverse phase preparative chromatography (Phenomenex Gemini-NX C18 OBD 5 uM 30×100 mm; 10-50% MeCN/water w/0.1% NH$_4$OH modifier over 20 min) gave 4-3 as a solid (45 mg, 37%). LRMS (ES) (M+H)$^+$: observed=680.6, calculated=680.7. $^1$H NMR (400 MHz, DMSO-d$_6$): δ 8.05 (br t, J=5.6 Hz, 1H), 7.30 (d, J=10.15 Hz, 1H), 6.21 (d, J=10.12 Hz, 1H), 6.00 (s, 1H), 5.55 (s, 1H), 5.37 (s, 1H), 4.70 (dd, J=17.2, 6.7 Hz, 1H), 4.29 (br t, J=6.4 Hz, 1H), 4.18-4.10 (complex, 2H), 3.87 (d, J=14.8 Hz, 1H), 3.74 (d, J=14.8 Hz, 1H), 3.69-3.64 (complex, 2H), 3.27-3.18 (complex, 2H), 2.91 (m, 1H), 2.61 (m, 1H), 2.39-2.05 (complex, 7H), 1.97-1.83 (complex, 2H), 1.80-1.69 (complex, 3H), 1.64-1.52 (complex, 3H), 1.48 (s, 3H), 1.47-1.30 (complex, 3H), 1.05 (m, 1H), 0.85 (s, 3H), 0.76 (d, J=7.13 Hz, 3H).

Example 5

The synthesis of dexamethasone linker 4-(2-(cyclooct-2-yn-1-yloxy)acetamido)phenyl (2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) hydrogen phosphate (5-3) was as follows.

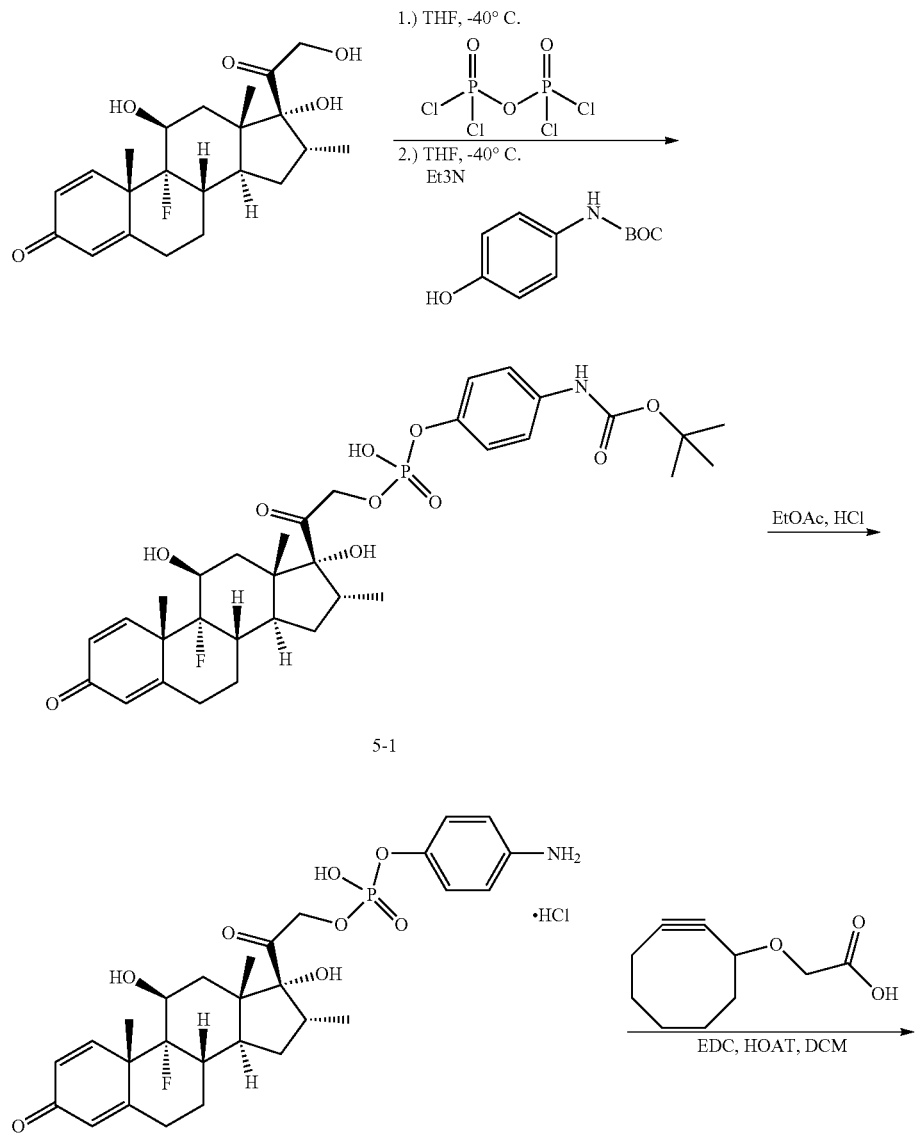

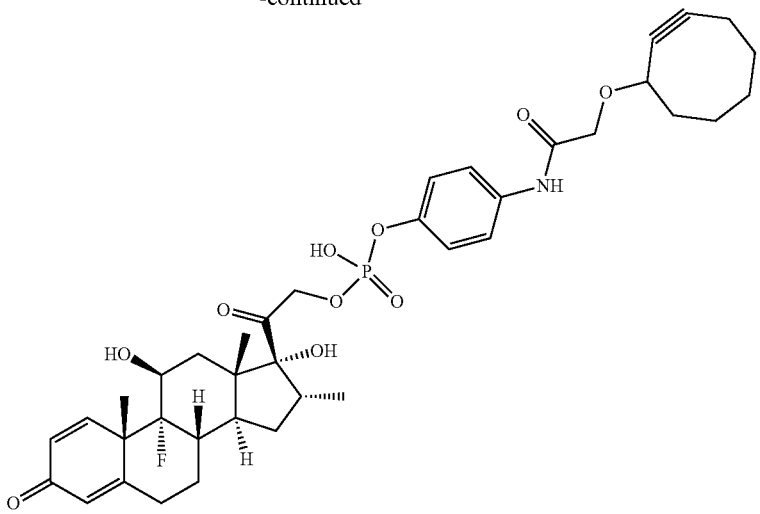

5-3

Step A: tert-butyl (4-(((2-((8S,9R,10S,11 S,13S, 14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethoxy) (hydroxy)phosphoryl)oxy)phenyl) carbamate (5-1)

To a stirred solution of dexamethasone (0.20 g, 0.51 mmol) in THF (1.0 mL) at −40° C. was added diphosphoryl chloride (0.24 g, 0.97 mmol) and the resulting mixture was stirred at −40° C. for 1 hr 15 min. To this was added N-BOC-4-aminophenol (0.32 g, 1.53 mmol) and triethylamine (0.56 mL, 4.0 mmol). The resulting mixture was stirred at −40° C. for 30 minutes. The reaction was quenched with water, and treated with saturated sodium bicarbonate solution until pH ~8. The solution was made acidic using 1N HCl solution and extracted several times with ethyl acetate. The combined organic phase was concentrated onto silica gel. Flash column separation using a 0-70% isopropanol/dichloromethane gradient gave 5-1 as a solid (370 mg, 88%). LRMS (ES) (M+H)⁺: observed=664.5, calculated=664.6.

Step B: 4-aminophenyl (2-((8S,9R,10S,11 S,13S, 14S,16R,17R)-9-fluoro-11,17-dihydroxy-10,13,16-trimethyl-3-oxo-6,7,8,9,10,11,12,13,14,15,16,17-dodecahydro-3H-cycl openta[a]phenanthren-17-yl)-2-oxoethyl) hydrogen phosphate, HCl (5-2)

The title compound was prepared from 5-1 according to the protocol outlined in Example 4 to produce 4-2 to afford 2-2. LRMS (ES) (M+H)⁺: observed=564.4, calculated=564.5

Step C: 4-(2-(cyclooct-2-yn-1-yloxy)acetamido) phenyl (2-((8S,9R,10S,11S,13S,14S,16R,17R)-9-fluoro-11,17-dihydroxy-10,13,16-trimethyl-3-oxo-6, 7,8,9,10,11,12,13,14,15,16,17-dodecahydro-3H-cyclopenta[a]phenanthren-17-yl)-2-oxoethyl) hydrogen phosphate (5-3)

The title compound was prepared from 5-2 according to the protocol outlined in Example 4 to produce 4-3 to afford 5-3. LRMS (ES) (M+H)⁺: observed=728.6, calculated=728.7 ¹H NMR (400 MHz, DMSO-d₆): δ 9.53 (s, 1H), 7.43 (d, J=8.54 Hz, 2H), 7.30 (d, J=10.14 Hz, 1H), 7.04 (d, J=8.54 Hz, 2H), 6.22 (dd, J=10.08, 1.92 Hz, 1H), 6.00 (s, 1H), 5.41 (s, 1H), 5.37 (d, J=4.22 Hz, 1H), 4.78 (dd, J=17.50, 6.20 Hz, 1H), 4.37 (t, J=5.59 Hz, 1H), 4.27 (dd, J=17.47, 9.02, 1H), 4.15-4.12 (m, 1H), 4.06 (d, J=14.53 Hz, 1H), 3.94 (d, J=14.59 Hz, 1H), 3.05 (q, J=7.26 Hz, 1H), 2.92 (m, 1H), 2.61 (m, 1H), 2.40-2.06 (complex, 7H), 1.98 (m, 1H), 1.87 (m, 1H), 1.82-1.73 (complex, 3H), 1.67-1.52 (complex, 3H), 1.48 (s, 3H), 1.43 (d, J=13.54 Hz, 2H), 1.35 (m, 1H), 1.05 (m, 1H), 0.84 (s, 3H), 0.76 (d, J=7.14 Hz, 3H).

Example 6

The synthesis of dexamethasone linker 2-((8 S,9R,10S,11 S,13 S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl hydrogen (2-(2-(cyclooct-2-yn-1-yloxy)acetamido)ethyl) phosphoramidate (6-2) was as follows.

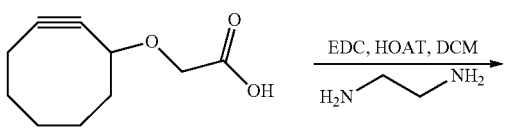

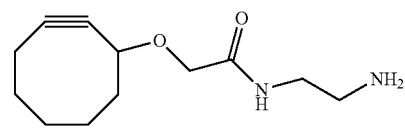

6-1

-continued

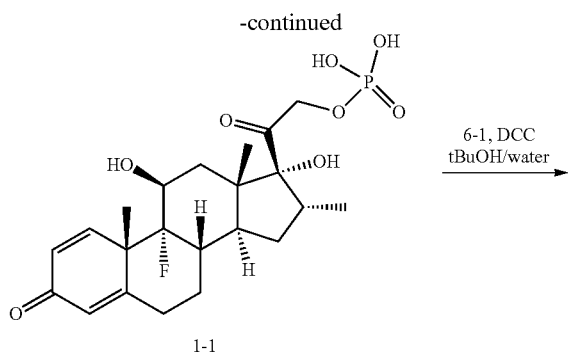

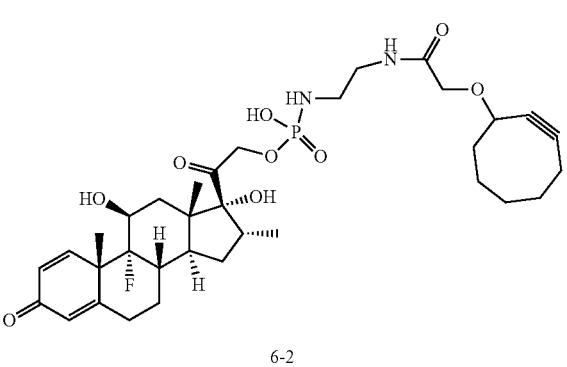

Step A: N-(2-aminoethyl)-2-(cyclooct-2-yn-1-yloxy) acetamide (6-1)

To a stirred solution of 2-(cyclooct-2-yn-1-yloxy)acetic acid (0.10 g, 0.55 mmol) in dichloromethane (2 mL) was added HOAT (0.075 g, 0.55 mmol) and EDC (0.126 g, 0.66 mmol). The resulting solution was stirred at room temperature for 20 minutes. This solution was added to 1,2-ethylenediamine (0.49 g, 8.23 mmol) in DCM (1 mL) dropwise. The mixture was concentrated and purified. (Phenomenex Gemini NX C18, 5 um particle size, 21.2 mm i.d. by 5 cm length, 10-50% CH3CN/water w/0.1% NH4OH modifier over 10 min at 40 mL/min) (50 mg, 40%).

Step B: 2-((8S,9R,10S,11 S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl hydrogen (2-(2-(cyclooct-2-yn-1-yloxy)acetamido) ethyl)phosphoramidate (6-2)

To a stirred solution of 6-1 (0.05 g, 0.22 mmol) and 1-1 (0.035 g, 0.074 mmol) in a solution of t-butanol (1.2 mL) and water (0.25 mL) was added DCC (0.06 g, 0.30 mmol) and the resulting mixture was heated to 100 C for 4 hr. The reaction mixture was allowed to cool and concentrated. The residue was dissolved in a 1:1:1 MeOH:water:MeCN solution and syringe filtered. The mixture was purified using reverse phase preparative chromatography (Phenomenex Gemini-NX C18 OBD 5 uM 30×100 mm; 5-45% MeCN/water w/0.1% NH$_4$OH modifier over 20 min) to give 6-2 as a solid (15 mg, 30%). LRMS (ES) (M+H)$^+$: observed=679.5, calculated=678.7.

Example 7

The synthesis of dexamethasone linker 2-(3-(2,5-dioxo-2,5-dihydro-1H-pyrrol-1-yl)propanamido)ethyl (2-((8 S,9R,10S,11S,13 S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) dihydrogen pyrophosphate (7-1) was as follows.

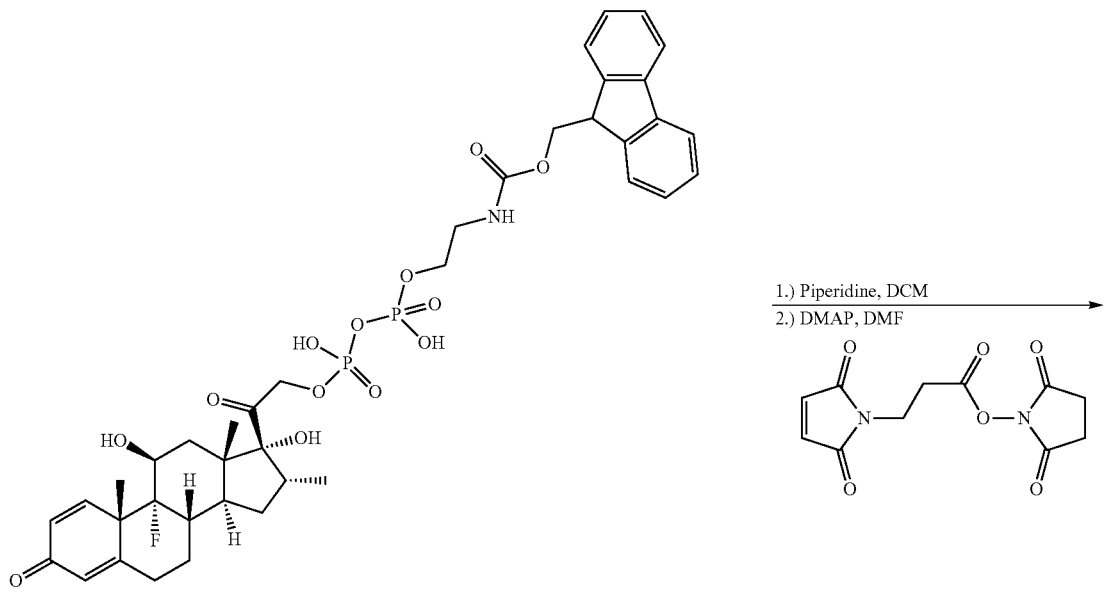

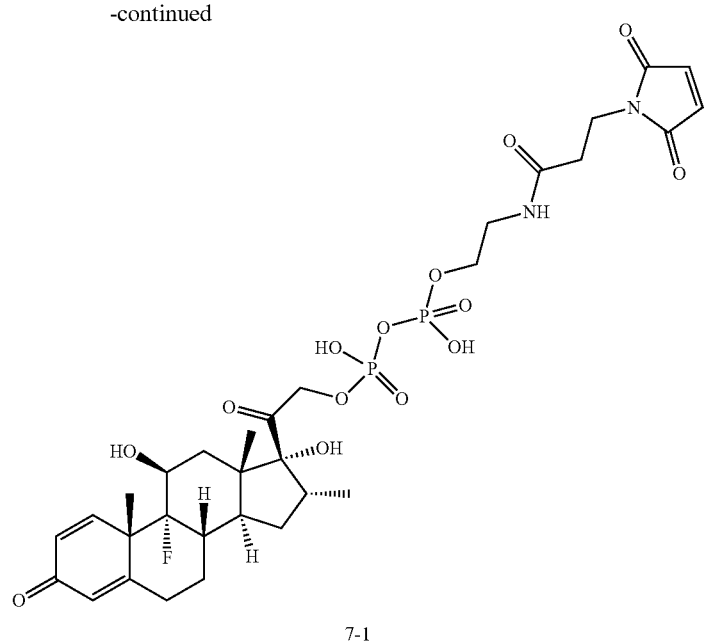

7-1

To a stirred solution of 1-3 (0.19 g, 0.23 mmol) in DCM (3 mL) was added piperidine (0.15 mL, 1.51 mmol) and the resulting mixture was stirred at room temperature for 3 hrs. The solution was concentrated to dryness. The crude mixture was taken into a 2:1:1 methanol:acetonitrile:water mixture and filtered. The filtrate was purified using reverse phase preparative chromatography (Phenomenex Gemini-NX C18 OBD 5 uM 30×100 mm; 5-35% MeCN/water w/0.1% NH$_4$OH modifier over 20 min). A portion of the resulting purified amine (0.07 g, 0.11 mmol) was dissolved in DMF (0.8 mL). To this solution was added 2,5-dioxopyrrolidin-1-yl 3-(2,5-dioxo-2,5-dihydro-1H-pyrrol-1-yl)propanoate (0.09 mg, 0.34 mmol) and DMAP (0.014 g, 0.11 mmol) and the resulting solution was stirred 20 minutes. The crude reaction mixture was directly purified using reverse phase preparative chromatography (Sunfire Prep C18 OBD 5 um 30×150 mm; 10-35% CH3CN/water w/0.1% TFA modifier over 20 min) gave 7-1 as a solid (13 mg, 15%). LRMS (ES) (M+H)$^+$: observed=747.2, calculated=746.6.

Example 8

The synthesis of dexamethasone linker ((2R,3S,4R,5R)-5-(2,4-dioxo-3,4-dihydropyrimidin-1(2H)-yl)-3-(((2-((8 S,9R,10S,11 S,13 S,14 S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethoxy)(hydroxy)phosphoryl)oxy)-4-hydroxytetrahydrofuran-2-yl)methyl (2-(2-(cyclooct-2-yn-1-yloxy)acetamido)ethyl)carbamate (8-5) was as follows.

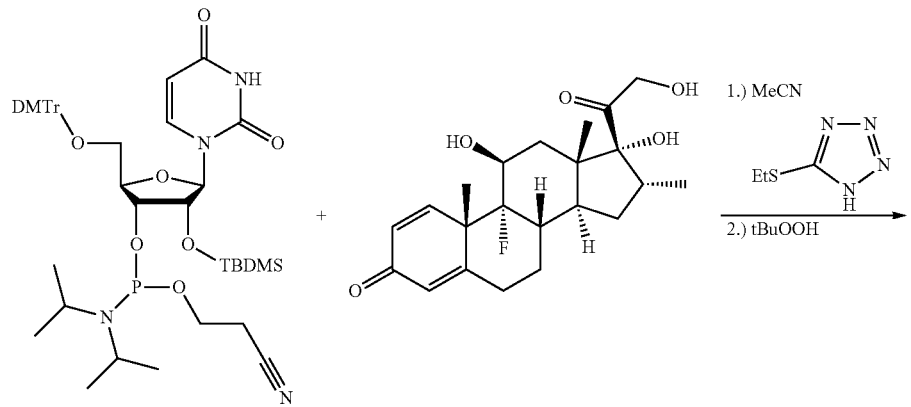

-continued
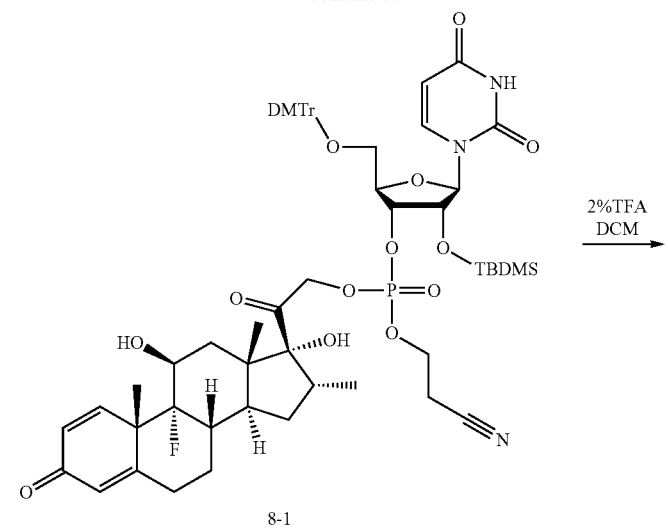
8-1
2%TFA
DCM
→
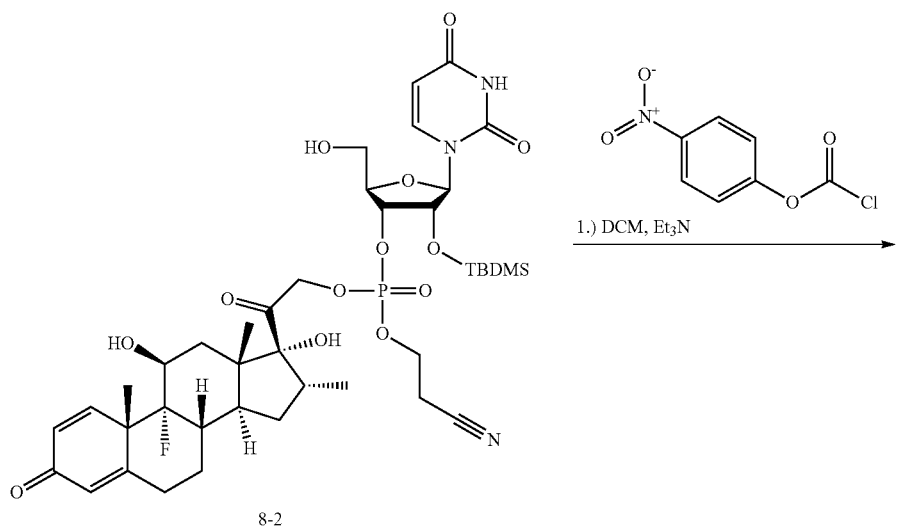
8-2
1.) DCM, Et₃N
→
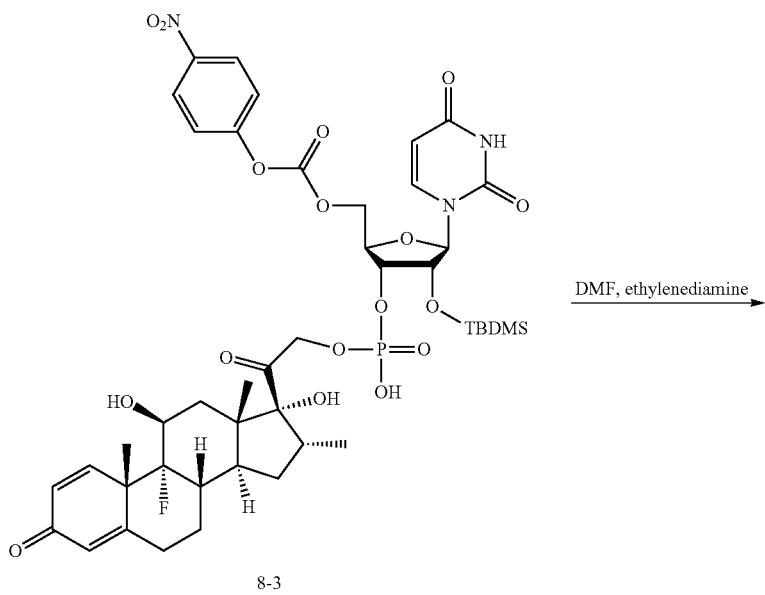
8-3
DMF, ethylenediamine
→

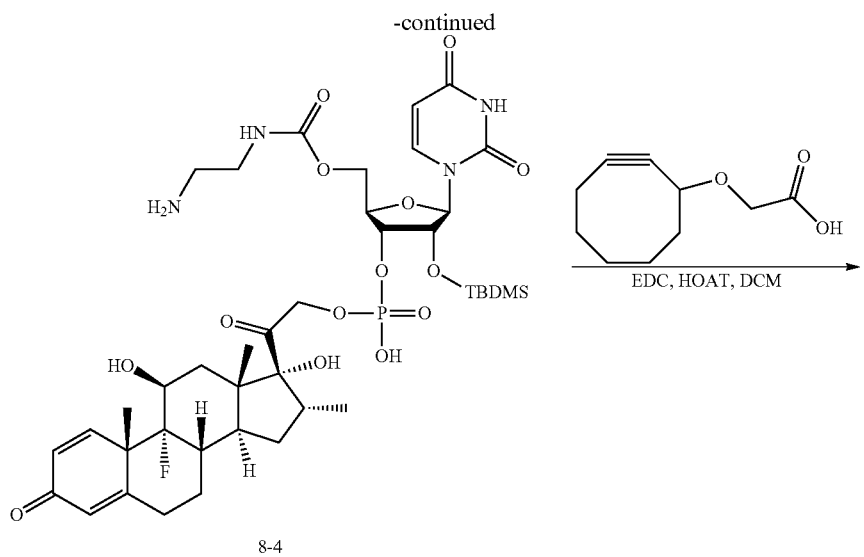

8-4

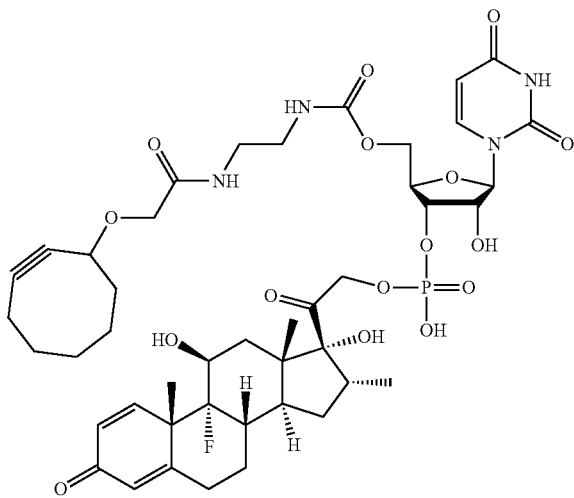

8-5

Step A: (2R,3R,4R,5R)-2-((bis(4-methoxyphenyl)(phenyl)methoxy)methyl)-4-((tert-butyldimethylsilyl)oxy)-5-(2,4-dioxo-3,4-dihydropyrimidin-(2H)-yl)tetrahydrofuran-3-yl (2-cyanoethyl) (2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) phosphite (8-1)

To a stirred mixture of (2R,3R,4R,5R)-2-((bis(4-methoxyphenyl)(phenyl)methoxy)methyl)-4-((tert-butyldimethylsilyl)oxy)-5-(2,4-dioxo-3,4-dihydropyrimidin-1 (2H)-yl)tetrahydrofuran-3-yl (2-cyanoethyl) diisopropylphosphoramidite (1.20 g, 1.40 mmol) and dexamethasone (0.50 g, 1.27 mmol) in acetonitrile (12 mL) was added 5-(ethylthio)-1H-tetrazole (0.33 g, 2.55 mmol). The resulting mixture was stirred for 20 minutes. To the homogenous solution that resulted was added 5M tert-butyl hydroperoxide (0.51 mL, 2.55 mmol). The reaction was stirred 1 hr at room temperature and concentrated onto silica gel. Flash column separation using a 0-100% ethyl acetate/hexane gradient gave 8-1 as a solid (1.67 g, 100%) LRMS (ES) (M+H)$^+$: observed=1168.3, calculated=1168.3.

Step B: (2R,3R,4R,5R)-4-((tert-butyldimethylsilyl)oxy)-5-(2,4-dioxo-3,4-dihydropyrimidin-1 (2H)-yl)-2-(hydroxymethyl)tetrahydrofuran-3-yl (2-cyanoethyl) (2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) phosphate (8-2)

To a stirred solution of 8-1 (1.48 g, 1.26 mmol) in DCM (30 mL) was added TFA (0.3 mL, 3.89 mmol) at room temperature. The reaction was stirred for 30 minutes, washed with saturated bicarbonate solution and the organic phase was concentrated onto silica gel. Flash column separation using a 0-10% isopropanol/DCM gradient gave 8-2 as a solid (0.79 g, 72%) LRMS (ES) (M+H)$^+$: observed=866.5, calculated=865.9.

Step C: ((2R,3R,4R,5R)-4-((tert-butyldimethylsilyl) oxy)-5-(2,4-dioxo-3,4-dihydropyrimidin-1 (2H)-yl)-3-(((2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethoxy) (hydroxy)phosphoryl)oxy)tetrahydrofuran-2-yl) methyl (4-nitrophenyl) carbonate (8-3)

To a stirred solution of 8-2 (0.30 g, 0.35 mmol) in DCM (5 mL) was added triethylamine (0.15 mL, 1.04 mmol) and 4-nitrophenyl carbonochloridate (0.15 g, 0.76 mmol) and the resulting solution was stirred at room temperature. Additional 4-nitrophenyl carbonochloridate was added until reaction was complete by LCMS. The reaction was directly loaded onto a silica gel column and flash column separation using a 0-50% isopropanol/DCM gradient gave 8-3 as a solid (0.32 g, 93%) LRMS (ES) (M+H)$^+$: observed=978.4, calculated=977.9.

Step D: ((2R,3R,4R,5R)-4-((tert-butyldimethylsilyl) oxy)-5-(2,4-dioxo-3,4-dihydropyrimidin-1 (2H)-yl)-3-(((2-((8S,9R,10S,1 S,3S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethoxy) (hydroxy)phosphoryl)oxy)tetrahydrofuran-2-yl) methyl (2-aminoethyl)carbamate (8-4)

To a stirred solution of ethylenediamine (0.28 mL, 4.17 mmol) in DMF (1 mL) was added a solution of 8-3 (0.20 g, 0.20 mmol) in DMF (1 mL) dropwise. The reaction was stirred at room temperature for 10 minutes, then purified directly using reverse phase preparative chromatography (Phenomenex Gemini-NX C18 OBD 5 uM 30×100 mm; 10-50% MeCN/water w/0.1% NH$_4$OH modifier over 20 min) to give 8-4 as a solid (115 mg, 61%). LRMS (ES) (M+H)$^+$: observed=899.5, calculated=898.9.

Step E: ((2R,3S,4R,5R)-5-(2,4-dioxo-3,4-dihydro-pyrimidin-1(2H)-yl)-3-(((2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethoxy)(hydroxy)phosphoryl)oxy)-4-hydroxytetrahydrofuran-2-yl)methyl (2-(2-(cyclooct-2-yn-1-yloxy)acetamido)ethyl)carbamate (8-5)

The title compound was prepared from 8-4 according to the protocol outlined in Example 4 to produce 4-3 to afford 8-5. LRMS (ES) (M+H)$^+$: observed=949.4, calculated=948.9

Example 9

The synthesis of Budesonide linker 2-(2-(cyclooct-2-yn-1-yloxy)acetamido)ethyl (2-((6aR,6bS,7S,8aS,8bS,11aR,12aS,12bS)-7-hydroxy-6a,8a-dimethyl-4-oxo-10-propyl-2,4,6a,6b,7,8,8a,8b,11a,12,12a,12b-dodecahydro-1H-naphtho[2',1':4,5]indeno[1,2-d][1,3]dioxol-8b-yl)-2-oxo-ethyl) dihydrogen pyrophosphate (9-4) was as follows.

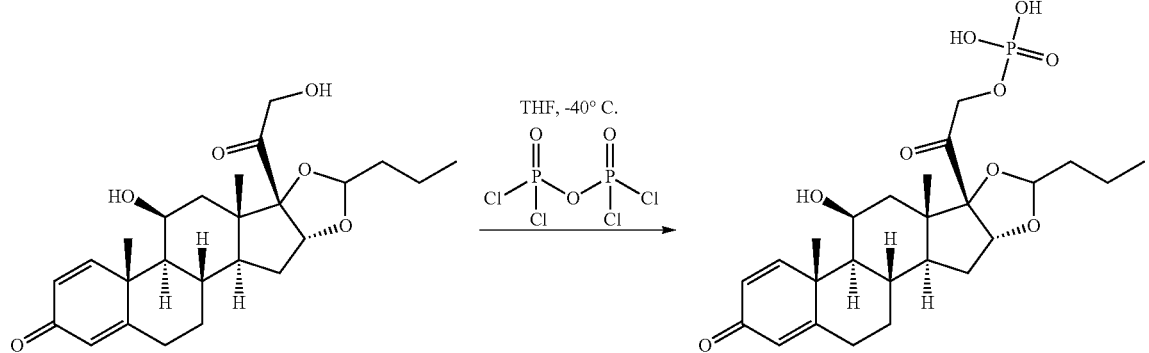

9-1

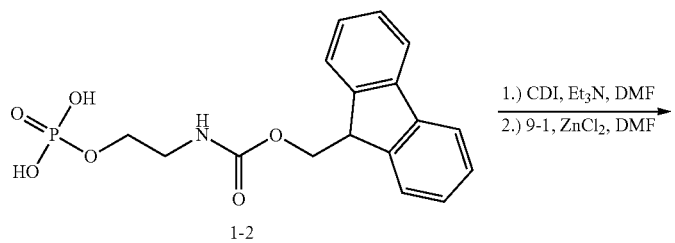

1-2

-continued
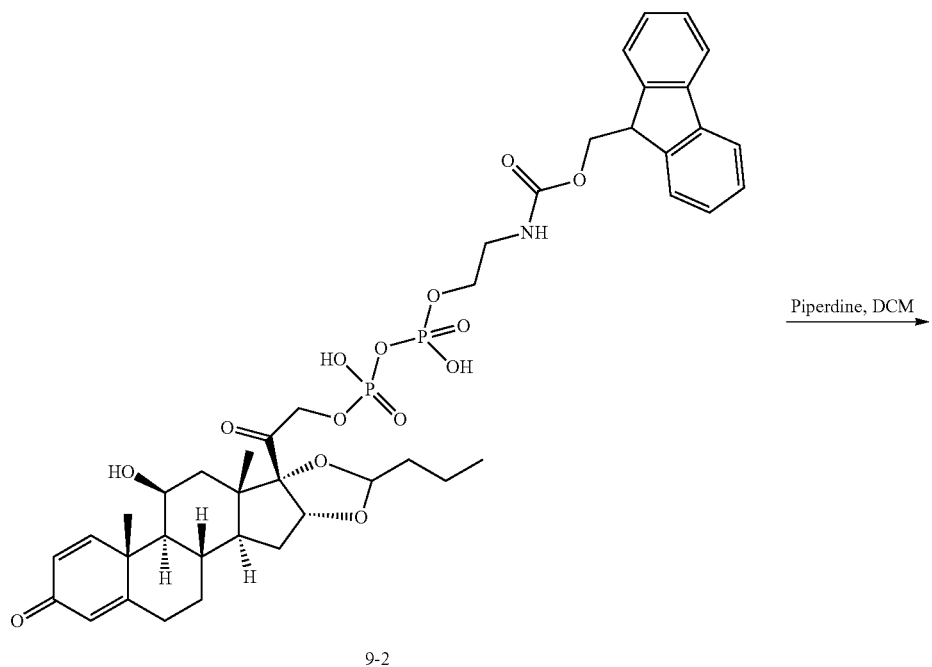
9-2
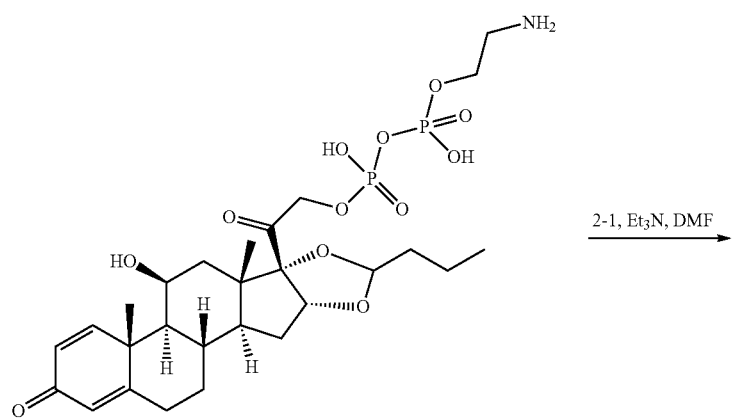
9-3

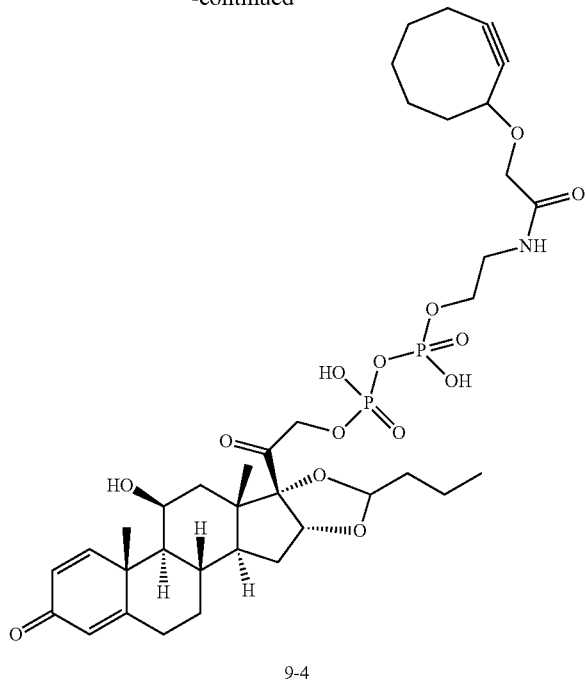

9-4

Step A: 2-((6aR,6bS,7S,8aS,8bS,11aR,12aS,12bS)-7-hydroxy-6a,8a-dimethyl-4-oxo-10-propyl-2,4,6a,6b,7,8,8a,8b,11a,12,12a,12b-dodecahydro-1H-naphtho[2',1':4,5]indeno[1,2-d][1,3]dioxol-8b-yl)-2-oxoethyl dihydrogen phosphate (9-1)

The title compound was prepared from budesonide according to the protocol outlined in Example 1 to produce 1-1 to afford 9-1. LRMS (ES) (M+H)$^+$: observed=511.2, calculated=510.5

Step B: (9H-fluoren-9-yl)methyl (2-((hydroxy((hydroxy(2-((6aR,6bS,7S,8aS,8bS,11aR,12aS,12bS)-7-hydroxy-6a,8a-dimethyl-4-oxo-10-propyl-2,4,6a,6b,7,8,8a,8b,11a,12,12a,12b-dodecahydro-1H-naphtho[2',1':4,5]indeno[1,2-d][1,3]dioxol-8b-yl)-2-oxoethoxy)phosphoryl)oxy)phosphoryl)oxy)ethyl)carbamate (9-2)

The title compound was prepared from 9-1 according to the protocol outlined in Example 1 to produce 1-3 to afford 9-2. LRMS (ES) (M+H)$^+$: observed=856.3, calculated=855.8

Step C: 2-aminoethyl (2-((6aR,6bS,7S,8aS,8bS,11aR,12aS,12bS)-7-hydroxy-6a,8a-dimethyl-4-oxo-10-propyl-2,4,6a,6b,7,8,8a,8b,11a,12,12a,12b-dodecahydro-1H-naphtho[2',1': 4,5]indeno[1,2-d][1,3]dioxol-8b-yl)-2-oxoethyl) dihydrogen pyrophosphate (9-3)

The title compound was prepared from 9-2 according to the protocol outlined in Example 2 to produce 2-6 to afford 9-3. LRMS (ES) (M+H)$^+$: observed=634.3, calculated=633.5

Step D: 2-(2-(cyclooct-2-yn-1-yloxy)acetamido)ethyl (2-((6aR,6bS,7S,8aS,8bS,11aR,12aS,12bS)-7-hydroxy-6a,8a-dimethyl-4-oxo-10-propyl-2,4,6a,6b,7, 8,8a,8b,11a,12,12a,12b-dodecahydro-1H-naphtho[2',1':4,5]indeno[1,2-d][1,3]dioxol-8b-yl)-2-oxoethyl) dihydrogen pyrophosphate (9-4)

The title compound was prepared from 9-3 according to the protocol outlined in Example 2-7 to afford 9-4. Mixture of isomers $^1$H NMR (499 MHz, DMSO): 0.86-0.83 (complex, 6 H); 0.89 (s, 6H); 0.99-0.90 (complex, 2H); 1.09 (t, J=7.0 Hz, 2H); 1.15 (t, J=7.2 Hz, 6H); 1.35-1.25 (complex, 6H); 1.39 (s, 6H); 2.32-1.46 (complex, 32H); 3.02 (q, J=7.0 Hz, 4H); 3.21 (br s, 2H); 3.81-3.73 (complex, 6H); 3.94-3.89 (complex, 2H); 4.33-4.25 (complex, 4H); 4.39 (d, J=18.4 Hz, 2H); 4.56 (t, J=4.3 Hz, 1H); 4.79-4.63 (complex, 3H); 5.01 (d, J=7.2 Hz, 1H); 5.17 (dd, J=4.9, 4.6 Hz, 1H); 5.91 (s, 2H); 6.15 (d, J=10.1 Hz, 2H); 7.31 (d, J=10.3 Hz, 2H); 8.84 (br s, 2H). LRMS (ES) (M+H)$^+$: observed=798.4, calculated=797.7

Example 10

The synthesis of Budesonide linker 2-(3-(2,5-dioxo-2,5-dihydro-1H-pyrrol-1-yl)propanamido)ethyl (2-((6aR,6bS,7S,8aS,8bS,11 aR,12aS,12bS)-7-hydroxy-6a,8a-dimethyl-4-oxo-10-propyl-2,4,6a,6b,7,8,8a,8b,11a,12,12a,12b-dodecahydro-1H-naphtho[2',1':4,5]indeno[1,2-d][1,3]dioxol-8b-yl)-2-oxoethyl) dihydrogen pyrophosphate (10-1) was as follows.

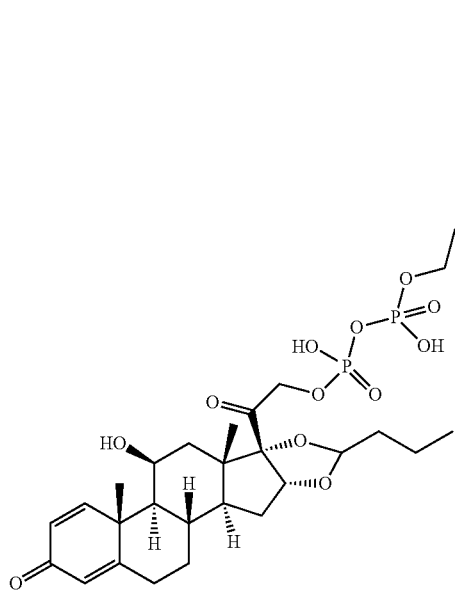

9-2

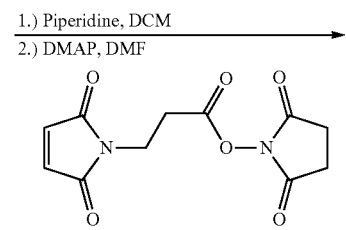

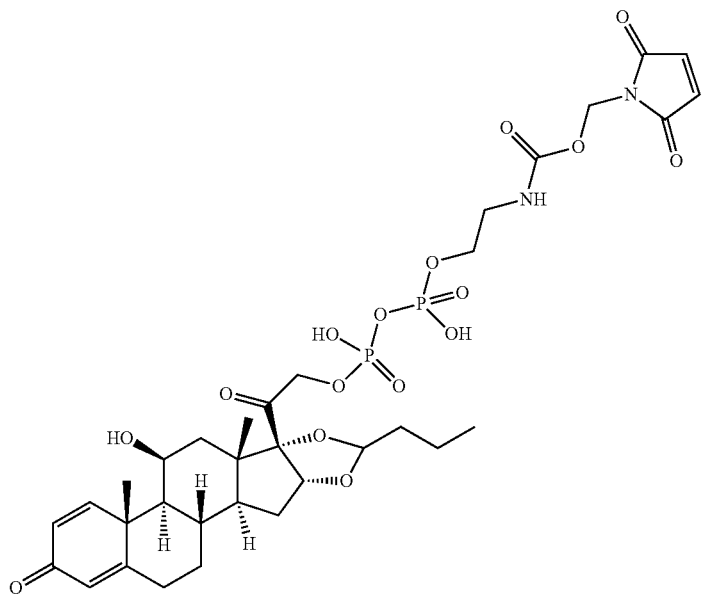

10-1

The title compound was prepared from 9-2 according to the protocol outlined in Example 7 to produce 7-1 to afford 10-1. LRMS (ES) (M+H)$^+$: observed=785.4, calculated=784.6

Example 11

The synthesis of Budesonide linker 1-(cyclooct-2-yn-1-yloxy)-2-oxo-6,9,12-trioxa-3-azatetradecan-14-yl (2-((6aR,6bS,7S,8aS,8bS,11aR,12aS,12bS)-7-hydroxy-6a,8a-dimethyl-4-oxo-10-propyl-2,4,6a,6b,7,8,8a,8b,11a,12,12a,12b-dodecahydro-1H-naphtho[2',1':4,5]indeno[1,2-d][1,3]dioxol-8b-yl)-2-oxoethyl) dihydrogen pyrophosphate (11-5) was as follows.

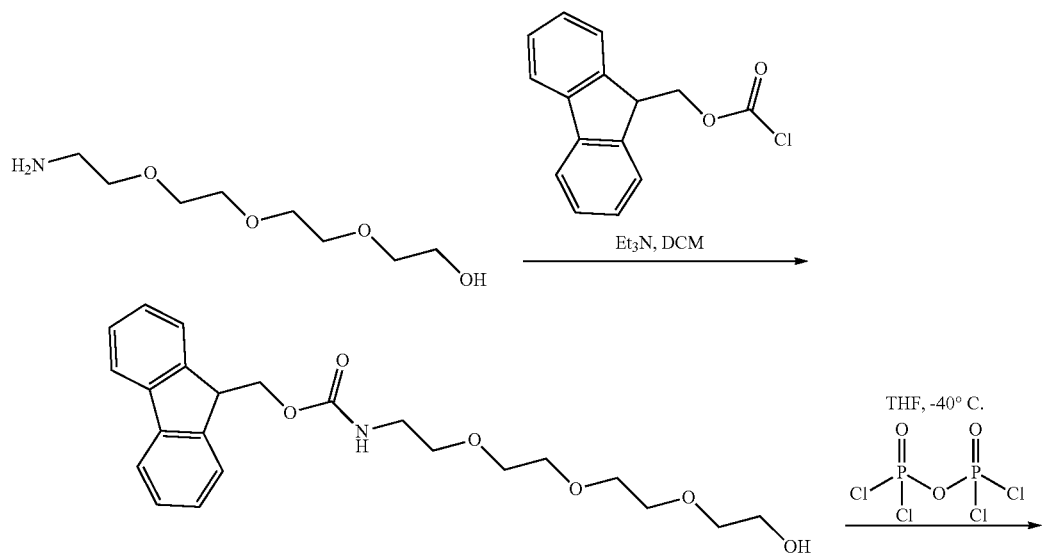
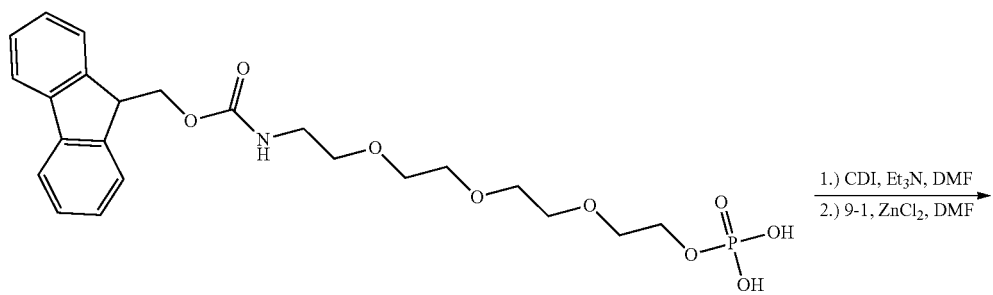
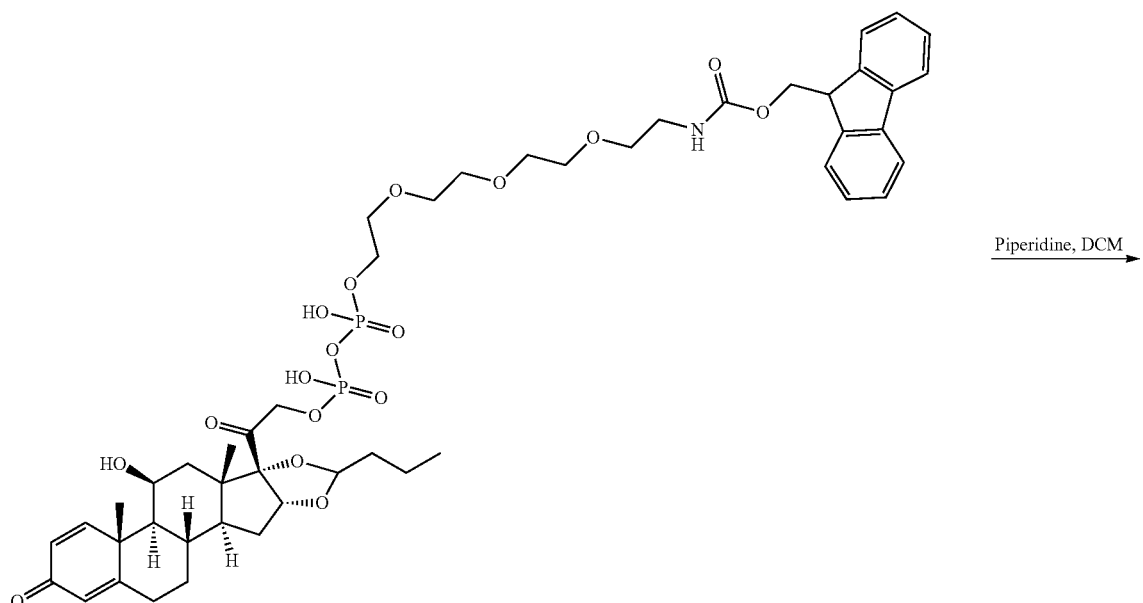

-continued
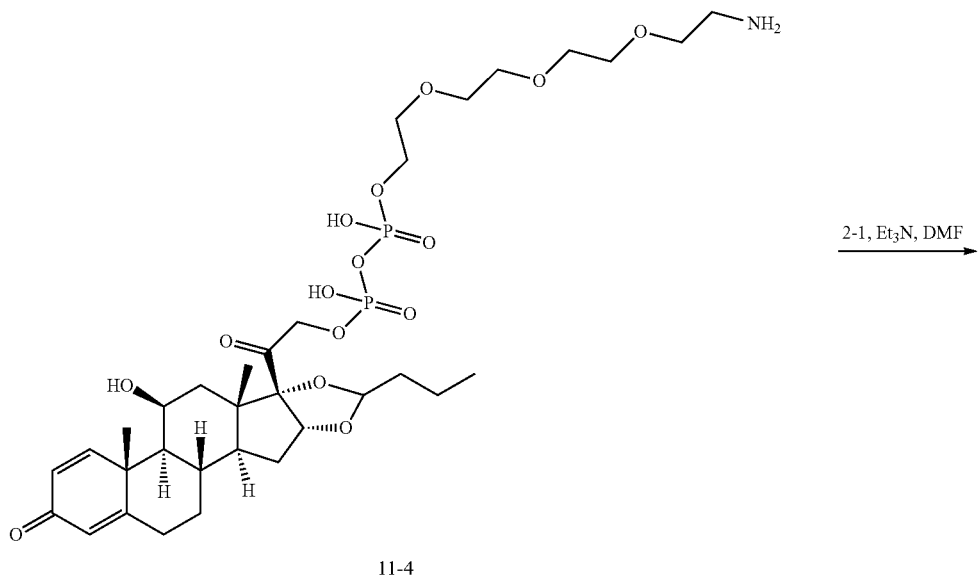
11-4
2-1, Et₃N, DMF
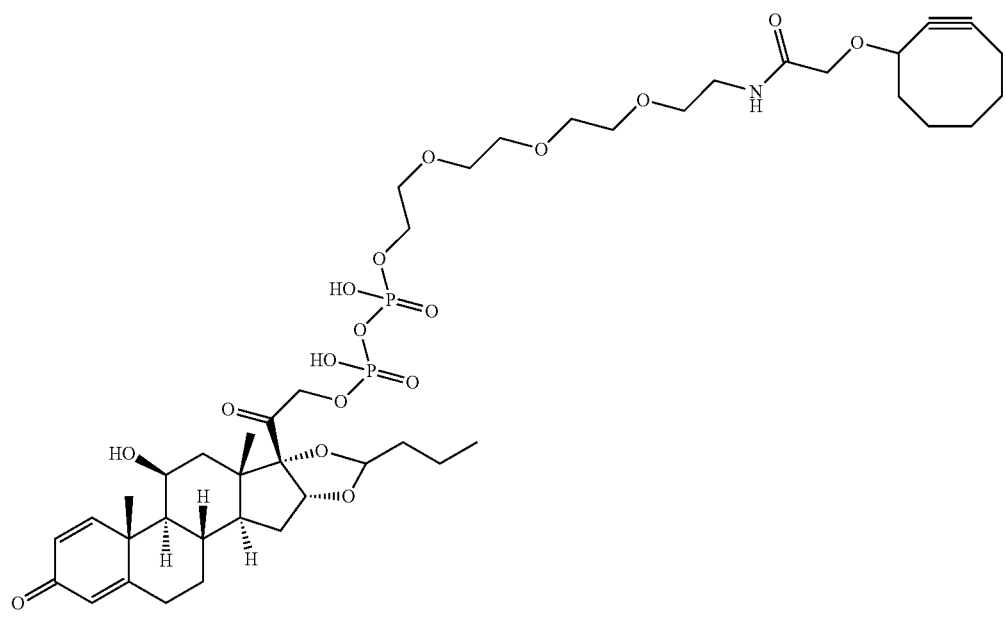
11-5

Step A: (9H-fluoren-9-yl)methyl (2-(2-(2-(2-hydroxyethoxy)ethoxy)ethoxy)ethyl)carbamate (11-1)

To a stirred solution of 2-(2-(2-(2-aminoethoxy)ethoxy)ethoxy)ethanol (1.00 g, 5.17 mmol) in DCM (15 mL) was added 9-fluorenylmethyl chloroformate (1.34 g, 5.17 mmol) and triethylamine (1.08 mL, 7.76 mmol). The resulting solution was stirred at room temperature for 10 minutes. The reaction was concentrated onto silica gel and flash column separation using a 0-10% isopropanol/dichloromethane gradient gave 11-1 as an oil (1.43 g, 66%) LRMS (ES) (M+H)+: observed=416.1, calculated=415.4.

Step B: (9H-fluoren-9-yl)methyl (2-(2-(2-(2-(phosphonooxy)ethoxy)ethoxy)ethoxy)ethyl)carbamate (11-2)

The title compound was prepared from 11-1 according to the protocol outlined in Example 1 to produce 1-1 to afford 11-2. LRMS (ES) (M+H)+: observed=496.3, calculated=495.4

Step C: (9H-fluoren-9-yl)methyl (2-(2-(2-(2-((hydroxy((hydroxy(2-((6aR,6bS,7S,8aS,8bS,1 aR,12aS,12bS)-7-hydroxy-6a,8a-dimethyl-4-oxo-10-propyl-2,4,6a,6b,7, 8,8a,8b,11a,12,12a,12b-dodecahydro-1H-naphtho[2',1':4,5]indeno[1,2-d][1,3]dioxol-8b-yl)-2-oxoethoxy)phosphoryl)oxy)phosphoryl)oxy)ethoxy)ethoxy)ethoxy)ethyl)carbamate (11-3)

The title compound was prepared from 11-2 and 9-1 according to the protocol outlined in Example 1 to produce 1-3 to afford 11-3. LRMS (ES) (M+H)+: observed=988.6, calculated=987.9

Step D: 2-(2-(2-(2-aminoethoxy)ethoxy)ethoxy)ethyl (2-(((6aR,6bS,7S,8aS,8bS,11aR,12aS,12bS)-7-hydroxy-6a,8a-dimethyl-4-oxo-10-propyl-2,4,6a,6b,7,8,8a,8b,11a,12,12a,12b-dodecahydro-1H-naphtho[2',1':4,5]indeno[1,2-di][1,3]dioxol-8b-yl)-2-oxoethyl) dihydrogen pyrophosphate (11-4)

The title compound was prepared from 11-3 according to the protocol outlined in Example 2 to produce 2-6 to afford 11-4. LRMS (ES) (M+H)+: observed=766.5, calculated=765.7

Step E: 1-(cyclooct-2-yn-1-yloxy)-2-oxo-6,9,12-trioxa-3-azatetradecan-14-yl (2-((6aR,6bS,7S,8aS,8bS,11aR,12aS,12bS)-7-hydroxy-6a,8a-dimethyl-4-oxo-10-propyl-2,4,6a,6b,7,8,8a,8b,11a,12,12a,12b-dodecahydro-H-naphtho[2',1':4,5]indeno[1,2-d][1,3]dioxol-8b-yl)-2-oxoethyl) dihydrogen pyrophosphate (11-5)

The title compound was prepared from 11-4 according to the protocol outlined in Example 2 to produce 2-7 to afford 11-5. LRMS (ES) (M+H)+: observed=930.6, calculated=929.9

Example 12

The synthesis of Budesonide linker 4-((2S)-2-((2S)-2-(2-(cyclooct-2-yn-1-yloxy)acetamido)-3-methylbutanamido)-5-ureidopentanamido)benzyl (2-((6aR,6b S,7S,8aS,8b S,11aR,12aS,12b S)-7-hydroxy-6a,8a-dimethyl-4-oxo-10-propyl-2,4,6a,6b,7,8,8a,8b,11a,12,12a,12b-dodecahydro-1H-naphtho[2',1':4,5]indeno[1,2-d][1,3]dioxol-8b-yl)-2-oxoethyl) hydrogen phosphate (12-3) was as follows.

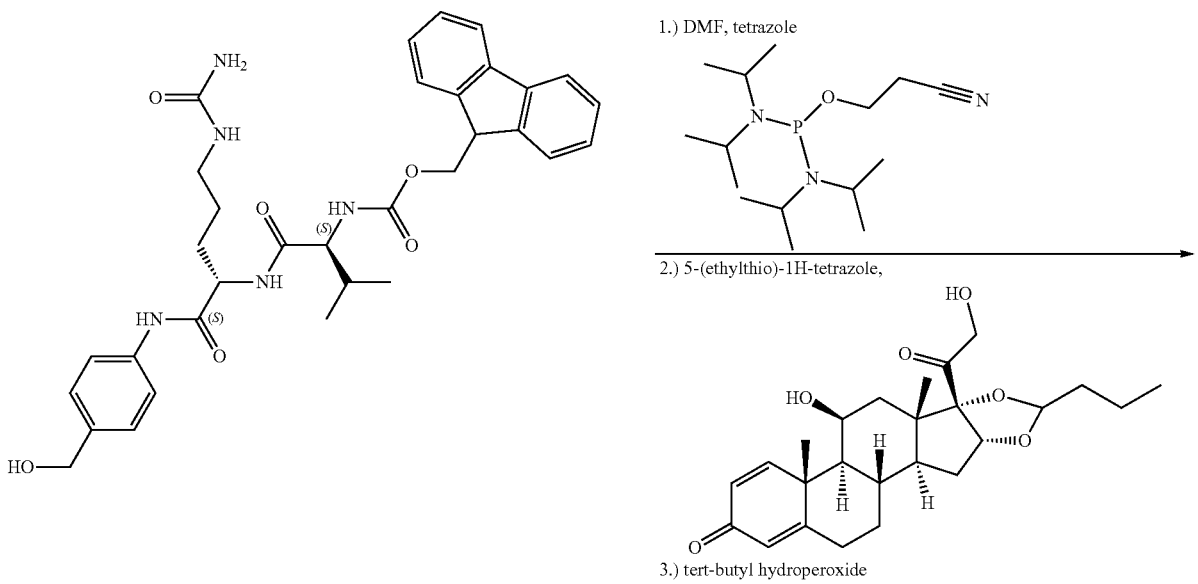

-continued
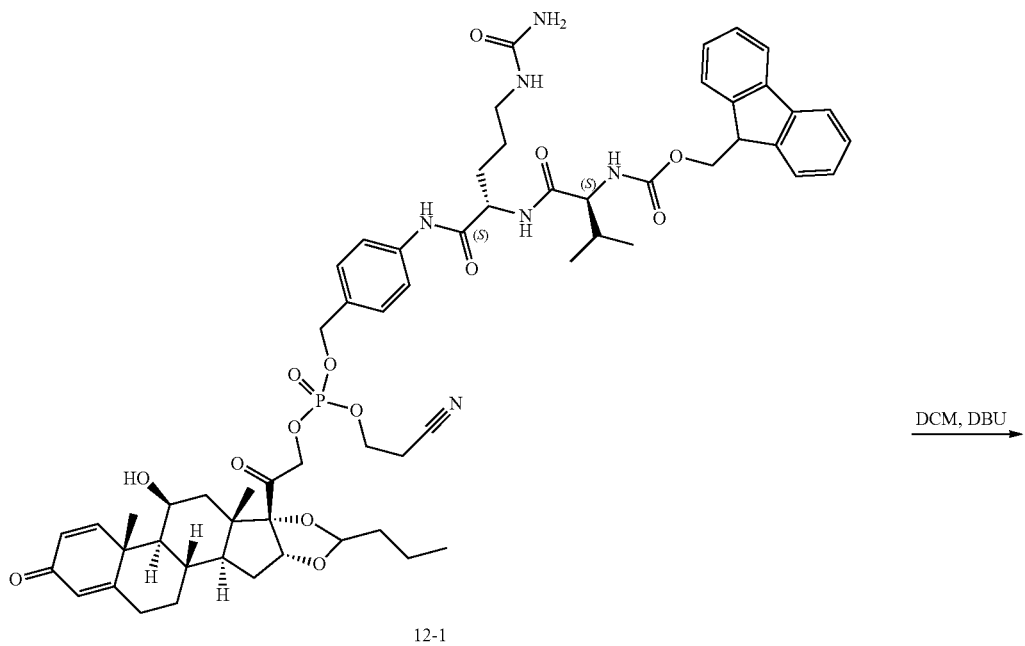
12-1
→ DCM, DBU
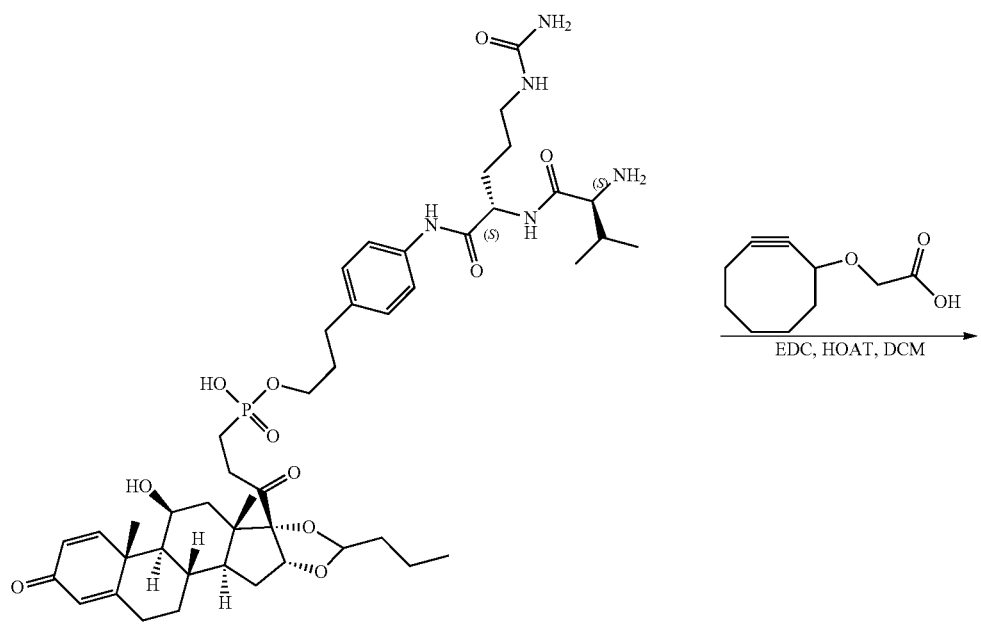
12-2
→ EDC, HOAT, DCM

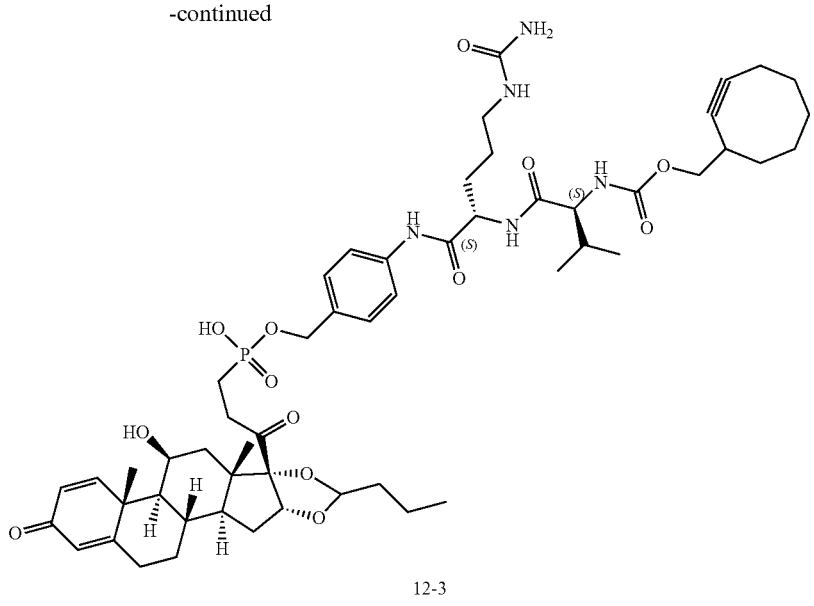

12-3

Step A: (9H-fluoren-9-yl)methyl ((2S)-1-(((2S)-1-((4-(((((2-cyanoethoxy) (2 (((6aR,6bS,7S,8aS,8bS,11aR,12aS,12bS)-7-hydroxy-6a,8a-dimethyl-4-oxo-10-propyl-2,4,6a,6b,7,8,8a,8b,11a,12,12a,12b-dodecahydro-1H-naphtho[2',1': 4,5]indeno[1,2-d][1,3]dioxol-8b-yl)-2-oxoethoxy)phosphoryl)oxy) methyl)phenyl)amino)-1-oxo-5-ureidopentan-2-yl) amino)-3-methyl-1-oxobutan-2-yl)carbamate (12-1)

To a stirred solution of (9H-fluoren-9-yl)methyl ((S)-1-(((S)-1-((4-(hydroxymethyl)phenyl)amino)-1-oxo-5-ureidopentan-2-yl)amino)-3-methyl-1-oxobutan-2-yl)carbamate (0.20 g, 0.33 mmol) in DMF (4.7 mL) was added 3-((bis (diisopropylamino)phosphino)oxy)propanenitrile (0.11 g, 0.37 mmol). To this mixture was added 0.45M tetrazole in acetonitrile (0.81 mL, 0.37 mmol) dropwise and the resulting mixture was stirred for 20 minutes at room temperature. To this was added Budesonide (0.22 g, 0.50 mmol) and 5-(ethylthio)-1H-tetrazole (0.09 g, 0.67 mmol) and allowed to stir to 30 minutes at room temperature. To this was added 6 M tertbutyl hydroperoxide in decane (0.12 mL, 0.73 mmol) and allowed to stir at room temperature for 1 hour. The crude reaction was loaded directly onto silica gel and flash column separation using a 0-100% ethyl acetate/hexane gradient followed by a 0-50% isopropanol/DCM gradient gave 12-1 as a solid. (0.10 g, 27%) LRMS (ES) (M+H)⁺: observed=1147.7, calculated=1147.2.

Step B: 4-((S)-2-((S)-2-amino-3-methylbutanamido)-5-ureidopentanamido)benzyl (2((6aR,6bS,7S,8aS,8bS,11aR,2aS,2bS)-7-hydroxy-6a,8a-dimethyl-4-oxo-10-propyl-2,4,6a,6b,7,8,8a,8b,11a,12,12a,12b-dodecahydro-1H-naphtho[2',1':4,5]indeno[1,2-d][1,3]dioxol-8b-yl)-2-oxoethyl) hydrogen phosphate (12-2)

To a stirred solution of 12-1 (0.10 g, 0.09 mmol) in DCM (1.8 mL) was added DBU (0.05 mL, 0.35 mmol) and the resulting solution was stirred 20 minutes at room temperature. The reaction was concentrated and dissolved in a 2:1:1 methanol:water:acetonitrile mixture and syringe filtered. The filtrate was purified using reverse phase preparative chromatography (Phenomenex Gemini-NX C18 OBD 5 uM 30×100 mm; 10-50% MeCN/water w/0.1% NH₄OH modifier over 20 min) to give 12-2 as a solid (42 mg, 53%). LRMS (ES) (M+H)⁺: observed=872.6, calculated=871.9.

Step C: 4-((2S)-2-((2S)-2-(2-(cyclooct-2-yn-1-yloxy)acetamido)-3-methylbutanamido)-5-ureidopentanamido)benzyl (2-((6aR,6bS,7S,8aS,8bS,11aR,12aS,12bS)-7-hydroxy-6a,8a-dimethyl-4-oxo-10-propyl-2,4,6a,6b,7,8,8a,8b,11a,12,12a,12b-dodecahydro-1H-naphtho[2',1': 4,5]indeno[1,2-d][1,3]dioxol-8b-yl)-2-oxoethyl) hydrogen phosphate (12-3)

The title compound was prepared from 12-2 according to the protocol outlined in Example 4 to produce 4-3 to afford 12-3. LRMS (ES) (M+H)⁺: observed=1036.8, calculated=1036.1

Example 13

The synthesis of Budesonide linker 2-((6aR,6bS,7S,8aS,8bS,11 aR,12aS,12bS)-7-hydroxy-6a,8a-dimethyl-4-oxo-10-propyl-2,4,6a,6b,7,8,8a,8b,11a,12,12a,12b-dodecahydro-1H-naphtho[2',1':4,5]indeno[1,2-d][1,3]dioxol-8b-yl)-2-oxoethyl acetate (13-1) was as follows.

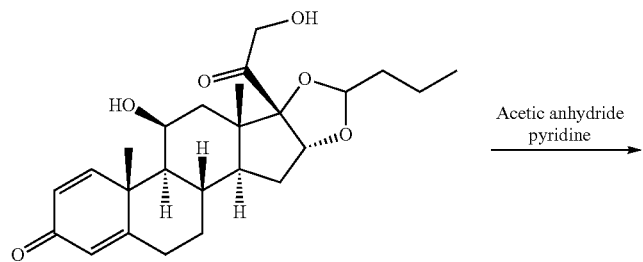
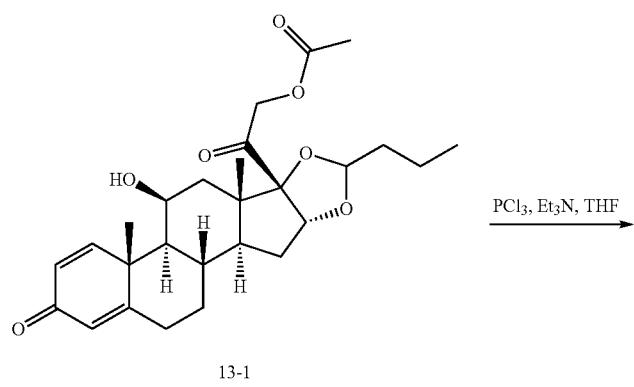
13-1
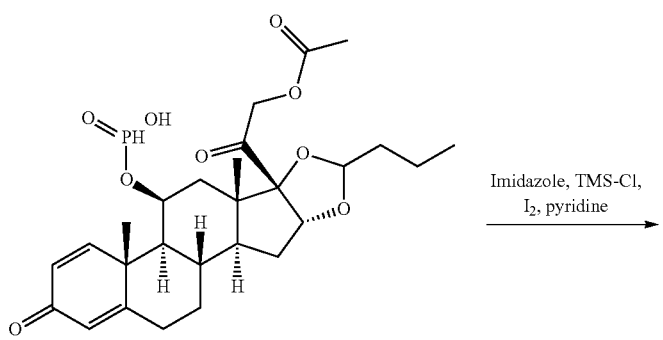
13-2
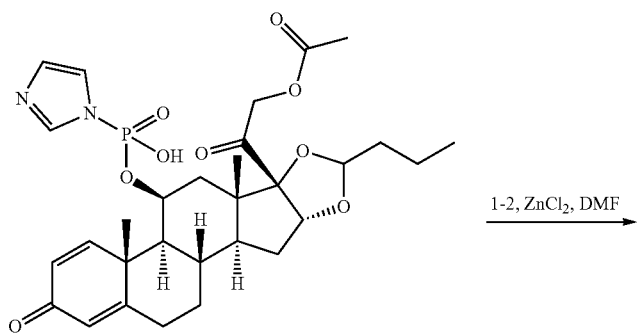
13-3

-continued
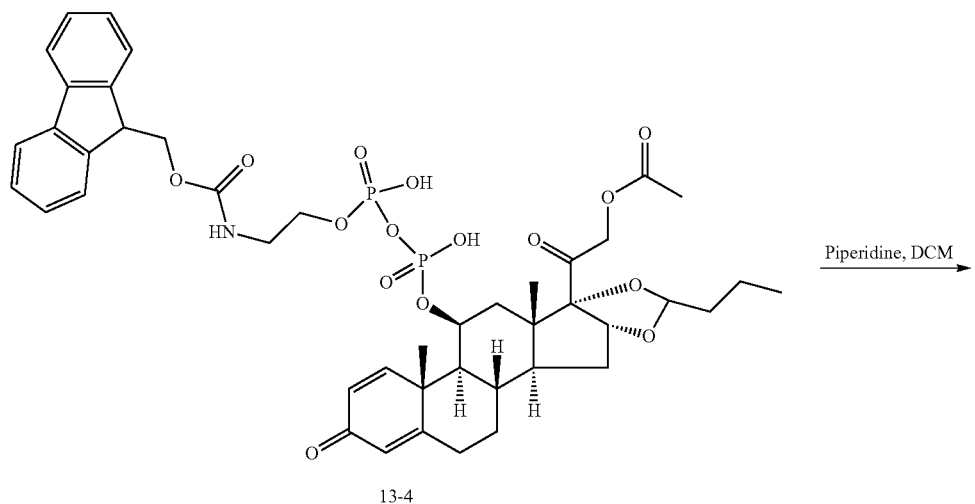
13-4
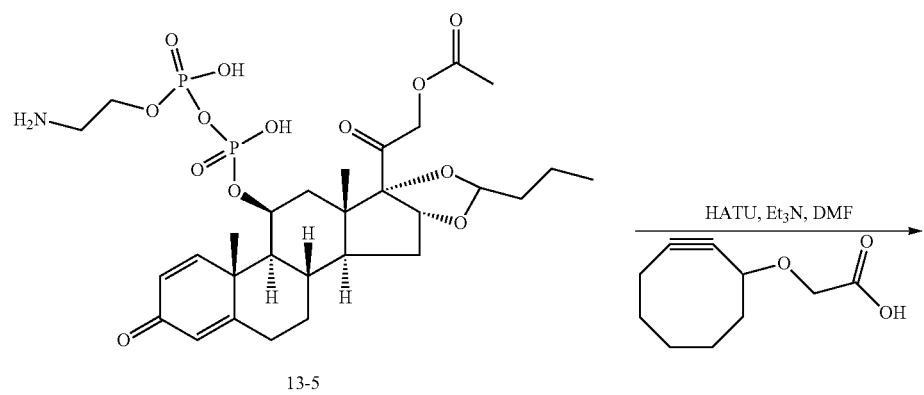
13-5
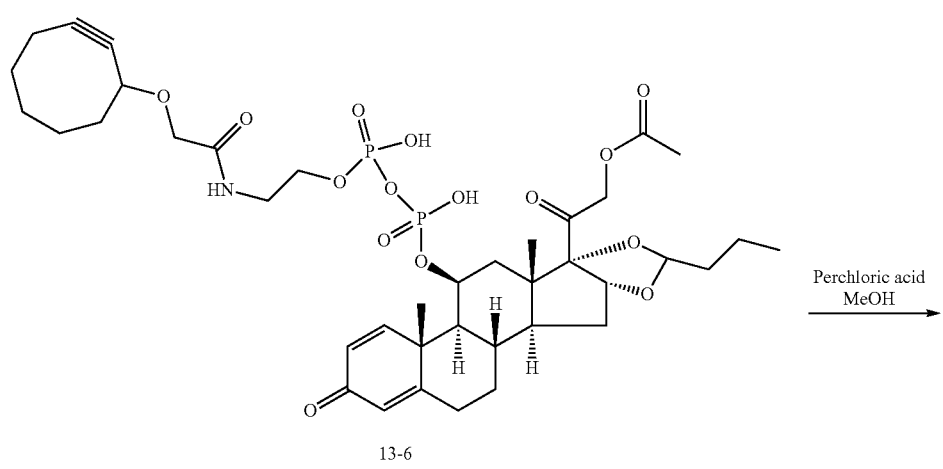
13-6

-continued

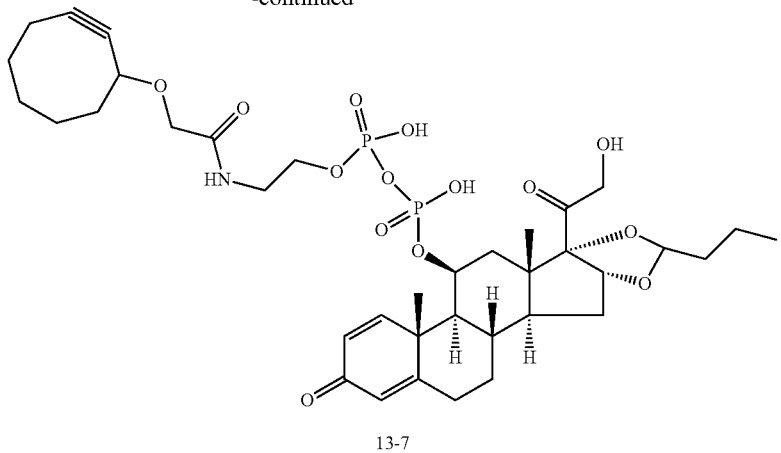

13-7

Step A: synthesis 2-((6aR,6bS,7S,8aS,8bS,11aR, 12aS,12bS)-7-hydroxy-6a,8a-dimethyl-4-oxo-10-propyl-2,4,6a,6b,7,8,8a,8b,11a,12,12a,12b-dodecahydro-1H-naphtho[2',1': 4,5]indeno[1,2-d][1,3]dioxol-8b-yl)-2-oxoethyl acetate (13-1)

To a stirred solution of budesonide (2.00 g, 4.65 mmol) in pyridine (20.0 mL) at room temperature was added acetic anhydride (2.0 mL, 21.20 mmol) and the resulting mixture was stirred for 2.5 hours. The reaction was chilled in an ice bath and quenched with saturated sodium bicarbonate solution (20.0 mL). The solution was extracted several times with ethyl acetate. The combined organic phase washed with brine, dried over sodium sulfate and concentrated to give 13-1 as a solid (2.30 g, 105%). LRMS (ES) (M+H)$^+$: observed=473.4, calculated=472.5.

Step B: 2-((6aR,6bS,7S,8aS,8bS,11aR,12aS,12bS)-7-((hydroxyhydrophosphoryl)oxy)-6a,8a-dimethyl-4-oxo-10-propyl-2,4,6a,6b,7,8,8a,8b,11a,12,12a,12b-dodecahydro-1H-naphtho[2',1':4,5]indeno[1,2-d][1,3]dioxol-8b-yl)-2-oxoethyl acetate (13-2)

To a stirred solution of 13-1 (0.50 g, 1.06 mmol) in THF (10.0 mL) at −78° C. was added phosphorus trichloride (0.18 mL, 2.12 mmol) dissolved in THF (2.0 mL) followed by triethylamine (0.74 mL, 5.29 mmol) dissolved in THF (2.0 mL). The resulting mixture was stirred at −78° C. for 10 minutes and allowed to warm to room temperature for 45 minutes. The reaction was chilled in an ice bath and quenched with water (0.50 mL). The solution was allowed to warm to room temperature and saturated sodium bicarbonate solution was added until pH 9 and stirred for 10 minutes. The mixture was acidified with 1N HCl and was extracted several times with ethyl acetate. The combined organic phase was dried over sodium sulfate and concentrated to give 13-2 as a solid (0.55 g, 97%). LRMS (ES) (M+H)$^+$: observed=537.3, calculated=536.5.

Step C: 2-((6aR,6bS,7S,8aS,8bS,11aR,12aS,12bS)-7-((hydroxy(1H-imidazol-1-yl) phosphoryl)oxy)-6a, 8a-dimethyl-4-oxo-10-propyl-2,4,6a,6b,7,8,8a,8b, 11a,12,12a,12b-dodecahydro-1H-naphtho[2',1':4,5] indeno[1,2-d][1,3]dioxol-8b-yl)-2-oxoethyl acetate (13-3)

To a stirred solution of 13-2 (0.55 g, 1.03 mmol) and imidazole (0.35 g, 5.13 mmol) in pyridine (8.0 mL) at room temperature was added TMS-Cl (1.31 mL, 10.25 mmol) and the resulting solution was stirred for 10 minutes. To this mixture was added iodine (0.52 g, 2.05 mmol) dissolved in pyridine (2 mL) and stirred room temperature for 50 minutes. The reaction was then cooled in and ice bath and quenched with water (0.5 mL). The reaction was concentrated, dissolved in aqueous acetonitrile and purified using reverse phase preparative chromatography (Phenomenex Gemini-NX C18 OBD 5 µM 30×100 mm; 10-50% MeCN/water w/0.10% NH$_4$OH modifier over 20 min) to give 13-3 as a solid (282 mg, 45%). LRMS (ES) (M+H)$^+$: observed=603.4, calculated=602.6.

Step D: 2-((6aR,6bS,7S,8aS,8bS,11aR,12aS,12bS)-7-(((((2-((((9H-fluoren-9-yl)methoxy)carbonyl)amino)ethoxy) (hydroxy)phosphoryl)oxy) (hydroxy)phosphoryl)oxy)-6a,8a-dimethyl-4-oxo-10-propyl-2, 4,6a,6b,7,8,8a,8b,11a,12,12a,12b-dodecahydro-1H-naphtho[2',1':4,5]indeno[1,2-d][1,3]dioxol-8b-yl)-2-oxoethyl acetate (13-4)

To a stirred solution of 13-3 (0.20 g, 0.33 mmol) and 1-2 (0.12 g, 0.33 mmol) in DMF (1.4 mL) was added ZnCl$_2$ (0.36 g, 2.66 mmol) and the mixture was allowed to stir at room temperature overnight. The reaction was diluted with 1 N HCl and extracted several times with ethyl acetate. The combined organic layers were concentrated, dissolved in aqueous acetonitrile and purified using reverse phase preparative chromatography (Phenomenex Gemini-NX C18 OBD 5 µM 30×100 mm; 10-50% MeCN/water w/0.1% NH$_4$OH modifier over 20 min) to give 13-4 as a solid (166 mg, 55%). LRMS (ES) (M+H)$^+$: observed=898.4, calculated=897.8.

Step E: 2-((6aR,6bS,7S,8aS,8bS,11aR,12aS,12bS)-7-(((((2-aminoethoxy) (hydroxy)phosphoryl)oxy) (hydroxy)phosphoryl)oxy)-6a,8a-dimethyl-4-oxo-10-propyl-2,4,6a,6b,7, 8,8a,8b,11a,12,12a,12b-dodecahydro-1H-naphtho[2',1':4,5]indeno[1,2-d][1, 3]dioxol-8b-yl)-2-oxoethyl acetate (13-5)

The title compound was prepared from 13-4 according to the protocol outlined in Example 2 to prepare 2-4 to afford 13-5. LRMS (ES) (M+H)$^+$: observed=676.4, calculated=675.6.

Step F: 2-(((6aR,6bS,7S,8aS,8bS,11aR,12aS,12bS)-7-(((((2-(2-(cyclooct-2-yn-1-yloxy)acetamido) ethoxy) (hydroxy)phosphoryl)oxy) (hydroxy)phosphoryl)oxy)-6a,8a-dimethyl-4-oxo-10-propyl-2,4,6a, 6b,7,8,8a,8b,11a,12,12a,12b-dodecahydro-1H-naphtho[2',1': 4,5]indeno[1,2-d][1,3]dioxol-8b-yl)-2-oxoethyl acetate (13-6)

To a stirred solution of 13-5 (0.037 g, 0.055 mmol) and 2-(cyclooct-2-yn-1-yloxy)acetic acid (0.032 g, 0.175 mmol) in DMF (0.8 mL) was added HATU (0.066 g, 0.175 mmol) and triethylamine (0.03 mL, 0.22 mmol). The reaction was stirred at room temperature for 20 minutes, then purified directly using reverse phase preparative chromatography (Phenomenex Gemini-NX C18 OBD 5 μM 30×100 mm; 10-50% MeCN/water w/0.1% NH$_4$OH modifier over 20 min) to give 13-6 as a solid (36 mg, 78%). LRMS (ES) (M+H)$^+$: observed=840.5, calculated=839.8.

Step G: 2-((6aR,6bS,7S,8aS,8bS,11 aR,12aS,12bS)-7-hydroxy-6a,8a-dimethyl-4-oxo-10-propyl-2,4,6a, 6b,7,8,8a,8b,11a,12,12a,12b-dodecahydro-1H-naphtho[2',1':4,5]indeno[1,2-d][1,3]dioxol-8b-yl)-2-oxoethyl acetate (13-7)

To a stirred solution of 13-6 (0.035 mg, 0.042 mmol) in methanol (0.50 mL) was added 70% perchloric acid (7.2 μL, 0.083 mmol) and the resulting solution was stirred room temperature overnight. The reaction was purified directly using reverse phase preparative chromatography (Phenomenex Gemini-NX C18 OBD 5 μM 30×100 mm; 10-50% MeCN/water w/0.1% NH$_4$OH modifier over 20 min) to give 13-7 as a solid (16 mg, 47%). LRMS (ES) (M+H)$^+$: observed=798.4, calculated=797.7.

Example 14

The synthesis of Fluticasone linker (6S,8S,9R,10S,11 S,13 S,14S,16R,17R)-11-(((((2-(2-(cyclooct-2-yn-1-yloxy) acetamido)ethoxy)(hydroxy)phosphoryl)oxy)(hydroxy) phosphoryl)oxy)-6,9-difluoro-17-(((fluoromethyl)thio)carbonyl)-10,13,16-trimethyl-3-oxo-6,7,8,9,10,11,12,13,14,15, 16,17-dodecahydro-3H-cyclopenta[a]phenanthren-17-yl propionate (14-5) was as follows.

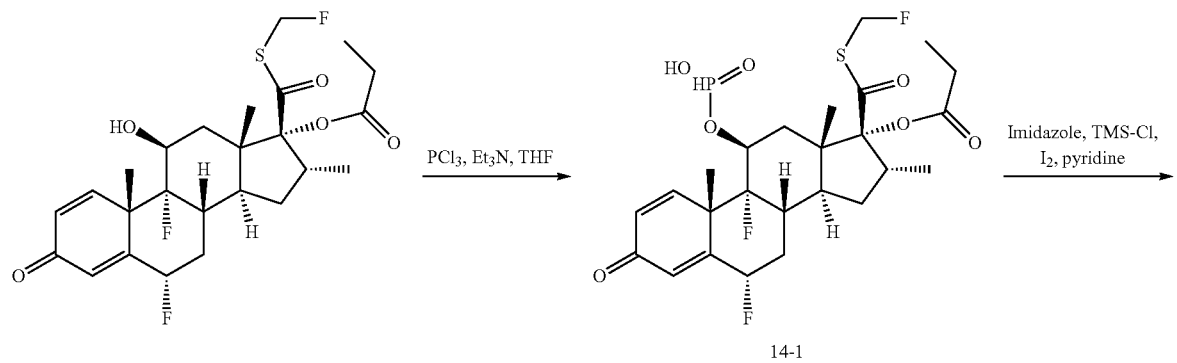

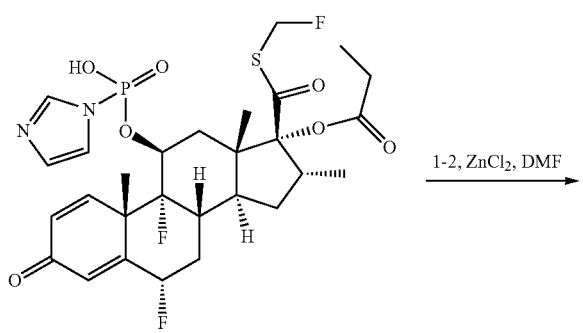

14-2

-continued
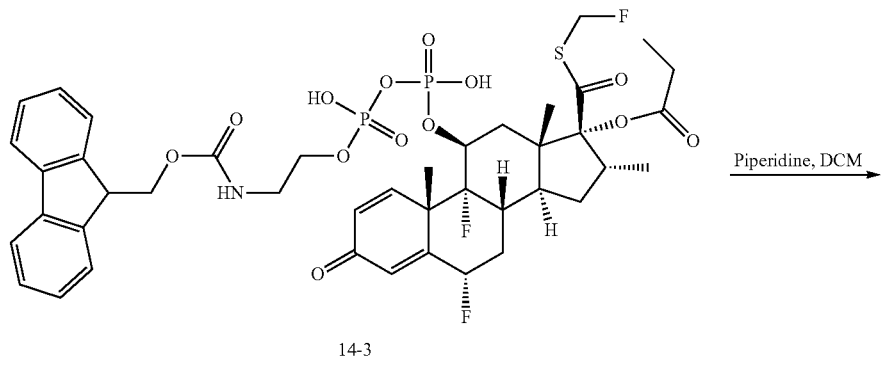
14-3
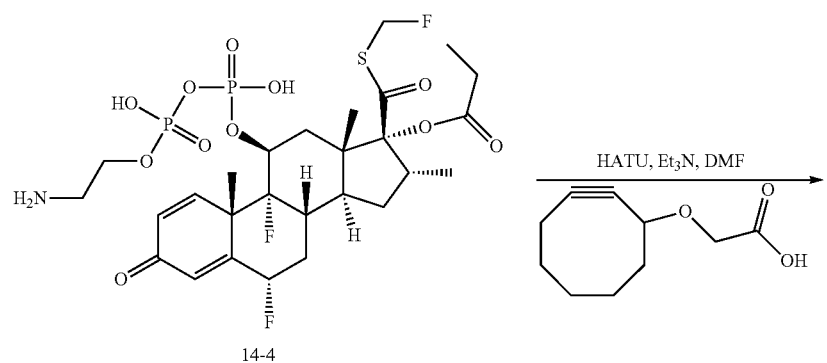
14-4
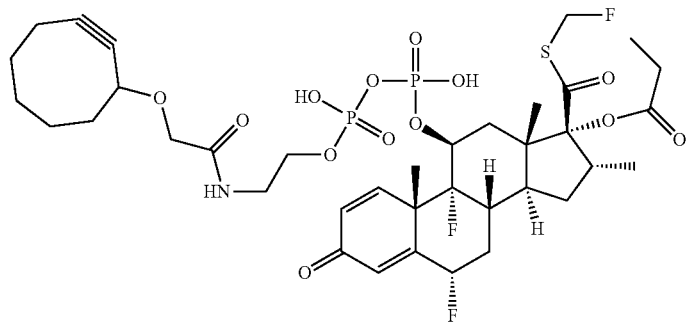
14-5

Step A: (6S,8S,9R,10S,11S,13S,14S,16R,17R)-6,9-difluoro-17-(((fluoromethyl)thio)carbonyl)-11-((hydroxyhydrophosphoryl)oxy)-10,13,16-trimethyl-3-oxo-6,7,8,9,10,11,12,13,14,15,16,17-dodecahydro-3H-cyclopenta[a]phenanthren-17-ylpropionate (14-1)

The title compound was prepared from fluticasone propionate according to the protocol outlined in Example 13 to prepare 13-2 to afford 14-1. LRMS (ES) (M+H)$^+$: observed=565.3, calculated=564.5.

Step B: (6S,8S,9R,10S,11S,13S,14S,16R,17R)-6,9-difluoro-17-(((fluoromethyl)thio)carbonyl)-11-((hydroxy(1H-imidazol-1-yl)phosphoryl)oxy)-10,13,16-trimethyl-3-oxo-6,7,8,9,10,11,12,13,14,15,16,17-dodecahydro-3H-cyclopenta[a]phenanthren-17-yl propionate (14-2)

The title compound was prepared from 14-1 according to the protocol outlined in Example 13 to prepare 13-3 to afford 14-2. LRMS (ES) (M+H)$^+$: observed=631.3, calculated=630.6.

Step C: (6S,8S,9R,10S,11S,13S,14S,16R,17R)-11-(((((2-((((9H-fluoren-9-yl)methoxy)carbonyl)amino)ethoxy) (hydroxy)phosphoryl)oxy) (hydroxy)phosphoryl)oxy)-6,9-difluoro-17-(((fluoromethyl)thio)carbonyl)-10,13,16-trimethyl-3-oxo-6,7,8,9,10,11,12,13,14,15,16,17-dodecahydro-3H-cyclopenta[a]phenanthren-17-yl propionate (14-3)

The title compound was prepared from 14-2 according to the protocol outlined in Example 13 to prepare 13-4 to afford 14-3. LRMS (ES) (M+H)$^+$: observed=943.4 (M+H+NH$_3$), calculated=925.8.

Step D: (6S,8S,9R,10S,11S,13S,14S,16R,17R)-11-(((((2-aminoethoxy)(hydroxy)phosphoryl)oxy) (hydroxy)phosphoryl)oxy)-6,9-difluoro-17-(((fluoromethyl)thio)carbonyl)-10,13,16-trimethyl-3-oxo-6,7,8,9,10,11,12,13,14,15,16,17-dodecahydro-3H-cyclopenta[a]phenanthren-17-yl propionate (14-4)

The title compound was prepared from 14-3 according to the protocol outlined in Example 2 to prepare 2-4 to afford 14-4. LRMS (ES) (M+H)$^+$: observed=704.3, calculated=703.6.

Step F: (6S,8S,9R,10S,11S,13S,14S,16R,17R)-11-(((((2-(2-(cyclooct-2-yn-1-yloxy)acetamido)ethoxy) (hydroxy)phosphoryl)oxy) (hydroxy)phosphoryl)oxy)-6,9-difluoro-17-(((fluoromethyl)thio)carbonyl)-10,13,16-trimethyl-3-oxo-6,7,8,9,10,11,12,13,14,15,16,17-dodecahydro-3H-cyclopenta[a]phenanthren-17-ylpropionate (14-5)

The title compound was prepared from 14-4 according to the protocol outlined in Example 13 to prepare 13-6 to afford 14-5. LRMS (ES) (M+H)$^+$: observed=868.4, calculated=867.8.

Example 15

The synthesis of Fluticasone linker (6S,8S,9R,10S,11S,13S,14S,16R,17R)-11-((((((2-(2-(cyclooct-2-yn-1-yloxy)acetamido)ethoxy)(hydroxy) phosphoryl)oxy)(hydroxy)phosphoryl)oxy)methoxy)-6,9-difluoro-17-(((fluoromethyl)thio)carbonyl)-10,13,16-trimethyl-3-oxo-6,7,8,9,10,11,12,13,14,15,16,17-dodecahydro-3H-cyclopenta[a]phenanthren-7-yl propionate (15-5) was as follows.

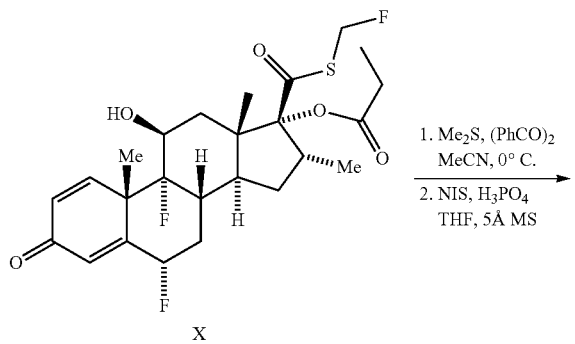

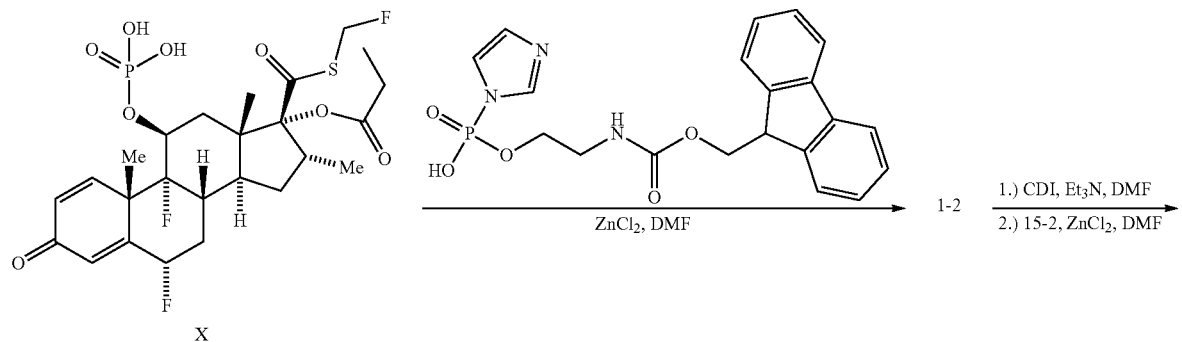

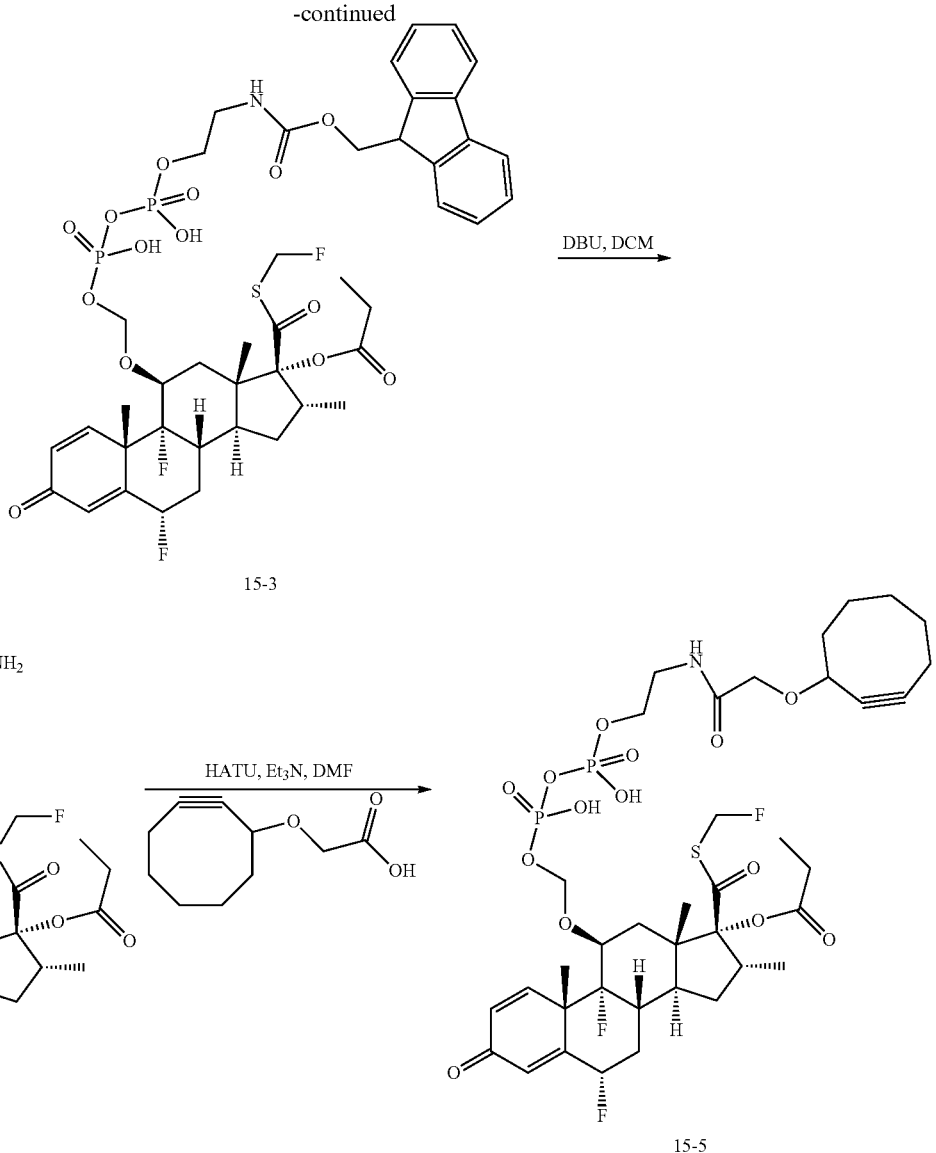

Step A: (6S,8S,9R,10S,11S,13S,14S,16R,17R)-6,9-difluoro-17-(((fluoromethyl)thio)carbonyl)-10,13,16-trimethyl-1-((methylthio)methoxy)-3-oxo-6,7,8,9,10,11,12,13,14,15,16,17-dodecahydro-3H-cyclopenta[a]phenanthren-17-yl propionate (15-1)

To a stirred solution of fluticasone propionate (0.50 g, 1.00 mmol) in MeCN (5.0 mL) at 0° C. was added dimethyl sulfide (0.59 mL, 8.00 mmol) followed by benzoyl peroxide (0.97 g, 4.00 mmol) added in four portions over 20 minutes. The resulting mixture was stirred at 0° C. for 1 hour. The reaction was concentrated, taken up in ethyl acetate and washed with saturated sodium bicarbonate. The combined organic phase was concentrated. The crude was purified directly using reverse phase preparative chromatography (Phenomenex Gemini-NX C18 OBD 5 uM 30×100 mm; 40-80% MeCN/water w/0.1% NH₄OH modifier over 20 min) to give to give 15-1 as a solid (0.07 g, 12.7%). LRMS (ES) (M+H)⁺: observed=561.3, calculated=560.6.

Step B: (6S,8S,9R,10S,11S,13S,14S,16R,17R)-6,9-difluoro-17-(((fluoromethyl)thio)carbonyl)-10,13,16-trimethyl-3-oxo-11-((phosphonooxy)methoxy)-6,7,8,9,10,11,12,13,14,15,16,17-dodecahydro-3H-cyclopenta[a]phenanthren-17-yl propionate (15-2)

Phosphoric acid (0.09 g, 0.89 mmol) was heated under nitrogen at 120° C. for 30 minutes. This was allowed to cool and to it was added molecular seives and 15-1 (0.07 g, 0.13 mmol). This mixture was dissolved in THF (1.3 mL) and NIS (0.04 g, 0.19 mmol) was added. The resulting solution was allowed to stir overnight at room temperature. The mixture was filtered and concentrated. The crude was purified directly using reverse phase preparative chromatography (Phenomenex Gemini-NX C18 OBD 5 uM 30×100 mm; 10-50% MeCN/water w/0.1% NH₄OH modifier over 20 min) to give to give 15-2 as a solid (0.05 g, 63%). LRMS (ES) (M+H)⁺: observed=611.3, calculated=610.5.

Step C: (6S,8S,9R,10S,11S,13S,14S,16R,17R)-11-((((((2-((((9H-fluoren-9-yl)methoxy)carbonyl)amino)ethoxy)(hydroxy)phosphoryl)oxy)(hydroxy)phosphoryl)oxy)methoxy)-6,9-difluoro-17-(((fluoromethyl)thio)carbonyl)-10,13,16-trimethyl-3-oxo-6,7,8,9,10,11,12,13,14,15,16,17-dodecahydro-3H-cyclopenta[a]phenanthren-17-yl propionate (15-3)

The title compound was prepared from 15-2 according to the protocol outlined in Example 1 to prepare 1-3 to afford 15-3. LRMS (ES) (M+H)+: observed=956.5, calculated=955.8.

Step D: (6S,8S,9R,10S,11S,13S,14S,16R,17R)-11-((((((2-aminoethoxy)(hydroxy)phosphoryl)oxy)(hydroxy)phosphoryl)oxy)methoxy)-6,9-difluoro-17-(((fluoromethyl)thio)carbonyl)-10,13,16-trimethyl-3-oxo-6,7,8,9,10,11,12,13,14,15,16,17-dodecahydro-3H-cyclopenta[a]phenanthren-17-yl propionate (15-4)

The title compound was prepared from 15-3 according to the protocol outlined in Example 12 to prepare 12-2 to afford 15-4. LRMS (ES) (M+H)+: observed=734.5, calculated=733.6.

Step E: (6S,8S,9R,10S,11S,13S,14S,16R,17R)-1-((((((2-(2-(cyclooct-2-yn-1-yloxy)acetamido)ethoxy)(hydroxy)phosphoryl)oxy)(hydroxy)phosphoryl)oxy)methoxy)-6,9-difluoro-17-(((fluoromethyl)thio)carbonyl)-10,13,16-trimethyl-3-oxo-6,7,8,9,10,11,12,13,14,15,16,17-dodecahydro-3H-cyclopenta[a]phenanthren-17-yl propionate (15-5)

The title compound was prepared from 15-4 according to the protocol outlined in Example 13 to prepare 13-6 to afford 15-5. LRMS (ES) (M+H)+: observed=898.4, calculated=897.8.

Example 16

The synthesis of Budesonide linker 1-(cyclooct-2-yn-1-yloxy)-2-oxo-3-aza-6,9,12,15,18,21,24,27,30,33,36,39,42,45,48,51,54,57,60,63,66,69,72-tricosaoxahenheptacont-74-yl (2-((6aR,6bS,7S,8aS,8bS,11aR,12aS,12bS)-7-hydroxy-6a,8a-dimethyl-4-oxo-10-propyl-2,4,6a,6b,7,8,8a,8b,11a,12,12a,12b-dodecahydro-1H-naphtho[2',1':4,5]indeno[1,2-d][1,3]dioxol-8b-yl)-2-oxoethyl) dihydrogen pyrophosphate (16-5) was as follows.

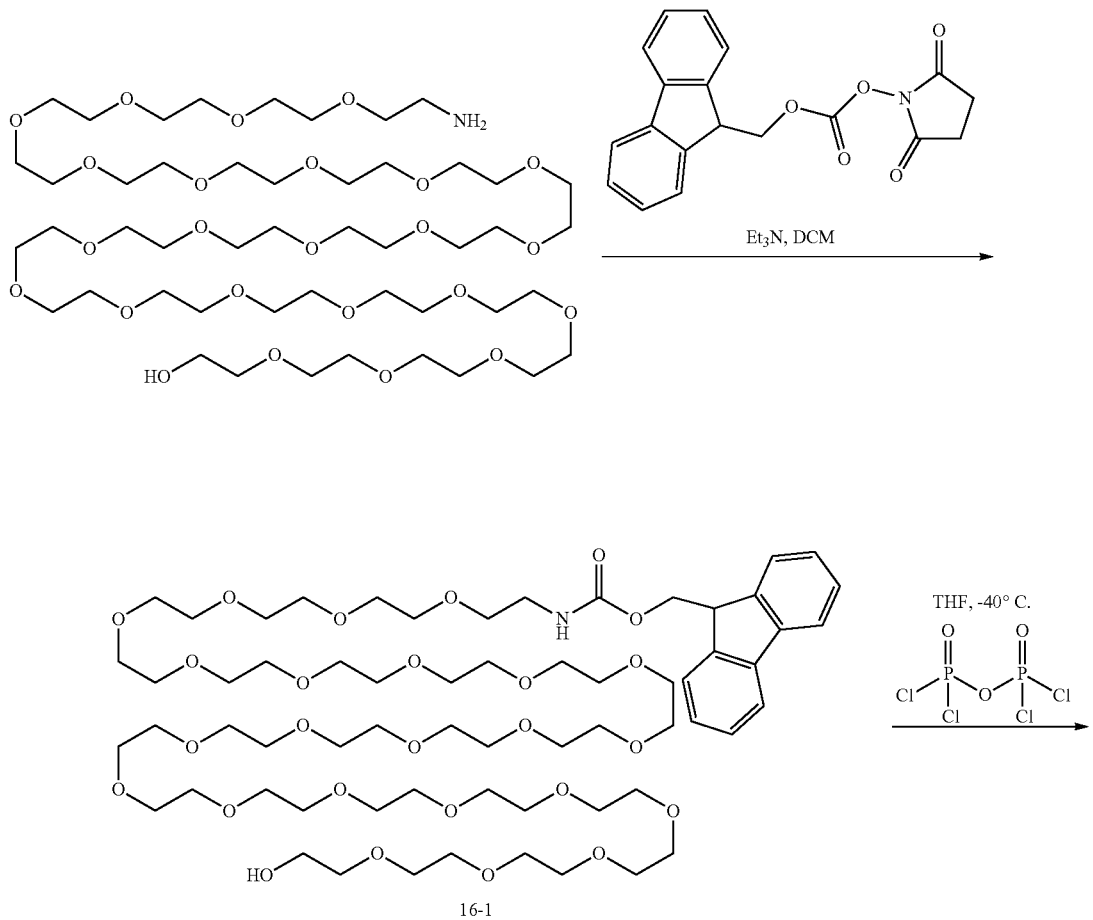

16-1

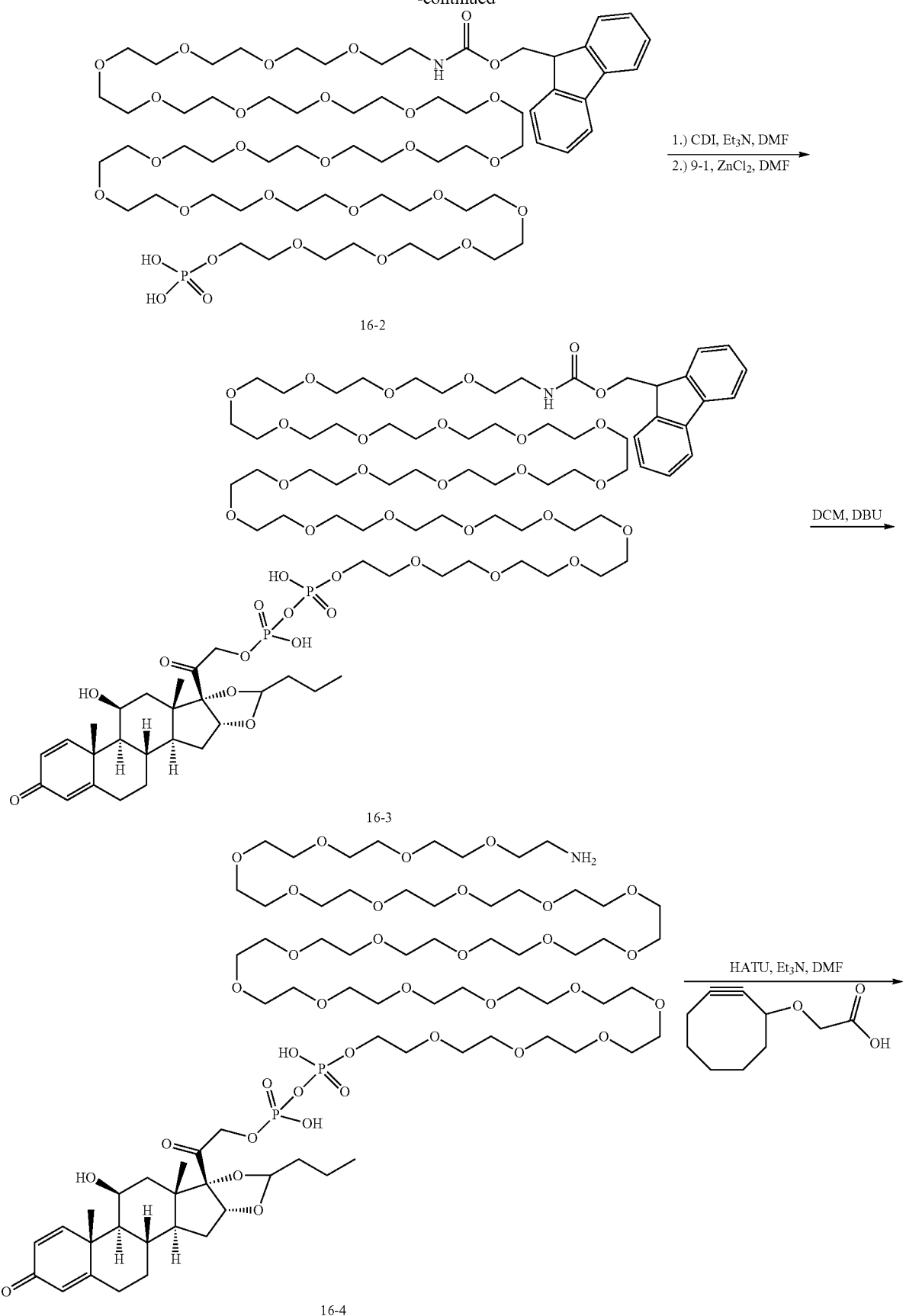

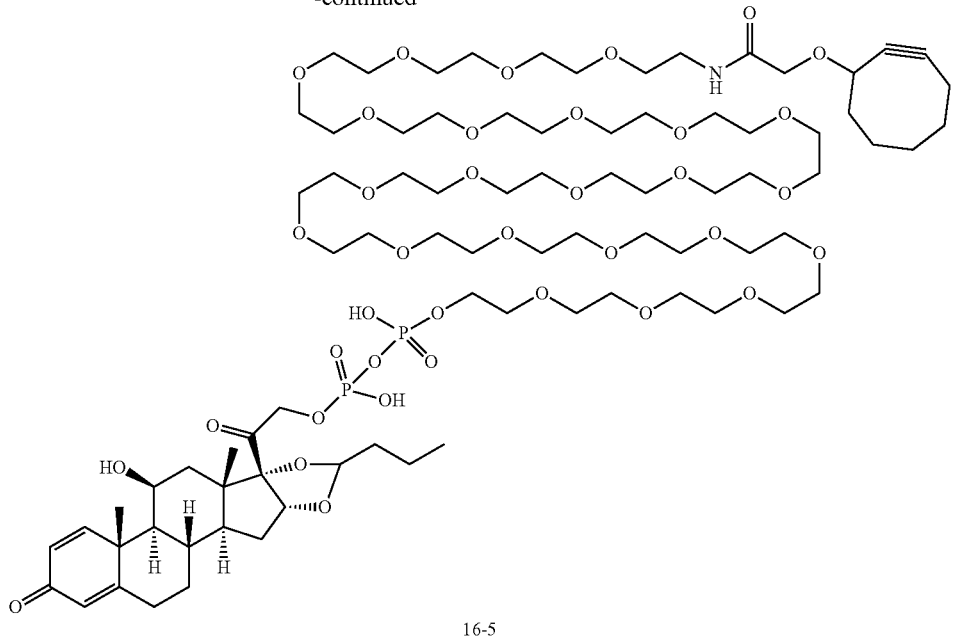

16-5

Step A: (9H-fluoren-9-yl)methyl (71-hydroxy-3,6,9, 12,15,18,21,24,27,30,33,36,39,42,45,48,51,54,57,60, 63,66,69-tricosaoxahenheptacontyl)carbamate (16-1)

The title compound was prepared from 71-amino-3,6,9, 12,15,18,21,24,27,30,33,36,39,42,45,48,51,54,57,60,63,66, 69-tricosaoxahenheptacontan-1-ol and (9H-fluoren-9-yl) methyl (2,5-dioxopyrrolidin-1-yl) carbonate according to the protocol outlined in Example 11 to produce 11-1 to afford 16-1. LRMS (ES) (M+H)+: observed=1314.1, calculated=1296.5

Step B: (9H-fluoren-9-yl)methyl (71-(phosphonooxy)-3,6,9,12,15,18,21,24,27,30,33,36,39,42,45, 48,51,54,57,60,63,66,69-tricosaoxahenheptacontyl) carbamate (16-2)

The title compound was prepared from 16-1 according to the protocol outlined in Example 1 to produce 1-1 to afford 16-2. LRMS (ES) (M+H)+: observed=1394.0, calculated=1376.5

Step C: (9H-fluoren-9-yl)methyl (71-((hydroxy((hydroxy(2-((6aR,6bS,7S,8aS,8bS,11aR,12aS,12bS)-7-hydroxy-6a,8a-dimethyl-4-oxo-10-propyl-2,4,6a,6b, 7,8,8a,8b,11a,12,12a,12b-dodecahydro-1H-naphtho [2',1':4,5]indeno[1,2-d][1,3]dioxol-8b-yl)-2-oxoethoxy)phosphoryl)oxy)phosphoryl)oxy)-3,6,9, 12,15,18,21,24,27,30,33,36,39,42,45,48,51,54,57,60, 63,66,69-tricosaoxahenheptacontyl)carbamate (16-3)

The title compound was prepared from 16-2 and 9-1 according to the protocol outlined in Example 1 to produce 1-3 to afford 16-3. LRMS (ES) (M+H)+: observed=1886.7, calculated=1869.0

Step D: 72-amino-3, 6, 9,12,15,18, 21, 24, 27,30, 33, 36, 39, 42, 45, 48, 51, 54, 57,60, 63, 66, 69-tricosaoxahenheptacontanyl (2-((6aR,6bS,7S,8aS,8bS, 11aR,12aS,12bS)-7-hydroxy-6a,8a-dimethyl-4-oxo-10-propyl-2,4,6a,6b,7,8,8a,8b,11a,12,12a,12b-dodecahydro-1H-naphtho[2',1':4,5]indeno[1,2-d][1, 3]dioxol-8b-yl)-2-oxoethyl) dihydrogen pyrophosphate (16-4)

The title compound was prepared from 16-3 according to the protocol outlined in Example 12 to produce 12-2 to afford 16-4. LRMS (ES) (M+H)+: observed=1664.0, calculated=1646.7

Step E: 1-(cyclooct-2-yn-1-yloxy)-2-oxo-3-aza-6, 9,12,15,18, 21, 24,27, 30, 33, 36, 39, 42, 45, 48, 51, 54,57, 60, 63, 66, 69,72-tricosaoxahenheptacont-74-yl (2-((6aR,6bS,7S,8aS,8bS,11aR,12aS, 12bS)-7-hydroxy-6a,8a-dimethyl-4-oxo-10-propyl-2, 4,6a,6b,7,8,8a,8b,11a,12,12a,12b-dodecahydro-1H-naphtho[2',1':4,5]indeno[1,2-d][1,3]dioxol-8b-yl)-2-oxoethyl) dihydrogen pyrophosphate (16-5)

The title compound was prepared from 16-4 according to the protocol outlined in Example 13 to produce 13-6 to afford 16-5. LRMS (ES) (M+H)+: observed=1828.7, calculated=1810.9

Example 17

The synthesis of Budesonide linker 4-((2S)-2-((2S)-2-(2-(cyclooct-2-yn-1-yloxy)acetamido)-3-methylbutanamido)-5-ureidopentanamido)benzyl (2-((6aR,6b S,7S,8aS,8b S,11 aR,12aS,12b S)-7-hydroxy-6a,8a-dimethyl-4-oxo-10-propyl-2,4,6a,6b,7,8,8a,8b,11a,12,12a,12b-dodecahydro-1H-naphtho[2',1':4,5]indeno[1,2-d][1,3]dioxol-8b-yl)-2-oxoethyl) dihydrogen pyrophosphate (17-2) was as follows.

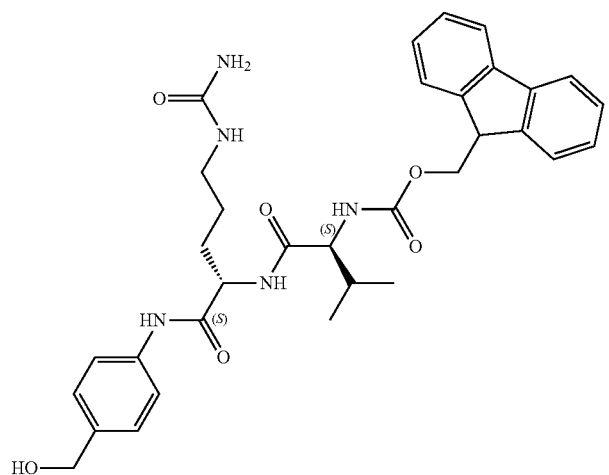
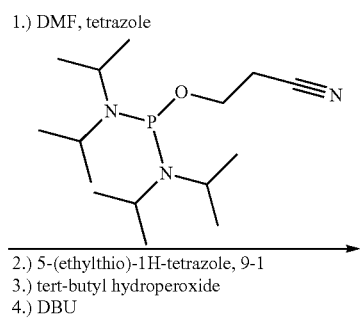
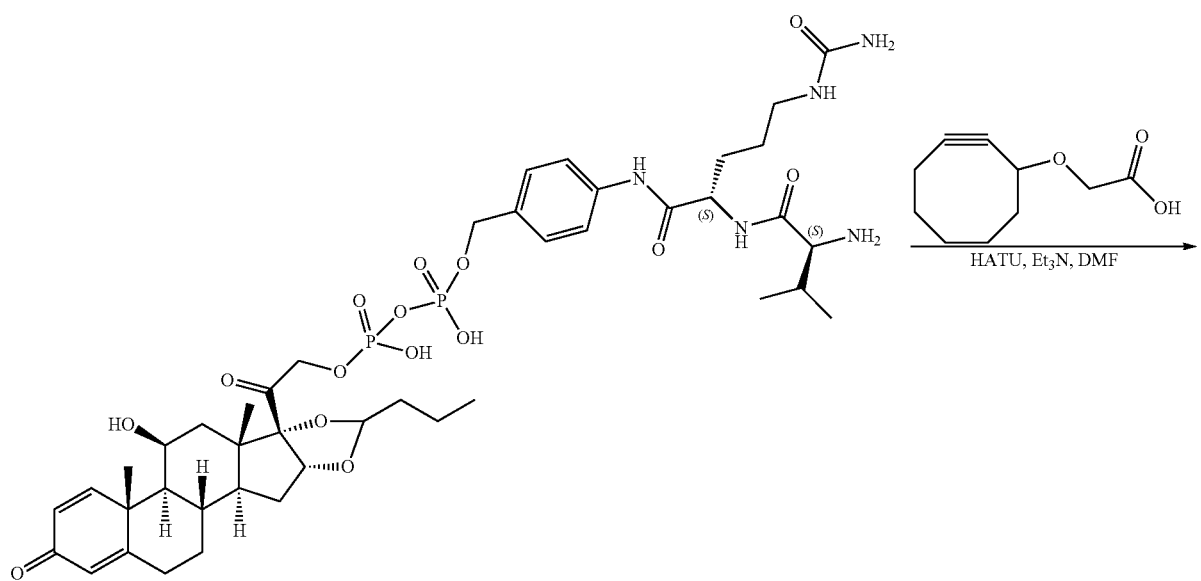
17-1
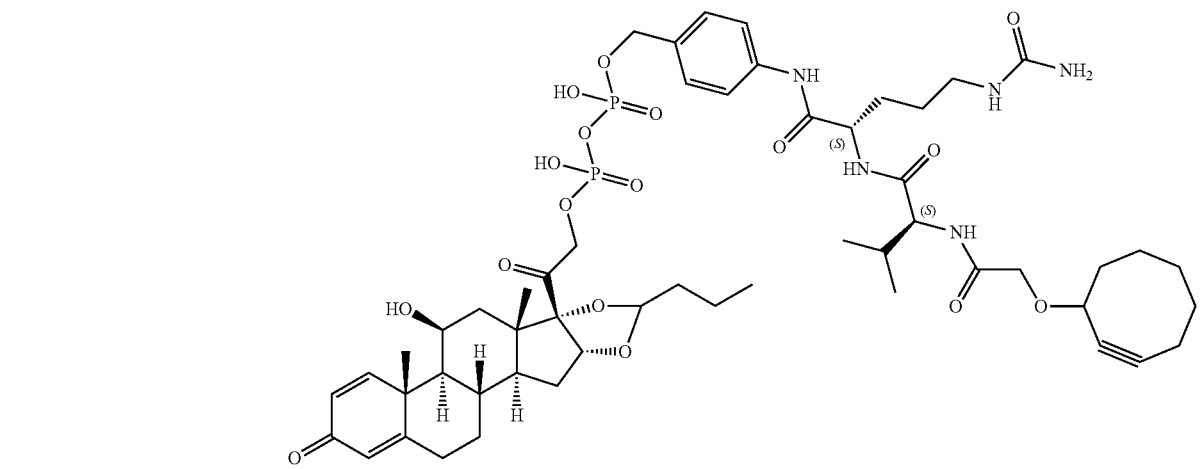
17-2

Step A: 4-((S)-2-((S)-2-amino-3-methylbutanamido)-5-ureidopentanamido)benzyl (2((6aR,6bS,7S,8aS,8bS,11aR,12aS,2bS)-7-hydroxy-6a,8a-dimethyl-4-oxo-10-propyl-2,4,6a,6b,7,8,8a,8b,11a,12,12a,12b-dodecahydro-1H-naphtho[2',1': 4,5]indeno[1,2-d][1,3]dioxol-8b-yl)-2-oxoethyl) dihydrogen pyrophosphate (17-1)

To a stirred solution of (9H-fluoren-9-yl)methyl ((S)-1-(((S)-1-((4(hydroxymethyl)phenyl)amino)-1-oxo-5-ureidopentan-2-yl)amino)-3-methyl-1-oxobutan-2-yl)carbamate (0.05 g, 0.083 mmol) in DMF (1.2 mL) was added 3-((bis(diisopropylamino)phosphino)oxy)propanenitrile (29 uL, 0.09 mmol). To this mixture was added 0.45M tetrazole in acetonitrile (0.20 mL, 0.09 mmol) dropwise and the resulting mixture was stirred for 20 minutes at room temperature. To this was added 9-1 (0.042 g, 0.083 mmol) and 5-(ethylthio)-1H-tetrazole (0.02 g, 0.16 mmol) and allowed to stir to 30 minutes at room temperature. To this was added 6 M tertbutyl hydroperoxide in decane (0.03 mL, 0.18 mmol) and allowed to stir at room temperature for 30 minutes. To this was added DBU (0.12 mL, 0.83 mmol) and the resulting solution was stirred overnight at room temperature. The crude reaction was purified by direct injection using reverse phase preparative chromatography (Phenomenex Gemini-NX C18 OBD 5 uM 30×100 mm; 5-40% MeCN/water w/0.1% $NH_4OH$ modifier over 20 min) to give 17-1 as a solid (18.5 mg, 23%). LRMS (ES) $(M+H)^+$: observed=952.6, calculated=951.9.

Step B: 4-((2S)-2-((2S)-2-(2-(cyclooct-2-yn-1-yloxy)acetamido)-3-methylbutanamido)-5-ureidopentanamido)benzyl (2-((6aR,6bS,7S,8aS,8bS,11aR,12aS,12bS)-7-hydroxy-6a,8a-dimethyl-4-oxo-10-propyl-2,4,6a,6b,7,8,8a,8b,11a,12,12a,12b-dodecahydro-H-naphtho[2',1': 4,5]indeno[1,2-d][1,3]dioxol-8b-yl)-2-oxoethyl) dihydrogen pyrophosphate (17-2)

The title compound was prepared from 17-1 according to the protocol outlined in Example 13 to produce 13-6 to afford 17-2. LRMS (ES) $(M+H)^+$: observed=1116.6, calculated=1116.1.

Example 18

The solubility of exemplary drug-linker conjugates in aqueous solutions was evaluated. Linkers utilized in drug conjugates may have aqueous solubility to enable conjugation in aqueous media amenable to protein solubilization. Furthermore, linkers with aqueous solubility are considered hydrophilic, and may confer to the drug conjugate a reduced propensity to aggregate relative to standard hydrophobic linkers in the literature. The following exemplary drug-linkers were tested in an aqueous solution comprising 20% acetonitrile ($MeCN/H_2O$) for solubility at a concentration of 10 mg/mL. As shown in Table 1, the exemplary linker-drug conjugates displayed high solubility, which may be a result of the contribution of the polarity and charge of the phosphate containing linker to the drug-linker conjugate.

TABLE 1

| Drug Linker | Measured Solubility in 20% $MeCN/H_2O$ |
| --- | --- |
| 1-4 | >10 mg/mL |
| 2-7 | >10 mg/mL |

TABLE 1-continued

| Drug Linker | Measured Solubility in 20% $MeCN/H_2O$ |
| --- | --- |
| 3-4 | >10 mg/mL |
| 4-3 | >10 mg/mL |
| 5-3 | >10 mg/mL |

Example 19

In Vitro Stability Studies of Exemplary Drug-Linkers in Blood and Lysosomal Lysates.

Exemplary dexamethasone-linkers 4-3, 5-3, 1-4, 3-4, and 2-7 were incubated in relevant biomatrices to measure their stability and propensity to release free drug (Tables 2 to 4).

The exemplary dexamethasone-linkers were studied for their stability (Table 1) and propensity to release dexamethasone (Table 2) in human blood. As shown in the tables, all the dexamethasone linkers were stable in blood with little detectable degradation or release of free dexamethasone.

TABLE 1

Time Course of Calculated Conc. for each compound in human whole blood (nM)

| Matrix | Time | Dexamethasone | 4-3 | 5-3 | 1.4 | 3-4 | 2-7 |
| --- | --- | --- | --- | --- | --- | --- | --- |
| | Matrix spiking | 2939 | 2821 | n/a | 3059 | n/a | 1059 |
| | 0 m | 1687 | 1539 | 1299 | 1617 | 1382 | 1040 |
| | 5 m | | | 1251 | | 1325 | |
| | 10 m | | | | | | |
| | 15 m | | | 1276 | | 1398 | |
| | 20 m | 2409 | 1861 | | | | 1390 |
| | 30 m | | | 1111 | | 1250 | |
| | 1 hr | 2224 | 1619 | 937 | 1421 | 1141 | 1515 |
| | 2 hr | | | 1480 | | 1703 | |
| | 3 hr | 1502 | 1677 | | | | 1899 |
| | 6 hr | 2792 | 2040 | | 1400 | | 123 |

TABLE-2

Time Course of Calculated Conc. for dexamethasone in human whole blood (nM)

| Matrix | Time | Dexamethasone | 4-3 | 5-3 | 1.4 | 3-4 | 2-7 |
| --- | --- | --- | --- | --- | --- | --- | --- |
| | Matrix Spiking | 2939 | 4 | 0 | 2 | 0 | 0 |
| | 0 m | 1687 | 0 | 0 | 0 | 0 | 0 |
| | 5 m | | | 0 | | 0 | |
| | 10 m | | | | | | |
| | 15 m | | | 0 | | 0 | |
| | 20 m | 2409 | 0 | | | | 0 |
| | 30 m | | | 0 | | 0 | |
| | 1 hr | 2224 | 0 | 0 | 0 | 0 | 0 |
| | 2 hr | | | 0 | | 0 | |
| | 3 hr | 1502 | 1 | | | | 0 |
| | 6 hr | 2792 | 3 | | 0 | | 0 |

General Experimental Procedure

Human Blood Incubation Human blood was collected the morning of the experiment from at least 3 individuals using K2EDTA as the anticoagulant. An equal volume from each individual was combined for use in the experiment. The experiment started no more than 2 hours after the blood collection. All drug-linker conjugates were solubilized in DMSO to form each 10 mM stock solution. Dosing solution for each linker was prepared by serial dilution of each stock solution using 1:3 acetonitrile:water. All solutions were kept on ice during the experiment.

Human blood was pre-warmed in a 37° C. water bath in an appropriate volume to collect samples over a time course from 0 through 6 hours. Incubating blood was mixed well just prior to sampling to give a homogenous mixture. Aliquots of blood were removed at appropriate time points, added to cold stopping solution, which was methanol containing an appropriate internal standard, and mixed rigorously. The samples were centrifuged at 4000 RPM for 10 minutes after which equal volumes of the supernatant fractions were diluted with cold deionized water. The samples were then ready for analysis. A time 0 sample was prepared by spiking blood, which had been pretreated with the same stopping reagent used above with the drug-linker. This sample is referred to in the tables as the matrix spiking.

Representative dexamethasone-linkers 4-3, 5-3, 1-4, 3-4, and 2-7 were studied for their stability (Table 4) and propensity to release dexamethasone (Table 5) in purified rat liver lysosomal lysates. Tables 4 and 5 show that the different dexamethasone-linkers released dexamethasone at different rates depending on the structure of the tuning element. For example, 3-4 was no longer detectable after 10 minutes incubation in the rat lysosomal extract whereas for 4-3 and 5-3 the dexamethasone was more slowly released with 5-3 releasing dexamethasone faster than 4-3.

TABLE 3

Time Course of Calculated Conc. for each compound in rat lysomal lysate (nM)

| Matrix | Time | Dexa-methasone | 4-3 | 5-3 | 1.4 | 3-4 | 2-7 |
|---|---|---|---|---|---|---|---|
| | Matrix spiking | 2059.0 | 1590.7 | 2555.29 | 2487.3 | 3128.83 | 2228 |
| | 0 m | 1456.4 | 888.8 | 1394.08 | 1148.2 | 1252 | 1327 |
| | 5 m | 1851.2 | 1156.1 | 1295.86 | 158.2 | 501.28 | 56 |
| | 10 m | 1640.8 | 983.4 | 1278.4 | 19.0 | 149.18 | 512 |
| | 15 m | 1666.7 | 1032.6 | 1407.73 | 3.7 | N/A | 0 |
| | 30 m | 1602.6 | 980.1 | 1175.39 | N/A | N/A | 37 |
| | 1 hr | 1576.8 | 882.4 | 970.65 | N/A | N/A | 0 |
| | 2 hr | 1681.0 | 880.1 | 743.45 | N/A | N/A | 0 |
| | 3 hr | 1689.7 | 903.8 | 500.41 | N/A | N/A | 0 |
| | 6 hr | 1689.8 | 858.9 | 221.03 | N/A | N/A | 0 |

TABLE 4

Time Course of Calculated Conc. for dexamethasone rat lysomeal lysate (nM)

| Matrix | Time | Dexa-methasone | 4-3 | 5-3 | 1.4 | 3-4 | 2-7 |
|---|---|---|---|---|---|---|---|
| | Matrix Spiking | 2059.0 | N/A | N/A | N/A | N/A | 17 |
| | 0 m | 1456.4 | 0.9 | N/A | 4.7 | 15.74 | 44 |
| | 5 m | 1851.2 | 14.5 | 10.25 | 320.7 | 100.44 | 415 |
| | 10 m | 1640.8 | 14.2 | 21.56 | 559.4 | 209.07 | 682 |
| | 15 m | 1666.7 | 22.3 | 31.68 | 831.7 | 285.67 | 808 |
| | 30 m | 1602.6 | 28.9 | 78.6 | 1059.6 | 425.28 | 1039 |
| | 1 hr | 1576.8 | 41.6 | 162.45 | 1148.8 | 526.5 | 1159 |
| | 2 hr | 1681.0 | 72.5 | 290.66 | 854.5 | 534.84 | 1309 |
| | 3 hr | 1689.7 | 90.2 | 379.36 | 841.9 | 584.61 | 1207 |
| | 6 hr | 1689.8 | 141.9 | 550.43 | 826.6 | 561.88 | 1155 |

General Experimental Procedure

Rat Lysosome Incubation.

Rat Liver lysosomes were available commercially with a pool of 6 animals. All linker compounds were solubilized in DMSO to form each 10 mM stock solution. Dosing solution for each linker was prepared by serial dilution of each stock solution using 1:3 acetonitrile: water. All solutions were kept on ice during the experiment.

Rat lysosomes were pre-warmed in a 37° C. water bath in an appropriate volume to collect samples over a time course from 0 minutes through 6 hours. Incubating lysosomes were mixed well just prior to sampling to give a homogenous mixture. Aliquots of lysosomes were removed at appropriate time points, added to cold stopping solution, which was methanol containing an appropriate internal standard, and mixed rigorously. The samples were centrifuged at 4000 RPM for 10 minutes after which equal volumes of supernatant were diluted with cold deionized water. The samples were ready for analysis. A time 0 sample was prepared by spiking the drug-linker to lysosomes which had been pretreated with the same stopping reagent as above. This sample is referred to as matrix spiking in the tables.

Liquid Chromatography—Tandem Mass Spectrometry Analysis

A Thermo LX-2 ultra-performance liquid chromatography system coupled with a Sciex API5000 triple quadrupole mass spectrometer was used for the analysis. The payload and drug-linkers were retained and separated by a C18 column and detected by the mass spectrometer. The standard curve for each analyte was prepared to obtain the quantitative results. Samples were kept in cold stack set at 5° C.

Example 20

Synthesis, Purification and Analysis of ADC Using Exemplary Drug-Linker 1-4

To establish the chemical reactivity of this linker design to form a drug conjugate, exemplary drug-linker 1-4 was conjugated to an anti-mouse CD25 antibody (IgG1) (mCD25) to produce antibody-drug conjugate ADC 12-1 or anti-human CD70 antibody (hCD70) to produce ADC 12-2. Specifically, the drug-linker was conjugated to the unnatural amino acid para-azidophenylalanine (pAzF) replacing the alanine at position 1 of CH1 of the antibody using copper-free 3+2 cycloaddition chemistry. Synthesis of antibodies containing an unnatural amino acid has been described in U.S. Pat. No. 7,632,924, incorporated herein by reference, and copper-free 3+2 cycloaddition chemistry has been described in U.S. Pat. No. 7,807,619, incorporated herein by reference. Conjugation, purification, and analysis confirmed synthesis of the Anti-CD25 antibody-drug conjugate ADC 12-1 and the anti-CD70 ADC 12-2.

Experimental for Conjugation of Phosphate Linker 1-4 to Antibodies.

Antibodies were purified over protein A column (NovaSep) followed by SP 650S column (Tosoh Biosciences). The heavy chain and light chain of the anti-CD25 antibody comprise SEQ ID NO:81 and SEQ ID NO:82, respectively, wherein X is pAzF. The heavy chain and light chain of the anti-CD70 antibody comprise SEQ ID NO:89 and SEQ ID NO:80, respectively, wherein X is pAzF.

Site Specific Conjugation Using Click (2+3) Chemistry.

Para-azidophenylalanine containing antibodies were buffer exchanged into 50 mM Histidine; 100 mM NaCl; 2.5% Trehalose; 0-20% Dimethylamine, pH 6.0 and concentrated to 1-20 mg/mL. 10-15 molar equivalents of cyclooctyne drug-linker were added and reacted for 16-72 hours at 28-30° C. The antibody conjugates were purified over a SP 650S column (Tosoh Biosciences) to remove excess reagents. The conjugates were buffer exchanged into 50 mM Histidine; 100 mM NaCl; 2.5% Trehalose; pH 6.0, 0.22 μm filtered, and stored at 4° C.

Conjugation Analysis.

Conjugation efficiency and DAR values were determined by reversed phase HPLC. The ADC was run over a Zorbax 300SB-C3 column, 4.6×150 mm (Agilent) at 80° C. and eluted with a linear gradient from 30% B to 90% B (A: water, 0.1% TFA; B: acetonitrile, 0.1% TFA). An Agilent 1200 series HPLC system and Chemstation software were used to resolve and quantify percentage of antibody conjugated with drug-linker.

Example 21

Serum Stability of ADC 12-1

Drug conjugates may be designed with a stable linker to ensure that the attached payload adopts the pharmacokinetic properties of the carrier. In the example of antibody drug conjugates, premature release of the payload will reduce the total payload delivered to a target cell. To establish the potential for circulatory stability of this linker design in the context of a drug conjugate, ADC 12-1 was incubated in mouse serum and monitored for degradation or loss of payload (dexamethasone). As shown in FIG. 2, no measurable loss of dexamethasone was observed over three weeks incubation in serum.

In Vitro Stability Study Design in DBA1 Mice Serum

For the in vitro stability study, the ADC 12-1 was spiked in DBA1 mice serum at 0.1 mg/mL. Samples were sealed under nitrogen, placed at 37° C. in a cell culture incubator and stored at −80° C. until analysis. Time points from 0 min to 21 days of incubation were evaluated.

In Vitro Stability—Free Payload Analysis

Samples were evaluated for free dexamethasone by LC-MS/MS. For the in vitro stability study, 40 μL of serum for each time point underwent protein precipitation with 400 μL acetonitrile containing dexamethasone-d4 (internal standard). Tubes were centrifuged at 14000 RPM (4° C.) for 10 minutes and the supernatant fraction removed and dried in a speed vac. Samples were reconstituted with methanol/water (50/50) and injected in an Acquity/TSQ Vantage triple quad mass spectrometer equipped with an Xbridge C18 column (Waters, Milford). Mobile phases consisted of buffers A (water:acetonitrile:formic acid, 95:5:0.1%) and B (acetonitrile:water:formic acid, 80:20:0.1%) and a linear gradient was performed with buffer B increasing from 30 to 65% in 3 minutes. Flow rate was set at 0.3 mL/minutes. Transitions for acetate adduct of dexamethasone and dexamethasone d-4 were 437>361 and 441>363, respectively. Compounds were detected using negative electrospray ionization. Free dexamethasone was not be detected in the in vitro stability serum samples over the period evaluated.

In Vitro Stability—Immunoprecipitation Coupled to Intact Mass Analysis

ADC 12-1 was pulled down from mice serum using immunoprecipitation (IP) with streptavidin magnetic beads (Dynabeads M-280) coupled to biotinylated CD25 (antigen). Beads were washed 3 times with 100 μL of TBS 1×. Two microliters of 1 mg/mL biotinylated CD25 was added to 30 μL of each sample (serum from each time point) and incubated for 10 minutes at room temperature (RT). Samples were added to the pre-washed beads and incubated for 30 minutes at RT under gentle shaking. The flow through was discarded and beads were washed twice with 0.02% Rapigest in TBS 1×. Elution was performed with 30 μL of TFA 0.1% and 5 μL of each sample was analyzed in an UPLC/Synapt G2-S (Waters, Milford) equipped with a POROS column (ABSciex) using reverse phase gradient.

Spectra deconvolution was performed using MaxEnt1 software (Waters, Milford) and results were compared against the intact mass obtained for the ADC from a stock solution (FIG. 3). FIG. 3 shows a deconvoluted intact mass spectrum for the ADC 12-1 stock solution. G0F, G1F and G2F in the figure refer to the carbohydrate isoforms on the antibody portion of the antibody-drug conjugate.

The deconvoluted spectra of the stock solution (FIG. 3) revealed that the antibody-drug conjugate 12-1 intact mass in its predominant DAR 2 form contained two G0F sugar motifs. Additional peaks at about 162 Da apart showed two other glycoforms containing G0F/G1F (peak at 148701 Da) and 2× G1F (peak at 148863 Da). The glycan profile is typical of that for an IgG.

FIG. 4A-4D shows the deconvoluted spectra of time points 1 hour, 8 hours, 14 days and 21 days from the in vitro stability study. The data analysis showed that no significant mass change occurred for the ADC over the incubation period evaluated in the study (Table 6: intact mass results for the in-vitro stability study).

TABLE 6

| In vitro Stability | |
|---|---|
| MW of the ADC 12-1 (2×G0F form) | Incubation Time |
| 148539 | 1 hour |
| 148539 | 8 hours |
| 148539 | 2 days |
| 148539 | 3 days |
| 148540 | 7 days |
| 148540 | 14 days |
| 148540 | 21 days |

In Vivo Stability of ADC 12-1

Effective linker designs will not only provide stable tethering to a carrier in drug conjugates, but should also have minimal to no effect on the pharmacokinetic properties of the carrier itself. To establish the potential of this linker design for in vivo circulatory stability and to understand its impact on the pharmacokinetics of the conjugated carrier in the context of a drug conjugate, ADC 12-1 was dosed to DB 1 mice and was monitored for degradation of the mAb, intactness of the antibody-drug conjugate, and loss of payload (dexamethasone). Importantly, the study showed that the inherent pharmacokinetics of naked (non-conjugated) anti-mouse CD25 was not adversely affected by the conjugation of two molecules of drug-linker 1-4 to the antibody. Furthermore, the study showed that no loss of drug linker and no measurable dexamethasone were observed over the course of the 5 day study. The data shows that drug-linker 1-4 was stable in circulation and retained payload on the carrier in this example of an antibody-drug conjugate.

In Vivo Pharmacokinetic (PK)/Stability Study

General Experimental for In Vivo PK Study of ADC 12-1

An in vivo study in DBA1 mice was performed in order to evaluate stability and pharmacokinetics of ADC 12-1. Naked antibody was administered intravenously in a single bolus to all groups. Group 1 was given a dose of 2 mpk; Group 2 and Group 3 were dosed 2 and 4 mpk of ADC 12-1, respectively. Plasma samples were taken from all three groups at 1, 2, 6, 16 hrs and 1, 2, 3, 5 days after dosing. At each of these time points, three animals per group were sacrificed to obtain plasma sample. Samples from group 1 were analyzed for total naked antibody contents, samples from groups 2 and 3 were submitted for total antibody, intact antibody and free-payload analysis. FIG. 5 shows the In vivo stability of ADC 12-1 following IV dosing to DBA1 mice.

In Vivo Pharmacokinetic (PK)/Stability Study—Free Payload Analysis

PK study samples were evaluated for free dexamethasone using the method described above. For increased sensitivity, 100 μL of serum from one mice of each time point was submitted to protein precipitation with acetonitrile. Free dexamethasone was not detected in any PK samples.

In Vivo Pharmacokinetic (PK)/Stability Study—Intact Antibody Drug Conjugate Mass Analysis Samples from the ADC 12-1 PK study were also evaluated for stability using immunoprecipitation coupled to intact mass analysis. 50 μL of each sample was processed as described above. The results showed no molecular weight change for the antibody-drug conjugate over the study time range (from 1 hour to 5 days) (FIG. 6A-6B, Table 7).

TABLE 7

In vivo PK/Stability Intact Mass Results

| Sample | MW of the 12-1 (2xG0F motif) | PK Group | Time Point |
| --- | --- | --- | --- |
| B1 | 148548 | G2 | 1 hour |
| C1 | 148547 | G2 | 1 hour |
| E1 | 148546 | G2 | 2 hours |
| F1 | 148548 | G2 | 2 hours |
| A2 | 148546 | G2 | 6 hours |
| C2 | 148546 | G2 | 16 hours |
| D2 | 148547 | G2 | 16 hours |
| F2 | 148545 | G2 | 1 day |
| G2 | 148548 | G2 | 1 day |
| A3 | 148546 | G2 | 2 days |
| D3 | 148548 | G2 | 3 days |
| G3 | 148550 | G2 | 5 days |
| H3 | 148542 | G2 | 5 days |
| B7 | 148542 | G3 | 1 hour |
| C7 | 148548 | G3 | 1 hour |
| E7 | 148547 | G3 | 2 hours |
| F7 | 148545 | G3 | 2 hours |
| A8 | 148547 | G3 | 6 hours |
| C8 | 148546 | G3 | 16 hours |
| D8 | 148546 | G3 | 16 hours |
| F8 | 148546 | G3 | 1 day |
| G8 | 148546 | G3 | 1 day |
| A9 | 148544 | G3 | 2 days |
| B9 | 148547 | G3 | 2 days |
| D9 | 148549 | G3 | 3 days |
| E9 | 148550 | G3 | 3 days |
| G9 | 148547 | G3 | 5 days |
| H9 | 148545 | G3 | 5 days |

In Vivo Pharmacokinetic (PK)/Stability Study Naked/Total mAb Analysis

Plasma samples from in vivo PK study were analyzed for naked Antibody/total Antibody ADC 12-1 concentrations using Meso Scale Discovery (MSD) based electro-chemiluminescence method. The capture reagent is recombinant mouse IL-2R alpha (CD25) for both assays. The detection reagent may be goat anti-rat IgG for naked antibody/total Antibody and anti-dex mAb (e.g., Rabbit polyclonal anti-dexamethasone (Abcam Cat # ab35000)) may be used to detect ADC 12-1, respectively. Briefly, 96 well MSD plates were coated with the capture reagent and then washed. Plates were blocked for 1 hour and washed again. Samples were then added and incubated for 2 hours. Following incubation, plates were washed, incubated with the detection antibody for 1 hour, and washed again. The reading buffer was added and the plates were read using MSD plate reader.

Example 22

In this example, anti-CD70 antibody 2H5 was conjugated to exemplary drug-linker 1-4 to produce ADC 12-2 (FIG. 1) as described for making ADC 12-1 in Example 20. In vitro activity and targeted delivery of ADC 12-2, naked antibody, and anti-hexon conjugate control were assessed by transfecting into 786-O (renal cell) and then measuring glucocorticoid-induced leucine zipper (GILZ) mRNA, a widely expressed dexamethasone-induced mRNA transcript. As shown in FIG. 7, ADC 12-2 displayed potent in vitro activity (0.7 ug/ml IP value) in 786-O cells that were confirmed to express CD70. This activity reflects dexamethasone conjugation and targeted delivery as the nonconjugated IgG variant and anti-hexon controls did not induce and observable GILZ in this cell line.

786-O cells were plated at 30K cells/well overnight at 37° C. in RPMI Media as suggested by ATCC (+10% HI FBS). Cells were stimulated with ADCs for 2, 6, or 24 hours at 37° C. Cells were lysed using RLT and RNA is isolated using RNeasy 96 Kits. PCR was used to measure GAPDH, PER1, or TSC22D3

Quantitation of Glucocorticoid-induced leucine zipper (GILZ) mRNA expression was determined as follows. Cellular quantitation of GILZ mRNA was conducted using the following method. Cells suspension were prepared in HBSS+2% FBS (assay buffer) and plated at $5 \times 10^4$ cells per well. Dosing solutions for free drug, ADCs and parental antibodies were prepared by serial dilution of each stock solution using 1:3 in HBSS+2% FBS supplemented with 1% final concentration of (50 mM Histidine, 100 mM NaCl, 5% Trehalose, pH 6.0), and incubated with cells final concentrations ranging from 20 to 0.002 μg/ml and 100 to 0.01 ng dexamethasone/ml for 18 hours. Cell lysis, cDNA synthesis, and real-time PCR were performed according to manufacturer's instructions using TaqMan Gene Expression Cells-to-$C_T$™ Kit (Invitrogen, Carlsbad, Calif.). Specific primers against human GILZ and GAPDH were purchased from the Life Technologies (Invitrogen, Carlsbad, Calif.). Real-time PCR reactions were performed on the Applied Biosystems 7900 HT Fast Real-Time PCR System. Thermal cycling conditions consisted of an initial UDG incubation hold (50° C., 2 min) denaturing and enzyme activation step (95° C., 2 min) followed by 40 cycles of denaturing (95° C., 15 s), annealing and extending (60° C., 1 min). The mRNA levels were normalized to GAPDH (internal control) using the formula Δ threshold cycle (CT)=CT target−CT reference. The differential expression signal were expressed as delta Ct (ΔCt) by subtracting the Ct values of the un-stimulated samples (containing only assay buffer or DMSO vehicle) from those of the stimulated samples and expressed as relative fold of change using the formula: $2^{\Delta\Delta CT}$.

Example 23

The example shows that conjugates comprising the phosphate-based links have little or no propensity to form aggregates.

Aggregation Assay

An SE-HPLC method was used to conduct the aggregation/% monomer analysis. An isocratic gradient using 0.2 M potassium phosphate, 0.25 M potassium chloride pH 6.0 was used as the mobile phase at a flowrate of 0.5 mL/min. The column used was a Sepax Zenix-C SEC-300, 3 μm, 300 A, 7.8×300 mm (Cat #233300-7830). Detection of signal was monitored at 214 nm (280 for FIO). For a representative run, the analyte load was 10 μg.

The results are shown in Table 8.

TABLE 8

| Sample Name | Drug-Linker | % High Molecular Weight (aggregate) | % Monomer |
|---|---|---|---|
| ADC 12-1 | Phos-21Dex365 (1-4) | 1.4 | 98.6 |
| ADC 12-2 | Phos-21Dex365 (1-4) | 0.9 | 99.1 |

Example 24

In this example, anti-CD74 antibody LL1 (or negative control IgG1 isotype) was conjugated to exemplary drug-linkers 1-4, 2-7, 3-4, 4-3, 5-3, 6-2, 9-4 to produce ADC 12-4, 12-5, 12-6, 12-7, 12-9, 12-10, 12-11, 12-12 (Table 9) as described for making ADC 12-1 in Example 20. The anti-CD74 antibody LL1 comprises a heavy chain (HC) having the amino acid sequence shown in SEQ ID NO:69 and a light chain (LC) having the amino acid sequence shown in SEQ ID NO:73. The amino acid at position 121 is para-azido phenylalanine (pAzF), which was the site for conjugating the exemplary drug-linkers using copper-free 3+2 cycloaddition chemistry to produce the ADCs. The construction of ADC 12-4 is illustrated in FIG. 1.

TABLE 9

| Antibody | Linker | ADC |
|---|---|---|
| Anti-hCD74 (LL1) | Linker 1-4 | ADC 12-4 |
| Anti-hCD74 (LL1) | Linker 2-7 | ADC 12-5 |
| Anti-hCD74 (LL1) | Linker 3-4 | ADC 12-6 |
| Anti-hCD74 (LL1) | Linker 4-3 | ADC 12-7 |
| Anti-hCD74 (LL1) | Linker 6-2 | ADC 12-9 |

TABLE 9-continued

| Antibody | Linker | ADC |
|---|---|---|
| Anti-hCD74 (LL1) | Linker 9-4 | ADC 12-10 |
| IgG1 (neg control) | Linker 1-4 | ADC 12-11 |
| IgG1 (neg control) | Linker 9-4 | ADC 12-12 |
| Anti-hCD74 (clone11) | Linker 9-4 | ADC 12-13 |
| Anti-hCD74 (clone11) | Linker 15-5 | ADC 12-14 |
| Anti-hCD74 (clone11) | Linker 16-5 | ADC 12-15 |

In vitro activity and targeted delivery of ADC 12-4, 12-5, 12-6, 12-7, 12-9, 12-10, the isotype-matched negative controls 12-11, 12-12, and naked anti-hCD74 (LL1) control were assessed in HUT-78 an SUDHL-6 cells (CD74 positive T and B lymphoma cell lines respectively) as well as 786-O cells (a CD74 negative renal carcinoma cell line). The cells were treated with individual ADC, anti-hCD74 antibody, or budesonide (Bud) for 18 hours and then glucocorticoid-induced leucine zipper (GILZ) mRNA, a glucocorticoid-regulated gene, was measured by RT-PCR. As shown in FIGS. 8 and 9, the tested ADCs displayed a range of potency in up-regulating GILZ mRNA in both HUT-78 and SUDHL-6 cells, with ADC 12-10 most active with an EC50 value of about 0.2 µg/mL in both cell lines (see Table 10). In contrast, the isotype-matched negative control ADCs did not induce measurable GILZ mRNA in both cell lines. Furthermore, all the ADCs did not induce measurable GILZ mRNA except at the highest concentration (30 µg/mL) in 786-O cells (FIG. 10). (The activity at the highest concentration in 786-O cells may be due to impurity of the sample or possible low CD74 expression in cells.). The overall activity profile of the ADC is consistent with targeted delivery of a payload (e.g. dexamethasone or budesonide) that is dependent on the binding and internalization of the antibody with its antigen on the cell surface, and on the efficiency of linker cleavage inside the cells.

TABLE 10

The Max effects and the $EC_{50}$ values of ADC and budesonide on human cell lines

| ADC or Antibody | HUT-78 cells | | SUDHL-6 cells | | 786-0 cells (CD74(—)) | |
|---|---|---|---|---|---|---|
| | Emax | $EC_{50}$ (µg/mL) | Emax | $EC_{50}$ (µg/mL) | Emax | $EC_{50}$ (µg/mL) |
| ADC 12-4 (LL1) | 3.95 | 1.08 | 3.44 | 0.99 | 1.71 | >30 |
| ADC 12-5 (LL1) | 4.13 | 1.32 | 3.4 | 0.4 | 1.34 | >30 |
| ADC 12-6 (LL1) | 4.61 | 1.87 | 3.33 | 0.47 | 2.26 | >30 |
| ADC 12-7 (LL1) | 1.93 | >30 | 1.52 | 14.3 | 1.73 | >30 |
| ADC 12-9 (LL1) | 2.55 | >30 | 6.48 | >30 | 4.02 | >30 |
| ADC 12-10 (LL1) | 6.47 | 0.2 | 5.89 | 0.21 | 3.52 | >30 |
| ADC 12-11 (IgG1) | 0.99 | N/A | 1.13 | >30 | 1.14 | >30 |
| ADC 12-12 (IgG1) | 0.99 | N/A | 1.28 | >30 | 2.66 | >30 |
| ADC12-13 (Clone 11) | 4.94 | 0.2 | 6.77 | 0.63 | 9.19 | >30 |
| CD74 Ab (LL1) | 1.34 | N/A | 1.02 | N/A | 1.02 | N/A |
| ADC 12-14 (Clone 11) | 8.36 | 0.055 | 14.2 | 0.023 | 18.78 | 4.45 |
| ADC 12-15 (Clone11) | 8.34 | 0.26 | 7.53 | 0.67 | 5.26 | >30 |
| Budesonide | 9.03 | 0.65 (nM) | 14.33 | 2.21 (nM) | 25.68 | 0.58 (nM) |
| Fluticasone Propionate | 10.27 | 0.45 (nM) | 15.78 | 0.52 (nM) | 25.38 | 0.46 (nM) |

N/A: $EC_{50}$ value can't be generated.

Materials and Methods

The HUT-78 (ATCC TIB-161), SUDHL-6 (ATCC CRL-2959) and 786-O (ATCC CRL-1932) cells were purchased from ATCC and maintained in culture medium as suggested by ATCC, in which Iscove's MDM/20% HI FBS for HUT-78 cells and RPMI-1640/10% FBS for SUDHL-6 and 786-O cells.

The quantitation of Glucocorticoid-induced leucine zipper (GILZ) mRNA expression was determined by real time-PCR. In brief, actively growing cells were harvested and then resuspended in the assay buffer (HBSS plus 2% FBS) at concentration of $1.1\times10^6$/ml. $5\times10^4$ cells/well in 45 µl volume were plated to Greiner 384 well v-bottom reagent plates (Ref #781280). Dosing solutions for free drug, ADCs and parental antibodies were prepared in the v-bottom Greiner reagent plates at 10-fold over the final concentration by serial dilution of each stock solution using 1:3 in HBSS+ 2% FBS supplemented with 1% final concentration of (50 mM Histidine, 100 mM NaCl, 5% Trehalose, pH 6.0), and 5 µl of the 10-fold solutions were added to each well to reach final concentrations ranging from 30 to 0.0005 µg/ml for ADC/parental antibody and 100 to 0.002 nM for dexamethasone or budesonide (11 concentrations). After 18 hour incubation, the cells were lysed, and the lysates were used for cDNA synthesis and real-time PCR, according to manufacturer's instructions in TaqMan Gene Expression Cells-to-$C_T$™ Kit (Invitrogen, Carlsbad, Calif.). Specific primers against human GILZ and GAPDH were purchased from the Life Technologies (Invitrogen, Carlsbad, Calif.). Real-time PCR reactions were performed on the Applied Biosystems 7900 HT Fast Real-Time PCR System. Thermal cycling conditions consisted of an initial UDG incubation hold (50° C., 2 min) denaturing and enzyme activation step (95° C., 2 min) followed by 40 cycles of denaturing (95° C., 15 s), annealing and extending (60° C., 1 min). The mRNA levels were normalized to GAPDH (internal control) using the formula Δ threshold cycle (CT)=CT target−CT reference. The differential expression signal were expressed as delta Ct (ΔCt) by subtracting the Ct values of the un-stimulated samples (containing only assay buffer or DMSO vehicle) from those of the stimulated samples and expressed as relative fold of change using the formula: $2^{\Delta\Delta CT}$. The graphs were generated in GraphPad Prism and the $EC_{50}$ values were calculated with non-linear regression curve fit of the data in GraphPad Prism.

Example 25

The anti-CD74 antibody LL1 (or negative control isotype) was conjugated to exemplary drug-linkers 15-5, 16-5, or 17-2 as described for making ADC 12-1 to make ADC 12-13, ADC 12-14, and ADC 12-15, respectively. The anti-CD74 antibody LL1 comprises a heavy chain (HC) having the amino acid sequence shown in SEQ ID NO:69 and a light chain (LC) having the amino acid sequence shown in SEQ ID NO:73. The amino acid at position 121 is para-azido phenylalanine (pAzF) and may serve as the site for conjugating the exemplary drug-linkers using copper-free 3+2 cycloaddition chemistry to produce the ADCs.

Table of Sequences

| SEQ ID NO: | Description | Amino Acid Sequence |
|---|---|---|
| 1 | Anti-CD25 LC CDR1 | RASQSVSSYLA |
| 2 | Anti-CD25 LC CDR2 | GASSRAT |
| 3 | Anti-CD25 LC CDR3 | QQYSSSPLT |
| 4 | Anti-CD25 HC CDR1 | RYIIN |
| 5 | Anti-CD25 HC CDR2 | RIIPILGVENYAQKFQG |
| 6 | Anti-CD25 HC CDR3 | KDWFDY |
| 7 | Anti-CD25 HC CDR1 | RYPIN |
| 8 | Anti-CD25 HC CDR2 | RIIPILGIADYAQRFQG |
| 9 | Anti-CD25 HC CDR3 | RDWGDY |
| 10 | Anti-CD25 LC CDR3 | QQYGSSPIT |
| 11 | Anti-CD25 HC CDR1 | RYAIN |
| 12 | Anti-CD25 HC CDR2 | RIIPILDIADYAQKFQD |
| 13 | Anti-CD25 HC CDR3 | KDWFDP |
| 14 | Anti-CD25 HC CDR1 | RYPIN |
| 15 | Anti-CD70 LC CDR1 | RASQSVSSYLA |
| 16 | Anti-CD70 LC CDR2 | YDASNRAT |
| 17 | Anti-CD70 LC CDR3 | QQRTNWPLT |
| 18 | Anti-CD70 HC CDR1 | SYIMH |
| 19 | Anti-CD70 HC CDR2 | VISYDGRNKYYADSVK |
| 20 | Anti-CD70 HC CDR3 | DTDGYDFDY |
| 21 | Anti-CD70 LC CDR1 | RASQGISSALA |
| 22 | Anti-CD70 LC CDR2 | DASSLES |
| 23 | Anti-CD70 LC CDR3 | QQFNSYPFT |
| 24 | Anti-CD70 HC CDR1 | YYAMH |
| 25 | Anti-CD70 HC CDR2 | VISYDGSIKYYADSVK |
| 26 | Anti-CD70 HC CDR3 | EGPYSNYLDY |
| 27 | Anti-CD70 LC CDR1 | RASQGISSWLA |
| 28 | Anti-CD70 LC CDR2 | AASSLQS |
| 29 | Anti-CD70 LC CDR3 | QQYNSYPLT |
| 30 | Anti-CD70 HC CDR1 | DYGMH |
| 31 | Anti-CD70 HC CDR2 | VIWYDGSNKYYADSVK |
| 32 | Anti-CD70 HC CDR3 | DSIVMVRGDY |
| 33 | Anti-CD70 LC CDR1 | RASQGISSWLA |
| 34 | Anti-CD70 LC CDR2 | AASSLQS |
| 35 | Anti-CD70 LC CDR3 | QQYNSYPLT |
| 36 | Anti-CD70 HC CDR1 | DHGMH |
| 37 | Anti-CD70 HC CDR2 | VIWYDGSNKYYADSVK |

Table of Sequences

| SEQ ID NO: | Description | Amino Acid Sequence |
|---|---|---|
| 38 | Anti-CD70 HC CDR3 | DSIMVRGDY |
| 39 | Anti-CD70 LC CDR2 | DASNRAT |
| 40 | Anti-CD70 LC CDR3 | QQRSNWPLT |
| 41 | Anti-CD70 HC CDR1 | SDYYWS |
| 42 | Anti-CD70 HC CDR2 | YIYYSGSTNYDPSLKS |
| 43 | Anti-CD70 HC CDR3 | GDGDYGGNCFDY |
| 44 | Anti-CD74 LC CDR1 | RSSQSLVHRNGNTYLH |
| 45 | Anti-CD74 LC CDR2 | TVSNRFS |
| 46 | Anti-CD74 LC CDR3 | SQSSHVPPT |
| 47 | Anti-CD74 HC CDR1 | NYGVN |
| 48 | Anti-CD74 HC CDR2 | WINPNTGEPTFDDDFKG |
| 49 | Anti-CD74 HC CDR3 | SRGKNEAWFAY |
| 50 | Anti-CD74 LC CDR1 | QGISSW |
| 51 | Anti-CD74 LC CDR3 | QQYNSYPLT |
| 52 | Anti-CD74 HC CDR1 | GFTFSSYA |
| 53 | Anti-CD74 HC CDR2 | ISYDGSNK |
| 54 | Anti-CD74 HC CDR3 | ASGRYYGSGSYSSYFD |
| 55 | Anti-CD74 HC CDR2 | ISYDGSIK |
| 56 | Anti-CD74 HC CDR3 | ARGREYTSQNIVILLD |
| 57 | Anti-CD74 HC CDR3 | ARGREITSQNIVILLD |
| 58 | Anti-CD74 HC CDR2 | IWYDGSNK |
| 59 | Anti-CD74 HC CDR3 | ARGGTLVRGAMYGTDV |
| 60 | Anti-CD163 LC CDR1 | ASQSVSSDV |
| 61 | Anti-CD163 LC CDR3 | QDYTSPRT |
| 62 | Anti-CD163 HC CDR1 | GYSITSDY |
| 63 | Anti-CD163 HC CDR3 | CVSGTYYFDYWG |
| 64 | Anti-CD163 LC CDR1 | ASQSVSHDV |
| 65 | Anti-CD163 LC CDR3 | QDYSSPRT |
| 66 | Glycosylation site at N297 of IgG1 | QYNS |
| 67 | Glycosylation site at N297 of IgG4 | QFNS |
| 68 | Mutated glycosylation site of IgG1 or IgG4 | QAQS |
| 69 | Anti-CD74 IgG1; X at position 121 is para-azido-phenylalanine (pAzF) (CDRs bold type; Fc underlined) | QVQLQQSGSELKKPGASVKVSCKAS GYTFTNYGVNWIKQAPGQGLQWMGW INPNTGEPTFDDDFKGRFAFSLDTS VSTAYLQISSLKADDTAVYFCSRSR GKNEAWFAYWGQGSLVTVSSXSTKG PSVFPLAPSSKSTSGGTAALGCLVK DYFPEPVTVSWNSGALTSGVHTFPA VLQSSGLYSLSSVVTVPSSSLGTQT YICNVNHKPSNTKVDKKVEPKSCDK THTCPPCPAPELLGGPSVFLFPPKP KDTLMISRTPEVTCVVVDVSHEDPE VKFNWYVDGVEVHNAKTKPREEQYN STYRVVSVLTVLHQDWLNGKEYKCK VSNKALPAPIEKTISKAKGQPREPQ VYTLPPSRDELTKNQVSLTCLVKGF YPSDIAVEWESNGQPENNYKTTPPV LDSDGSFFLYSKLTVDKSRWQQGNV FSCSVMHEALHNHYTQKSLSLSPGK |
| 70 | Anti-CD74 IgG4; X at position 121 is para-azido-phenylalanine (pAzF) (CDRs bold type; Fc underlined) | QVQLQQSGSELKKPGASVKVSCKAS GYTFTNYGVNWIKQAPGQGLQWMGW INPNTGEPTFDDDFKGRFAFSLDTS VSTAYLQISSLKADDTAVYFCSRSR GKNEAWFAYWGQGSLVTVSSXSTKG PSVFPLAPCSRSTSESTAALGCLVK DYFPEPVTVSWNSGALTSGVHTFPA VLQSSGLYSLSSVVTVPSSSLGTKT YTCNVDHKPSNTKVDKRVESKYGPP CPPCPAPEFLGGPSVFLFPPKPKDT LMISRTPEVTCVVVDVSQEDPEVQF NWYVDGVEVHNAKTKPREEQFNSTY RVVSVLTVLHQDWLNGKEYKCKVSN KGLPSSIEKTISKAKGQPREPQVYT LPPSQEEMTKNQVSLTCLVKGFYPS DIAVEWESNGQPENNYKTTPPVLDS DGSFFLYSRLTVDKSRWQEGNVFSC SVMHEALHNHYTQKSLSLSLGK |
| 71 | Anti-CD74 IgG1 (CDRs bold type; Fc underlined) | QVQLQQSGSELKKPGASVKVSCKAS GYTFTNYGVNWIKQAPGQGLQWMGW INPNTGEPTFDDDFKGRFAFSLDTS VSTAYLQISSLKADDTAVYFCSRSR GKNEAWFAYWGQGSLVTVSSASTKG PSVFPLAPSSKSTSGGTAALGCLVK DYFPEPVTVSWNSGALTSGVHTFPA VLQSSGLYSLSSVVTVPSSSLGTQT YICNVNHKPSNTKVDKKVEPKSCDK THTCPPCPAPELLGGPSVFLFPPKP KDTLMISRTPEVTCVVVDVSHEDPE VKFNWYVDGVEVHNAKTKPREEQYN STYRVVSVLTVLHQDWLNGKEYKCK VSNKALPAPIEKTISKAKGQPREPQ VYTLPPSRDELTKNQVSLTCLVKGF YPSDIAVEWESNGQPENNYKTTPPV LDSDGSFFLYSKLTVDKSRWQQGNV FSCSVMHEALHNHYTQKSLSLSPGK |
| 72 | Anti-CD74 IgG4 (CDRs bold type; Fc underlined) | QVQLQQSGSELKKPGASVKVSCKAS GYTFTNYGVNWIKQAPGQGLQWMGW INPNTGEPTFDDDFKGRFAFSLDTS VSTAYLQISSLKADDTAVYFCSRSR GKNEAWFAYWGQGSLVTVSSASTKG PSVFPLAPCSRSTSESTAALGCLVK DYFPEPVTVSWNSGALTSGVHTFPA VLQSSGLYSLSSVVTVPSSSLGTKT YTCNVDHKPSNTKVDKRVESKYGPP CPPCPAPEFLGGPSVFLFPPKPKDT LMISRTPEVTCVVVDVSQEDPEVQF NWYVDGVEVHNAKTKPREEQFNSTY RVVSVLTVLHQDWLNGKEYKCKVSN KGLPSSIEKTISKAKGQPREPQVYT LPPSQEEMTKNQVSLTCLVKGFYPS DIAVEWESNGQPENNYKTTPPVLDS DGSFFLYSRLTVDKSRWQEGNVFSC SVMHEALHNHYTQKSLSLSLGK |
| 73 | Anti-CD74 LC (CDRs bold type) | DIQLTQSPLSLPVTLGQPASISCRS SQSLVHRNGNTYLHWFQQRPGQSPR LLIYTVSNRFSGVPDRFSGSGSGTD FTLKISRVEAEDVGVYFCSQSSHVP |

Table of Sequences

| SEQ ID NO: | Description | Amino Acid Sequence |
|---|---|---|
| | | PTFGAGTRLEIKRTVAAPSVFIFPP SDEQLKSGTASVVCLLNNFYPREAK VQWKVDNALQSGNSQESVTEQDSKD STYSLSSTLTLSKADYEKHKVYACE VTHQGLSSPVTKSFNRGEC |
| 74 | Anti-CD74 IgG1; X at position 126 is para-azido-phenylalanine (pAzF)(CDRs bold type; Fc underlined) | QVQLVESGGGVVQPGRSLRLSCAAS GFTFSSYAMHWVRQAPGKGLEWVAV ISYDGSIKYYADSVKGRFTISRDNS KNTLYLQMNSLRVEDTAVFYCARGR EEITSQNIVILLDYWGQGTLVTVTS XSTKGPSVFPLAPSSKSTSGGTAAL GCLVKDYFPEPVTVSWNSGALTSGV HTFPAVLQSSGLYSLSSVVTVPSSS LGTQTYICNVNHKPSNTKVDKKVEP KSCDKTHTCPPCPAPELLGGPSVFL FPPKPKDTLMISRTPEVTCVVVDVS HEDPEVKFNWYVDGVEVHNAKTKPR EEQYNSTYRVVSVLTVLHQDWLNGK EYKCKVSNKALPAPIEKTISKAKGQ PREPQVYTLPPSRDELTKNQVSLTC LVKGFYPSDIAVEWESNGQPENNYK TTPPVLDSDGSFFLYSKLTVDKSRW QQGNVFSCSVMHEALHNHYTQKSLS LSPGK |
| 75 | Anti-CD74 IgG4; X at position 126 is para-azido-phenylalanine (pAzF) (CDRs bold type; Fc underlined) | QVQLVESGGGVVQPGRSLRLSCAAS GFTFSSYAMHWVRQAPGKGLEWVAV ISYDGSIKYYADSVKGRFTISRDNS KNTLYLQMNSLRVEDTAVFYCARGR EEITSQNIVILLDYWGQGTLVTVTS XSTKGPSVFPLAPCSRSTSESTAAL GCLVKDYFPEPVTVSWNSGALTSGV HTFPAVLQSSGLYSLSSVVTVPSSS LGTKTYTCNVDHKPSNTKVDKRVES KYGPPCPPCPAPEFLGGPSVFLFPP KPKDTLMISRTPEVTCVVVDVSQED PEVQFNWYVDGVEVHNAKTKPREEQ FNSTYRVVSVLTVLHQDWLNGKEYK CKVSNKGLPSSIEKTISKAKGQPRE PQVYTLPPSQEEMTKNQVSLTCLVK GFYPSDIAVEWESNGQPENNYKTTP PVLDSDGSFFLYSRLTVDKSRWQEG NVFSCSVMHEALHNHYTQKSLSLSL GK |
| 76 | Anti-CD74 IgG1 (CDRs bold type; Fc underlined) | QVQLVESGGGVVQPGRSLRLSCAAS GFTFSSYAMHWVRQAPGKGLEWVAV ISYDGSIKYYADSVKGRFTISRDNS KNTLYLQMNSLRVEDTAVFYCARGR EEITSQNIVILLDYWGQGTLVTVTS ASTKGPSVFPLAPSSKSTSGGTAAL GCLVKDYFPEPVTVSWNSGALTSGV HTFPAVLQSSGLYSLSSVVTVPSSS LGTQTYICNVNHKPSNTKVDKKVEP KSCDKTHTCPPCPAPELLGGPSVFL FPPKPKDTLMISRTPEVTCVVVDVS HEDPEVKFNWYVDGVEVHNAKTKPR EEQYNSTYRVVSVLTVLHQDWLNGK EYKCKVSNKALPAPIEKTISKAKGQ PREPQVYTLPPSRDELTKNQVSLTC LVKGFYPSDIAVEWESNGQPENNYK TTPPVLDSDGSFFLYSKLTVDKSRW QQGNVFSCSVMHEALHNHYTQKSLS LSPGK |
| 77 | Anti-CD74 IgG4 (CDRs bold type; Fc underlined) | QVQLVESGGGVVQPGRSLRLSCAAS GFTFSSYAMHWVRQAPGKGLEWVAV ISYDGSIKYYADSVKGRFTISRDNS KNTLYLQMNSLRVEDTAVFYCARGR EEITSQNIVILLDYWGQGTLVTVTS ASTKGPSVFPLAPCSRSTSESTAAL GCLVKDYFPEPVTVSWNSGALTSGV HTFPAVLQSSGLYSLSSVVTVPSSS LGTKTYTCNVDHKPSNTKVDKRVES KYGPPCPPCPAPEFLGGPSVFLFPP KPKDTLMISRTPEVTCVVVDVSQED PEVQFNWYVDGVEVHNAKTKPREEQ FNSTYRVVSVLTVLHQDWLNGKEYK CKVSNKGLPSSIEKTISKAKGQPRE PQVYTLPPSQEEMTKNQVSLTCLVK GFYPSDIAVEWESNGQPENNYKTTP PVLDSDGSFFLYSRLTVDKSRWQEG NVFSCSVMHEALHNHYTQKSLSLSL GK |
| 78 | Anti-CD74 LC (CDRs bold type) | DIQMTQSPSSLSASVGDRVTITCRA SQGISSWLAWYQQKPEKAPKSLIYA ASSLQSGVPSRFSGSGSGTDFTLTI SSLQPEDFATYYCQQYNSYPLTFGG GTKVEIKRTVAAPSVFIFPPSDEQL KSGTASVVCLLNNFYPREAKVQWKV DNALQSGNSQESVTEQDSKDSTYSL SSTLTLSKADYEKHKVYACEVTHQG LSSPVTKSFNRGEC |
| 79 | Anti-CD70 2H5 IgG1 X at position 119 is para-azido-phenylalanine (pAF) (CDRs bold type; Fc underlined) | QVQLVESGGGVVQPGRSLRLSCAAS GFTFSSYIMHWVRQAPGKGLEWVAV ISYDGRNKYYADSVKGRFTISRDNS KNTLYLQMNSLRAEDTAVYYCARDT DGYDFDYWGQGTLVTVSSXSTKGPS VFPLAPSSKSTSGGTAALGCLVKDY FPEPVTVSWNSGALTSGVHTFPAVL QSSGLYSLSSVVTVPSSSLGTQTYI CNVNHKPSNTKVDKKVEPKSCDKTH TCPPCPAPELLGGPSVFLFPPKPKD TLMISRTPEVTCVVVDVSHEDPEVK FNWYVDGVEVHNAKTKPREEQYNST YRVVSVLTVLHQDWLNGKEYKCKVS NKALPAPIEKTISKAKGQPREPQVY TLPPSRDELTKNQVSLTCLVKGFYP SDIAVEWESNGQPENNYKTTPPVLD SDGSFFLYSKLTVDKSRWQQGNVFS CSVMHEALHNHYTQKSLSLSPG |
| 80 | Anti-CD70 Kappa light chain (CDRs bold type) | EIVLTQSPATLSLSPGERATLSCRA SQSVSSYLAWYQQKPGQAPRLLIYD ASNRATGIPARFSGSGSGTDFTLTI SSLEPEDFAVYYCQQRTNWPLTFGG GTKVEIKRTVAAPSVFIFPPSDEQL KSGTASVVCLLNNFYPREAKVQWKV DNALQSGNSQESVTEQDSKDSTYSL SSTLTLSKADYEKHKVYACEVTHQG LSSPVTKSFNRGEC |
| 81 | Anti-murine CD25 muIgG1 D265A X at position 115 is para-azido-phenylalanine (pAF) | QVKLLQSGAALVKPGASVKMSCKAS GYSFPDSWVTWVKQSHGKSLEWIGD IFPNSGATNFNEKFKGKATLTVDKS TSTAYMELSRLTSEDSAIYYCTRLD YGYWGQGVMVTVSSXKTTPPSVYPL APGSAAQTNSMVTLGCLVKGYFPEP VTVTWNSGSLSSGVHTFPAVLQSDL YTLSSSVTVPSSTWPSETVTCNVAH PASSTKVDKKIVPRDCGCKPCICTV PEVSSVFIFPPKPKDVLTITLTPKV TCVVVAISKDDPEVQFSWFVDDVEV HTAQTQPREEQFNSTFRSVSELPIM HQDWLNGKEFKCRVNSAAFPAPIEK TISKTKGRPKAPQVYTIPPPKEQMA KDKVSLTCMITDFFPEDITVEWQWN GQPAENYKNTQPIMDTGSYFVYSK LNVQKSNWEAGNTFTCSVLHEGLHN HHTEKSLSHSPGK |

Table of Sequences

| SEQ ID NO: | Description | Amino Acid Sequence |
|---|---|---|
| 82 | Anti-murine CD25 muKappa | DVVLTQTPPTLSATIGQSVSISCRSSQSLLHSNGNTYLNWLLQRPGQPPQLLIYLASRLESGVPNRFSGSGSGTDFTLKISGVEAEDLGVYYCVQSSHFPNTEGVGTKLELKRADAAPTVSIFPPSSEQLTSGGASVVCFLNNFYPKDINVKWKIDGSERQNGVLNSWTDQDSKDSTYSMSSTLTLTKDEYERHNSYTCEATHKTSTSPIVKSFNRNEC |

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

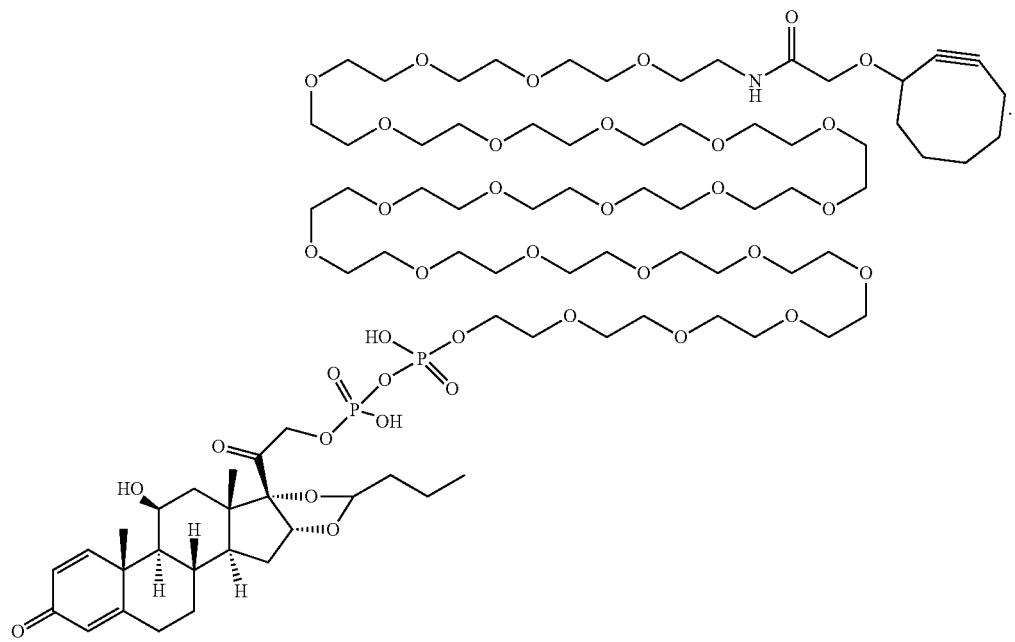

What is claimed is:

1. A composition comprising a compound having formula (I)

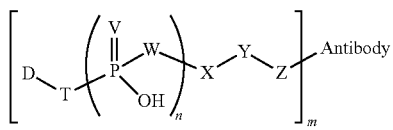

wherein V is selected from O and S;

W is selected from O, N, and $CH_2$;

X is a tuning element selected from a covalent bond; a carbon atom; a heteroatom;

an optionally substituted group selected from the group consisting of acyl, aliphatic, heteroaliphatic, aryl, heteroaryl, and heterocyclic; nucleoside, protease sensitive group, cathepsin B sensitive group, or glycosidase sensitive group;

Y is selected from a covalent bond or a bivalent, straight or branched, saturated or unsaturated, optionally substituted $C_{1-30}$ hydrocarbon chain wherein one or more methylene units of Y are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group;

T is an NR, $CR_2$, O, or S;

D is an anti-inflammatory agent;

Antibody is an antibody that binds a CD74 protein and comprises a heavy chain (HC) comprising an amino acid sequence selected from SEQ ID NO:69, 70, 71, and 72 and a light chain (LC) comprising the amino acid sequence of SEQ ID NO:7;

Z is a linkage formed between (i) a reactive functional group selected from the group consisting of maleimide and strained cycloalkyne, and (ii) the side chain of an amino acid in the heavy chain or light chain of the antibody;

each occurrence of R is independently hydrogen, a suitable protecting group, an acyl moiety, arylalkyl moiety, aliphatic moiety, aryl moiety, heteroaryl moiety, or heteroaliphatic moiety;

n is 1, 2, 3, or 4;

m is 1, 2, 3, 4, 5, 6, 7, 8, 9, or 10;

and a pharmaceutically acceptable carrier.

2. The composition of claim 1, wherein the anti-inflammatory agent comprises a glucocorticoid receptor agonist.

3. The composition of claim 1, wherein the anti-inflammatory agent comprises Cortisol, cortisone acetate, beclometasone, prednisone, prednisolone, methylprednisolone, betamethasone, trimcinolone, budesonide, dexamethasone, fluticasone, or mometasone.

4. The composition of claim 1, wherein the antibody comprises the heavy chain comprising SEQ ID NO: 69 or SEQ ID NO: 70 and the reactive functional group comprises the strained cycloalkyne.

5. A method for treating an inflammatory disease or disorder by providing to a subject having the disease or disorder a composition comprising a compound having formula (I)

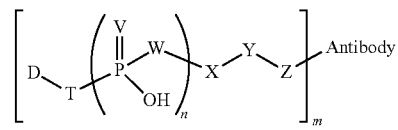

wherein V is selected from O and S;

W is selected from O, N, and $CH_2$;

X is a tuning element selected from a covalent bond; a carbon atom; a heteroatom; an optionally substituted group selected from the group consisting of acyl, aliphatic, heteroaliphatic, aryl, heteroaryl, and heterocyclic; nucleoside, protease sensitive group, cathepsin B sensitive group, or glycosidase sensitive group;

Y is selected from a covalent bond or a bivalent, straight or branched, saturated or unsaturated, optionally substituted $C_{1-30}$ hydrocarbon chain wherein one or more methylene units of Y are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group;

T is an NR, $CR_2$, O, or S;

D is an anti-inflammatory agent;

Antibody is an antibody that binds a CD74 protein and comprises a heavy chain (HC) comprising an amino acid sequence selected from SEQ ID NO:69, 70, 71, and 72 and a light chain (LC) comprising the amino acid sequence of SEQ ID NO:73;

Z is a linkage formed between (i) a reactive functional group selected from the group consisting of maleimide and strained cycloalkyne and (ii) the side chain of an amino acid in the heavy chain or light chain of the antibody;

each occurrence of R is independently hydrogen, a suitable protecting group, an acyl moiety, arylalkyl moiety, aliphatic moiety, aryl moiety, heteroaryl moiety, or heteroaliphatic moiety;

n is 1, 2, 3, or 4;

m is 1, 2, 3, 4, 5, 6, 7, 8, 9, or 10;

and a pharmaceutically acceptable carrier to treat the inflammatory disease or disorder.

6. The method of claim 5, wherein the anti-inflammatory agent comprises a glucocorticoid receptor agonist.

7. The method of claim 5, wherein the anti-inflammatory agent comprises Cortisol, cortisone acetate, beclometasone, prednisone, prednisolone, methylprednisolone, betamethasone, trimcinolone, budesonide, dexamethasone, fluticasone, or mometasone.

8. The method of claim 5, wherein the antibody comprises the heavy chain comprising SEQ ID NO: 69 or SEQ ID NO:70 and the reactive functional group comprises the strained cycloalkyne.

9. The method of claim 5, wherein the inflammatory disease or disorder comprises Alzheimer's disease, ankylosing spondylitis arthritis (osteoarthritis, rheumatoid arthritis (RA), psoriatic arthritis), asthma, atherosclerosis, Crohn's disease, colitis, dermatitis, diverticulitis, fibromyalgia, hepatitis, irritable bowel syndrome (IBS), systemic lupus erythematous (SLE), nephritis, Parkinson's disease, or ulcerative colitis.

10. An antibody drug conjugate comprising
(a) an antibody that binds a CD74 protein, the antibody comprising a heavy chain (HC) comprising an amino acid sequence selected from SEQ ID NO:69 or 70 and a light chain (LC) comprising the amino acid sequence of SEQ ID NO:73, wherein the antibody comprises a para-azidophenylalanine (pAzF) conjugated to a molecule selected from the group of molecules consisting of
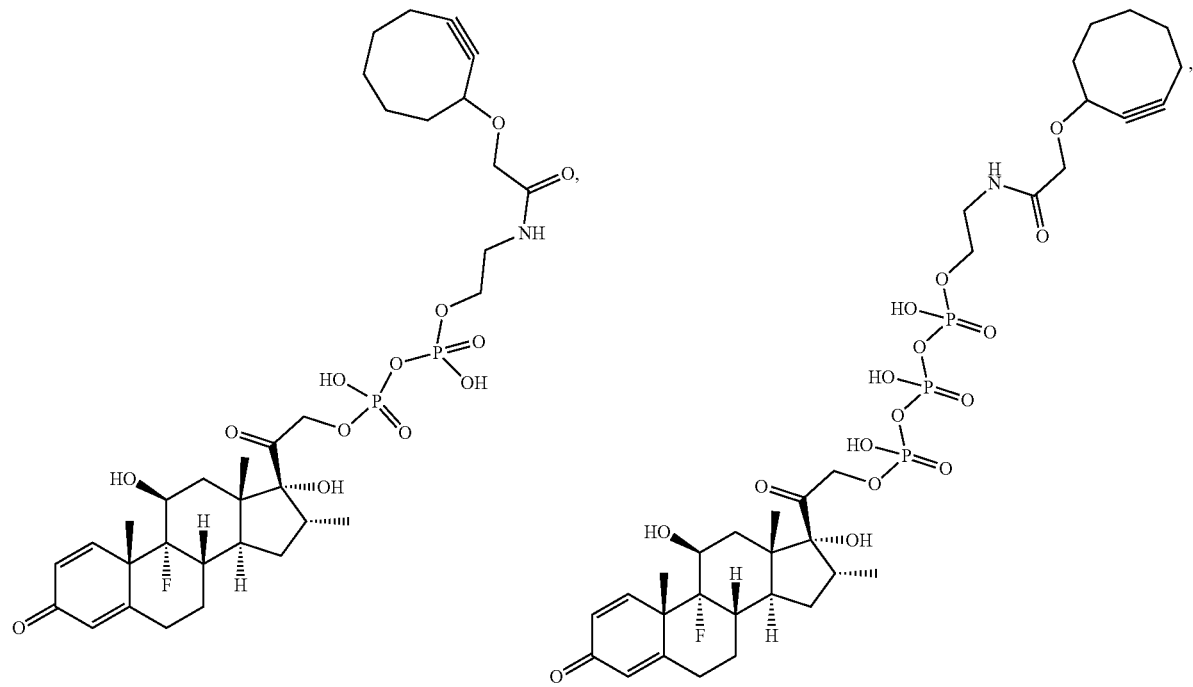
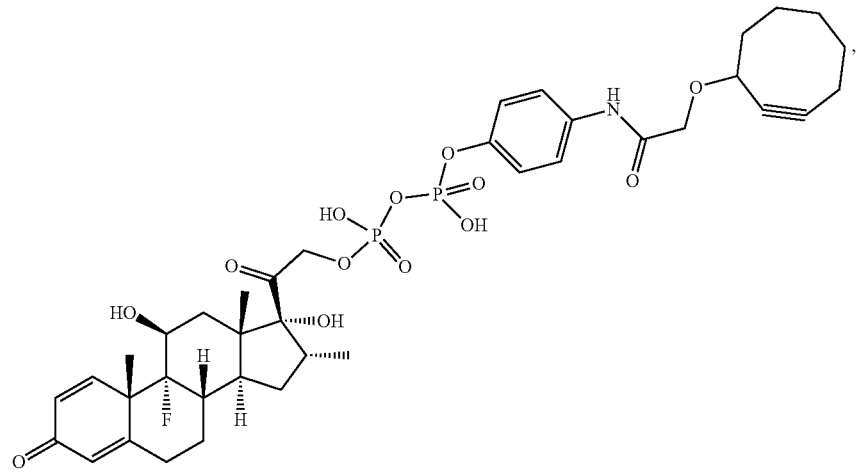
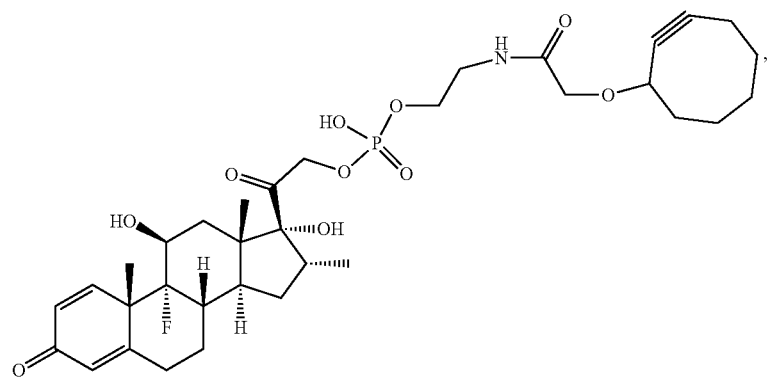

5-3
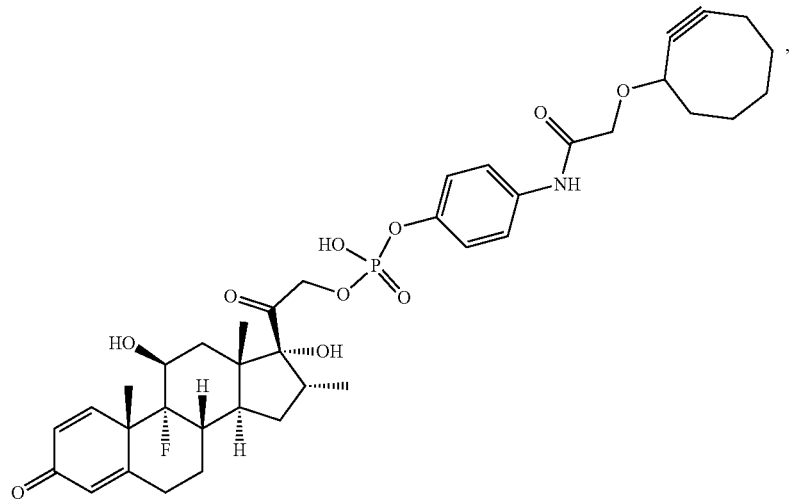
6-2
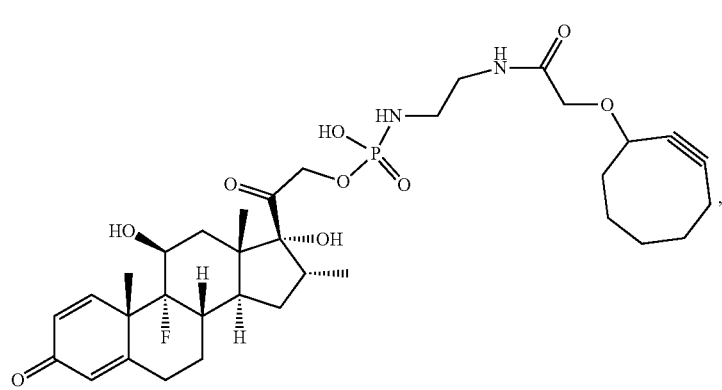
8-5
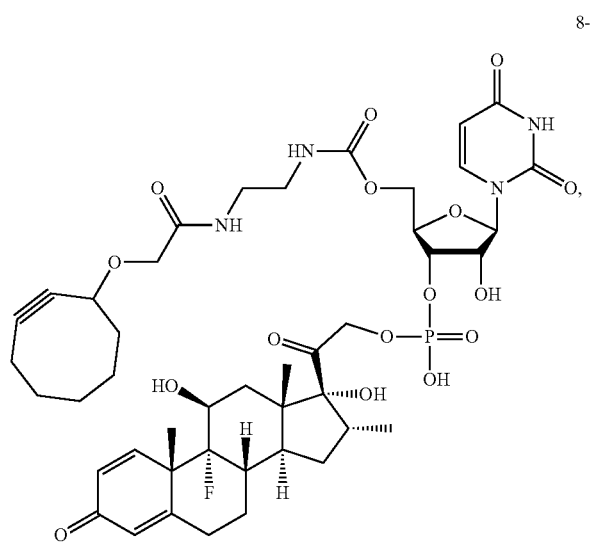
9-4
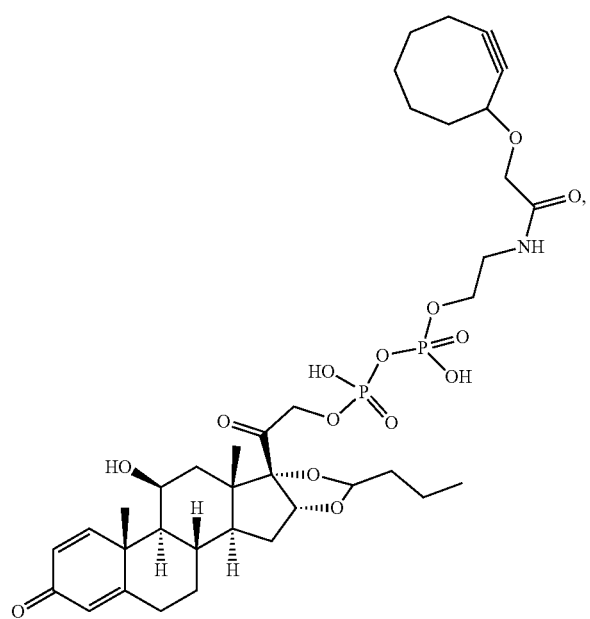

11-5
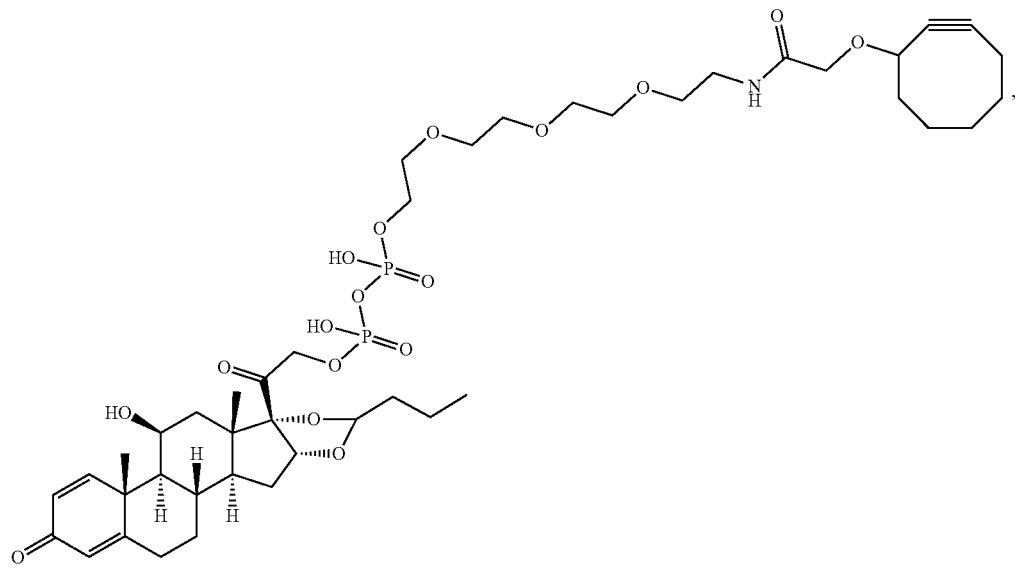
12-3
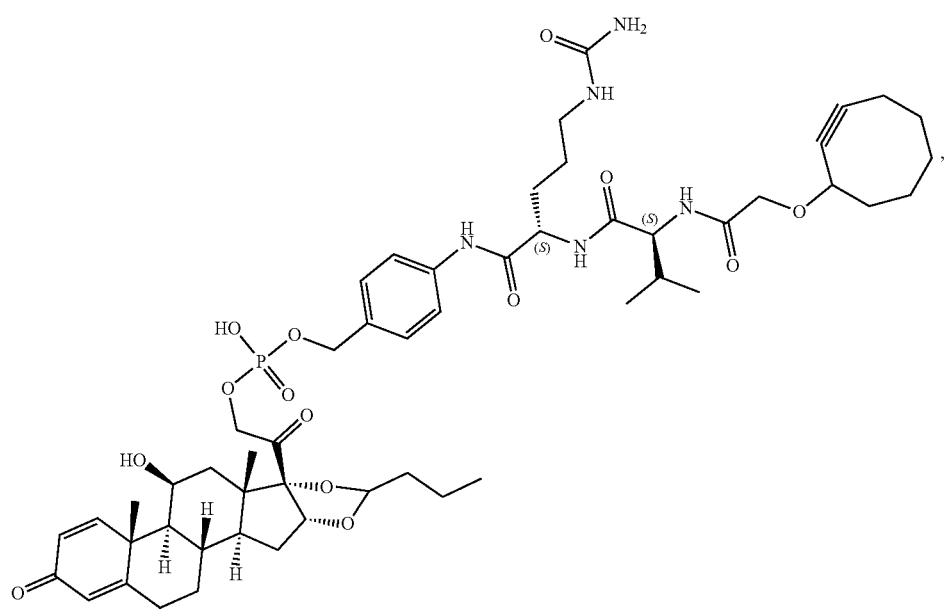
13-7
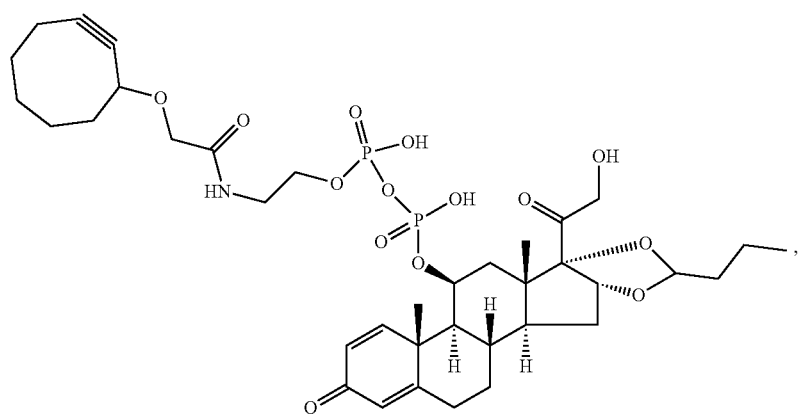

-continued
14-5
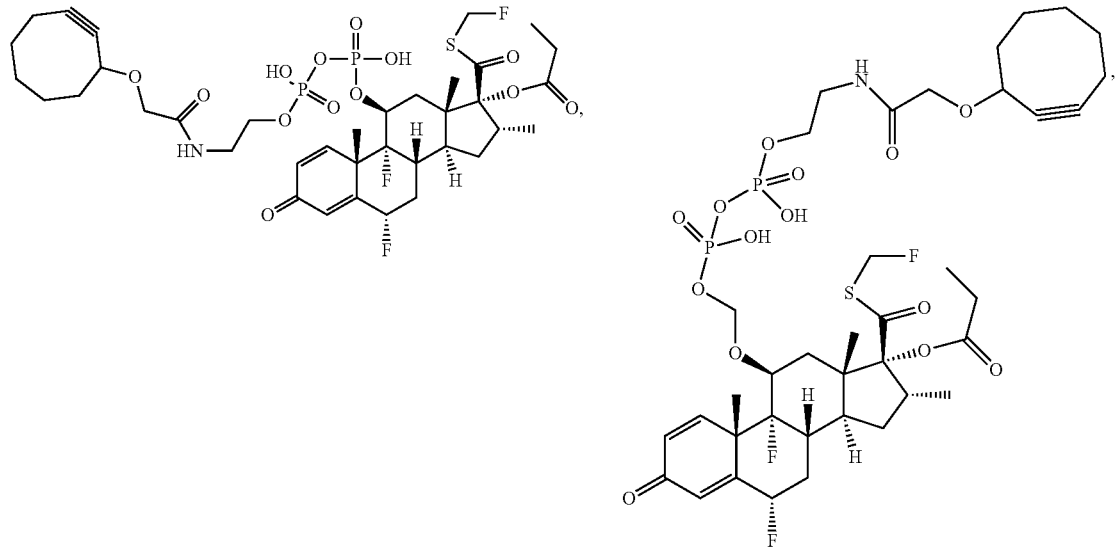
15-5
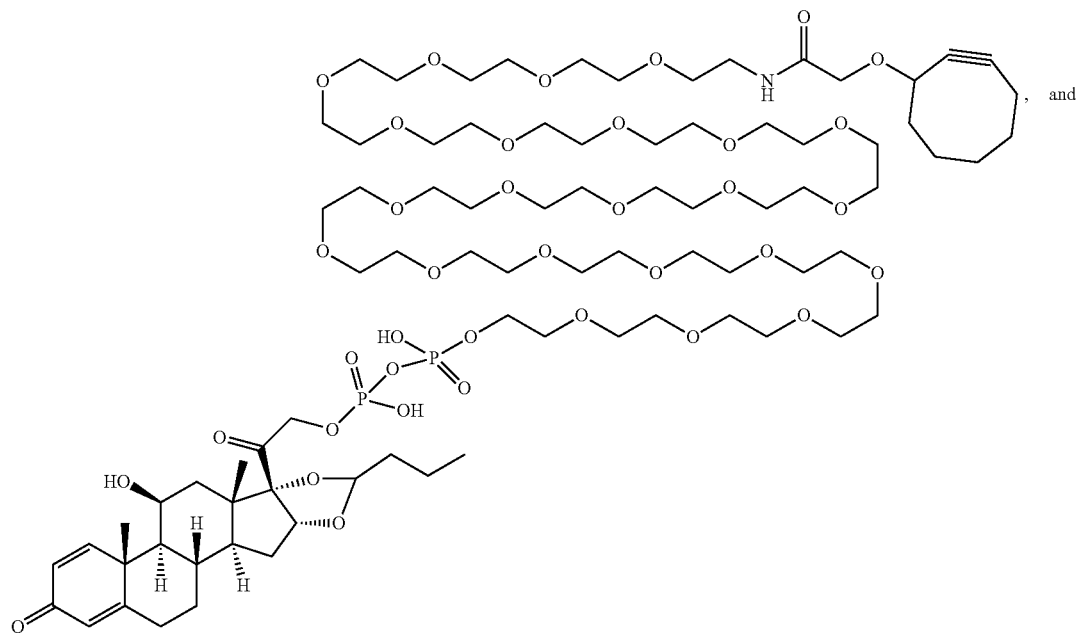
16-5
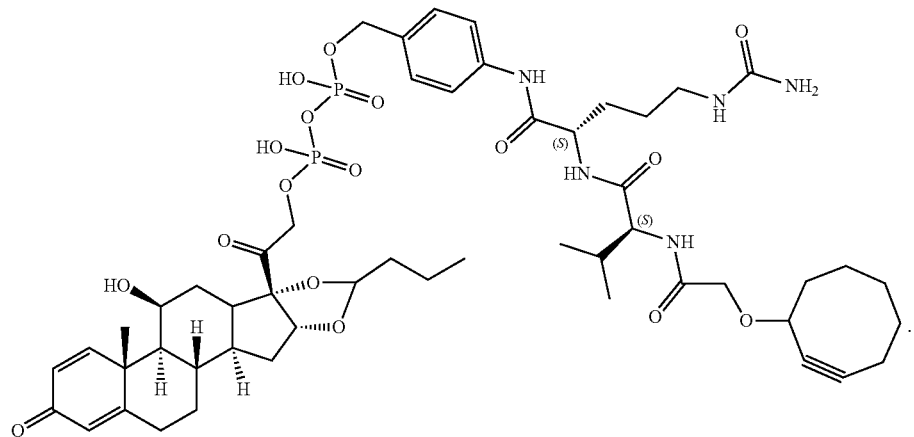
, and
17-2
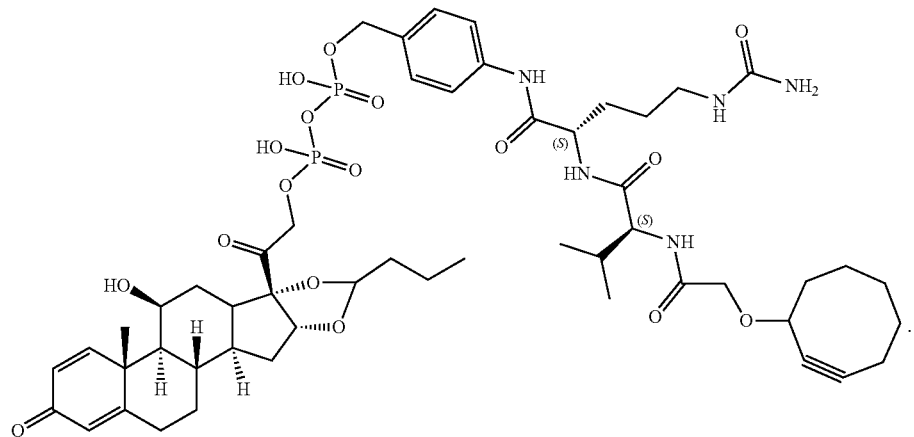

11. The composition of claim 4, wherein the strained cycloalkyne is cyclooctyne.
12. The method of claim 8, wherein the strained cycloalkyne is cyclooctyne.
13. The antibody drug conjugate of claim 10, wherein the molecule
14. The antibody drug conjugate of claim 10, wherein the molecule is
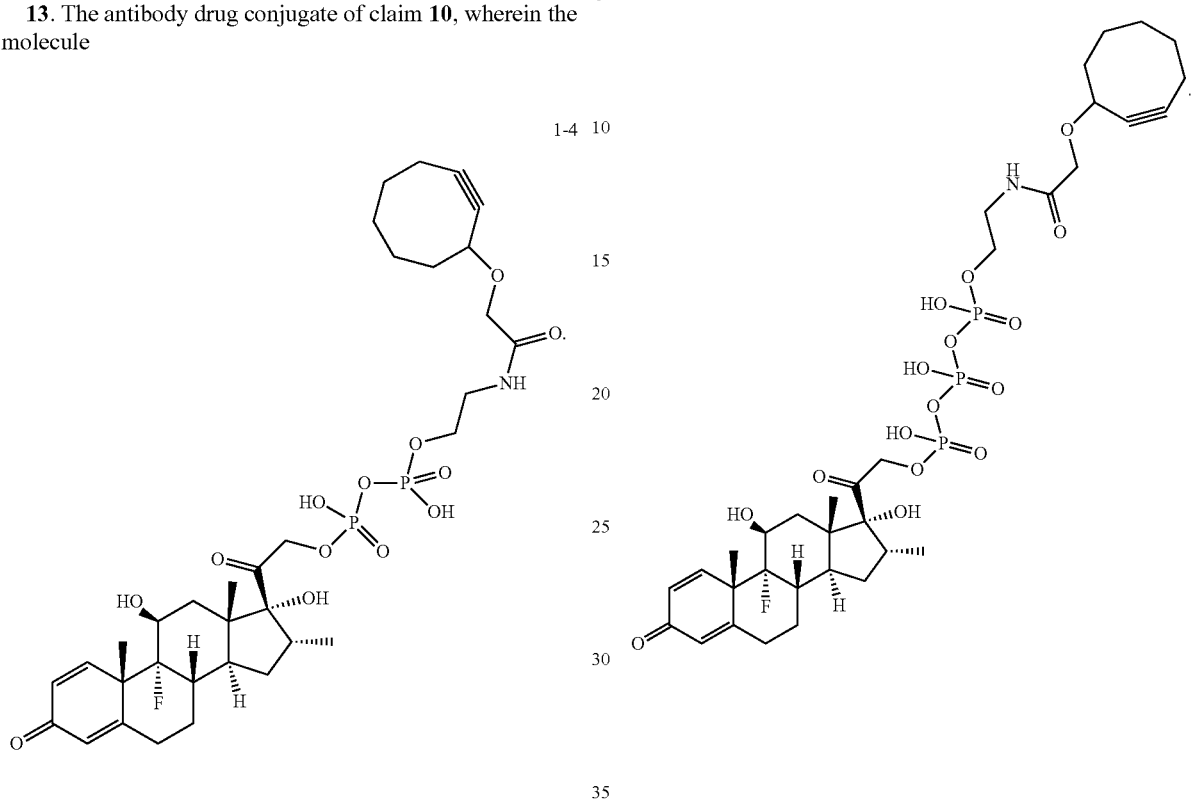
15. The antibody drug conjugate of claim 10, wherein the molecule is
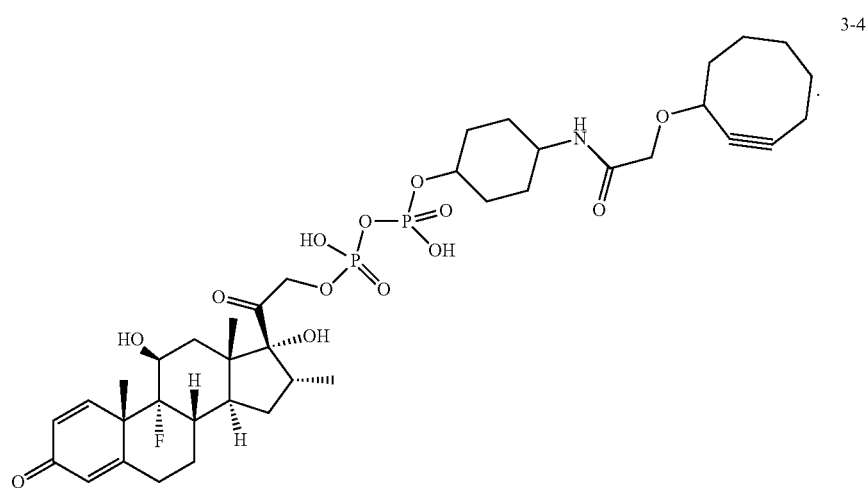

16. The antibody drug conjugate of claim 10, wherein the molecule is
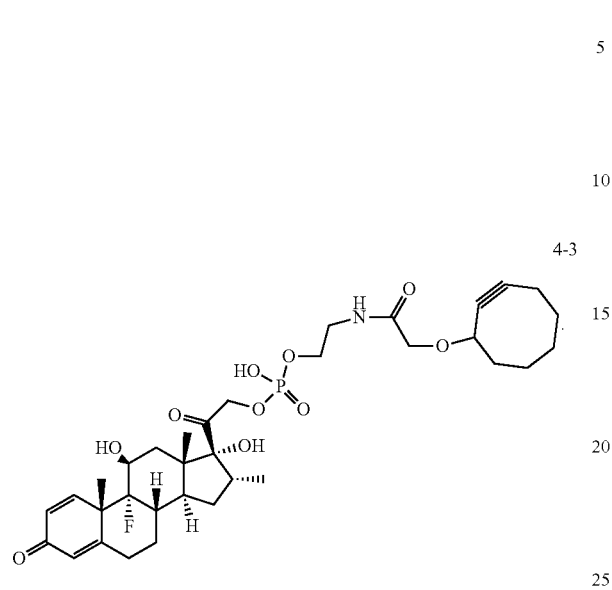
4-3
17. The antibody drug conjugate of claim 10, wherein the molecule is
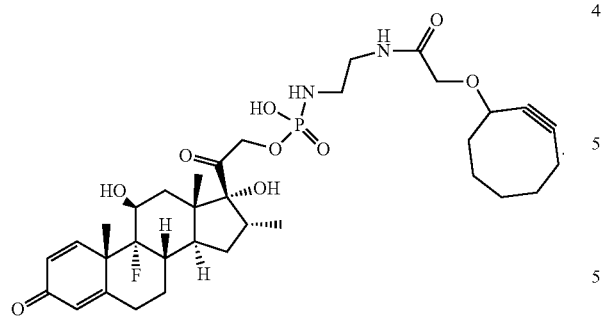
6-2
18. The antibody drug conjugate of claim 10, wherein the molecule is
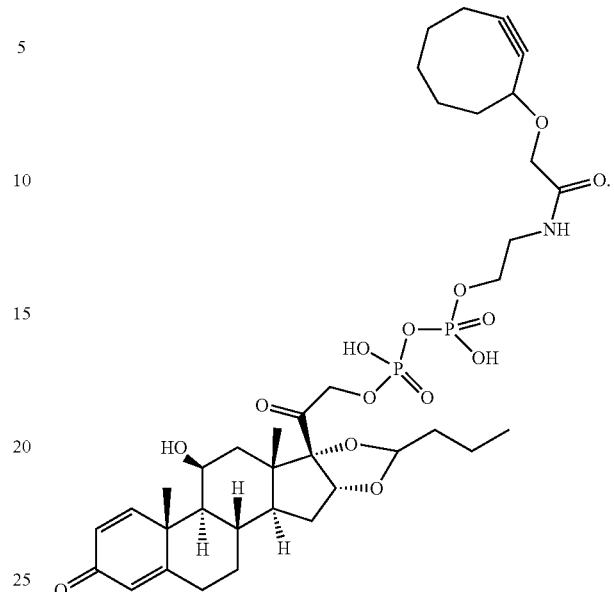
9-4
19. The antibody drug conjugate of claim 10, wherein the molecule is
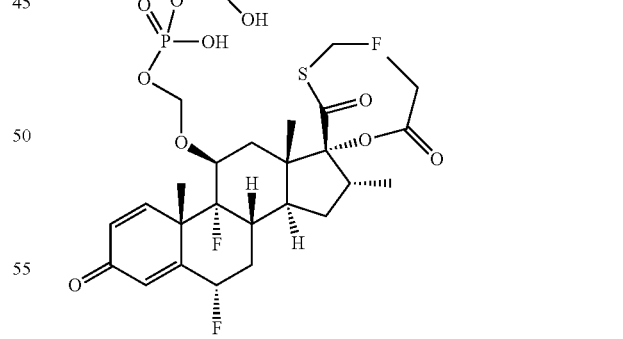
15-5
20. The antibody drug conjugate of claim 10, wherein the molecule is

SEQUENCE LISTING

```
<160> NUMBER OF SEQ ID NOS: 82

<210> SEQ ID NO 1
<211> LENGTH: 12
<212> TYPE: PRT
<213> ORGANISM: Artificial Sequence
<220> FEATURE:
<223> OTHER INFORMATION: Anti-CD25 LC CDR1

<400> SEQUENCE: 1

Arg Ala Ser Gln Ser Val Ser Ser Ser Tyr Leu Ala
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Anti-CD25 LC CDR2

<400> SEQUENCE: 2

Gly Ala Ser Ser Arg Ala Thr
1               5

<210> SEQ ID NO 3
<211> LENGTH: 9
<212> TYPE: PRT
<213> ORGANISM: Artificial Sequence
<220> FEATURE:
<223> OTHER INFORMATION: Anti-CD25 LC CDR3

<400> SEQUENCE: 3

Gln Gln Tyr Ser Ser Ser Pro Leu Thr
1               5

<210> SEQ ID NO 4
<211> LENGTH: 5
<212> TYPE: PRT
<213> ORGANISM: Artificial Sequence
<220> FEATURE:
<223> OTHER INFORMATION: Anti-CD25 HC CDR1

<400> SEQUENCE: 4

Arg Tyr Ile Ile Asn
1               5

<210> SEQ ID NO 5
<211> LENGTH: 17
```

```
<212> TYPE: PRT
<213> ORGANISM: Artificial Sequence
<220> FEATURE:
<223> OTHER INFORMATION: Anti-CD25 HC CDR2

<400> SEQUENCE: 5

Arg Ile Ile Pro Ile Leu Gly Val Glu Asn Tyr Ala Gln Lys Phe Gln
1               5                   10                  15
Gly

<210> SEQ ID NO 6
<211> LENGTH: 6
<212> TYPE: PRT
<213> ORGANISM: Artificial Sequence
<220> FEATURE:
<223> OTHER INFORMATION: Anti-CD25 HC CDR3

<400> SEQUENCE: 6

Lys Asp Trp Phe Asp Tyr
1               5

<210> SEQ ID NO 7
<211> LENGTH: 5
<212> TYPE: PRT
<213> ORGANISM: Artificial Sequence
<220> FEATURE:
<223> OTHER INFORMATION: Anti-CD25 HC CDR1

<400> SEQUENCE: 7

Arg Tyr Pro Ile Asn
1               5

<210> SEQ ID NO 8
<211> LENGTH: 17
<212> TYPE: PRT
<213> ORGANISM: Artificial Sequence
<220> FEATURE:
<223> OTHER INFORMATION: Anti-CD25 HC CDR2

<400> SEQUENCE: 8

Arg Ile Ile Pro Ile Leu Gly Ile Ala Asp Tyr Ala Gln Arg Phe Gln
1               5                   10                  15
Gly

<210> SEQ ID NO 9
<211> LENGTH: 6
<212> TYPE: PRT
<213> ORGANISM: Artificial Sequence
<220> FEATURE:
<223> OTHER INFORMATION: Anti-CD25 HC CDR3

<400> SEQUENCE: 9

Arg Asp Trp Gly Asp Tyr
1               5

<210> SEQ ID NO 10
<211> LENGTH: 9
<212> TYPE: PRT
<213> ORGANISM: Artificial Sequence
<220> FEATURE:
<223> OTHER INFORMATION: Anti-CD25 LC CDR3

<400> SEQUENCE: 10

Gln Gln Tyr Gly Ser Ser Pro Ile Thr
1               5
```

```
<210> SEQ ID NO 11
<211> LENGTH: 5
<212> TYPE: PRT
<213> ORGANISM: Artificial Sequence
<220> FEATURE:
<223> OTHER INFORMATION: Anti-CD25 HC CDR1

<400> SEQUENCE: 11

Arg Tyr Ala Ile Asn
1               5

<210> SEQ ID NO 12
<211> LENGTH: 17
<212> TYPE: PRT
<213> ORGANISM: Artificial Sequence
<220> FEATURE:
<223> OTHER INFORMATION: Anti-CD25 HC CDR2

<400> SEQUENCE: 12

Arg Ile Ile Pro Ile Leu Asp Ile Ala Asp Tyr Ala Gln Lys Phe Gln
1               5                   10                  15

Asp

<210> SEQ ID NO 13
<211> LENGTH: 6
<212> TYPE: PRT
<213> ORGANISM: Artificial Sequence
<220> FEATURE:
<223> OTHER INFORMATION: Anti-CD25 HC CDR3

<400> SEQUENCE: 13

Lys Asp Trp Phe Asp Pro
1               5

<210> SEQ ID NO 14
<211> LENGTH: 5
<212> TYPE: PRT
<213> ORGANISM: Artificial Sequence
<220> FEATURE:
<223> OTHER INFORMATION: Anti-CD25 HC CDR1

<400> SEQUENCE: 14

Arg Tyr Pro Ile Asn
1               5

<210> SEQ ID NO 15
<211> LENGTH: 11
<212> TYPE: PRT
<213> ORGANISM: Artificial Sequence
<220> FEATURE:
<223> OTHER INFORMATION: Anti-CD70 LC CDR1

<400> SEQUENCE: 15

Arg Ala Ser Gln Ser Val Ser Ser Tyr Leu Ala
1               5                   10

<210> SEQ ID NO 16
<211> LENGTH: 8
<212> TYPE: PRT
<213> ORGANISM: Artificial Sequence
<220> FEATURE:
<223> OTHER INFORMATION: Anti-CD70 LC CDR2

<400> SEQUENCE: 16

Tyr Asp Ala Ser Asn Arg Ala Thr
1               5
```

```
<210> SEQ ID NO 17
<211> LENGTH: 9
<212> TYPE: PRT
<213> ORGANISM: Artificial Sequence
<220> FEATURE:
<223> OTHER INFORMATION: Anti-CD70 LC CDR3

<400> SEQUENCE: 17

Gln Gln Arg Thr Asn Trp Pro Leu Thr
1               5

<210> SEQ ID NO 18
<211> LENGTH: 5
<212> TYPE: PRT
<213> ORGANISM: Artificial Sequence
<220> FEATURE:
<223> OTHER INFORMATION: Anti-CD70 HC CDR1

<400> SEQUENCE: 18

Ser Tyr Ile Met His
1               5

<210> SEQ ID NO 19
<211> LENGTH: 16
<212> TYPE: PRT
<213> ORGANISM: Artificial Sequence
<220> FEATURE:
<223> OTHER INFORMATION: Anti-CD70 HC CDR2

<400> SEQUENCE: 19

Val Ile Ser Tyr Asp Gly Arg Asn Lys Tyr Tyr Ala Asp Ser Val Lys
1               5                   10                  15

<210> SEQ ID NO 20
<211> LENGTH: 9
<212> TYPE: PRT
<213> ORGANISM: Artificial Sequence
<220> FEATURE:
<223> OTHER INFORMATION: Anti-CD70 HC CDR3

<400> SEQUENCE: 20

Asp Thr Asp Gly Tyr Asp Phe Asp Tyr
1               5

<210> SEQ ID NO 21
<211> LENGTH: 11
<212> TYPE: PRT
<213> ORGANISM: Artificial Sequence
<220> FEATURE:
<223> OTHER INFORMATION: Anti-CD70 LC CDR1

<400> SEQUENCE: 21

Arg Ala Ser Gln Gly Ile Ser Ser Ala Leu Ala
1               5                   10

<210> SEQ ID NO 22
<211> LENGTH: 7
<212> TYPE: PRT
<213> ORGANISM: Artificial Sequence
<220> FEATURE:
<223> OTHER INFORMATION: Anti-CD70 LC CDR2

<400> SEQUENCE: 22

Asp Ala Ser Ser Leu Glu Ser
1               5
```

```
<210> SEQ ID NO 23
<211> LENGTH: 9
<212> TYPE: PRT
<213> ORGANISM: Artificial Sequence
<220> FEATURE:
<223> OTHER INFORMATION: Anti-CD70 LC CDR3

<400> SEQUENCE: 23

Gln Gln Phe Asn Ser Tyr Pro Phe Thr
1               5

<210> SEQ ID NO 24
<211> LENGTH: 5
<212> TYPE: PRT
<213> ORGANISM: Artificial Sequence
<220> FEATURE:
<223> OTHER INFORMATION: Anti-CD70 HC CDR1

<400> SEQUENCE: 24

Tyr Tyr Ala Met His
1               5

<210> SEQ ID NO 25
<211> LENGTH: 16
<212> TYPE: PRT
<213> ORGANISM: Artificial Sequence
<220> FEATURE:
<223> OTHER INFORMATION: Anti-CD70 HC CDR2

<400> SEQUENCE: 25

Val Ile Ser Tyr Asp Gly Ser Ile Lys Tyr Tyr Ala Asp Ser Val Lys
1               5                   10                  15

<210> SEQ ID NO 26
<211> LENGTH: 10
<212> TYPE: PRT
<213> ORGANISM: Artificial Sequence
<220> FEATURE:
<223> OTHER INFORMATION: Anti-CD70 HC CDR3

<400> SEQUENCE: 26

Glu Gly Pro Tyr Ser Asn Tyr Leu Asp Tyr
1               5                   10

<210> SEQ ID NO 27
<211> LENGTH: 11
<212> TYPE: PRT
<213> ORGANISM: Artificial Sequence
<220> FEATURE:
<223> OTHER INFORMATION: Anti-CD70 LC CDR1

<400> SEQUENCE: 27

Arg Ala Ser Gln Gly Ile Ser Ser Trp Leu Ala
1               5                   10

<210> SEQ ID NO 28
<211> LENGTH: 7
<212> TYPE: PRT
<213> ORGANISM: Artificial Sequence
<220> FEATURE:
<223> OTHER INFORMATION: Anti-CD70 LC CDR2

<400> SEQUENCE: 28

Ala Ala Ser Ser Leu Gln Ser
1               5
```

```
<210> SEQ ID NO 29
<211> LENGTH: 9
<212> TYPE: PRT
<213> ORGANISM: Artificial Sequence
<220> FEATURE:
<223> OTHER INFORMATION: Anti-CD70 LC CDR3

<400> SEQUENCE: 29

Gln Gln Tyr Asn Ser Tyr Pro Leu Thr
1               5

<210> SEQ ID NO 30
<211> LENGTH: 5
<212> TYPE: PRT
<213> ORGANISM: Artificial Sequence
<220> FEATURE:
<223> OTHER INFORMATION: Anti-CD70 HC CDR1

<400> SEQUENCE: 30

Asp Tyr Gly Met His
1               5

<210> SEQ ID NO 31
<211> LENGTH: 16
<212> TYPE: PRT
<213> ORGANISM: Artificial Sequence
<220> FEATURE:
<223> OTHER INFORMATION: Anti-CD70 HC CDR2

<400> SEQUENCE: 31

Val Ile Trp Tyr Asp Gly Ser Asn Lys Tyr Tyr Ala Asp Ser Val Lys
1               5                   10                  15

<210> SEQ ID NO 32
<211> LENGTH: 10
<212> TYPE: PRT
<213> ORGANISM: Artificial Sequence
<220> FEATURE:
<223> OTHER INFORMATION: Anti-CD70 HC CDR3

<400> SEQUENCE: 32

Asp Ser Ile Val Met Val Arg Gly Asp Tyr
1               5                   10

<210> SEQ ID NO 33
<211> LENGTH: 11
<212> TYPE: PRT
<213> ORGANISM: Artificial Sequence
<220> FEATURE:
<223> OTHER INFORMATION: Anti-CD70 LC CDR1

<400> SEQUENCE: 33

Arg Ala Ser Gln Gly Ile Ser Ser Trp Leu Ala
1               5                   10

<210> SEQ ID NO 34
<211> LENGTH: 7
<212> TYPE: PRT
<213> ORGANISM: Artificial Sequence
<220> FEATURE:
<223> OTHER INFORMATION: Anti-CD70 LC CDR2

<400> SEQUENCE: 34

Ala Ala Ser Ser Leu Gln Ser
1               5

<210> SEQ ID NO 35
```

```
<211> LENGTH: 9
<212> TYPE: PRT
<213> ORGANISM: Artificial Sequence
<220> FEATURE:
<223> OTHER INFORMATION: Anti-CD70 LC CDR3

<400> SEQUENCE: 35

Gln Gln Tyr Asn Ser Tyr Pro Leu Thr
1               5

<210> SEQ ID NO 36
<211> LENGTH: 5
<212> TYPE: PRT
<213> ORGANISM: Artificial Sequence
<220> FEATURE:
<223> OTHER INFORMATION: Anti-CD70 HC CDR1

<400> SEQUENCE: 36

Asp His Gly Met His
1               5

<210> SEQ ID NO 37
<211> LENGTH: 16
<212> TYPE: PRT
<213> ORGANISM: Artificial Sequence
<220> FEATURE:
<223> OTHER INFORMATION: Anti-CD70 HC CDR2

<400> SEQUENCE: 37

Val Ile Trp Tyr Asp Gly Ser Asn Lys Tyr Tyr Ala Asp Ser Val Lys
1               5                   10                  15

<210> SEQ ID NO 38
<211> LENGTH: 9
<212> TYPE: PRT
<213> ORGANISM: Artificial Sequence
<220> FEATURE:
<223> OTHER INFORMATION: Anti-CD70 HC CDR3

<400> SEQUENCE: 38

Asp Ser Ile Met Val Arg Gly Asp Tyr
1               5

<210> SEQ ID NO 39
<211> LENGTH: 7
<212> TYPE: PRT
<213> ORGANISM: Artificial Sequence
<220> FEATURE:
<223> OTHER INFORMATION: Anti-CD70 LC CDR2

<400> SEQUENCE: 39

Asp Ala Ser Asn Arg Ala Thr
1               5

<210> SEQ ID NO 40
<211> LENGTH: 9
<212> TYPE: PRT
<213> ORGANISM: Artificial Sequence
<220> FEATURE:
<223> OTHER INFORMATION: Anti-CD70 LC CDR3

<400> SEQUENCE: 40

Gln Gln Arg Ser Asn Trp Pro Leu Thr
1               5

<210> SEQ ID NO 41
<211> LENGTH: 7
```

```
<212> TYPE: PRT
<213> ORGANISM: Artificial Sequence
<220> FEATURE:
<223> OTHER INFORMATION: Anti-CD70 HC CDR1

<400> SEQUENCE: 41

Ser Asp Tyr Tyr Tyr Trp Ser
1               5

<210> SEQ ID NO 42
<211> LENGTH: 16
<212> TYPE: PRT
<213> ORGANISM: Artificial Sequence
<220> FEATURE:
<223> OTHER INFORMATION: Anti-CD70 HC CDR2

<400> SEQUENCE: 42

Tyr Ile Tyr Tyr Ser Gly Ser Thr Asn Tyr Asp Pro Ser Leu Lys Ser
1               5                   10                  15

<210> SEQ ID NO 43
<211> LENGTH: 12
<212> TYPE: PRT
<213> ORGANISM: Artificial Sequence
<220> FEATURE:
<223> OTHER INFORMATION: Anti-CD70 HC CDR3

<400> SEQUENCE: 43

Gly Asp Gly Asp Tyr Gly Gly Asn Cys Phe Asp Tyr
1               5                   10

<210> SEQ ID NO 44
<211> LENGTH: 16
<212> TYPE: PRT
<213> ORGANISM: Artificial Sequence
<220> FEATURE:
<223> OTHER INFORMATION: Anti-CD74 LC CDR1

<400> SEQUENCE: 44

Arg Ser Ser Gln Ser Leu Val His Arg Asn Gly Asn Thr Tyr Leu His
1               5                   10                  15

<210> SEQ ID NO 45
<211> LENGTH: 7
<212> TYPE: PRT
<213> ORGANISM: Artificial Sequence
<220> FEATURE:
<223> OTHER INFORMATION: Anti-CD74 LC CDR2

<400> SEQUENCE: 45

Thr Val Ser Asn Arg Phe Ser
1               5

<210> SEQ ID NO 46
<211> LENGTH: 9
<212> TYPE: PRT
<213> ORGANISM: Artificial Sequence
<220> FEATURE:
<223> OTHER INFORMATION: Anti-CD74 LC CDR3

<400> SEQUENCE: 46

Ser Gln Ser Ser His Val Pro Pro Thr
1               5

<210> SEQ ID NO 47
<211> LENGTH: 5
<212> TYPE: PRT
```

```
<213> ORGANISM: Artificial Sequence
<220> FEATURE:
<223> OTHER INFORMATION: Anti-CD74 HC CDR1

<400> SEQUENCE: 47

Asn Tyr Gly Val Asn
1               5

<210> SEQ ID NO 48
<211> LENGTH: 17
<212> TYPE: PRT
<213> ORGANISM: Artificial Sequence
<220> FEATURE:
<223> OTHER INFORMATION: Anti-CD74 HC CDR2

<400> SEQUENCE: 48

Trp Ile Asn Pro Asn Thr Gly Glu Pro Thr Phe Asp Asp Asp Phe Lys
1               5                   10                  15

Gly

<210> SEQ ID NO 49
<211> LENGTH: 11
<212> TYPE: PRT
<213> ORGANISM: Artificial Sequence
<220> FEATURE:
<223> OTHER INFORMATION: Anti-CD74 HC CDR3

<400> SEQUENCE: 49

Ser Arg Gly Lys Asn Glu Ala Trp Phe Ala Tyr
1               5                   10

<210> SEQ ID NO 50
<211> LENGTH: 6
<212> TYPE: PRT
<213> ORGANISM: Artificial Sequence
<220> FEATURE:
<223> OTHER INFORMATION: Anti-CD74 LC CDR1

<400> SEQUENCE: 50

Gln Gly Ile Ser Ser Trp
1               5

<210> SEQ ID NO 51
<211> LENGTH: 9
<212> TYPE: PRT
<213> ORGANISM: Artificial Sequence
<220> FEATURE:
<223> OTHER INFORMATION: Anti-CD74 LC CDR3

<400> SEQUENCE: 51

Gln Gln Tyr Asn Ser Tyr Pro Leu Thr
1               5

<210> SEQ ID NO 52
<211> LENGTH: 8
<212> TYPE: PRT
<213> ORGANISM: Artificial Sequence
<220> FEATURE:
<223> OTHER INFORMATION: Anti-CD74 HC CDR1

<400> SEQUENCE: 52

Gly Phe Thr Phe Ser Ser Tyr Ala
1               5

<210> SEQ ID NO 53
<211> LENGTH: 8
```

```
<212> TYPE: PRT
<213> ORGANISM: Artificial Sequence
<220> FEATURE:
<223> OTHER INFORMATION: Anti-CD74 HC CDR2

<400> SEQUENCE: 53

Ile Ser Tyr Asp Gly Ser Asn Lys
1               5

<210> SEQ ID NO 54
<211> LENGTH: 16
<212> TYPE: PRT
<213> ORGANISM: Artificial Sequence
<220> FEATURE:
<223> OTHER INFORMATION: Anti-CD74 HC CDR3

<400> SEQUENCE: 54

Ala Ser Gly Arg Tyr Tyr Gly Ser Gly Ser Tyr Ser Ser Tyr Phe Asp
1               5                   10                  15

<210> SEQ ID NO 55
<211> LENGTH: 8
<212> TYPE: PRT
<213> ORGANISM: Artificial Sequence
<220> FEATURE:
<223> OTHER INFORMATION: Anti-CD74 HC CDR2

<400> SEQUENCE: 55

Ile Ser Tyr Asp Gly Ser Ile Lys
1               5

<210> SEQ ID NO 56
<211> LENGTH: 16
<212> TYPE: PRT
<213> ORGANISM: Artificial Sequence
<220> FEATURE:
<223> OTHER INFORMATION: Anti-CD74 HC CDR3

<400> SEQUENCE: 56

Ala Arg Gly Arg Glu Tyr Thr Ser Gln Asn Ile Val Ile Leu Leu Asp
1               5                   10                  15

<210> SEQ ID NO 57
<211> LENGTH: 16
<212> TYPE: PRT
<213> ORGANISM: Artificial Sequence
<220> FEATURE:
<223> OTHER INFORMATION: Anti-CD74 HC CDR3

<400> SEQUENCE: 57

Ala Arg Gly Arg Glu Ile Thr Ser Gln Asn Ile Val Ile Leu Leu Asp
1               5                   10                  15

<210> SEQ ID NO 58
<211> LENGTH: 8
<212> TYPE: PRT
<213> ORGANISM: Artificial Sequence
<220> FEATURE:
<223> OTHER INFORMATION: Anti-CD74 HC CDR2

<400> SEQUENCE: 58

Ile Trp Tyr Asp Gly Ser Asn Lys
1               5

<210> SEQ ID NO 59
<211> LENGTH: 16
<212> TYPE: PRT
```

```
<213> ORGANISM: Artificial Sequence
<220> FEATURE:
<223> OTHER INFORMATION: Anti-CD74 HC CDR3

<400> SEQUENCE: 59

Ala Arg Gly Gly Thr Leu Val Arg Gly Ala Met Tyr Gly Thr Asp Val
1               5                   10                  15

<210> SEQ ID NO 60
<211> LENGTH: 9
<212> TYPE: PRT
<213> ORGANISM: Artificial Sequence
<220> FEATURE:
<223> OTHER INFORMATION: Anti-CD163 LC CDR1

<400> SEQUENCE: 60

Ala Ser Gln Ser Val Ser Ser Asp Val
1               5

<210> SEQ ID NO 61
<211> LENGTH: 8
<212> TYPE: PRT
<213> ORGANISM: Artificial Sequence
<220> FEATURE:
<223> OTHER INFORMATION: Anti-CD163 LC CDR3

<400> SEQUENCE: 61

Gln Asp Tyr Thr Ser Pro Arg Thr
1               5

<210> SEQ ID NO 62
<211> LENGTH: 8
<212> TYPE: PRT
<213> ORGANISM: Artificial Sequence
<220> FEATURE:
<223> OTHER INFORMATION: Anti-CD163 HC CDR1

<400> SEQUENCE: 62

Gly Tyr Ser Ile Thr Ser Asp Tyr
1               5

<210> SEQ ID NO 63
<211> LENGTH: 12
<212> TYPE: PRT
<213> ORGANISM: Artificial Sequence
<220> FEATURE:
<223> OTHER INFORMATION: Anti-CD163 HC CDR3

<400> SEQUENCE: 63

Cys Val Ser Gly Thr Tyr Tyr Phe Asp Tyr Trp Gly
1               5                   10

<210> SEQ ID NO 64
<211> LENGTH: 9
<212> TYPE: PRT
<213> ORGANISM: Artificial Sequence
<220> FEATURE:
<223> OTHER INFORMATION: Anti-CD163 LC CDR1

<400> SEQUENCE: 64

Ala Ser Gln Ser Val Ser His Asp Val
1               5

<210> SEQ ID NO 65
<211> LENGTH: 8
<212> TYPE: PRT
<213> ORGANISM: Artificial Sequence
```

<220> FEATURE:
<223> OTHER INFORMATION: Anti-CD163 LC CDR3

<400> SEQUENCE: 65

Gln Asp Tyr Ser Ser Pro Arg Thr
1               5

<210> SEQ ID NO 66
<211> LENGTH: 4
<212> TYPE: PRT
<213> ORGANISM: Artificial Sequence
<220> FEATURE:
<223> OTHER INFORMATION: Glycosylation site atN297 of IgG1

<400> SEQUENCE: 66

Gln Tyr Asn Ser
1

<210> SEQ ID NO 67
<211> LENGTH: 4
<212> TYPE: PRT
<213> ORGANISM: Artificial Sequence
<220> FEATURE:
<223> OTHER INFORMATION: Glycosylation site atN297 of IgG4

<400> SEQUENCE: 67

Gln Phe Asn Ser
1

<210> SEQ ID NO 68
<211> LENGTH: 4
<212> TYPE: PRT
<213> ORGANISM: Artificial Sequence
<220> FEATURE:
<223> OTHER INFORMATION: Mutated glycosylation site of IgG1 or IgG4

<400> SEQUENCE: 68

Gln Ala Gln Ser
1

<210> SEQ ID NO 69
<211> LENGTH: 450
<212> TYPE: PRT
<213> ORGANISM: Artificial Sequence
<220> FEATURE:
<223> OTHER INFORMATION: Anti-CD74 IgG1
<220> FEATURE:
<221> NAME/KEY: MISC_FEATURE
<222> LOCATION: (121)..(121)
<223> OTHER INFORMATION: Xaa at position 121 is para-azido phenylalanine
      (pAzF)

<400> SEQUENCE: 69

Gln Val Gln Leu Gln Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Val Asn Trp Ile Lys Gln Ala Pro Gly Gln Gly Leu Gln Trp Met
        35                  40                  45

Gly Trp Ile Asn Pro Asn Thr Gly Glu Pro Thr Phe Asp Asp Asp Phe
    50                  55                  60

Lys Gly Arg Phe Ala Phe Ser Leu Asp Thr Ser Val Ser Thr Ala Tyr
65                  70                  75                  80

Leu Gln Ile Ser Ser Leu Lys Ala Asp Asp Thr Ala Val Tyr Phe Cys
                85                  90                  95

```
Ser Arg Ser Arg Gly Lys Asn Glu Ala Trp Phe Ala Tyr Trp Gly Gln
            100                 105                 110

Gly Ser Leu Val Thr Val Ser Xaa Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 70
<211> LENGTH: 447
<212> TYPE: PRT
<213> ORGANISM: Artificial Sequence
<220> FEATURE:
<223> OTHER INFORMATION: Anti-CD74 IgG4
<220> FEATURE:
<221> NAME/KEY: MISC_FEATURE
```

<222> LOCATION: (121)..(121)
<223> OTHER INFORMATION: Xaa at position 121 is para-azido-phenylalanine
      (pAzF)

<400> SEQUENCE: 70

```
Gln Val Gln Leu Gln Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Val Asn Trp Ile Lys Gln Ala Pro Gly Gln Gly Leu Gln Trp Met
        35                  40                  45

Gly Trp Ile Asn Pro Asn Thr Gly Glu Pro Thr Phe Asp Asp Asp Phe
50                  55                  60

Lys Gly Arg Phe Ala Phe Ser Leu Asp Thr Ser Val Ser Thr Ala Tyr
65                  70                  75                  80

Leu Gln Ile Ser Ser Leu Lys Ala Asp Asp Thr Ala Val Tyr Phe Cys
                85                  90                  95

Ser Arg Ser Arg Gly Lys Asn Glu Ala Trp Phe Ala Tyr Trp Gly Gln
            100                 105                 110

Gly Ser Leu Val Thr Val Ser Ser Xaa Ser Thr Lys Gly Pro Ser Val
        115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
```

```
                385                 390                 395                 400
Asp Gly Ser Phe Phe Leu Tyr Ser Arg Leu Thr Val Asp Lys Ser Arg
                    405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly Lys
            435                 440                 445

<210> SEQ ID NO 71
<211> LENGTH: 450
<212> TYPE: PRT
<213> ORGANISM: Artificial Sequence
<220> FEATURE:
<223> OTHER INFORMATION: Anti-CD74 IgG1

<400> SEQUENCE: 71

Gln Val Gln Leu Gln Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Val Asn Trp Ile Lys Gln Ala Pro Gly Gln Gly Leu Gln Trp Met
        35                  40                  45

Gly Trp Ile Asn Pro Asn Thr Gly Glu Pro Thr Phe Asp Asp Asp Phe
    50                  55                  60

Lys Gly Arg Phe Ala Phe Ser Leu Asp Thr Ser Val Ser Thr Ala Tyr
65                  70                  75                  80

Leu Gln Ile Ser Ser Leu Lys Ala Asp Asp Thr Ala Val Tyr Phe Cys
                85                  90                  95

Ser Arg Ser Arg Gly Lys Asn Glu Ala Trp Phe Ala Tyr Trp Gly Gln
            100                 105                 110

Gly Ser Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
```

```
305                 310                 315                 320
Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 72
<211> LENGTH: 447
<212> TYPE: PRT
<213> ORGANISM: Artificial Sequence
<220> FEATURE:
<223> OTHER INFORMATION: Anti-CD74 IgG4

<400> SEQUENCE: 72

Gln Val Gln Leu Gln Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Val Asn Trp Ile Lys Gln Ala Pro Gly Gln Gly Leu Gln Trp Met
        35                  40                  45

Gly Trp Ile Asn Pro Asn Thr Gly Glu Pro Thr Phe Asp Asp Asp Phe
    50                  55                  60

Lys Gly Arg Phe Ala Phe Ser Leu Asp Thr Ser Val Ser Thr Ala Tyr
65                  70                  75                  80

Leu Gln Ile Ser Ser Leu Lys Ala Asp Asp Thr Ala Val Tyr Phe Cys
                85                  90                  95

Ser Arg Ser Arg Gly Lys Asn Glu Ala Trp Phe Ala Tyr Trp Gly Gln
            100                 105                 110

Gly Ser Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
```

```
            210                 215                 220
Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
                260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 73
<211> LENGTH: 219
<212> TYPE: PRT
<213> ORGANISM: Artificial Sequence
<220> FEATURE:
<223> OTHER INFORMATION: Anti-CD74 LC

<400> SEQUENCE: 73

Asp Ile Gln Leu Thr Gln Ser Pro Leu Ser Leu Pro Val Thr Leu Gly
1               5                   10                  15

Gln Pro Ala Ser Ile Ser Cys Arg Ser Ser Gln Ser Leu Val His Arg
            20                  25                  30

Asn Gly Asn Thr Tyr Leu His Trp Phe Gln Gln Arg Pro Gly Gln Ser
        35                  40                  45

Pro Arg Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Ser His Val Pro Pro Thr Phe Gly Ala Gly Thr Arg Leu Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
```

```
               130                 135                 140
Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 74
<211> LENGTH: 455
<212> TYPE: PRT
<213> ORGANISM: Artificial Sequence
<220> FEATURE:
<223> OTHER INFORMATION: Anti-CD74 IgG1
<220> FEATURE:
<221> NAME/KEY: MISC_FEATURE
<222> LOCATION: (126)..(126)
<223> OTHER INFORMATION: Xaa at position 126 is para-azido-phenylalanine
      (pAzF)

<400> SEQUENCE: 74

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Ile Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Phe Tyr Cys
                85                  90                  95

Ala Arg Gly Arg Glu Glu Ile Thr Ser Gln Asn Ile Val Ile Leu Leu
            100                 105                 110

Asp Tyr Trp Gly Gln Gly Thr Leu Val Thr Val Thr Ser Xaa Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255
```

-continued

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 75
<211> LENGTH: 907
<212> TYPE: PRT
<213> ORGANISM: Artificial Sequence
<220> FEATURE:
<223> OTHER INFORMATION: Anti-CD74 IgG4
<220> FEATURE:
<221> NAME/KEY: MISC_FEATURE
<222> LOCATION: (126)..(126)
<223> OTHER INFORMATION: Xaa at position 126 is para-azido-phenylalanine
      (pAzF)

<400> SEQUENCE: 75

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Ile Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Phe Tyr Cys
                85                  90                  95

Ala Arg Gly Arg Glu Glu Ile Thr Ser Gln Asn Ile Val Ile Leu Leu
            100                 105                 110

Asp Tyr Trp Gly Gln Gly Thr Leu Val Thr Val Thr Ser Xaa Ser Thr
        115                 120                 125

```
Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly Lys Gln Val Gln Leu Val Glu Ser Gly Gly Gly Val Val
    450                 455                 460

Gln Pro Gly Arg Ser Leu Arg Leu Ser Cys Ala Ala Ser Gly Phe Thr
465                 470                 475                 480

Phe Ser Ser Tyr Ala Met His Trp Val Arg Gln Ala Pro Gly Lys Gly
                485                 490                 495

Leu Glu Trp Val Ala Val Ile Ser Tyr Asp Gly Ser Ile Lys Tyr Tyr
            500                 505                 510

Ala Asp Ser Val Lys Gly Arg Phe Thr Ile Ser Arg Asp Asn Ser Lys
        515                 520                 525

Asn Thr Leu Tyr Leu Gln Met Asn Ser Leu Arg Val Glu Asp Thr Ala
    530                 535                 540

Val Phe Tyr Cys Ala Arg Gly Arg Glu Glu Ile Thr Ser Gln Asn Ile
```

```
                545                 550                 555                 560
Val Ile Leu Leu Asp Tyr Trp Gly Gln Gly Thr Leu Val Thr Val Thr
                    565                 570                 575

Ser Ala Ser Thr Lys Gly Pro Ser Val Phe Pro Leu Ala Pro Ser Ser
                    580                 585                 590

Lys Ser Thr Ser Gly Gly Thr Ala Ala Leu Gly Cys Leu Val Lys Asp
                    595                 600                 605

Tyr Phe Pro Glu Pro Val Thr Val Ser Trp Asn Ser Gly Ala Leu Thr
                    610                 615                 620

Ser Gly Val His Thr Phe Pro Ala Val Leu Gln Ser Ser Gly Leu Tyr
625                 630                 635                 640

Ser Leu Ser Ser Val Val Thr Val Pro Ser Ser Ser Leu Gly Thr Gln
                    645                 650                 655

Thr Tyr Ile Cys Asn Val Asn His Lys Pro Ser Asn Thr Lys Val Asp
                    660                 665                 670

Lys Lys Val Glu Pro Lys Ser Cys Asp Lys Thr His Thr Cys Pro Pro
                    675                 680                 685

Cys Pro Ala Pro Glu Leu Leu Gly Gly Pro Ser Val Phe Leu Phe Pro
690                 695                 700

Pro Lys Pro Lys Asp Thr Leu Met Ile Ser Arg Thr Pro Glu Val Thr
705                 710                 715                 720

Cys Val Val Val Asp Val Ser His Glu Asp Pro Glu Val Lys Phe Asn
                    725                 730                 735

Trp Tyr Val Asp Gly Val Glu Val His Asn Ala Lys Thr Lys Pro Arg
                    740                 745                 750

Glu Glu Gln Tyr Asn Ser Thr Tyr Arg Val Val Ser Val Leu Thr Val
                    755                 760                 765

Leu His Gln Asp Trp Leu Asn Gly Lys Glu Tyr Lys Cys Lys Val Ser
                    770                 775                 780

Asn Lys Ala Leu Pro Ala Pro Ile Glu Lys Thr Ile Ser Lys Ala Lys
785                 790                 795                 800

Gly Gln Pro Arg Glu Pro Gln Val Tyr Thr Leu Pro Pro Ser Arg Asp
                    805                 810                 815

Glu Leu Thr Lys Asn Gln Val Ser Leu Thr Cys Leu Val Lys Gly Phe
                    820                 825                 830

Tyr Pro Ser Asp Ile Ala Val Glu Trp Glu Ser Asn Gly Gln Pro Glu
                    835                 840                 845

Asn Asn Tyr Lys Thr Thr Pro Pro Val Leu Asp Ser Asp Gly Ser Phe
850                 855                 860

Phe Leu Tyr Ser Lys Leu Thr Val Asp Lys Ser Arg Trp Gln Gln Gly
865                 870                 875                 880

Asn Val Phe Ser Cys Ser Val Met His Glu Ala Leu His Asn His Tyr
                    885                 890                 895

Thr Gln Lys Ser Leu Ser Leu Ser Pro Gly Lys
                    900                 905

<210> SEQ ID NO 76
<211> LENGTH: 455
<212> TYPE: PRT
<213> ORGANISM: Artificial Sequence
<220> FEATURE:
<223> OTHER INFORMATION: Anti-CD74 IgG1

<400> SEQUENCE: 76

Gln Val Gln Leu Val Glu Ser Gly Gly Gly Val Val Gln Pro Gly Arg
```

```
1               5                   10                  15
Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
            35                  40                  45

Ala Val Ile Ser Tyr Asp Gly Ser Ile Lys Tyr Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Phe Tyr Cys
            85                  90                  95

Ala Arg Gly Arg Glu Glu Ile Thr Ser Gln Asn Ile Val Ile Leu Leu
            100                 105                 110

Asp Tyr Trp Gly Gln Gly Thr Leu Val Thr Val Thr Ser Ala Ser Thr
            115                 120                 125

Lys Gly Pro Ser Val Phe Pro Leu Ala Pro Ser Ser Lys Ser Thr Ser
            130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
            165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
            195                 200                 205

Asn Val Asn His Lys Pro Ser Asn Thr Lys Val Asp Lys Lys Val Glu
            210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
            245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
            290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
            325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
            355                 360                 365

Asn Gln Val Ser Leu Thr Cys Leu Val Lys Gly Phe Tyr Pro Ser Asp
            370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
            405                 410                 415

Lys Leu Thr Val Asp Lys Ser Arg Trp Gln Gln Gly Asn Val Phe Ser
            420                 425                 430
```

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 77
<211> LENGTH: 452
<212> TYPE: PRT
<213> ORGANISM: Artificial Sequence
<220> FEATURE:
<223> OTHER INFORMATION: Anti-CD74 IgG4

<400> SEQUENCE: 77

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Ile Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Phe Tyr Cys
                85                  90                  95

Ala Arg Gly Arg Glu Glu Ile Thr Ser Gln Asn Ile Val Ile Leu Leu
            100                 105                 110

Asp Tyr Trp Gly Gln Gly Thr Leu Val Thr Val Thr Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

```
Ile Glu Lys Thr Ile Ser Lys Ala Lys Gly Gln Pro Arg Glu Pro Gln
            340                 345                 350

Val Tyr Thr Leu Pro Pro Ser Gln Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
            435                 440                 445

Ser Leu Gly Lys
    450

<210> SEQ ID NO 78
<211> LENGTH: 214
<212> TYPE: PRT
<213> ORGANISM: Artificial Sequence
<220> FEATURE:
<223> OTHER INFORMATION: Anti-CD74 LC

<400> SEQUENCE: 78

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 79
```

```
<211> LENGTH: 447
<212> TYPE: PRT
<213> ORGANISM: Artificial Sequence
<220> FEATURE:
<223> OTHER INFORMATION: Anti-CD70 2H5 IgG1
<220> FEATURE:
<221> NAME/KEY: MISC_FEATURE
<222> LOCATION: (119)..(119)
<223> OTHER INFORMATION: Xaa at position 119 is para-azido-phenylalanine
      (pAF)

<400> SEQUENCE: 79
```

| | | | | | | | | | | | | | | |
|---|---|---|---|---|---|---|---|---|---|---|---|---|---|---|
| Gln | Val | Gln | Leu | Val | Glu | Ser | Gly | Gly | Gly | Val | Val | Gln | Pro | Gly | Arg |
| 1 | | | | 5 | | | | | 10 | | | | | 15 | |

Ser Leu Arg Leu Ser Cys Ala Ala Ser Gly Phe Thr Phe Ser Ser Tyr
            20                  25                  30

Ile Met His Trp Val Arg Gln Ala Pro Gly Lys Gly Leu Glu Trp Val
        35                  40                  45

Ala Val Ile Ser Tyr Asp Gly Arg Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Thr Asp Gly Tyr Asp Phe Asp Tyr Trp Gly Gln Gly Thr
            100                 105                 110

Leu Val Thr Val Ser Ser Xaa Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

```
Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 80
<211> LENGTH: 652
<212> TYPE: PRT
<213> ORGANISM: Artificial Sequence
<220> FEATURE:
<223> OTHER INFORMATION: Anti-CD70 Kappa light chain
<220> FEATURE:
<221> NAME/KEY: MISC_FEATURE
<222> LOCATION: (329)..(329)
<223> OTHER INFORMATION: Xaa can be any naturaqlly occuring amino acid

<400> SEQUENCE: 80

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Thr Asn Trp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gln Val Lys Leu Leu Gln Ser Gly Ala Ala
    210                 215                 220

Leu Val Lys Pro Gly Ala Ser Val Lys Met Ser Cys Lys Ala Ser Gly
225                 230                 235                 240

Tyr Ser Phe Pro Asp Ser Trp Val Thr Trp Val Lys Gln Ser His Gly
                245                 250                 255
```

```
Lys Ser Leu Glu Trp Ile Gly Asp Ile Phe Pro Asn Ser Gly Ala Thr
            260                 265                 270

Asn Phe Asn Glu Lys Phe Lys Gly Lys Ala Thr Leu Thr Val Asp Lys
        275                 280                 285

Ser Thr Ser Thr Ala Tyr Met Glu Leu Ser Arg Leu Thr Ser Glu Asp
    290                 295                 300

Ser Ala Ile Tyr Tyr Cys Thr Arg Leu Asp Tyr Gly Tyr Trp Gly Gln
305                 310                 315                 320

Gly Val Met Val Thr Val Ser Ser Xaa Lys Thr Thr Pro Pro Ser Val
                325                 330                 335

Tyr Pro Leu Ala Pro Gly Ser Ala Ala Gln Thr Asn Ser Met Val Thr
                340                 345                 350

Leu Gly Cys Leu Val Lys Gly Tyr Phe Pro Glu Pro Val Thr Val Thr
                355                 360                 365

Trp Asn Ser Gly Ser Leu Ser Ser Gly Val His Thr Phe Pro Ala Val
            370                 375                 380

Leu Gln Ser Asp Leu Tyr Thr Leu Ser Ser Ser Val Thr Val Pro Ser
385                 390                 395                 400

Ser Thr Trp Pro Ser Glu Thr Val Thr Cys Asn Val Ala His Pro Ala
                405                 410                 415

Ser Ser Thr Lys Val Asp Lys Lys Ile Val Pro Arg Asp Cys Gly Cys
                420                 425                 430

Lys Pro Cys Ile Cys Thr Val Pro Glu Val Ser Ser Val Phe Ile Phe
            435                 440                 445

Pro Pro Lys Pro Lys Asp Val Leu Thr Ile Thr Leu Thr Pro Lys Val
450                 455                 460

Thr Cys Val Val Val Ala Ile Ser Lys Asp Asp Pro Glu Val Gln Phe
465                 470                 475                 480

Ser Trp Phe Val Asp Asp Val Glu Val His Thr Ala Gln Thr Gln Pro
                485                 490                 495

Arg Glu Glu Gln Phe Asn Ser Thr Phe Arg Ser Val Ser Glu Leu Pro
                500                 505                 510

Ile Met His Gln Asp Trp Leu Asn Gly Lys Glu Phe Lys Cys Arg Val
                515                 520                 525

Asn Ser Ala Ala Phe Pro Ala Pro Ile Glu Lys Thr Ile Ser Lys Thr
            530                 535                 540

Lys Gly Arg Pro Lys Ala Pro Gln Val Tyr Thr Ile Pro Pro Pro Lys
545                 550                 555                 560

Glu Gln Met Ala Lys Asp Lys Val Ser Leu Thr Cys Met Ile Thr Asp
                565                 570                 575

Phe Phe Pro Glu Asp Ile Thr Val Glu Trp Gln Trp Asn Gly Gln Pro
                580                 585                 590

Ala Glu Asn Tyr Lys Asn Thr Gln Pro Ile Met Asp Thr Asp Gly Ser
            595                 600                 605

Tyr Phe Val Tyr Ser Lys Leu Asn Val Gln Lys Ser Asn Trp Glu Ala
            610                 615                 620

Gly Asn Thr Phe Thr Cys Ser Val Leu His Glu Gly Leu His Asn His
625                 630                 635                 640

His Thr Glu Lys Ser Leu Ser His Ser Pro Gly Lys
                645                 650

<210> SEQ ID NO 81
<211> LENGTH: 438
```

<212> TYPE: PRT
<213> ORGANISM: Artificial Sequence
<220> FEATURE:
<223> OTHER INFORMATION: Anti-murine CD25 muIgG1 D265A
<220> FEATURE:
<221> NAME/KEY: MISC_FEATURE
<222> LOCATION: (115)..(115)
<223> OTHER INFORMATION: Xaa at position 115 is para-azido-phenylalanine (pAF)

<400> SEQUENCE: 81

```
Gln Val Lys Leu Leu Gln Ser Gly Ala Ala Leu Val Lys Pro Gly Ala
1               5                   10                  15

Ser Val Lys Met Ser Cys Lys Ala Ser Gly Tyr Ser Phe Pro Asp Ser
            20                  25                  30

Trp Val Thr Trp Val Lys Gln Ser His Gly Lys Ser Leu Glu Trp Ile
        35                  40                  45

Gly Asp Ile Phe Pro Asn Ser Gly Ala Thr Asn Phe Asn Glu Lys Phe
50                  55                  60

Lys Gly Lys Ala Thr Leu Thr Val Asp Lys Ser Thr Ser Thr Ala Tyr
65                  70                  75                  80

Met Glu Leu Ser Arg Leu Thr Ser Glu Asp Ser Ala Ile Tyr Tyr Cys
                85                  90                  95

Thr Arg Leu Asp Tyr Gly Tyr Trp Gly Gln Gly Val Met Val Thr Val
            100                 105                 110

Ser Ser Xaa Lys Thr Thr Pro Pro Ser Val Tyr Pro Leu Ala Pro Gly
        115                 120                 125

Ser Ala Ala Gln Thr Asn Ser Met Val Thr Leu Gly Cys Leu Val Lys
130                 135                 140

Gly Tyr Phe Pro Glu Pro Val Thr Val Thr Trp Asn Ser Gly Ser Leu
145                 150                 155                 160

Ser Ser Gly Val His Thr Phe Pro Ala Val Leu Gln Ser Asp Leu Tyr
                165                 170                 175

Thr Leu Ser Ser Ser Val Thr Val Pro Ser Ser Thr Trp Pro Ser Glu
            180                 185                 190

Thr Val Thr Cys Asn Val Ala His Pro Ala Ser Ser Thr Lys Val Asp
        195                 200                 205

Lys Lys Ile Val Pro Arg Asp Cys Gly Cys Lys Pro Cys Ile Cys Thr
210                 215                 220

Val Pro Glu Val Ser Ser Val Phe Ile Phe Pro Pro Lys Pro Lys Asp
225                 230                 235                 240

Val Leu Thr Ile Thr Leu Thr Pro Lys Val Thr Cys Val Val Val Ala
                245                 250                 255

Ile Ser Lys Asp Asp Pro Glu Val Gln Phe Ser Trp Phe Val Asp Asp
            260                 265                 270

Val Glu Val His Thr Ala Gln Thr Gln Pro Arg Glu Glu Gln Phe Asn
        275                 280                 285

Ser Thr Phe Arg Ser Val Ser Glu Leu Pro Ile Met His Gln Asp Trp
290                 295                 300

Leu Asn Gly Lys Glu Phe Lys Cys Arg Val Asn Ser Ala Ala Phe Pro
305                 310                 315                 320

Ala Pro Ile Glu Lys Thr Ile Ser Lys Thr Lys Gly Arg Pro Lys Ala
                325                 330                 335

Pro Gln Val Tyr Thr Ile Pro Pro Lys Glu Gln Met Ala Lys Asp
            340                 345                 350

Lys Val Ser Leu Thr Cys Met Ile Thr Asp Phe Phe Pro Glu Asp Ile
```

```
                    355                 360                 365
Thr Val Glu Trp Gln Trp Asn Gly Gln Pro Ala Glu Asn Tyr Lys Asn
        370                 375                 380

Thr Gln Pro Ile Met Asp Thr Asp Gly Ser Tyr Phe Val Tyr Ser Lys
385                 390                 395                 400

Leu Asn Val Gln Lys Ser Asn Trp Glu Ala Gly Asn Thr Phe Thr Cys
                405                 410                 415

Ser Val Leu His Glu Gly Leu His Asn His His Thr Glu Lys Ser Leu
        420                 425                 430

Ser His Ser Pro Gly Lys
        435

<210> SEQ ID NO 82
<211> LENGTH: 219
<212> TYPE: PRT
<213> ORGANISM: Artificial Sequence
<220> FEATURE:
<223> OTHER INFORMATION: Anti-murine CD25 muKappa

<400> SEQUENCE: 82

Asp Val Val Leu Thr Gln Thr Pro Pro Thr Leu Ser Ala Thr Ile Gly
1               5                   10                  15

Gln Ser Val Ser Ile Ser Cys Arg Ser Ser Gln Ser Leu Leu His Ser
            20                  25                  30

Asn Gly Asn Thr Tyr Leu Asn Trp Leu Leu Gln Arg Pro Gly Gln Pro
        35                  40                  45

Pro Gln Leu Leu Ile Tyr Leu Ala Ser Arg Leu Glu Ser Gly Val Pro
    50                  55                  60

Asn Arg Phe Ser Gly Ser Gly Ser Gly Thr Asp Phe Thr Leu Lys Ile
65                  70                  75                  80

Ser Gly Val Glu Ala Glu Asp Leu Gly Val Tyr Tyr Cys Val Gln Ser
                85                  90                  95

Ser His Phe Pro Asn Thr Phe Gly Val Gly Thr Lys Leu Glu Leu Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215
```